US010851358B2

(12) United States Patent
Jantz et al.

(10) Patent No.: US 10,851,358 B2
(45) Date of Patent: *Dec. 1, 2020

(54) ENGINEERED MEGANUCLEASES SPECIFIC FOR RECOGNITION SEQUENCES IN THE HEPATITIS B VIRUS GENOME

(71) Applicant: Precision BioSciences, Inc., Durham, NC (US)

(72) Inventors: Derek Jantz, Durham, NC (US); James Jefferson Smith, Morrisville, NC (US)

(73) Assignee: Precision BioSciences, Inc., Durham, NC (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/852,296

(22) Filed: Apr. 17, 2020

(65) Prior Publication Data

US 2020/0239864 A1 Jul. 30, 2020

Related U.S. Application Data

(63) Continuation of application No. 16/342,169, filed as application No. PCT/US2017/056638 on Oct. 13, 2017, now Pat. No. 10,662,416.

(60) Provisional application No. 62/527,159, filed on Jun. 30, 2017, provisional application No. 62/527,196, filed on Jun. 30, 2017, provisional application No. 62/452,506, filed on Jan. 31, 2017, provisional application No. 62/408,356, filed on Oct. 14, 2016.

(51) Int. Cl.

| | |
|---|---|
| ***C12N 15/86*** | (2006.01) |
| ***C12N 15/52*** | (2006.01) |
| ***C12N 9/22*** | (2006.01) |
| ***A61P 31/20*** | (2006.01) |
| ***A61K 9/51*** | (2006.01) |
| *A61K 38/43* | (2006.01) |
| *A61K 38/00* | (2006.01) |

(52) U.S. Cl.

CPC .................. *C12N 9/22* (2013.01); *A61K 9/51* (2013.01); *A61K 38/43* (2013.01); *A61P 31/20* (2018.01); *C12N 15/52* (2013.01); *C12N 15/86* (2013.01); *A61K 38/00* (2013.01); *C12N 2730/10122* (2013.01); *C12N 2750/14141* (2013.01)

(58) Field of Classification Search

CPC ........... C12N 9/22; C12N 15/52; C12N 15/86

See application file for complete search history.

(56) References Cited

U.S. PATENT DOCUMENTS

2019/0017075 A1* 1/2019 Bartsevich .............. A61P 35/00
2019/0142973 A1* 5/2019 Jantz .................... C12N 15/102 514/14.1

* cited by examiner

*Primary Examiner* — Maryam Monshipouri

(74) *Attorney, Agent, or Firm* — Wolf, Greenfield & Sacks, P.C.

(57) ABSTRACT

The present invention encompasses engineered meganucleases which recognize and cleave a recognition sequence within an open reading frame (ORF) of the genome of at least two genotypes of the Hepatitis B virus (HBV). The present invention also encompasses methods of using such engineered meganucleases in a pharmaceutical composition and in methods for treating or reducing the symptoms of a HBV infection, or treating hepatocellular carcinoma (HCC). Further, the invention encompasses pharmaceutical compositions comprising engineered meganuclease proteins, nucleic acids encoding engineered meganucleases, and the use of such compositions for treating HBV infections or HCC.

13 Claims, 21 Drawing Sheets

Specification includes a Sequence Listing.

|              |       HBV1       |      HBV2        |              |
|              |    Half-Site     |    Half-Site     |              |
| HBV 1-2      | CCCCTGCTC        | TACAGGCGG        | SEQ ID NO:10 |
| Recognition Sequence | GGGGACGAG | ATGTCCGCC    | SEQ ID NO:11 |

|              |       HBV5       |      HBV6        |              |
|              |    Half-Site     |    Half-Site     |              |
| HBV 5-6      | GATGATGTG        | TGGGGGCCA        | SEQ ID NO:12 |
| Recognition Sequence | CTACTACAC | ACCCCCGGT    | SEQ ID NO:13 |

|              |       HBV7       |      HBV8        |              |
|              |    Half-Site     |    Half-Site     |              |
| HBV 7-8      | TTTGCTGAC        | CCCCACTG         | SEQ ID NO:14 |
| Recognition Sequence | AAACGACTG | GGGGTGAC     | SEQ ID NO:15 |

|              |       HBV11      |      HBV12       |              |
|              |    Half-Site     |    Half-Site     |              |
| HBV 11-12    | TGCCGATCC        | TGCGGAACT        | SEQ ID NO:16 |
| Recognition Sequence | ACGGCTAGG | ACGCCTTGA    | SEQ ID NO:17 |

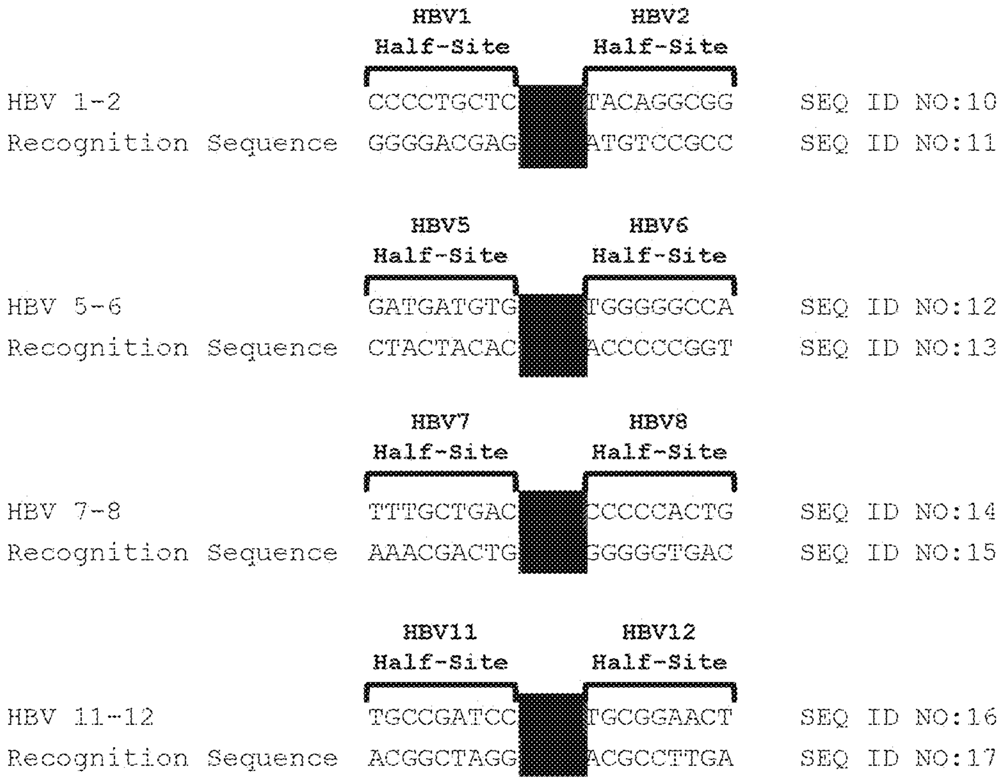

FIGURE 2

| HBV 1-2 | 185-206 of SEQ ID NO: 3 | SEQ ID NO: |
|---|---|---|
| Genotype A | CCCCTGCTCGTGTTACAGGCGG | 10 |
| Genotype B | CCCCTGCTCGTGTTACAGGCGG | 10 |
| Genotype C | CCCCTGCTCGTGTTACAGGCGG | 10 |
| Genotype D | CCCCT**T**CTCGTGTTACAGGCGG | 84 |
| Genotype E | CCCCTGCTCGTGTTACAGGCGG | 10 |
| Genotype F | CCCCTGCTCGTGTTACAGGCGG | 10 |
| Genotype G | CCCCTGCTCGTGTTACAGGCGG | 10 |

| HBV 5-6 | 742-763 of SEQ ID NO: 3 | SEQ ID NO: |
|---|---|---|
| Genotype A | GATGATGTGGTATTGGGGGCCA | 12 |
| Genotype B | GATGATGTGGTATTGGGGGCCA | 12 |
| Genotype C | GATGATGTGGTATTGGGGGCCA | 12 |
| Genotype D | GATGATGTGGTATTGGGGGCCA | 12 |
| Genotype E | GATGATGTGGTATTGGGGGCCA | 12 |
| Genotype F | GATGAT**C**TGGTATTGGGGGCCA | 85 |
| Genotype G | GATGATGTGGTATTGGGGGCCA | 12 |

| HBV 7-8 | 1183-1204 of SEQ ID NO: 3 | SEQ ID NO: |
|---|---|---|
| Genotype A | TTTGCTGACGCAACCCCCACTG | 14 |
| Genotype B | TTTGCTGACGCAACCCCCACTG | 14 |
| Genotype C | TTTGCTGACGCAACCCCCACTG | 14 |
| Genotype D | TTTGCTGACGCAACCCCCACTG | 14 |
| Genotype E | TTTGCTGA**T**GCAACCCCCACTG | 86 |
| Genotype F | TTTGCTGACGCAACCCCCACTG | 14 |
| Genotype G | TTTGCTGACGCAACCCCCACTG | 14 |

| HBV 11-12 | 1259-1280 of SEQ ID NO: 3 | SEQ ID NO: |
|---|---|---|
| Genotype A | TGCCGATCCATACTGCGGAACT | 16 |
| Genotype B | TGCCGATCCATACTGCGGAACT | 16 |
| Genotype C | TGCCGATCCATACTGCGGAACT | 16 |
| Genotype D | TGCCGATCCATACTGCGGAACT | 16 |
| Genotype E | TGCCGATCCATACTGCGGAACT | 16 |
| Genotype F | TGCCGATCCATACTGCGGAACT | 16 |
| Genotype G | TGCCGATCCATACTGCGGAACT | 16 |

FIGURE 4

C.
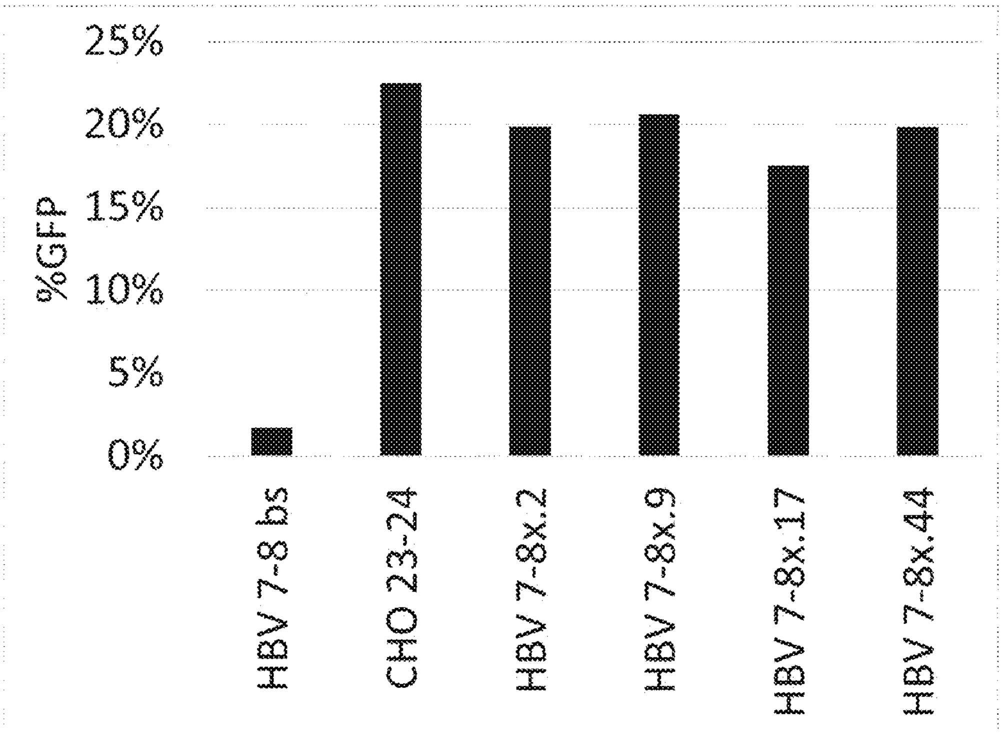
D.
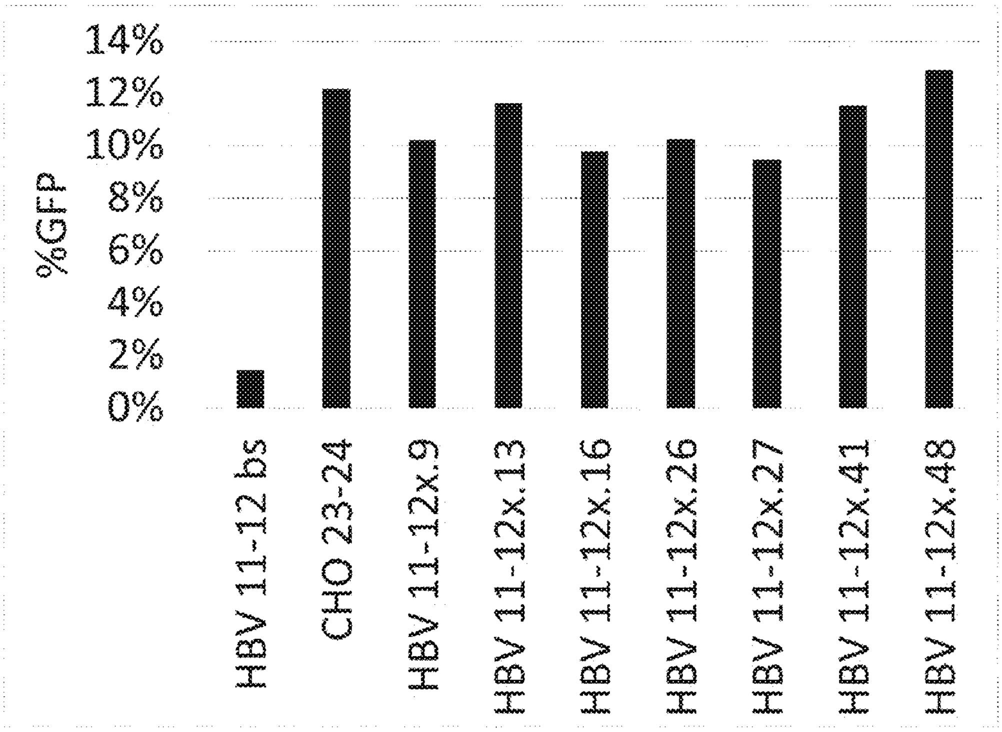
FIGURE 7 (cont.)

A.
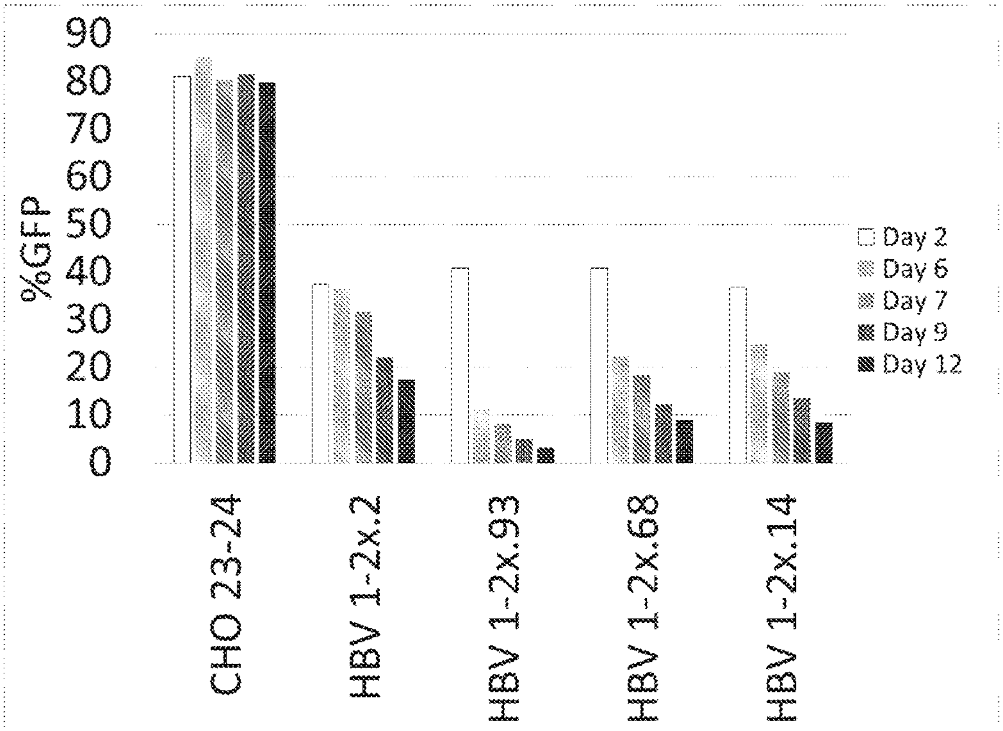
B.
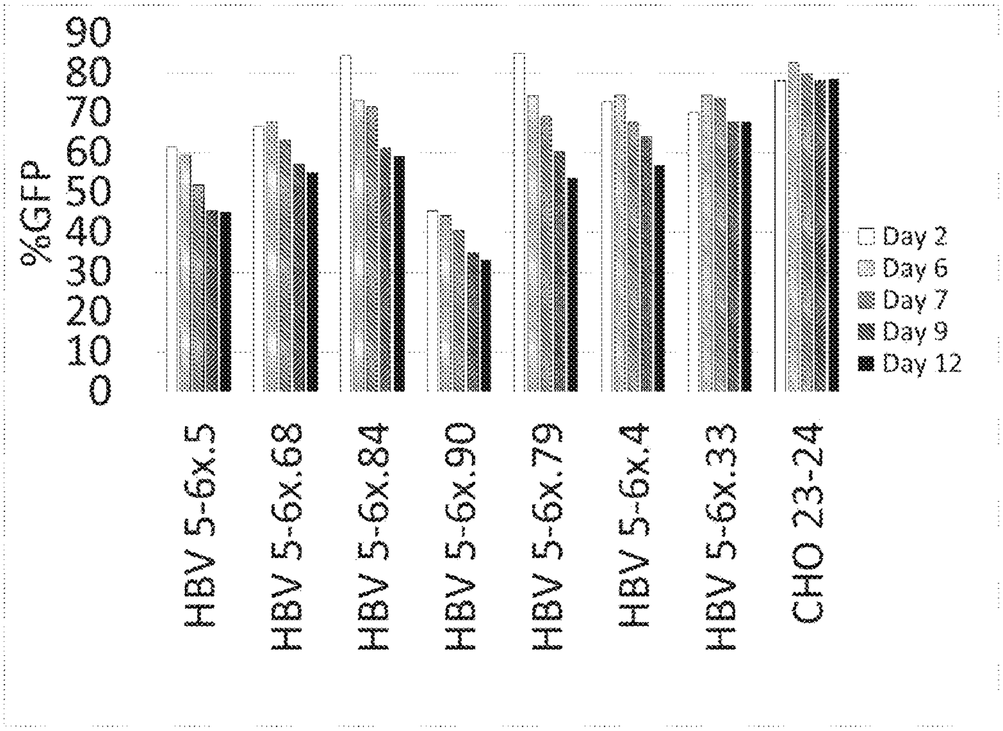
FIGURE 8

C.
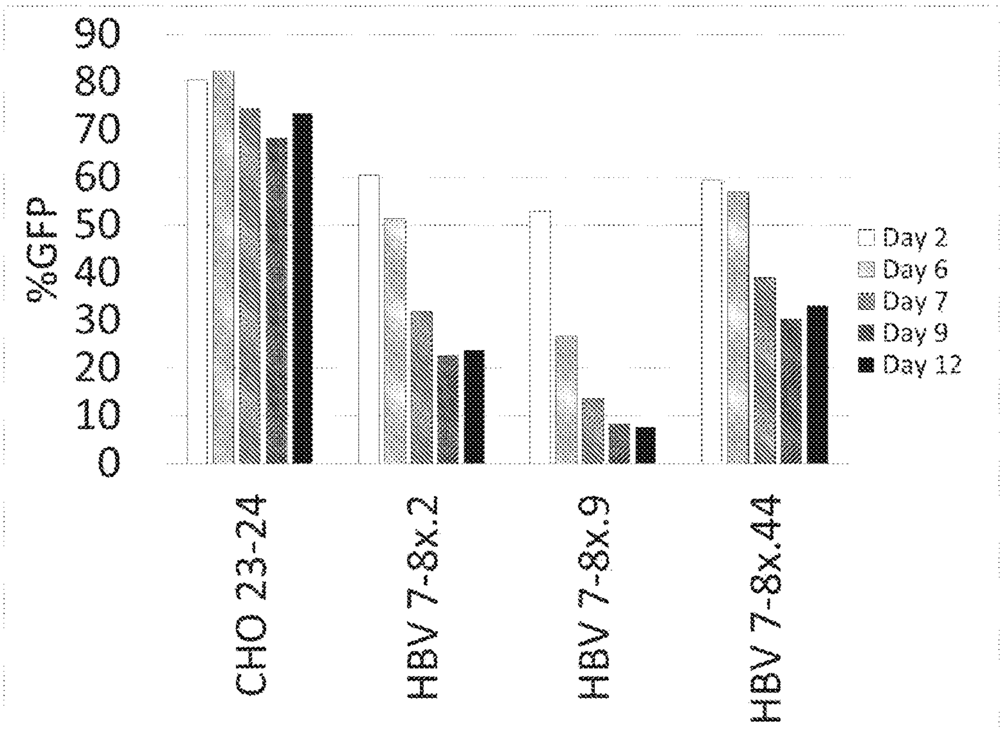
D.
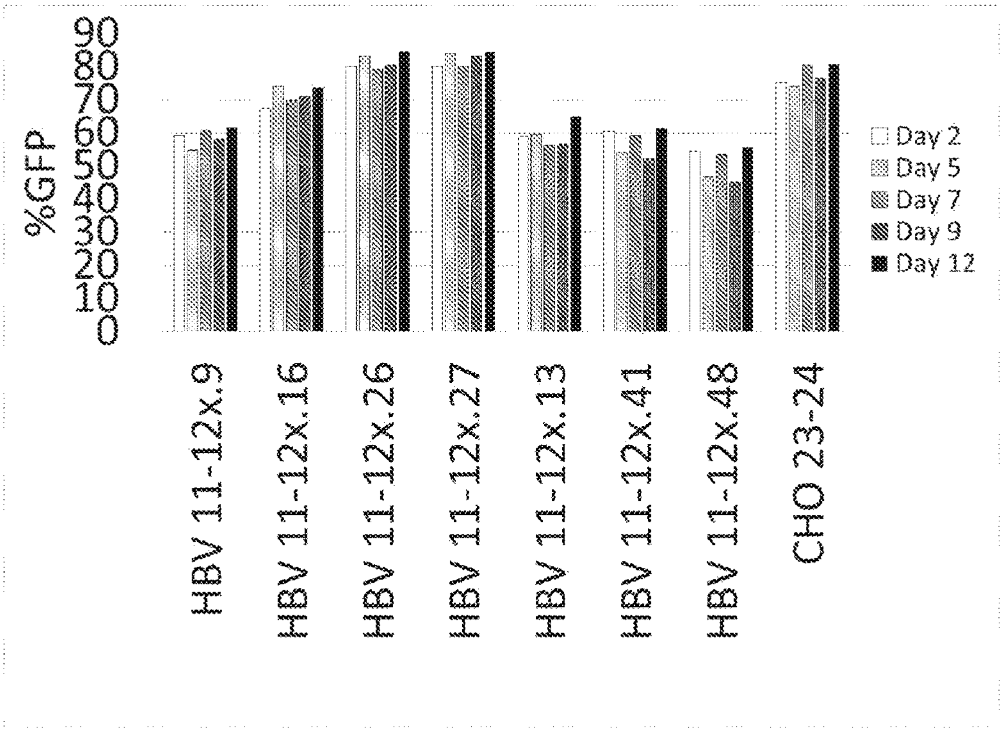
FIGURE 8 (cont.)

A.

B.

C.

C.

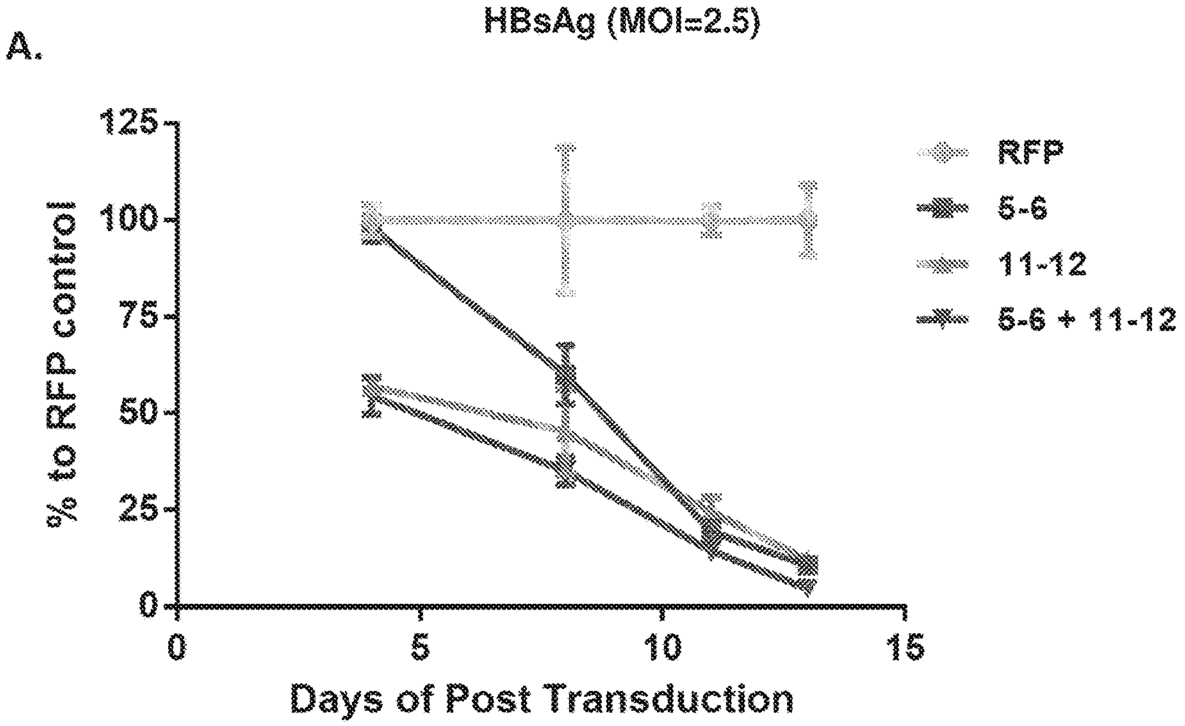
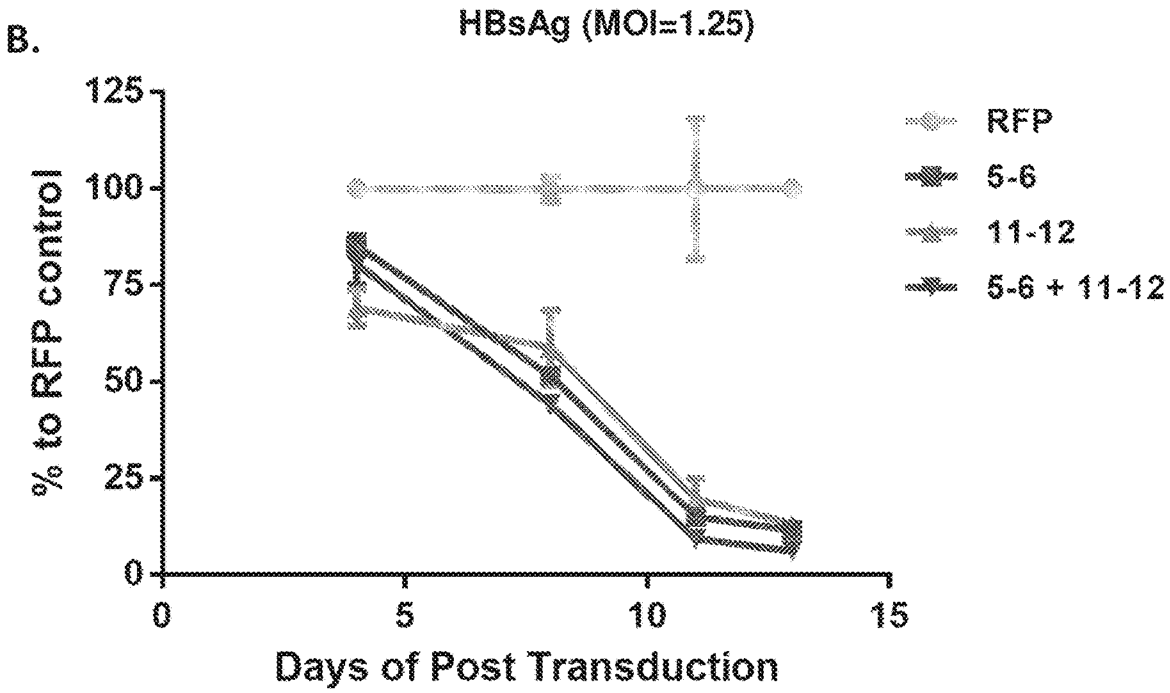
FIGURE 14

C.
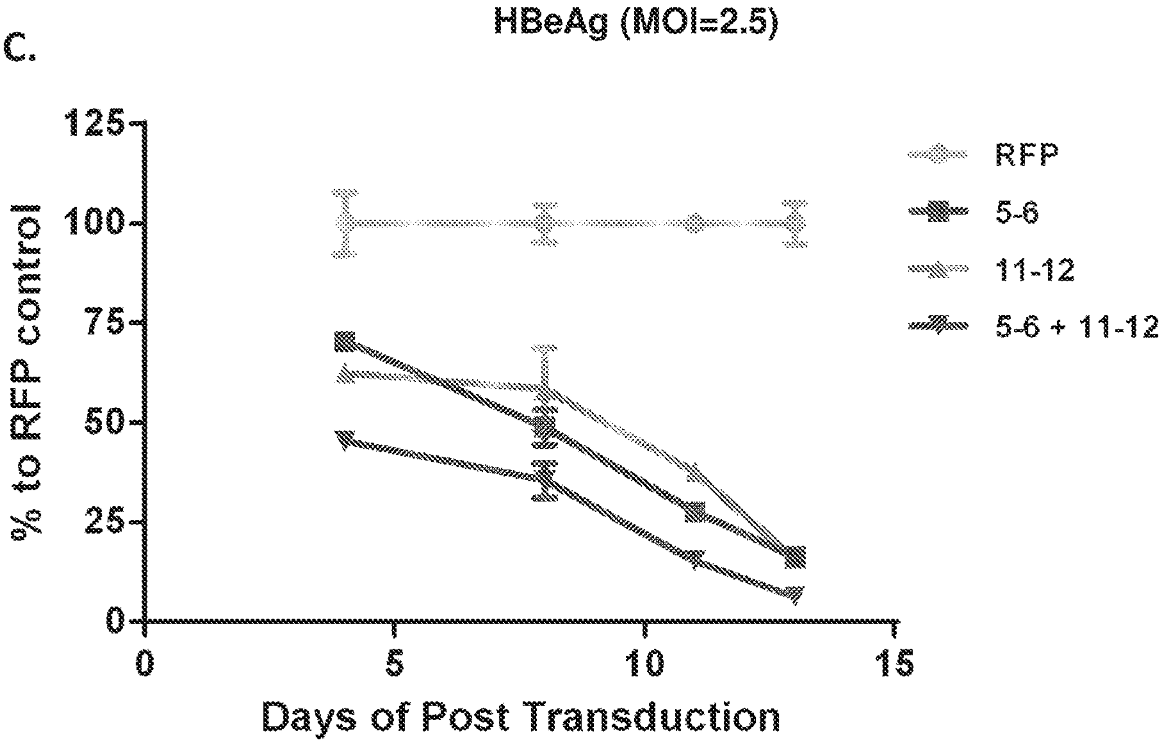
D.
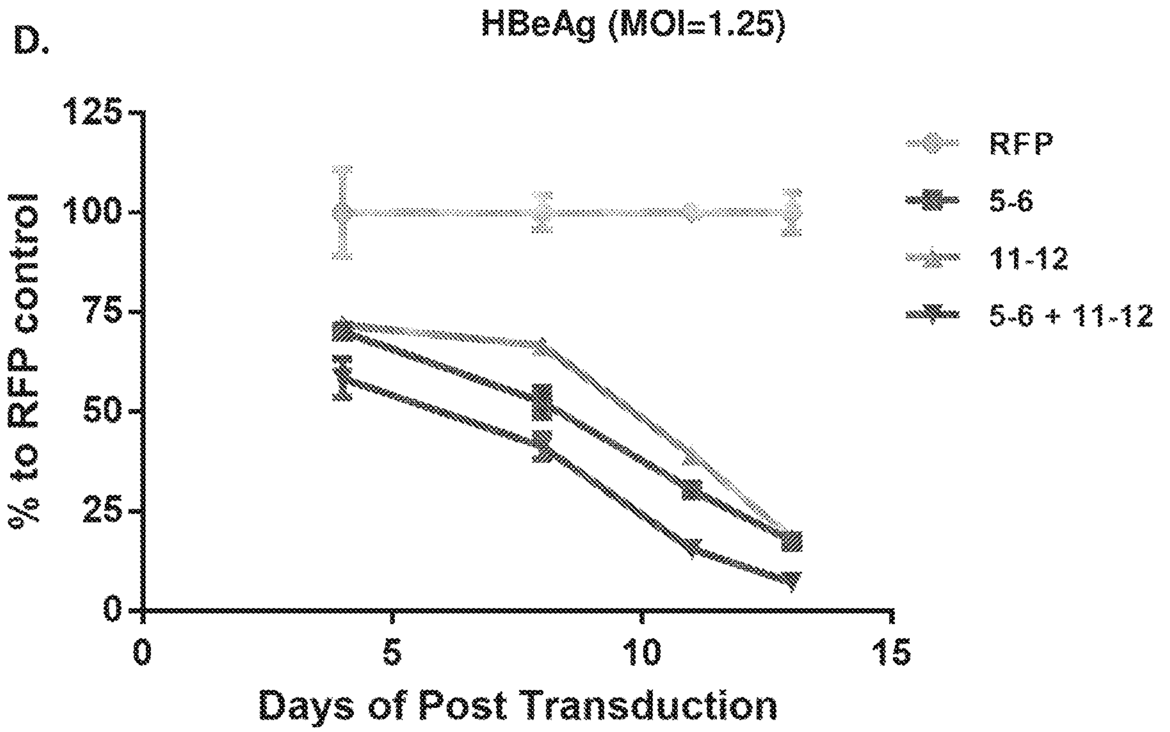
FIGURE 14 (cont.)

SEQUENCE LISTING

```
<160> NUMBER OF SEQ ID NOS: 86

<210> SEQ ID NO 1
<211> LENGTH: 163
<212> TYPE: PRT
<213> ORGANISM: Chlamydomonas reinhardtii
<220> FEATURE:
<221> NAME/KEY: wild-type I-CreI meganuclease
<222> LOCATION: (1)..(163)

<400> SEQUENCE: 1

Met Asn Thr Lys Tyr Asn Lys Glu Phe Leu Leu Tyr Leu Ala Gly Phe
1               5                   10                  15

Val Asp Gly Asp Gly Ser Ile Ile Ala Gln Ile Lys Pro Asn Gln Ser
            20                  25                  30

Tyr Lys Phe Lys His Gln Leu Ser Leu Ala Phe Gln Val Thr Gln Lys
        35                  40                  45

Thr Gln Arg Arg Trp Phe Leu Asp Lys Leu Val Asp Glu Ile Gly Val
    50                  55                  60

Gly Tyr Val Arg Asp Arg Gly Ser Val Ser Asp Tyr Ile Leu Ser Glu
65                  70                  75                  80

Ile Lys Pro Leu His Asn Phe Leu Thr Gln Leu Gln Pro Phe Leu Lys
                85                  90                  95

Leu Lys Gln Lys Gln Ala Asn Leu Val Leu Lys Ile Ile Trp Arg Leu
            100                 105                 110

Pro Ser Ala Lys Glu Ser Pro Asp Lys Phe Leu Glu Val Cys Thr Trp
        115                 120                 125

Val Asp Gln Ile Ala Ala Leu Asn Asp Ser Lys Thr Arg Lys Thr Thr
    130                 135                 140

Ser Glu Thr Val Arg Ala Val Leu Asp Ser Leu Ser Glu Lys Lys Lys
145                 150                 155                 160

Ser Ser Pro


<210> SEQ ID NO 2
<211> LENGTH: 9
<212> TYPE: PRT
<213> ORGANISM: Chlamydomonas reinhardtii
<220> FEATURE:
<221> NAME/KEY: LAGLIDADG
```

<222> LOCATION: (1)..(9)

<400> SEQUENCE: 2

Leu Ala Gly Leu Ile Asp Ala Asp Gly
1 5

<210> SEQ ID NO 3
<211> LENGTH: 3221
<212> TYPE: DNA
<213> ORGANISM: Hepatitis B virus
<220> FEATURE:
<221> NAME/KEY: HBV genotype A
<222> LOCATION: (1)..(3221)

<400> SEQUENCE: 3
ttccactgcc ttccaccaag ctctgcagga tcccagagtc aggggtctgt attttcctgc 60
tggtggctcc agttcaggaa cagtaaaccc tgctccgaat attgcctctc acatctcgtc 120
aatctccgcg aggactgggg accctgtggc gaacatggag aacatcacat caggattcct 180
aggacccctg ctcgtgttac aggcggggtt tttcttgttg acaagaatcc tcacaatacc 240
gcagagtcta gactcgtggt ggacttctct caattttcta gggggatcac ccgtgtgtct 300
tggccaaaat tcgcagtccc caacctccaa tcactcacca acctcctgtc ctccaatttg 360
tcctggttat cgctggatgt gtctgcggcg ttttatcata ttcctcttca tcctgctgct 420
atgcctcatc ttcttattgg ttcttctgga ttatcaaggt atgttgcccg tttgtcctct 480
aattccagga tcaacaacaa ccagtacggg accatgcaaa acctgcacga ctcctgctca 540
aggcaactct atgtttccct catgttgctg tacaaaacct acggatggaa attgcacctg 600
tattcccatc ccatcgtcct gggctttcgc aaaataccta tgggagtggg cctcagtccg 660
tttctcttgg ctcagtttac tagtgccatt tgttcagtgg ttcgtagggc tttcccccac 720
tgtttggctt tcagctatat ggatgatgtg gtattggggg ccaagtctgt acagcatcgt 780
gagtcccttt ataccgctgt taccaatttt cttttgtctc tgggtataca tttaaaccct 840
aacaaaacaa aaagatgggg ttattcccta aacttcatgg gttacataat tggaagttgg 900
ggaactttgc cacaggatca tattgtacaa aagatcaaac actgttttag aaaacttcct 960
gttaacaggc ctattgattg gaaagtatgt caaagaattg tgggtctttt gggctttgct 1020
gctccattta cacaatgtgg atatcctgcc ttaatgcctt tgtatgcatg tatacaagct 1080
aaacaggctt tcactttctc gccaacttac aaggcctttc taagtaaaca gtacatgaac 1140
ctttaccccg ttgctcggca acggcctggt ctgtgccaag tgtttgctga cgcaaccccc 1200
actggctggg gcttggccat aggccatcag cgcatgcgtg gaacctttgt ggctcctctg 1260
ccgatccata ctgcggaact cctagccgct tgttttgctc gcagccggtc tggagcaaag 1320
ctcatcggaa ctgacaattc tgtcgtcctc tcgcggaaat atacatcgtt tccatggctg 1380
ctaggctgtg ctgccaactg gatccttcgc ggaacgtcct ttgtctacgt cccgtcggcg 1440
ctgaatcccg cggacgaccc ctctcggggc cgcttgggac tctctcgtcc ccttctccgt 1500
ctgccgttcc agccgaccac ggggcgcacc tctctttacg cggtctcccc gtctgtgcct 1560
tctcatctgc cggtccgtgt gcacttcgct tcacctctgc acgttgcatg gagaccaccg 1620
tgaacgccca tcagatcctg cccaaggtct tacataagag gactcttgga ctcccagcaa 1680
tgtcaacgac cgaccttgag gcctacttca aagactgtgt gtttaaggac tgggaggagc 1740
tgggggagga gattaggtta aaggtctttg tattaggagg ctgtaggcat aaattggtct 1800
gcgcaccagc accatgcaac tttttcacct ctgcctaatc atctcttgta catgtcccac 1860

```
tgttcaagcc tccaagctgt gccttgggtg gctttggggc atggacattg acccttataa   1920
agaatttgga gctactgtgg agttactctc gtttttgcct tctgacttct ttccttccgt   1980
cagagatctc ctagacaccg cctcagctct gtatcgagaa gccttagagt ctcctgagca   2040
ttgctcacct caccatactg cactcaggca agccattctc tgctgggggg aattgatgac   2100
tctagctacc tgggtgggta ataatttgga agatccagca tccagggatc tagtagtcaa   2160
ttatgttaat actaacatgg gtttaaagat caggcaacta ttgtggtttc atatatcttg   2220
ccttactttt ggaagagaga ctgtacttga atatttggtc tctttcggag tgtggattcg   2280
cactcctcca gcctatagac caccaaatgc ccctatctta tcaacaattc cggaaactac   2340
tgttgttaga cgacgggacc gaggcaggtc ccctagaaga agaactccct cgcctcgcag   2400
acgcagatct caatcgccgc gtcgcagaag atctcaatct cgggaatctc aatgttagta   2460
ttccttggac tcataaggtg ggaaacttta cggggcttta ttcctctaca gtacctatct   2520
ttaatcctga atggcaaact ccttcctttc ctaagattca tttacaagag gacattatta   2580
ataggtgtca acaatttgtg ggccctctca ctgtaaatga aaagagaaga ttgaaattaa   2640
ttatgcctgc tagattctat cctacccaca ctaaatattt gcccttagac aaaggaatta   2700
aaccttatta tccagatcag gtagttaatc attacttcca aaccagacat tatttacata   2760
ctctttggaa ggctggtatt ctatataaga gggaaaccac acgtagcgca tcattttgcg   2820
ggtcaccata ttcttgggaa caagagctac agcatgggag gttggtcatc aaaacctcgc   2880
aaaggcatgg ggacgaatct ttctgttccc aaccctctgg gattctttcc cgatcatcag   2940
ttggaccctg cattcggagc caactcaaac aatccagatt gggacttcaa ccccatcaag   3000
gaccactggc caacagccaa ccaggtagga gtgggagcat tcgggccagg gctcacccct   3060
ccacacggcg gtattttggg gggagccct caggctcagg gcatattgac cacagtgtca   3120
acaattcctc ctcctgcctc caccaatcgg cagtcaggaa ggcagcctac tcccatctct   3180
ccacctctaa gagacagtca tcctcaggcc atgcagtgga a                      3221
```

```
<210> SEQ ID NO 4
<211> LENGTH: 3214
<212> TYPE: DNA
<213> ORGANISM: Hepatitis B virus
<220> FEATURE:
<221> NAME/KEY: HBV genotype B
<222> LOCATION: (1)..(3214)

<400> SEQUENCE: 4
```

```
tccaccactt tccaccaaac tcttcaagat cccagagtca gggccctgta ctttcctgct     60
ggtggctcca gttcaggaac agtgagccct gctcagacta ctgtctctgc catatcgtca    120
atcttatcga agactgggga ccctgtaccg aacatggaga acatcgcatc aggactccta    180
ggacccctgc tcgtgttaca ggcggggttt ttcttgttga caaaaatcct cacaatacca    240
cagagtctag actcgtggtg gacttctctc aattttctag ggggaamacc cgtgtgtctt    300
ggccaaaatt cgcagtccca aatctccagt cactcacyaa cctgttgtcc tccaatttgt    360
cctggttatc gctggatgtg tctgcggcgt tttatcatct tcctytgcat cctgctgcta    420
tgcctcatct tcttgttggt tcttctggac tatcraggta tgttgcccgt ttgtcctcwa    480
mttccaggat cawcaacaac cagcaccgga ccatgcaaaa cctgcacgac tcctgctcaa    540
ggaacctcta tryktccctc atgttgctgt acaaaaccta cggacggaaa ctgcacctgt    600
attcccatcc catcatcttg ggctttcgca aaatacctat gggagtsggc ctcagyccgt    660
```

-continued

```
ttctcttggc tcagtttact agcgccattt gttcagtggt tcgtagggct ttcccccact    720
gtctggcttt cagttatatg gatgatgtgg tattgggggc caagtctgta caacatcttg    780
agtcccttta tgccgctgtt accaatttyc ttttgtcttt gggtatacay ttgaaccctc    840
acaaaacaaa aagatgggga tattccctta acttcatggg atatgtaatt gggtgttggg    900
gcacattgcc acaggaacat attgtacaaa aaatcaaaat gtgttttmgg aaacttcctg    960
taaacagacc tattgattgg aaagtatgtc aacgaattgt gggtcttttg ggtttgccg    1020
cccctttcac gcaatgtgga tatcctgctt tratgccttt atatgcatgt atacaagcaa   1080
aacaggcttt tactttctcg ccaacttaca aggcctttct aagtaaacag tatctgaacc   1140
tttaccccgt tactcggcaa cggtctggtc tgtgccaagt gtttgctgac gcaaccccca   1200
ctggttgggg cttggccata ggccwtcagc gcatgcgtgg aacctttgtg tctcctctgc   1260
cgatccatac tgcggaactc ctagccgctt gttttgctcg cagcaggtct ggggcaaaac   1320
tcatcgggac tgacaattct gtcgtgctct cccgcaagta tacatcgttc ccatggctgc   1380
taggctgtgc tgccaactgg atcctgcgcg ggacgtcctt tgtttacgtc ccgtcggcgc   1440
tgaatcccgc ggacgacccc tcccggggcc gcttggggct ctaccgcccg cttctccgcc   1500
tgttgtaccg tccgaccacg gggcgcacct ctctttacgc ggactccccg tctgtgcctt   1560
ctcatctrcc ggaccgtgtg cacttcgctt cacctctgca cgtcgcatgg agaccaccgt   1620
gaacgcccac cggaacctgc ccaaggtctt gcataagagg actcttggac tttccgcaat   1680
gtcaacgacc gaccttgagg catacttcaa agactgtgtg tttamtgagt gggaggagtt   1740
gggggaggag aktaggttaa aggtctttgt actaggaggc tgtaggcata aattggtgtg   1800
ttcaccagca ccatgcaact ttttcacctc tgcctaatca tctcwtgttc atgtcctact   1860
gttcaagcct ccaagctgtg ccttgggtgg ctttagggca tggacattga cccgtataaa   1920
gaatttggag cttctgtgga gttactctct tttttgcctm mtgacttctt tccttctatt   1980
cgagatctcc tcgacaccgc ctctgctttg tatcgggagg ccttagagtc tccggaacat   2040
tgttcacctc accatacggc actcaggcaa gctattctgt gttggggtga gttgatgaat   2100
ctagccacct gggtgggaag taatttggaa gatccagcat ccagggaatt agtmgttagc   2160
tatgtcaacg ttaatatggg cmtaaaaatc agacaactat tgtggtttca catttcctgt   2220
cttacttttg ggaragamac tgttcttgaa tatttggtgt cttttggagt gtggattcgc   2280
actcctcctg catatagacc aycaaatgcc cctatcttat caacacttcc ggaaactact   2340
gttgttagac gaagaggcag gtcccctaga agaagaactc cctcgcctcg cagacgaagg   2400
tctcaatcgc cgcgtcgcag aagatctcaa tctcgggaat ctcaatgtta gtattccttg   2460
gacacataag gtgggaaact ttacggggct ttattcttct acggtacctt gctttaatcc   2520
taawtggcaa actccttctt ttcctgacat tcatttgcag gaggacattg ttgatagatg   2580
taagcamttt gtggggcccc ttacagtaaa tgaaaacagg agactaaaat taattatgcc   2640
tgctaggttt tatcccaatg ttaccaaata tttgccctta gataaaggga tcaaacctta   2700
ttatccagag catgtagtta atcattactt ccagacgaga cattatttac ayactctttg   2760
gaaggcgggt atcytatata aaagagagtc cacacgtagc gcctcatttt gcggatcacc   2820
atattcttgg gaacaagatc tacagcatgg gaggttggtc ttccaaacct cgaaaaggca   2880
tggggacaaa tctttctgtc cccaatcccc tgggattctt cccmgatcat cagttggacc   2940
ctgcattcaa agccaactca saaaatccag attgggacct caacccgcac aaggacaact   3000
```

-continued

```
ggccggacgc caacaaggtg ggagtgggag cattcgggcc agggttcatc cctccccatg   3060

ggggactgtt ggggtggarc cctcaggctc agggcatact cacaactgtg ccagcagctc   3120

ctcctcctgc ctccaccaat cggcagtcag gaaggcagcc tactccctta tctccacctc   3180

taagggacac tcatcctcag gccatgcagt ggaa                               3214


<210> SEQ ID NO 5
<211> LENGTH: 3214
<212> TYPE: DNA
<213> ORGANISM: Hepatitis B virus
<220> FEATURE:
<221> NAME/KEY: HBV genotype C
<222> LOCATION: (1)..(3214)

<400> SEQUENCE: 5

tccacaacat tccaccaagc tctgctagat cccagagtga ggggcctata ttttcctgct     60

ggtggctcca gttccggaac agtaaaccct gttccgacta ctgcctcacc catatcgtca    120

atcttctcga ggactgggga ccctgcaccg aacatggaga gcacaacatc aggattccta    180

ggacccctgc tcgtgttaca ggcggggttt ttcttgttga caagaatcct cacaatacca    240

cagagtctag actcgtggtg gacttctctc aattttctag ggggagcacc cacgtgtcct    300

ggccaaaatt cgcagtcccc aacctccaat cactcaccaa cctcttgtcc tccaatttgt    360

cctggctatc gctggatgtg tctgcggcgt tttatcatat tcctcttcat cctgctgcta    420

tgcctcatct tcttgttggt tcttctggac taccaaggta tgttgcccgt ttgtcctcta    480

cttccaggaa catcaactac cagcacggga ccatgcaaga cctgcacgat tcctgctcaa    540

ggaacctcta tgtttccctc ttgttgctgt acaaaacctt cggacggaaa ctgcacttgt    600

attcccatcc catcatcctg ggctttcgca agattcctat gggagtgggc cttagtccgt    660

ttctcctggc tcagtttact agtgccattt gttcagtggt tcgcagggct ttcccccact    720

gtttggcttt cagttatatg gatgatgtgg tattgggggc caagtctgta caacatcttg    780

agtccctttt tacctctatt accaattttc ttttgtcgtt gggtatacat ttgaacccta    840

ataaaaccaa acgttggggc tactccctta acttcatggg atatgtaatt ggaagttggg    900

ggactttacc acaggaacat attgtattaa aaatcaagca atgttttcgg aaactgcctg    960

taaatagacc tattgattgg aaagtatgtc aaagaattgt gggtcttttg ggctttgctg   1020

ccccttttac acaatgtggc tatcctgcct tgatgccttt atatgcatgt atacaatcta   1080

agcaggcttt cactttctcg ccaacttaca aggcctttct gtgtcaacaa tacctgcacc   1140

tttaccccgt tgcccggcaa cggtcaggtc tctgccaagt gtttgctgac gcaaccccca   1200

ctggatgggg cttggccata ggccatcggc gcatgcgtgg aacctttgtg gctcctctgc   1260

cgatccatac tgcggaactc ctagcagctt gttttgctcg cagccggtct ggagcaaaac   1320

ttatcgggac tgacaactct gttgtcctct ctcggaaata cacctccttc ccatggctgc   1380

tcgggtgtgc tgccaactgg atcctgcgcg ggacgtcctt tgtctacgtc ccgtcggcgc   1440

tgaatcccgc ggacgacccg tctcggggcc gtttgggcct ctaccgtccc cttcttcatc   1500

tgctgttcca gccgactacg gggcgcacct ctctttacgc ggtctccccg tctgtgcctt   1560

ctcatctgcc ggaccgtgtg cacttcgctt cacctctgca cgtcgcatgg agaccaccgt   1620

gaatgcccac caggtcttgc ccaagctctt acataagagg actcttggac tctcagcaat   1680

gtcaacgacc gaccttgaag catacttcaa agactgtttg tttaaggact gggaggagtt   1740

gggggaggag attaggttaa aggtctttgt actaggaggc tgtaggcata aattggtctg   1800
```

-continued

```
ttcaccagca ccatgcaact ttttcacctc tgcctaatca tctcatgttc atgtcctact   1860
gttcaagcct ccaagctgtg ccttgggtgg ctttggggca tggacattga cccgtataaa   1920
gaatttggag cttctgtgga gttactctct tttttgcctt ctgacttctt tccttctatt   1980
cgagatctcc tcgacaccgc ctctgctctg tatcgggagg ccttagagtc tccggaacat   2040
tgttcacctc accatacagc actcaggcaa gctattctct gttggggtga gttgatgaat   2100
ctggccacct gggtgggaag taatttggaa gacccagcat ccagggaatt agtagtcagc   2160
tatgtcaatg ttaatatggg cctaaaaatc agacaactat tgtggtttca catttcctgt   2220
cttacttttg gaagagaaac tgttcttgag tatttggtgt cttttggagt gtggattcgc   2280
actcctccag cttacagacc accaaatgcc cctatcttat caacacttcc ggaaactact   2340
gttgttagac gacgaggcag gtcccctaga agaagaactc cctcgcctcg cagacgaagg   2400
tctcaatcgc cgcgtcgcag aagatctcaa tctcgggaat ctcaatgtta gtatcccttg   2460
gactcataag gtgggaaact ttactgggct ttattcttct actgttcctg tctttaatcc   2520
tgagtggcaa actccctcct ttcctaacat tcatttacag gaagacatta ttaatagatg   2580
tcaacaatat gtgggccctc ttacagttaa tgaaaaaagg agattaaaat taattatgcc   2640
tgctaggttc tatcctaacc ttaccaaata tttgcccttg gataaaggca ttaaacctta   2700
ttatcctgaa catgcagtta atcattactt caaaactagg cattatttac atactctgtg   2760
gaaggctggc attctatata aaagagaaac tacacgcagc gcttcatttt gtgggtcacc   2820
atattcttgg gaacaagagc tacagcatgg gaggttggtc ttccaaacct cgacaaggca   2880
tggggacgaa tctttctgtt cccaatcctc tgggattctt tcccgatcac cagttggacc   2940
ctgcgttcgg agccaactca aacaatccag attgggactt caaccccaac aaggatcact   3000
ggccagaggc aaatcaggta ggagcgggag cattcgggcc agggttcacc ccaccacacg   3060
gcggtctttt ggggtggagc cctcaggctc agggcatatt gacaacagtg ccagcagcgc   3120
ctcctcctgc ctccaccaat cggcagtcag gaagacagcc tactcccatc tctccacctc   3180
taagagacag tcatcctcag gccatgcagt ggaa                               3214
```

<210> SEQ ID NO 6
<211> LENGTH: 3182
<212> TYPE: DNA
<213> ORGANISM: Hepatitis B virus
<220> FEATURE:
<221> NAME/KEY: HBV genotype D
<222> LOCATION: (1)..(3182)

<400> SEQUENCE: 6

```
ttccacaacc tttcaccaaa ctctgcaaga tcccagagtg agaggcctgt atttccctgc     60
tggtggctcc agttcaggag cagtaaaccc tgttccgact actgcctctc ccttatcgtc    120
aatcttctcg aggattgggg accctgcgct gaacatggag aacatcacat caggattcct    180
aggacccctt ctcgtgttac aggcggggtt tttcttgttg acaagaatcc tcacaatacc    240
gcagagtcta gactcgtggt ggacttctct caattttcta gggggaacta ccgtgtgtct    300
tggccaaaat tcgcagtccc caacctccaa tcactcacca acctcctgtc ctccaacttg    360
tcctggttat cgctggatgt gtctgcggcg ttttatcatc ttcctcttca tcctgctgct    420
atgcctcatc ttcttgttgg ttcttctgga ctatcaaggt atgttgcccg tttgtcctct    480
aattccagga tcctcaacca ccagcacggg accatgccga acctgcatga ctactgctca    540
aggaacctct atgtatccct cctgttgctg taccaaacct tcggacggaa attgcacctg    600
```

-continued

```
tattcccatc ccatcatcct gggctttcgg aaaattccta tgggagtggg cctcagcccg    660
tttctcctgg ctcagtttac tagtgccatt tgttcagtgg ttcgtagggc tttcccccac    720
tgtttggctt tcagttatat ggatgatgtg gtattggggg ccaagtctgt acagcatctt    780
gagtcccttt ttaccgctgt taccaatttt cttttgtctt tgggtataca tttaaaccct    840
aacaaaacaa agagatgggg ttactctctg aattttatgg gttatgtcat tggaagttat    900
gggtccttgc cacaagaaca catcatacaa aaaatcaaag aatgttttag aaaacttcct    960
attaacaggc ctattgattg gaaagtatgt caacgaattg tgggtctttt gggttttgct   1020
gccccattta cacaatgtgg ttatcctgcg ttaatgccct tgtatgcatg tattcaatct   1080
aagcaggctt tcactttctc gccaacttac aaggcctttc tgtgtaaaca atacctgaac   1140
ctttaccccg ttgcccggca acggccaggt ctgtgccaag tgtttgctga cgcaaccccc   1200
actggctggg gcttggtcat gggccatcag cgcgtgcgtg gaaccttttc ggctcctctg   1260
ccgatccata ctgcggaact cctagccgct tgttttgctc gcagcaggtc tggagcaaac   1320
attatcggga ctgataactc tgttgtcctc tcccgcaaat atacatcgta tccatggctg   1380
ctaggctgtg ctgccaactg gatcctgcgc gggacgtcct ttgtttacgt cccgtcggcg   1440
ctgaatcctg cggacgaccc ttctcggggt cgcttgagac tctctcgtcc ccttctccgt   1500
ctgccgttcc gaccgaccac ggggcgcacc tctctttacg cggactcccc gtctgtgcct   1560
tctcatctgc cggaccgtgt gcacttcgct tcacctctgc acgtcgcatg gagaccaccg   1620
tgaacgccca ccgaatgttg cccaaggtct tacataagag gactcttgga ctctctgcaa   1680
tgtcaacgac cgaccttgag gcatacttca aagactgttt gtttaaagac tgggaggagt   1740
tgggggagga gattagatta aaggtctttg tactaggagg ctgtaggcat aaattggtct   1800
gcgcaccggc gccatgcacc tttttcacct ctgcctaatc atctcttgtt catgtcctac   1860
tgttcaagcc tccaagctgt gccttgggtg gctttggggc atggacatcg acccttataa   1920
agaatttgga gctactgtgg agttactctc gtttttgcct tctgacttct ttccttcagt   1980
acgagatctt ctagataccg cctcagctct gtatcgggaa gccttagagt ctcctgagca   2040
ttgttcacct caccatactg cactcaggca agcaattctt tgctgggggg aactaatgac   2100
tctagctacc tgggtgggtg ttaatttgga agatccagca tctagagacc tagtagtcag   2160
ttatgtcaac actaatatgg gcctaaagtt caggcaactc ttgtggtttc acatttcttg   2220
tctcactttt ggaagagaaa ccgttataga gtatttggtg tctttcggag tgtggattcg   2280
cactcctcca gcttatagac caccaaatgc ccctatccta tcaacacttc cggaaactac   2340
tgttgttaga cgacgaggca ggtcccctag aagaagaact ccctcgcctc gcagacgaag   2400
gtctcaatcg ccgcgtcgca gaagatctca atctcgggaa cctcaatgtt agtattcctt   2460
ggactcataa ggtggggaac tttactggtc tttattcttc tactgtacct gtctttaatc   2520
ctcattggaa aacaccatct ttcctaata tacatttaca ccaagacatt atcaaaaaat    2580
gtgaacagtt tgtaggccca cttacagtta atgagaaaag aagattgcaa ttgattatgc   2640
ctgctaggtt ttatccaaag gttaccaaat atttaccatt ggataagggt attaaacctt   2700
attatccaga acatctagtt aatcattact tccaaactag acactattta cacactctat   2760
ggaaggcggg tatattatat aagagagaaa caacacatag cgcctcattt tgtgggtcac   2820
catattcttg ggaacaagat ctacagcatg gggcagaatc tttccaccag caatcctctg   2880
ggattctttc ccgaccacca gttggatcca gccttcagag caaacacagc aaatccagat   2940
tgggacttca atcccaacaa ggacacctgg ccagacgcca acaaggtagg agctggagca   3000
```

```
ttcgggctgg gtttcactcc accgcacgga ggccttttgg ggtggagctc tcaggctcag   3060

ggcatactac aaactttgcc agcaaatccg cctcctgcct ccaccaatcg ccagacagga   3120

aggcagccta ccccgctgtc tccacctttg agaaacactc atcctcaggc catgcagtgg   3180

aa                                                                  3182
```

<210> SEQ ID NO 7
<211> LENGTH: 3212
<212> TYPE: DNA
<213> ORGANISM: Hepatitis B virus
<220> FEATURE:
<221> NAME/KEY: HBV genotype E
<222> LOCATION: (1)..(3212)

<400> SEQUENCE: 7

```
ttccacaaca ttccaccaag ctcascagga tcccagagta agrggcctgt atyttcctgc     60

tggtggctcc agttccggaa cagtgaaccc tgttccgact actgcctcac tcatctcgtc    120

aatcttctcg aggattgggg accctgcacc gaacatggaa ggcatcacat caggattcct    180

aggacccctg ctcgtgttac aggcggggtt tttcttgttg acaaaaatcc tcacaatacc    240

gcagagtcta gactcgtggt ggacttctct caattttcya ggggaagctc ccgtgtgtcg    300

tggccaaaat tcgcagtycc caacctccaa tcactcacca acctcttgtc ctccaatttg    360

tcctggctat cgctggatgt gtctgcggcg ttttatcatc ttcctcttca tcctgctgct    420

atgcctcatc ttcttgttgg ttcttctgga ctatcaaggt atgttgcccg tttgtcctct    480

aattccagga tcatcaacca ccagtacggg accctgccga acctgcacga ctcttgctca    540

aggaacctct atgtttccct catgttgctg ttcaaaacct tcggacggaa attgcacttg    600

tattcccatc ccatcatcat gggctttcgg aaaattccta tgggagtggg cctcagcccg    660

tttctcctgg ctcagtttac tagtgccatt tgttcagtgg ttcgccgggc tttcccccac    720

tgtctggctt tcagttatat ggatgatgtg gtattggggg ccaagtctgt acaacatctt    780

gagtcccttt atacctctgt taccaatttt cttttgtctt tgggtataca tttaaatcct    840

aacaaaacaa aaagatgggg atattcccta aatttcatgg gttatgttat tggtagttgg    900

gggtcattac cacaggaaca catcagaatg aaaatcaaag actgttttag aaaactccct    960

gttaaccggc ctattgattg gaaagtatgt caaagaattg tgggtctctt gggctttgct   1020

gcccctttta cacaatgtgg atatcctgct ttaatgcctc tgtatgcgtg tattcaatct   1080

aagcaggctt tcactttctc gccaacttac aaggcctttc tgtgtaaaca atacctgaac   1140

ctttaccccg ttgcccggca acggccaggt ctgtgccaag tgtttgctga tgcaaccccc   1200

actggttggg gcttggccat aggccatcag cgcatgcgtg gaacctttgy ggctcctctg   1260

ccgatccata ctgcggaact cctggccgct tgttttgctc gcagcaggtc tggagcgaaa   1320

cttattggaa cggataattc tgtcgttctc tcccggaaat atacatcatt tccatggctg   1380

ctaggctgtg ctgccaactg gatcctgcga gggacgtcct ttgtctacgt cccgtcagcg   1440

ctgaatcctg cggacgaccc gtctcggggt cgcttgggga tctatcgtcc ccttctccgt   1500

ctgccgttcc ggccgaccac ggggcgcacc tctctttacg cggtctcccc gtctgtgcct   1560

tctcatctgc cggaccgtgt gcacttcgct tcacctctgc acgtcgcatg gaaaccaccg   1620

tgaacgccca ccaaatcttg cccaaggtct tatataagag gactcttgga ctctctgcaa   1680

tgtcaacgac cgaccttgag gcatacttca aagactgctt gtttaaagac tgggaggagt   1740

tgggggagga gattagatta atgatctttg tactaggagg ctgtaggcat aaattggtct   1800
```

gcgcaccagc accatgcaac tttttcacct ctgcctaatc atctcttgtt catgtcctac 1860
tgttcaagcc tccaagctgt gccttgggtg gctttaggac atggacattg acccttataa 1920
agaatttgga gctwctgtgg agttactctc ktttttgcct catgacttct ttccttcaat 1980
aagagatctt ctagataccg ccacagctct gtatcgggat gccttagaat ctcctgagca 2040
ttgttcacct caccacacgg cactcaggca agccattctt tgctgggggg atgtaatgaa 2100
tctagctacc tgggtgggtg taaatttgga agatccagca tccagggacc tggtagtcgg 2160
ttatgtcaat actaatatgg gcctaaagtt cagacaatta ttgtggtttc acacttcctg 2220
tctcactttt ggaagagaaa ccgtcttaga gtatttggtg tcttttggag tgtggattcg 2280
cactcctcca ccttatagac caccaaatgc ccctatctta tcaacacttc cggagactac 2340
tgttgttaga cgaagaggca ggtcccctag aagaagaact ccctcrcctc gcagacgtag 2400
atctcaatcg ccgcgtcgca gaagatctca atctccagct tcccgatgtt agtattcctt 2460
ggactcacaa ggtgggaaat ttacggggc tttactcttc tactatacct gtctttaatc 2520
ctaactggaa aactccatct ttcctgata ttcatttgca ccaggacatt attaacaaat 2580
gtgaacaatt tgtaggtccc ctaacagtaa atgaaaaacg aagattmaac ttagtcatgc 2640
ctgctagatt ttttcccatc tctacgaaat atttgcctct agagaaaggt ataaaaccct 2700
attatccaga taatgtagtt aatcattact tccaaaccag acactattta cataccctat 2760
ggaaggcggg tatcttatat aaaagagaaa ctgcacgtag cgcctcattt tgtgggtcac 2820
catattcttg ggaacaagag ctacatcatg ggtctttctt ggacggtccc tctcgaatgg 2880
gggaagaatc attccaccac caatcctctg ggattttttc ccgaccacca gttggatcca 2940
gcattcagag caaacaccag aaatccagat tgggaccaca atcccaacaa agaccactgg 3000
acagaagcca acaaggtagg agtgggagca ttcgggccgg ggttcactcc cccacacgga 3060
ggccttttgg ggtggagccc tcaggctcaa ggcatgctaa aaacattgcc agcagatccg 3120
cctcctgcct ccaccaatcg gcagtcagga aggcagccta ccccaatcac tccacctttg 3180
agagacactc atcctcaggc catrcagtgg aa 3212

<210> SEQ ID NO 8
<211> LENGTH: 3205
<212> TYPE: DNA
<213> ORGANISM: Hepatitis B virus
<220> FEATURE:
<221> NAME/KEY: HBV genotype F
<222> LOCATION: (1)..(3205)

<400> SEQUENCE: 8
ttccatcagg ctctgttgga tcccagggta agggctctgt atcttcctgc tggtggctcc 60
agttcaggaa cacaaaaccc tgctccgact attgcctctc tcacatcctc aatcttctcg 120
acgactgggg gccctgctat gaacatggac aacattacat caggactcct aggacccctg 180
ctcgtgttac aggcggtgtg tttcttgttg acaaaaatcc tcacaatacc acagagtcta 240
gactcgtggt ggacttctct caattttcta gggggactac ccgggtgtcc tggccaaaat 300
tcgcagtccc caacctccaa tcacttacca acctcctgtc ctccaacttg tcctggctat 360
cgttggatgt gtctgcggcg ttttatcatc ttcctcttca tcctgctgct atgcctcatc 420
ttcttgttgg ttcttctgga ctaccagggt atgttgcccg tttgtcctct acttccagga 480
tccacgacca ccagcacggg accctgcaaa acctgcacaa ctcttgcaca aggaacctct 540
atgtttccct cctgttgctg ttcaaaaccc tcggacggaa actgcacttg tattcccatc 600

-continued

```
ccatcatcct gggctttagg aaaataccta tgggagtggg cctcagcccg tttctcatgg    660
ctcagtttac tagtgcaatt tgttcagtgg tgcgtagggc tttcccccac tgtctggctt    720
ttagttatat tgatgatctg gtattggggg ccaaatctgt gcagcacctt gagtcccttt    780
ataccgctgt taccaatttt ctgttatctg tgggtatcca tttaaatact tctaaaacta    840
agagatgggg ttacacccta cattttatgg gttatgtcat tggtagttgg ggatcattac    900
ctcaagatca tattgtacac aaaatcaaag aatgttttcg gaaactgcct gtaaatcgtc    960
caattgattg gaaagtctgt caacgcattg tgggtctttt gggctttgct gcccctttca   1020
cacaatgtgg ttatcctgct ctcatgcctc tgtatgcttg tattactgct aaacaggctt   1080
ttgtttttc gccaacttac aaggcctttc tctgtaaaca atacatgaac ctttaccccg    1140
ttgccaggca acggccgggc ctgtgccaag tgtttgctga cgcaaccccc actggttggg   1200
gcttggccat tggccatcag cgcatgcgtg gaacctttgt ggctcctctg ccgatccata   1260
ctgcggaact ccttgcagct tgtttcgctc gcagcaggtc tggagcgact ctcatcggca   1320
cggacaactc tgttgtcctc tctaggaagt acacctcctt cccatggctg ctcgggtgtg   1380
ctgcaaactg gatcctgcgc gggacgtcct ttgtttacgt cccgtcggcg ctgaatcccg   1440
cggacgaccc ctcccggggc cgcttggggc tgtaccgccc tcttctccgt ctgccgttcc   1500
agccgacaac gggtcgcacc tctctttacg cggactcccc gtctgttcct tctcatctgc   1560
cggaccgtgt gcacttcgct tcacctctgc acgtcgcatg gagaccaccg tgaacgcccc   1620
ttggagtttg ccaacagtct tacataagag gactcttgga ctttcaggag ggtcaatgac   1680
ccggattgca gaatacatca aagactgtgt atttaaggac tgggaggagt tgggggagga   1740
gactaggtta atgatctttg tactaggagg ctgtaggcat aaattggtct gttcaccagc   1800
accatgcaac tttttcacct ctgcctaatc atcttttgtt catgtcctac tgttcaagcc   1860
tccaagctgt gccttgggtg gctttgggac atggacattg acccttataa agaatttggc   1920
gcttctgtgg agttactctc tttttgcct tctgatttct ttccatcggt tcgggaccta    1980
ctcgacaccg cttcagccct ttaccgggat gctttagagt cacctgaaca ttgcactccc   2040
catcacactg ccctcaggca agttattttg tgctggggtg agttaatgac tttggcttcc   2100
tgggtgggca ataacttgga agaccctgct gccagggatt tagtagttaa ctatgttaac   2160
actaacatgg gcctaaaaat tagacaacta ctgtggtttc acatttcctg ccttactttt   2220
ggaagagata tagttcttga gtatttggtg tcctttggag tgtggattcg cactcctcct   2280
gcttacagac cacaaaatgc ccctatccta tccacacttc cggaaactac tgttgttaga   2340
cgacgaggca ggtcccctag aagaagaact ccctcgcctc gcagacgaag atctcaatcg   2400
ccgcgtcgcc gaagatctca atctccagct tcccaatgtt agtattcctt ggactcataa   2460
ggtgggaaat tttacggggc tttactcttc tactgtgcct gcttttaatc ctgactggtt   2520
aactccttct tttcctaata ttcatttaca tcaagaccta atttctaaat gtgaacaatt   2580
tgtaggccca ctcactaaaa atgaattaag gaggttaaaa ttggttatgc cagctagatt   2640
ttatcctaag gttaccaaat attttcctat ggagaaagga atcaagcctt attatcctga   2700
gcatgcagtt aatcattact ttaaaacaag acattatttg catactttat ggaaggcggg   2760
aattttatat aagagagaat ccacacgtag cgcatcattt tgtgggtcac catattcctg   2820
ggaacaagag ctacagcatg ggagcacctc tctcaacgac aagaagaggc atgggacaga   2880
atctttctgt gcccaatcct ctgggattct ttccagacca tcagctggat ccgctattca   2940
```

-continued

```
aagcaaattc cagcagtccc gactgggact tcaacacaaa caaggacagt tggccaatgg   3000

caaacaaggt aggagtggga gcatacggtc cagggttcac acccccacac ggtggcctgc   3060

tggggtggag ccctcaggca caaggtatgt taacaacctt gccagcagat ccgcctcctg   3120

cttccaccaa tcggcggtcc gggagaaagc caaccccagt ctctccacct ctaagagaca   3180

ctcatccaca ggcaatgcag tggaa                                         3205
```

<210> SEQ ID NO 9
<211> LENGTH: 3247
<212> TYPE: DNA
<213> ORGANISM: Hepatitis B virus
<220> FEATURE:
<221> NAME/KEY: HBV genotype G
<222> LOCATION: (1)..(3247)

<400> SEQUENCE: 9

```
tctacagcat tccaccaagc tctacaaaat cccaaagtca ggggcctgta ttttcctgct     60

ggtggctcca gttcagggat agtgaaccct gttccgacta ttgcctctca catctcgtca    120

atcttctcca ggattgggga ccctgcaccg aacatggaga acatcacatc aggattccta    180

ggacccctgc tcgtgttaca ggcggggttt ttcttgttga caagaatcct cacaataccg    240

cagaatctag actcgtggtg gacttctctc aattttctag gggagtgcc cgtgtgtcct     300

ggcctaaatt cgcagtcccc aacctccaat cactcaccaa tctcctgtcc tccaacttgt    360

cctggctatc gctggatgtg tctgcggcgt tttatcatat tcctcttcat cctgctgcta    420

tgcctcatct tcttgttggt tcttctggac tatcaaggta tgttgcccgt ttgtcctctg    480

attccaggat cctcgaccac cagtacggga ccctgcaaaa cctgcacgac tcctgctcaa    540

ggcaactcta tgtatccctc atgttgctgt acaaaacctt cggacggaaa ttgcacctgt    600

attcccatcc catcatcttg ggctttcgca aaatacctat gggagtgggc ctcagtccgt    660

ttctcttggc tcagtttact agtgccattt gttcagtggt tcgtagggct ttcccccact    720

gtctggcttt cagctatatg gatgatgtgg tattgggggc caaatctgta caacatcttg    780

agtcccttta taccgctgtt accaattttc ttttgtcttt gggtatacat ctaaacccta    840

acaaaacaaa aagatggggt tattccttaa attttatggg atatgtaatt ggaagttggg    900

gtactttgcc acaagaacac atcacacaga aaattaagca atgttttcgg aaactccctg    960

ttaacaggcc aattgattgg aaagtctgtc aacgaataac tggtctgttg ggtttcgctg   1020

ctccttttac ccaatgtggt taccctgcct taatgccttt atatgcatgt atacaagcta   1080

agcaggcttt tactttctcg ccaacttata aggcctttct ctgtaaacaa tacatgaacc   1140

tttaccccgt tgctaggcaa cggcccggtc tgtgccaagt gtttgctgac gcaaccccca   1200

ctggttgggg cttggccatc ggccatcagc gcatgcgtgg aacctttgtg gctcctctgc   1260

cgatccatac tgcggaactc ctagctgctt gttttgctcg cagccggtct ggagcaaaac   1320

tcattgggac tgacaattct gtcgtccttt ctcggaaata tacatccttt ccatggctgc   1380

taggctgtgc tgccaactgg atccttcgcg ggacgtcctt tgtttacgtc ccgtcagcgc   1440

tgaatccagc ggacgacccc tcccggggcc gtttggggct ctgtcgcccc cttctccgtc   1500

tgccgttcct gccgaccacg gggcgcacct ctctttacgc ggtctccccg tctgttcctt   1560

ctcatctgcc ggaccgtgtg cacttcgctt cacctctgca cgttacatgg aaaccgccat   1620

gaacacctct catcatctgc caaggcagtt atataagagg actcttggac tgtttgttat   1680

gtcaacaacc ggggtggaga aatacttcaa ggactgtgtt tttgctgagt gggaagaatt   1740
```

-continued aggcaatgag tccaggttaa tgacctttgt attaggaggc tgtaggcata aattggtctg 1800
cgcaccagca ccatgtaact tttcacctc tgcctaatca tctcttgttc atgtcctact 1860
gttcaagcct ccaagctgtg ccttgggtgg ctttagggca tggatagaac aactttgcca 1920
tatggccttt ttggcttaga cattgaccct tataaagaat ttggagctac tgtggagttg 1980
ctctcgtttt tgccttctga ctttttcccg tctgttcgtg atcttctcga caccgcttca 2040
gctttgtacc gggaatcctt agagtcctct gatcattgtt cgcctcacca tacagcactc 2100
aggcaagcaa tcctgtgctg gggtgagttg atgactctag ccacctgggt gggtaataat 2160
ttggaagatc cagcatccag agatttggtg gtcaattatg ttaatactaa tatgggttta 2220
aaaatcaggc aactattgtg gtttcacatt tcctgtctta cttttgggag agaaaccgtt 2280
cttgagtatt tggtgtcttt tggagtgtgg attcgcactc ctcctgctta tagaccacca 2340
aatgccccta tcctatcaac acttccggag actactgttg ttagacgaag aggcaggtcc 2400
cctcgaagaa gaactccctc gcctcgcaga cgaagatctc aatcgccgcg tcgcagaaga 2460
tctgcatctc cagcttccca atgttagtat tccttggact cacaaggtgg gaaactttac 2520
ggggctgtat tcttctacta tacctgtctt taatcctgat tggcaaactc cttcttttcc 2580
aaatatccat ttgcatcaag acattataac taaatgtgaa caatttgtgg gccctctcac 2640
agtaaatgag aaacgaagat taaaactagt tatgcctgcc agatttttcc caaactctac 2700
taaatattta ccattagaca aaggtatcaa accgtattat ccagaaaatg tagttaatca 2760
ttacttccag accagacatt atttacatac cctttggaag gcgggtattc tatataagag 2820
agaaacatcc cgtagcgctt cattttgtgg gtcaccatat acttgggaac aagatctaca 2880
gcatggggct ttcttggacg gtccctctcg agtggggaaa gaacctttcc accagcaatc 2940
ctctaggatt ccttcccgat caccagttgg acccagcatt cagagcaaat accaacaatc 3000
cagattggga cttcaatccc aaaaaggacc cttggccaga ggccaacaag gtaggagttg 3060
gagcctatgg acccgggttc acccctccac acggaggcct tttggggtgg agccctcagt 3120
ctcagggcac actaacaact ttgccagcag atccgcctcc tgcctccacc aatcgtcagt 3180
cagggaggca gccgactccc atctctccac cactaagaga cagtcatcct caggccatgc 3240
agtggaa 3247

<210> SEQ ID NO 10
<211> LENGTH: 22
<212> TYPE: DNA
<213> ORGANISM: Hepatitis B virus
<220> FEATURE:
<221> NAME/KEY: HBV 1-2 recognition sequence (sense)
<222> LOCATION: (1)..(22)

<400> SEQUENCE: 10
cccctgctcg tgttacaggc gg 22

<210> SEQ ID NO 11
<211> LENGTH: 22
<212> TYPE: DNA
<213> ORGANISM: Hepatitis B virus
<220> FEATURE:
<221> NAME/KEY: HBV 1-2 recognition sequence (antisense)
<222> LOCATION: (1)..(22)

<400> SEQUENCE: 11
ggggacgagc acaatgtccg cc 22

```
<210> SEQ ID NO 12
<211> LENGTH: 22
<212> TYPE: DNA
<213> ORGANISM: Hepatitis B virus
<220> FEATURE:
<221> NAME/KEY: HBV 5-6 recognition sequence (sense)
<222> LOCATION: (1)..(22)

<400> SEQUENCE: 12

gatgatgtgg tattgggggc ca                                              22


<210> SEQ ID NO 13
<211> LENGTH: 22
<212> TYPE: DNA
<213> ORGANISM: Hepatitis B virus
<220> FEATURE:
<221> NAME/KEY: HBV 5-6 recognition sequence (antisense)
<222> LOCATION: (1)..(22)

<400> SEQUENCE: 13

ctactacacc ataacccccg gt                                              22


<210> SEQ ID NO 14
<211> LENGTH: 22
<212> TYPE: DNA
<213> ORGANISM: Hepatitis B virus
<220> FEATURE:
<221> NAME/KEY: HBV 7-8 recognition sequence (sense)
<222> LOCATION: (1)..(22)

<400> SEQUENCE: 14

tttgctgacg caacccccac tg                                              22


<210> SEQ ID NO 15
<211> LENGTH: 22
<212> TYPE: DNA
<213> ORGANISM: Hepatitis B virus
<220> FEATURE:
<221> NAME/KEY: HBV 7-8 recognition sequence (antisense)
<222> LOCATION: (1)..(22)

<400> SEQUENCE: 15

aaacgactgc gttgggggtg ac                                              22


<210> SEQ ID NO 16
<211> LENGTH: 22
<212> TYPE: DNA
<213> ORGANISM: Hepatitis B virus
<220> FEATURE:
<221> NAME/KEY: HBV 11-12 recognition sequence (sense)
<222> LOCATION: (1)..(22)

<400> SEQUENCE: 16

tgccgatcca tactgcggaa ct                                              22


<210> SEQ ID NO 17
<211> LENGTH: 22
<212> TYPE: DNA
<213> ORGANISM: Hepatitis B virus
<220> FEATURE:
<221> NAME/KEY: HBV 11-12 recognition sequence (antisense)
<222> LOCATION: (1)..(22)

<400> SEQUENCE: 17

acggctaggt atgacgcctt ga                                              22


<210> SEQ ID NO 18
```

<211> LENGTH: 354
<212> TYPE: PRT
<213> ORGANISM: Artificial
<220> FEATURE:
<223> OTHER INFORMATION: Synthetic Sequence
<220> FEATURE:
<221> NAME/KEY: HBV 1-2x.2
<222> LOCATION: (1)..(354)
<223> OTHER INFORMATION: full sequence

<400> SEQUENCE: 18

```
Met Asn Thr Lys Tyr Asn Lys Glu Phe Leu Leu Tyr Leu Ala Gly Phe
1               5                   10                  15

Val Asp Gly Asp Gly Ser Ile Phe Ala Cys Ile Arg Pro Val Gln Trp
            20                  25                  30

Ser Lys Phe Lys His Ser Leu Glu Leu Cys Phe Thr Val Thr Gln Lys
        35                  40                  45

Thr Gln Arg Arg Trp Phe Leu Asp Lys Leu Val Asp Glu Ile Gly Val
    50                  55                  60

Gly Tyr Val His Asp Tyr Gly Ser Val Ser Ala Tyr Arg Leu Ser Gln
65                  70                  75                  80

Ile Lys Pro Leu His Asn Phe Leu Thr Gln Leu Gln Pro Phe Leu Lys
                85                  90                  95

Leu Lys Gln Lys Gln Ala Asn Leu Val Leu Lys Ile Ile Glu Gln Leu
            100                 105                 110

Pro Ser Ala Lys Glu Ser Pro Asp Lys Phe Leu Glu Val Cys Thr Trp
        115                 120                 125

Val Asp Gln Ile Ala Ala Leu Asn Asp Ser Lys Thr Arg Lys Thr Thr
    130                 135                 140

Ser Glu Thr Val Arg Ala Val Leu Asp Ser Leu Pro Gly Ser Val Gly
145                 150                 155                 160

Gly Leu Ser Pro Ser Gln Ala Ser Ser Ala Ala Ser Ser Ala Ser Ser
                165                 170                 175

Ser Pro Gly Ser Gly Ile Ser Glu Ala Leu Arg Ala Gly Ala Gly Ser
            180                 185                 190

Gly Thr Gly Tyr Asn Lys Glu Phe Leu Leu Tyr Leu Ala Gly Phe Val
        195                 200                 205

Asp Gly Asp Gly Ser Ile Tyr Ala Ser Ile Arg Pro Ser Gln Asp Gln
    210                 215                 220

Lys Phe Lys His Arg Leu Ile Leu Val Phe Ala Val Ser Gln Lys Thr
225                 230                 235                 240

Gln Arg Arg Trp Phe Leu Asp Lys Leu Val Asp Glu Ile Gly Val Gly
                245                 250                 255

Tyr Val Arg Asp Thr Gly Ser Val Ser Glu Tyr Arg Leu Ser Glu Ile
            260                 265                 270

Lys Pro Leu His Asn Phe Leu Thr Gln Leu Gln Pro Phe Leu Lys Leu
        275                 280                 285

Lys Gln Lys Gln Ala Asn Leu Val Leu Lys Ile Ile Glu Gln Leu Pro
    290                 295                 300

Ser Ala Lys Glu Ser Pro Asp Lys Phe Leu Glu Val Cys Thr Trp Val
305                 310                 315                 320

Asp Gln Ile Ala Ala Leu Asn Asp Ser Lys Thr Arg Lys Thr Thr Ser
                325                 330                 335

Glu Thr Val Arg Ala Val Leu Asp Ser Leu Ser Glu Lys Lys Lys Ser
            340                 345                 350

Ser Pro
```

-continued

<210> SEQ ID NO 19
<211> LENGTH: 354
<212> TYPE: PRT
<213> ORGANISM: Artificial
<220> FEATURE:
<223> OTHER INFORMATION: Synthetic Sequence
<220> FEATURE:
<221> NAME/KEY: HBV 1-2x.14
<222> LOCATION: (1)..(354)
<223> OTHER INFORMATION: full sequence

<400> SEQUENCE: 19

```
Met Asn Thr Lys Tyr Asn Lys Glu Phe Leu Leu Tyr Leu Ala Gly Phe
1               5                   10                  15

Val Asp Gly Asp Gly Ser Ile Tyr Ala Cys Ile Ala Pro Arg Gln Trp
            20                  25                  30

Ser Lys Phe Lys His Ser Leu Glu Leu Arg Phe Ala Val Phe Gln Lys
        35                  40                  45

Thr Gln Arg Arg Trp Phe Leu Asp Lys Leu Val Asp Glu Ile Gly Val
    50                  55                  60

Gly Tyr Val Ser Asp Tyr Gly Ser Val Ser Arg Tyr His Leu Ser Glu
65                  70                  75                  80

Ile Lys Pro Leu His Asn Phe Leu Thr Gln Leu Gln Pro Phe Leu Lys
                85                  90                  95

Leu Lys Gln Lys Gln Ala Asn Leu Val Leu Lys Ile Ile Glu Gln Leu
            100                 105                 110

Pro Ser Ala Lys Glu Ser Pro Asp Lys Phe Leu Glu Val Cys Thr Trp
        115                 120                 125

Val Asp Gln Ile Ala Ala Leu Asn Asp Ser Lys Thr Arg Lys Thr Thr
    130                 135                 140

Ser Glu Thr Val Arg Ala Val Leu Asp Ser Leu Pro Gly Ser Val Gly
145                 150                 155                 160

Gly Leu Ser Pro Ser Gln Ala Ser Ser Ala Ala Ser Ser Ala Ser Ser
                165                 170                 175

Ser Pro Gly Ser Gly Ile Ser Glu Ala Leu Arg Ala Gly Ala Gly Ser
            180                 185                 190

Gly Thr Gly Tyr Asn Lys Glu Phe Leu Leu Tyr Leu Ala Gly Phe Val
        195                 200                 205

Asp Gly Asp Gly Ser Ile Tyr Ala Cys Ile Arg Pro Ala Gln Asp Ser
    210                 215                 220

Lys Phe Lys His Arg Leu Ile Leu Ala Leu Glu Val Gly Gln Lys Thr
225                 230                 235                 240

Arg Arg Arg Trp Phe Leu Asp Lys Leu Val Asp Glu Ile Gly Val Gly
                245                 250                 255

Tyr Val Val Asp Asn Gly Ser Val Ser Arg Tyr Ile Leu Ser Gln Ile
            260                 265                 270

Lys Pro Leu His Asn Phe Leu Thr Gln Leu Gln Pro Phe Leu Lys Leu
        275                 280                 285

Lys Gln Lys Gln Ala Asn Leu Val Leu Lys Ile Ile Glu Gln Leu Pro
    290                 295                 300

Ser Ala Lys Glu Ser Pro Asp Lys Phe Leu Glu Val Cys Thr Trp Val
305                 310                 315                 320

Asp Gln Ile Ala Ala Leu Asn Asp Ser Lys Thr Arg Lys Thr Thr Ser
                325                 330                 335

Glu Thr Val Arg Ala Val Leu Asp Ser Leu Ser Glu Lys Lys Lys Ser
```

340 345 350

Ser Pro

<210> SEQ ID NO 20
<211> LENGTH: 354
<212> TYPE: PRT
<213> ORGANISM: Artificial
<220> FEATURE:
<223> OTHER INFORMATION: Synthetic Sequence
<220> FEATURE:
<221> NAME/KEY: HBV 1-2x.68
<222> LOCATION: (1)..(354)
<223> OTHER INFORMATION: full sequence

<400> SEQUENCE: 20

Met Asn Thr Lys Tyr Asn Lys Glu Phe Leu Leu Tyr Leu Ala Gly Phe
1 5 10 15

Val Asp Gly Asp Gly Ser Ile Tyr Ala Cys Ile Arg Pro Asp Gln Ser
20 25 30

Ser Lys Phe Lys His Arg Leu Val Leu Gly Phe Glu Val Gly Gln Lys
35 40 45

Thr Arg Arg Arg Trp Phe Leu Asp Lys Leu Val Asp Glu Ile Gly Val
50 55 60

Gly Tyr Val Val Asp Asn Gly Ser Val Ser Arg Tyr Ile Leu Ser Glu
65 70 75 80

Ile Lys Pro Leu His Asn Phe Leu Thr Gln Leu Gln Pro Phe Leu Lys
85 90 95

Leu Lys Gln Lys Gln Ala Asn Leu Val Leu Lys Ile Ile Glu Gln Leu
100 105 110

Pro Ser Ala Lys Glu Ser Pro Asp Lys Phe Leu Glu Val Cys Thr Trp
115 120 125

Val Asp Gln Ile Ala Ala Leu Asn Asp Ser Lys Thr Arg Lys Thr Thr
130 135 140

Ser Glu Thr Val Arg Ala Val Leu Asp Ser Leu Pro Gly Ser Val Gly
145 150 155 160

Gly Leu Ser Pro Ser Gln Ala Ser Ser Ala Ala Ser Ser Ala Ser Ser
165 170 175

Ser Pro Gly Ser Gly Ile Ser Glu Ala Leu Arg Ala Gly Ala Gly Ser
180 185 190

Gly Thr Gly Tyr Asn Lys Glu Phe Leu Leu Tyr Leu Ala Gly Phe Val
195 200 205

Asp Gly Asp Gly Ser Ile Tyr Ala Cys Ile Ala Pro Arg Gln Trp Ser
210 215 220

Lys Phe Lys His Ser Leu Glu Leu Arg Phe Ala Val Phe Gln Lys Thr
225 230 235 240

Gln Arg Arg Trp Phe Leu Asp Lys Leu Val Asp Glu Ile Gly Val Gly
245 250 255

Tyr Val Ser Asp Tyr Gly Ser Val Ser Arg Tyr His Leu Ser Glu Ile
260 265 270

Lys Pro Leu His Asn Phe Leu Thr Gln Leu Gln Pro Phe Leu Lys Leu
275 280 285

Lys Gln Lys Gln Ala Asn Leu Val Leu Lys Ile Ile Glu Gln Leu Pro
290 295 300

Ser Ala Lys Glu Ser Pro Asp Lys Phe Leu Glu Val Cys Thr Trp Val
305 310 315 320

Asp Gln Ile Ala Ala Leu Asn Asp Ser Lys Thr Arg Lys Thr Thr Ser

```
                325                 330                 335

Glu Thr Val Arg Ala Val Leu Asp Ser Leu Ser Glu Lys Lys Lys Ser
            340                 345                 350

Ser Pro


<210> SEQ ID NO 21
<211> LENGTH: 354
<212> TYPE: PRT
<213> ORGANISM: Artificial Sequence
<220> FEATURE:
<223> OTHER INFORMATION: Synthetic Sequence
<220> FEATURE:
<221> NAME/KEY: HBV 1-2x.93
<222> LOCATION: (1)..(354)
<223> OTHER INFORMATION: full sequence

<400> SEQUENCE: 21

Met Asn Thr Lys Tyr Asn Lys Glu Phe Leu Leu Tyr Leu Ala Gly Phe
1               5                   10                  15

Val Asp Gly Asp Gly Ser Ile Tyr Ala Thr Ile Arg Pro Asp Gln Thr
            20                  25                  30

Tyr Lys Phe Lys His Arg Leu Ile Leu Gln Phe Ala Val Ser Gln Lys
        35                  40                  45

Thr Gln Arg Arg Trp Phe Leu Asp Lys Leu Val Asp Glu Ile Gly Val
    50                  55                  60

Gly Tyr Val Arg Asp Thr Gly Ser Val Ser Glu Tyr Arg Leu Ser Gln
65                  70                  75                  80

Ile Lys Pro Leu His Asn Phe Leu Thr Gln Leu Gln Pro Phe Leu Lys
                85                  90                  95

Leu Lys Gln Lys Gln Ala Asn Leu Val Leu Lys Ile Ile Glu Gln Leu
            100                 105                 110

Pro Ser Ala Lys Glu Ser Pro Asp Lys Phe Leu Glu Val Cys Thr Trp
        115                 120                 125

Val Asp Gln Ile Ala Ala Leu Asn Asp Ser Lys Thr Arg Lys Thr Thr
    130                 135                 140

Ser Glu Thr Val Arg Ala Val Leu Asp Ser Leu Pro Gly Ser Val Gly
145                 150                 155                 160

Gly Leu Ser Pro Ser Gln Ala Ser Ser Ala Ala Ser Ser Ala Ser Ser
                165                 170                 175

Ser Pro Gly Ser Gly Ile Ser Glu Ala Leu Arg Ala Gly Ala Gly Ser
            180                 185                 190

Gly Thr Gly Tyr Asn Lys Glu Phe Leu Leu Tyr Leu Ala Gly Phe Val
        195                 200                 205

Asp Gly Asp Gly Ser Ile Phe Ala Cys Ile Arg Pro Val Gln Trp Ser
    210                 215                 220

Lys Phe Lys His Ser Leu Glu Leu Cys Phe Thr Val Thr Gln Lys Thr
225                 230                 235                 240

Gln Arg Arg Trp Phe Leu Asp Lys Leu Val Asp Glu Ile Gly Val Gly
                245                 250                 255

Tyr Val His Asp Tyr Gly Ser Val Ser Ala Tyr Arg Leu Ser Gln Ile
            260                 265                 270

Lys Pro Leu His Asn Phe Leu Thr Gln Leu Gln Pro Phe Leu Lys Leu
        275                 280                 285

Lys Gln Lys Gln Ala Asn Leu Val Leu Lys Ile Ile Glu Gln Leu Pro
    290                 295                 300

Ser Ala Lys Glu Ser Pro Asp Lys Phe Leu Glu Val Cys Thr Trp Val
```

```
305                 310                 315                 320

Asp Gln Ile Ala Ala Leu Asn Asp Ser Lys Thr Arg Lys Thr Thr Ser
                325                 330                 335

Glu Thr Val Arg Ala Val Leu Asp Ser Leu Ser Glu Lys Lys Lys Ser
            340                 345                 350

Ser Pro


<210> SEQ ID NO 22
<211> LENGTH: 354
<212> TYPE: PRT
<213> ORGANISM: Artificial Sequence
<220> FEATURE:
<223> OTHER INFORMATION: Synthetic Sequence
<220> FEATURE:
<221> NAME/KEY: HBV 5-6x.33
<222> LOCATION: (1)..(354)
<223> OTHER INFORMATION: full sequence

<400> SEQUENCE: 22

Met Asn Thr Lys Tyr Asn Lys Glu Phe Leu Leu Tyr Leu Ala Gly Phe
1               5                   10                  15

Val Asp Gly Asp Gly Ser Ile Tyr Ala Arg Ile Arg Pro Ser Gln Ser
            20                  25                  30

Ser Lys Phe Lys His Lys Leu Thr Leu Val Phe Ala Val Ala Gln Lys
        35                  40                  45

Thr Gln Arg Arg Trp Phe Leu Asp Lys Leu Val Asp Glu Ile Gly Val
    50                  55                  60

Gly Tyr Val His Asp Glu Gly Ser Val Ser Gln Tyr Arg Leu Ser Gln
65                  70                  75                  80

Ile Lys Pro Leu His Asn Phe Leu Thr Gln Leu Gln Pro Phe Leu Lys
                85                  90                  95

Leu Lys Gln Lys Gln Ala Asn Leu Val Leu Lys Ile Ile Glu Gln Leu
            100                 105                 110

Pro Ser Ala Lys Glu Ser Pro Asp Lys Phe Leu Glu Val Cys Thr Trp
        115                 120                 125

Val Asp Gln Ile Ala Ala Leu Asn Asp Ser Lys Thr Arg Lys Thr Thr
    130                 135                 140

Ser Glu Thr Val Arg Ala Val Leu Asp Ser Leu Pro Gly Ser Val Gly
145                 150                 155                 160

Gly Leu Ser Pro Ser Gln Ala Ser Ser Ala Ala Ser Ser Ala Ser Ser
                165                 170                 175

Ser Pro Gly Ser Gly Ile Ser Glu Ala Leu Arg Ala Gly Ala Gly Ser
            180                 185                 190

Gly Thr Gly Tyr Asn Lys Glu Phe Leu Leu Tyr Leu Ala Gly Phe Val
        195                 200                 205

Asp Gly Asp Gly Ser Ile Trp Ala Thr Ile Glu Pro Leu Gln Lys Arg
    210                 215                 220

Lys Phe Lys His Ala Leu His Leu Met Phe Thr Val Ser Gln Lys Thr
225                 230                 235                 240

Gln Arg Arg Trp Phe Leu Asp Lys Leu Val Asp Glu Ile Gly Val Gly
                245                 250                 255

Tyr Val Ile Asp Gln Gly Ser Val Ser Glu Tyr Arg Leu Ser Gln Ile
            260                 265                 270

Lys Pro Leu His Asn Phe Leu Thr Gln Leu Gln Pro Phe Leu Lys Leu
        275                 280                 285

Lys Gln Lys Gln Ala Asn Leu Val Leu Lys Ile Ile Glu Gln Leu Pro
```

```
    290                 295                 300

Ser Ala Lys Glu Ser Pro Asp Lys Phe Leu Glu Val Cys Thr Trp Val
305                 310                 315                 320

Asp Gln Ile Ala Ala Leu Asn Asp Ser Lys Thr Arg Lys Thr Thr Ser
                325                 330                 335

Glu Thr Val Arg Ala Val Leu Asp Ser Leu Ser Glu Lys Lys Lys Ser
            340                 345                 350

Ser Pro


<210> SEQ ID NO 23
<211> LENGTH: 354
<212> TYPE: PRT
<213> ORGANISM: Artificial Sequence
<220> FEATURE:
<223> OTHER INFORMATION: Synthetic Sequence
<220> FEATURE:
<221> NAME/KEY: HBV 5-6x.84
<222> LOCATION: (1)..(354)
<223> OTHER INFORMATION: full sequence

<400> SEQUENCE: 23

Met Asn Thr Lys Tyr Asn Lys Glu Phe Leu Leu Tyr Leu Ala Gly Phe
1               5                   10                  15

Val Asp Gly Asp Gly Ser Ile Phe Ala Arg Ile Arg Pro Gly Gln Asp
            20                  25                  30

Tyr Lys Phe Lys His Asn Leu Val Leu Thr Phe Arg Val Ala Gln Lys
        35                  40                  45

Thr Gln Arg Arg Trp Phe Leu Asp Lys Leu Val Asp Glu Ile Gly Val
    50                  55                  60

Gly Tyr Val Leu Asp Glu Gly Ser Val Ser Gln Tyr Tyr Leu Ser Glu
65                  70                  75                  80

Ile Lys Pro Leu His Asn Phe Leu Thr Gln Leu Gln Pro Phe Leu Lys
                85                  90                  95

Leu Lys Gln Lys Gln Ala Asn Leu Val Leu Lys Ile Ile Glu Gln Leu
            100                 105                 110

Pro Ser Ala Lys Glu Ser Pro Asp Lys Phe Leu Glu Val Cys Thr Trp
        115                 120                 125

Val Asp Gln Ile Ala Ala Leu Asn Asp Ser Lys Thr Arg Lys Thr Thr
    130                 135                 140

Ser Glu Thr Val Arg Ala Val Leu Asp Ser Leu Pro Gly Ser Val Gly
145                 150                 155                 160

Gly Leu Ser Pro Ser Gln Ala Ser Ser Ala Ala Ser Ser Ala Ser Ser
                165                 170                 175

Ser Pro Gly Ser Gly Ile Ser Glu Ala Leu Arg Ala Gly Ala Gly Ser
            180                 185                 190

Gly Thr Gly Tyr Asn Lys Glu Phe Leu Leu Tyr Leu Ala Gly Phe Val
        195                 200                 205

Asp Gly Asp Gly Ser Ile Asn Ala Ser Ile Glu Pro Val Gln Lys Pro
    210                 215                 220

Lys Phe Lys His Thr Leu His Leu Arg Phe Glu Val Ser Gln Lys Thr
225                 230                 235                 240

Gln Arg Arg Trp Phe Leu Asp Lys Leu Val Asp Glu Ile Gly Val Gly
                245                 250                 255

Tyr Val Tyr Asp Gln Gly Ser Val Ser Ser Tyr Arg Leu Ser Glu Ile
            260                 265                 270

Lys Pro Leu His Asn Phe Leu Thr Gln Leu Gln Pro Phe Leu Lys Leu
```

```
        275                 280                 285

Lys Gln Lys Gln Ala Asn Leu Val Leu Lys Ile Ile Glu Gln Leu Pro
    290                 295                 300

Ser Ala Lys Glu Ser Pro Asp Lys Phe Leu Glu Val Cys Thr Trp Val
305                 310                 315                 320

Asp Gln Ile Ala Ala Leu Asn Asp Ser Lys Thr Arg Lys Thr Thr Ser
                325                 330                 335

Glu Thr Val Arg Ala Val Leu Asp Ser Leu Ser Glu Lys Lys Lys Ser
            340                 345                 350

Ser Pro


<210> SEQ ID NO 24
<211> LENGTH: 354
<212> TYPE: PRT
<213> ORGANISM: Artificial Sequence
<220> FEATURE:
<223> OTHER INFORMATION: Synthetic Sequence
<220> FEATURE:
<221> NAME/KEY: HBV 5-6x.90
<222> LOCATION: (1)..(354)
<223> OTHER INFORMATION: full sequence

<400> SEQUENCE: 24

Met Asn Thr Lys Tyr Asn Lys Glu Phe Leu Leu Tyr Leu Ala Gly Phe
1               5                   10                  15

Val Asp Gly Asp Gly Ser Ile Tyr Ala Arg Ile Arg Pro Arg Gln Asn
            20                  25                  30

Phe Lys Phe Lys His Ala Leu Val Leu Gln Phe Arg Val Ser Gln Lys
        35                  40                  45

Thr Gln Arg Arg Trp Phe Leu Asp Lys Leu Val Asp Glu Ile Gly Val
    50                  55                  60

Gly Tyr Val Leu Asp Glu Gly Ser Val Ser Gln Tyr Tyr Leu Ser Gln
65                  70                  75                  80

Ile Lys Pro Leu His Asn Phe Leu Thr Gln Leu Gln Pro Phe Leu Lys
                85                  90                  95

Leu Lys Gln Lys Gln Ala Asn Leu Val Leu Lys Ile Ile Glu Gln Leu
            100                 105                 110

Pro Ser Ala Lys Glu Ser Pro Asp Lys Phe Leu Glu Val Cys Thr Trp
        115                 120                 125

Val Asp Gln Ile Ala Ala Leu Asn Asp Ser Lys Thr Arg Lys Thr Thr
    130                 135                 140

Ser Glu Thr Val Arg Ala Val Leu Asp Ser Leu Pro Gly Ser Val Gly
145                 150                 155                 160

Gly Leu Ser Pro Ser Gln Ala Ser Ser Ala Ala Ser Ser Ala Ser Ser
                165                 170                 175

Ser Pro Gly Ser Gly Ile Ser Glu Ala Leu Arg Ala Gly Ala Gly Ser
            180                 185                 190

Gly Thr Gly Tyr Asn Lys Glu Phe Leu Leu Tyr Leu Ala Gly Phe Val
        195                 200                 205

Asp Gly Asp Gly Ser Ile Val Ala Gln Ile His Pro Ala Gln Lys Asn
    210                 215                 220

Lys Phe Lys His Gly Leu Arg Leu Gln Phe Tyr Val Tyr Gln Lys Thr
225                 230                 235                 240

Gln Arg Arg Trp Phe Leu Asp Lys Leu Val Asp Glu Ile Gly Val Gly
                245                 250                 255

Tyr Val Tyr Asp Gln Gly Ser Val Ser Cys Tyr Arg Leu Ser Gln Ile
```

```
            260                 265                 270

Lys Pro Leu His Asn Phe Leu Thr Gln Leu Gln Pro Phe Leu Lys Leu
        275                 280                 285

Lys Gln Lys Gln Ala Asn Leu Val Leu Lys Ile Ile Glu Gln Leu Pro
    290                 295                 300

Ser Ala Lys Glu Ser Pro Asp Lys Phe Leu Glu Val Cys Thr Trp Val
305                 310                 315                 320

Asp Gln Ile Ala Ala Leu Asn Asp Ser Lys Thr Arg Lys Thr Thr Ser
                325                 330                 335

Glu Thr Val Arg Ala Val Leu Asp Ser Leu Ser Glu Lys Lys Lys Ser
            340                 345                 350

Ser Pro


<210> SEQ ID NO 25
<211> LENGTH: 354
<212> TYPE: PRT
<213> ORGANISM: Artificial Sequence
<220> FEATURE:
<223> OTHER INFORMATION: Synthetic Sequence
<220> FEATURE:
<221> NAME/KEY: HBV 5-6x.4
<222> LOCATION: (1)..(354)
<223> OTHER INFORMATION: full sequence

<400> SEQUENCE: 25

Met Asn Thr Lys Tyr Asn Lys Glu Phe Leu Leu Tyr Leu Ala Gly Phe
1               5                   10                  15

Val Asp Gly Asp Gly Ser Ile Tyr Ala Thr Ile Gln Pro Val Gln Thr
            20                  25                  30

Arg Lys Phe Lys His Ile Leu Arg Leu Trp Phe Thr Val His Gln Lys
        35                  40                  45

Thr Gln Arg Arg Trp Phe Leu Asp Lys Leu Val Asp Glu Ile Gly Val
    50                  55                  60

Gly Tyr Val Val Asp Ala Gly Ser Val Ser Glu Tyr Arg Leu Ser Glu
65                  70                  75                  80

Ile Lys Pro Leu His Asn Phe Leu Thr Gln Leu Gln Pro Phe Leu Lys
                85                  90                  95

Leu Lys Gln Lys Gln Ala Asn Leu Val Leu Lys Ile Ile Glu Gln Leu
            100                 105                 110

Pro Ser Ala Lys Glu Ser Pro Asp Lys Phe Leu Glu Val Cys Thr Trp
        115                 120                 125

Val Asp Gln Ile Ala Ala Leu Asn Asp Ser Lys Thr Arg Lys Thr Thr
    130                 135                 140

Ser Glu Thr Val Arg Ala Val Leu Asp Ser Leu Pro Gly Ser Val Gly
145                 150                 155                 160

Gly Leu Ser Pro Ser Gln Ala Ser Ser Ala Ala Ser Ser Ala Ser Ser
                165                 170                 175

Ser Pro Gly Ser Gly Ile Ser Glu Ala Leu Arg Ala Gly Ala Gly Ser
            180                 185                 190

Gly Thr Gly Tyr Asn Lys Glu Phe Leu Leu Tyr Leu Ala Gly Phe Val
        195                 200                 205

Asp Gly Asp Gly Ser Ile Tyr Ala Arg Ile Arg Pro Thr Gln Gly Ser
    210                 215                 220

Lys Phe Lys His Lys Leu Thr Leu Cys Phe Arg Val Ala Gln Lys Thr
225                 230                 235                 240

Gln Arg Arg Trp Phe Leu Asp Lys Leu Val Asp Glu Ile Gly Val Gly
```

```
                245                 250                 255

Tyr Val Leu Asp Glu Gly Ser Val Ser Gln Tyr Tyr Leu Ser Gln Ile
            260                 265                 270

Lys Pro Leu His Asn Phe Leu Thr Gln Leu Gln Pro Phe Leu Lys Leu
        275                 280                 285

Lys Gln Lys Gln Ala Asn Leu Val Leu Lys Ile Ile Glu Gln Leu Pro
    290                 295                 300

Ser Ala Lys Glu Ser Pro Asp Lys Phe Leu Glu Val Cys Thr Trp Val
305                 310                 315                 320

Asp Gln Ile Ala Ala Leu Asn Asp Ser Lys Thr Arg Lys Thr Thr Ser
                325                 330                 335

Glu Thr Val Arg Ala Val Leu Asp Ser Leu Ser Glu Lys Lys Lys Ser
            340                 345                 350

Ser Pro


<210> SEQ ID NO 26
<211> LENGTH: 351
<212> TYPE: PRT
<213> ORGANISM: Artificial Sequence
<220> FEATURE:
<223> OTHER INFORMATION: Synthetic Sequence
<220> FEATURE:
<221> NAME/KEY: HBV 5-6x.5
<222> LOCATION: (1)..(351)
<223> OTHER INFORMATION: full sequence

<400> SEQUENCE: 26

Met Asn Thr Lys Tyr Asn Lys Glu Phe Leu Leu Tyr Leu Ala Gly Phe
1               5                   10                  15

Val Asp Gly Asp Gly Ser Ile Tyr Ala Thr Ile His Pro Thr Gln Lys
            20                  25                  30

Ala Lys Phe Lys His Val Leu Ala Leu Arg Phe Ser Val Cys Gln Lys
        35                  40                  45

Thr Gln Arg Arg Trp Phe Leu Asp Lys Leu Val Asp Glu Ile Gly Val
    50                  55                  60

Gly Tyr Val Tyr Asp Leu Gly Ser Val Ser Glu Tyr Arg Leu Ser Gln
65                  70                  75                  80

Ile Lys Pro Leu His Asn Phe Leu Thr Gln Leu Gln Pro Phe Leu Lys
                85                  90                  95

Leu Lys Gln Lys Gln Ala Asn Leu Val Leu Lys Ile Ile Glu Gln Leu
            100                 105                 110

Pro Ser Ala Lys Glu Ser Pro Asp Lys Phe Leu Glu Val Cys Thr Trp
        115                 120                 125

Val Asp Gln Ile Ala Ala Leu Asn Asp Ser Lys Thr Arg Lys Thr Thr
    130                 135                 140

Ser Glu Thr Val Arg Ala Val Leu Asp Ser Leu Pro Gly Ser Val Gly
145                 150                 155                 160

Gly Leu Ser Pro Ser Gln Ala Ser Ser Ala Ala Ser Ser Ala Ser Ser
                165                 170                 175

Ser Pro Gly Ser Gly Ile Ser Glu Ala Leu Arg Ala Gly Ala Gly Ser
            180                 185                 190

Tyr Asn Lys Glu Phe Leu Leu Tyr Leu Ala Gly Phe Val Asp Gly Asp
        195                 200                 205

Gly Ser Ile Tyr Ala Arg Ile Arg Pro Leu Gln His Gly Lys Phe Lys
    210                 215                 220

His Lys Leu His Leu Ala Phe Arg Val Ala Gln Lys Thr Gln Arg Arg
```

```
225                 230                 235                 240

Trp Phe Leu Asp Lys Leu Val Asp Glu Ile Gly Val Gly Tyr Val Phe
                245                 250                 255

Asp Asp Gly Ser Val Ser Gln Tyr Thr Leu Ser Gln Ile Lys Pro Leu
            260                 265                 270

His Asn Phe Leu Thr Gln Leu Gln Pro Phe Leu Lys Leu Lys Gln Lys
        275                 280                 285

Gln Ala Asn Leu Val Leu Lys Ile Ile Glu Gln Leu Pro Ser Ala Lys
    290                 295                 300

Glu Ser Pro Asp Lys Phe Leu Glu Val Cys Thr Trp Val Asp Gln Ile
305                 310                 315                 320

Ala Ala Leu Asn Asp Ser Lys Thr Arg Lys Thr Thr Ser Glu Thr Val
                325                 330                 335

Arg Ala Val Leu Asp Ser Leu Ser Glu Lys Lys Lys Ser Ser Pro
            340                 345                 350


<210> SEQ ID NO 27
<211> LENGTH: 354
<212> TYPE: PRT
<213> ORGANISM: Artificial Sequence
<220> FEATURE:
<223> OTHER INFORMATION: Synthetic Sequence
<220> FEATURE:
<221> NAME/KEY: HBV 5-6x.68
<222> LOCATION: (1)..(354)
<223> OTHER INFORMATION: full sequence

<400> SEQUENCE: 27

Met Asn Thr Lys Tyr Asn Lys Glu Phe Leu Leu Tyr Leu Ala Gly Phe
1               5                   10                  15

Val Asp Gly Asp Gly Ser Ile Tyr Ala Gln Ile Met Pro Arg Gln Arg
            20                  25                  30

Ala Lys Phe Lys His Val Leu Lys Leu Asn Phe Ala Val Cys Gln Lys
        35                  40                  45

Thr Gln Arg Arg Trp Phe Leu Asp Lys Leu Val Asp Glu Ile Gly Val
    50                  55                  60

Gly Tyr Val Thr Asp Gln Gly Ser Val Ser Glu Tyr Arg Leu Ser Glu
65                  70                  75                  80

Ile Lys Pro Leu His Asn Phe Leu Thr Gln Leu Gln Pro Phe Leu Lys
                85                  90                  95

Leu Lys Gln Lys Gln Ala Asn Leu Val Leu Lys Ile Ile Glu Gln Leu
            100                 105                 110

Pro Ser Ala Lys Glu Ser Pro Asp Lys Phe Leu Glu Val Cys Thr Trp
        115                 120                 125

Val Asp Gln Ile Ala Ala Leu Asn Asp Ser Lys Thr Arg Lys Thr Thr
    130                 135                 140

Ser Glu Thr Val Arg Ala Val Leu Asp Ser Leu Pro Gly Ser Val Gly
145                 150                 155                 160

Gly Leu Ser Pro Ser Gln Ala Ser Ser Ala Ala Ser Ser Ala Ser Ser
                165                 170                 175

Ser Pro Gly Ser Gly Ile Ser Glu Ala Leu Arg Ala Gly Ala Gly Ser
            180                 185                 190

Gly Thr Gly Tyr Asn Lys Glu Phe Leu Leu Tyr Leu Ala Gly Phe Val
        195                 200                 205

Asp Gly Asp Gly Ser Ile Tyr Ala Arg Ile Arg Pro Arg Gln Ser Ser
    210                 215                 220
```

```
Lys Phe Lys His Arg Leu Leu Leu Phe Phe Arg Val Ser Gln Lys Thr
225                 230                 235                 240

Gln Arg Arg Trp Phe Leu Asp Lys Leu Val Asp Glu Ile Gly Val Gly
                245                 250                 255

Tyr Val Leu Asp Glu Gly Ser Val Ser Gln Tyr Tyr Leu Ser Glu Ile
            260                 265                 270

Lys Pro Leu His Asn Phe Leu Thr Gln Leu Gln Pro Phe Leu Lys Leu
        275                 280                 285

Lys Gln Lys Gln Ala Asn Leu Val Leu Lys Ile Ile Glu Gln Leu Pro
    290                 295                 300

Ser Ala Lys Glu Ser Pro Asp Lys Phe Leu Glu Val Cys Thr Trp Val
305                 310                 315                 320

Asp Gln Ile Ala Ala Leu Asn Asp Ser Lys Thr Arg Lys Thr Thr Ser
                325                 330                 335

Glu Thr Val Arg Ala Val Leu Asp Ser Leu Ser Glu Lys Lys Lys Ser
            340                 345                 350

Ser Pro


<210> SEQ ID NO 28
<211> LENGTH: 354
<212> TYPE: PRT
<213> ORGANISM: Artificial Sequence
<220> FEATURE:
<223> OTHER INFORMATION: Synthetic Sequence
<220> FEATURE:
<221> NAME/KEY: HBV 5-6x.79
<222> LOCATION: (1)..(354)
<223> OTHER INFORMATION: full sequence

<400> SEQUENCE: 28

Met Asn Thr Lys Tyr Asn Lys Glu Phe Leu Leu Tyr Leu Ala Gly Phe
1               5                   10                  15

Val Asp Gly Asp Gly Ser Ile Tyr Ala Thr Ile Glu Pro Val Gln Lys
            20                  25                  30

Asn Lys Phe Lys His Gln Leu Arg Leu Cys Phe Ala Val Cys Gln Lys
        35                  40                  45

Thr Gln Arg Arg Trp Phe Leu Asp Lys Leu Val Asp Glu Ile Gly Val
    50                  55                  60

Gly Tyr Val Cys Asp Thr Gly Ser Val Ser Glu Tyr Arg Leu Ser Gln
65                  70                  75                  80

Ile Lys Pro Leu His Asn Phe Leu Thr Gln Leu Gln Pro Phe Leu Lys
                85                  90                  95

Leu Lys Gln Lys Gln Ala Asn Leu Val Leu Lys Ile Ile Glu Gln Leu
            100                 105                 110

Pro Ser Ala Lys Glu Ser Pro Asp Lys Phe Leu Glu Val Cys Thr Trp
        115                 120                 125

Val Asp Gln Ile Ala Ala Leu Asn Asp Ser Lys Thr Arg Lys Thr Thr
    130                 135                 140

Ser Glu Thr Val Arg Ala Val Leu Asp Ser Leu Pro Gly Ser Val Gly
145                 150                 155                 160

Gly Leu Ser Pro Ser Gln Ala Ser Ser Ala Ala Ser Ser Ala Ser Ser
                165                 170                 175

Ser Pro Gly Ser Gly Ile Ser Glu Ala Leu Arg Ala Gly Ala Gly Ser
            180                 185                 190

Gly Thr Gly Tyr Asn Lys Glu Phe Leu Leu Tyr Leu Ala Gly Phe Val
        195                 200                 205
```

```
Asp Gly Asp Gly Ser Ile Tyr Ala Arg Ile Arg Pro Cys Gln Gly Cys
    210                 215                 220

Lys Phe Lys His Ala Leu Lys Leu Thr Phe Arg Val Ala Gln Lys Thr
225                 230                 235                 240

Gln Arg Arg Trp Phe Leu Asp Lys Leu Val Asp Glu Ile Gly Val Gly
                245                 250                 255

Tyr Val Cys Asp Glu Gly Ser Val Ser Gln Tyr Tyr Leu Ser Gln Ile
            260                 265                 270

Lys Pro Leu His Asn Phe Leu Thr Gln Leu Gln Pro Phe Leu Lys Leu
        275                 280                 285

Lys Gln Lys Gln Ala Asn Leu Val Leu Lys Ile Ile Glu Gln Leu Pro
    290                 295                 300

Ser Ala Lys Glu Ser Pro Asp Lys Phe Leu Glu Val Cys Thr Trp Val
305                 310                 315                 320

Asp Gln Ile Ala Ala Leu Asn Asp Ser Lys Thr Arg Lys Thr Thr Ser
                325                 330                 335

Glu Thr Val Arg Ala Val Leu Asp Ser Leu Ser Glu Lys Lys Lys Ser
            340                 345                 350

Ser Pro


<210> SEQ ID NO 29
<211> LENGTH: 354
<212> TYPE: PRT
<213> ORGANISM: Artificial Sequence
<220> FEATURE:
<223> OTHER INFORMATION: Synthetic Sequence
<220> FEATURE:
<221> NAME/KEY: HBV 7-8x.2
<222> LOCATION: (1)..(354)
<223> OTHER INFORMATION: full sequence

<400> SEQUENCE: 29

Met Asn Thr Lys Tyr Asn Lys Glu Phe Leu Leu Tyr Leu Ala Gly Phe
1               5                   10                  15

Val Asp Gly Asp Gly Ser Ile Tyr Ala Thr Ile Ser Pro Ala Gln Ala
            20                  25                  30

Tyr Lys Phe Lys His Arg Leu Gly Leu Phe Phe Glu Val Asp Gln Lys
        35                  40                  45

Thr Gln Arg Arg Trp Phe Leu Asp Lys Leu Val Asp Glu Ile Gly Val
    50                  55                  60

Gly Tyr Val His Asp Arg Gly Ser Val Ser Arg Tyr Lys Leu Ser Glu
65                  70                  75                  80

Ile Lys Pro Leu His Asn Phe Leu Thr Gln Leu Gln Pro Phe Leu Lys
                85                  90                  95

Leu Lys Gln Lys Gln Ala Asn Leu Val Leu Lys Ile Ile Glu Gln Leu
            100                 105                 110

Pro Ser Ala Lys Glu Ser Pro Asp Lys Phe Leu Glu Val Cys Thr Trp
        115                 120                 125

Val Asp Gln Ile Ala Ala Leu Asn Asp Ser Lys Thr Arg Lys Thr Thr
    130                 135                 140

Ser Glu Thr Val Arg Ala Val Leu Asp Ser Leu Pro Gly Ser Val Gly
145                 150                 155                 160

Gly Leu Ser Pro Ser Gln Ala Ser Ser Ala Ala Ser Ser Ala Ser Ser
                165                 170                 175

Ser Pro Gly Ser Gly Ile Ser Glu Ala Leu Arg Ala Gly Ala Gly Ser
            180                 185                 190
```

```
Gly Thr Gly Tyr Asn Lys Glu Phe Leu Leu Tyr Leu Ala Gly Phe Val
        195                 200                 205

Asp Gly Asp Gly Ser Ile Tyr Ala Arg Ile Val Pro Cys Gln Arg Ser
    210                 215                 220

Lys Phe Lys His Ala Leu Arg Leu Glu Phe Thr Val Arg Gln Lys Thr
225                 230                 235                 240

Arg Arg Arg Trp Ile Leu Asp Lys Leu Val Asp Glu Ile Gly Val Gly
                245                 250                 255

Tyr Val Tyr Asp Ser Gly Ser Val Ser Arg Tyr Tyr Leu Ser Gln Ile
            260                 265                 270

Lys Pro Leu His Asn Phe Leu Thr Gln Leu Gln Pro Phe Leu Lys Leu
        275                 280                 285

Lys Gln Lys Gln Ala Asn Leu Val Leu Lys Ile Ile Glu Gln Leu Pro
    290                 295                 300

Ser Ala Lys Glu Ser Pro Asp Lys Phe Leu Glu Val Cys Thr Trp Val
305                 310                 315                 320

Asp Gln Ile Ala Ala Leu Asn Asp Ser Lys Thr Arg Lys Thr Thr Ser
                325                 330                 335

Glu Thr Val Arg Ala Val Leu Asp Ser Leu Ser Glu Lys Lys Lys Ser
            340                 345                 350

Ser Pro


<210> SEQ ID NO 30
<211> LENGTH: 354
<212> TYPE: PRT
<213> ORGANISM: Artificial Sequence
<220> FEATURE:
<223> OTHER INFORMATION: Synthetic Sequence
<220> FEATURE:
<221> NAME/KEY: HBV 7-8x.9
<222> LOCATION: (1)..(354)
<223> OTHER INFORMATION: full sequence

<400> SEQUENCE: 30

Met Asn Thr Lys Tyr Asn Lys Glu Phe Leu Leu Tyr Leu Ala Gly Phe
1               5                   10                  15

Val Asp Gly Asp Gly Ser Ile Tyr Ala Thr Ile Ser Pro Ala Gln Ala
            20                  25                  30

Tyr Lys Phe Lys His Arg Leu Gly Leu Phe Phe Glu Val Asp Gln Lys
        35                  40                  45

Thr Gln Arg Arg Trp Phe Leu Asp Lys Leu Val Asp Glu Ile Gly Val
    50                  55                  60

Gly Tyr Val His Asp Arg Gly Ser Val Ser Arg Tyr Lys Leu Ser Gln
65                  70                  75                  80

Ile Lys Pro Leu His Asn Phe Leu Thr Gln Leu Gln Pro Phe Leu Lys
                85                  90                  95

Leu Lys Gln Lys Gln Ala Asn Leu Val Leu Lys Ile Ile Glu Gln Leu
            100                 105                 110

Pro Ser Ala Lys Glu Ser Pro Asp Lys Phe Leu Glu Val Cys Thr Trp
        115                 120                 125

Val Asp Gln Ile Ala Ala Leu Asn Asp Ser Lys Thr Arg Lys Thr Thr
    130                 135                 140

Ser Glu Thr Val Arg Ala Val Leu Asp Ser Leu Pro Gly Ser Val Gly
145                 150                 155                 160

Gly Leu Ser Pro Ser Gln Ala Ser Ser Ala Ala Ser Ser Ala Ser Ser
                165                 170                 175
```

```
Ser Pro Gly Ser Gly Ile Ser Glu Ala Leu Arg Ala Gly Ala Gly Ser
            180                 185                 190

Gly Thr Gly Tyr Asn Lys Glu Phe Leu Leu Tyr Leu Ala Gly Phe Val
        195                 200                 205

Asp Gly Asp Gly Ser Ile Tyr Ala Arg Ile Val Pro Cys Gln Arg Ser
    210                 215                 220

Lys Phe Lys His Ala Leu Arg Leu Glu Phe Thr Val Arg Gln Lys Thr
225                 230                 235                 240

Arg Arg Arg Trp Ile Leu Asp Lys Leu Val Asp Glu Ile Gly Val Gly
                245                 250                 255

Tyr Val Phe Asp Asp Gly Ser Val Ser Arg Tyr Tyr Leu Ser Gln Ile
            260                 265                 270

Lys Pro Leu His Asn Phe Leu Thr Gln Leu Gln Pro Phe Leu Lys Leu
        275                 280                 285

Lys Gln Lys Gln Ala Asn Leu Val Leu Lys Ile Ile Glu Gln Leu Pro
    290                 295                 300

Ser Ala Lys Glu Ser Pro Asp Lys Phe Leu Glu Val Cys Thr Trp Val
305                 310                 315                 320

Asp Gln Ile Ala Ala Leu Asn Asp Ser Lys Thr Arg Lys Thr Thr Ser
                325                 330                 335

Glu Thr Val Arg Ala Val Leu Asp Ser Leu Ser Glu Lys Lys Lys Ser
            340                 345                 350

Ser Pro


<210> SEQ ID NO 31
<211> LENGTH: 354
<212> TYPE: PRT
<213> ORGANISM: Artificial Sequence
<220> FEATURE:
<223> OTHER INFORMATION: Synthetic Sequence
<220> FEATURE:
<221> NAME/KEY: HBV 7-8x.17
<222> LOCATION: (1)..(354)
<223> OTHER INFORMATION: full sequence

<400> SEQUENCE: 31

Met Asn Thr Lys Tyr Asn Lys Glu Phe Leu Leu Tyr Leu Ala Gly Phe
1               5                   10                  15

Val Asp Gly Asp Gly Ser Ile Tyr Ala Thr Ile Ser Pro Ala Gln Ala
            20                  25                  30

Tyr Lys Phe Lys His Arg Leu Gly Leu Phe Phe Glu Val Asp Gln Lys
        35                  40                  45

Thr Gln Arg Arg Trp Phe Leu Asp Lys Leu Val Asp Glu Ile Gly Val
    50                  55                  60

Gly Tyr Val His Asp Arg Gly Ser Val Ser Arg Tyr Lys Leu Ser Gln
65                  70                  75                  80

Ile Lys Pro Leu His Asn Phe Leu Thr Gln Leu Gln Pro Phe Leu Lys
                85                  90                  95

Leu Lys Gln Lys Gln Ala Asn Leu Val Leu Lys Ile Ile Glu Gln Leu
            100                 105                 110

Pro Ser Ala Lys Glu Ser Pro Asp Lys Phe Leu Glu Val Cys Thr Trp
        115                 120                 125

Val Asp Gln Ile Ala Ala Leu Asn Asp Ser Lys Thr Arg Lys Thr Thr
    130                 135                 140

Ser Glu Thr Val Arg Ala Val Leu Asp Ser Leu Pro Gly Ser Val Gly
145                 150                 155                 160
```

```
Gly Leu Ser Pro Ser Gln Ala Ser Ser Ala Ala Ser Ser Ala Ser Ser
                165                 170                 175

Ser Pro Gly Ser Gly Ile Ser Glu Ala Leu Arg Ala Gly Ala Gly Ser
            180                 185                 190

Gly Thr Gly Tyr Asn Lys Glu Phe Leu Leu Tyr Leu Ala Gly Phe Val
        195                 200                 205

Asp Gly Asp Gly Ser Ile Tyr Ala Arg Ile Val Pro Cys Gln Arg Ser
    210                 215                 220

Lys Phe Lys His Ala Leu Arg Leu Glu Phe Thr Val Arg Gln Lys Thr
225                 230                 235                 240

Arg Arg Arg Trp Ile Leu Asp Lys Leu Val Asp Glu Ile Gly Val Gly
                245                 250                 255

Tyr Val Phe Asp Asp Gly Ser Val Ser Arg Tyr Tyr Leu Ser Gln Ile
            260                 265                 270

Lys Pro Leu His Asn Phe Leu Thr Gln Leu Gln Pro Phe Leu Lys Leu
        275                 280                 285

Lys Gln Lys Gln Ala Asn Leu Val Leu Lys Ile Ile Glu Gln Leu Pro
    290                 295                 300

Ser Ala Lys Glu Ser Pro Asp Lys Phe Leu Glu Val Cys Thr Trp Val
305                 310                 315                 320

Asp Gln Ile Ala Ala Leu Asn Asp Ser Lys Thr Arg Lys Thr Thr Ser
                325                 330                 335

Glu Thr Val Arg Ala Val Leu Asp Arg Leu Ser Glu Lys Lys Lys Ser
            340                 345                 350

Ser Pro


<210> SEQ ID NO 32
<211> LENGTH: 354
<212> TYPE: PRT
<213> ORGANISM: Artificial Sequence
<220> FEATURE:
<223> OTHER INFORMATION: Synthetic Sequence
<220> FEATURE:
<221> NAME/KEY: HBV 7-8x.44
<222> LOCATION: (1)..(354)
<223> OTHER INFORMATION: full sequence

<400> SEQUENCE: 32

Met Asn Thr Lys Tyr Asn Lys Glu Phe Leu Leu Tyr Leu Ala Gly Phe
1               5                   10                  15

Val Asp Gly Asp Gly Ser Ile Tyr Ala Thr Ile Ser Pro Ala Gln Ala
            20                  25                  30

Tyr Lys Phe Lys His Arg Leu Gly Leu Phe Phe Glu Val Asp Gln Lys
        35                  40                  45

Thr Gln Arg Arg Trp Phe Leu Asp Lys Leu Val Asp Glu Ile Gly Val
    50                  55                  60

Gly Tyr Val His Asp Arg Gly Ser Val Ser Arg Tyr Lys Leu Ser Gln
65                  70                  75                  80

Ile Lys Pro Leu His Asn Phe Leu Thr Gln Leu Gln Pro Phe Leu Lys
                85                  90                  95

Leu Lys Gln Lys Gln Ala Asn Leu Val Leu Lys Ile Ile Glu Gln Leu
            100                 105                 110

Pro Ser Ala Lys Glu Ser Pro Asp Lys Phe Leu Glu Val Cys Thr Trp
        115                 120                 125

Val Asp Gln Ile Ala Ala Leu Asn Asp Ser Lys Thr Arg Lys Thr Thr
    130                 135                 140
```

-continued

```
Ser Glu Thr Val Arg Ala Val Leu Asp Ser Leu Pro Gly Ser Val Gly
145                 150                 155                 160

Gly Leu Ser Pro Ser Gln Ala Ser Ser Ala Ala Ser Ser Ala Ser Ser
                165                 170                 175

Ser Pro Gly Ser Gly Ile Ser Glu Ala Leu Arg Ala Gly Ala Gly Ser
            180                 185                 190

Gly Thr Gly Tyr Asn Lys Glu Phe Leu Leu Tyr Leu Ala Gly Phe Val
        195                 200                 205

Asp Gly Asp Gly Ser Ile Tyr Ala Arg Ile Val Pro Cys Gln Arg Ser
    210                 215                 220

Lys Phe Lys His Ala Leu Arg Leu Glu Phe Ala Val Arg Gln Lys Thr
225                 230                 235                 240

Gln Arg Arg Trp Ile Leu Asp Lys Leu Val Asp Glu Ile Gly Val Gly
                245                 250                 255

Tyr Val Phe Asp Asp Gly Ser Val Ser Arg Tyr Tyr Leu Ser Glu Ile
            260                 265                 270

Lys Pro Leu His Asn Phe Leu Thr Gln Leu Gln Pro Phe Leu Lys Leu
        275                 280                 285

Lys Gln Lys Gln Ala Asn Leu Val Leu Lys Ile Ile Glu Gln Leu Pro
    290                 295                 300

Ser Ala Lys Glu Ser Pro Asp Lys Phe Leu Glu Val Cys Thr Trp Val
305                 310                 315                 320

Asp Gln Ile Ala Ala Leu Asn Asp Ser Lys Thr Arg Lys Thr Thr Ser
                325                 330                 335

Glu Thr Val Arg Ala Val Leu Asp Ser Leu Ser Glu Lys Lys Lys Ser
            340                 345                 350

Ser Pro
```

<210> SEQ ID NO 33
<211> LENGTH: 354
<212> TYPE: PRT
<213> ORGANISM: Artificial Sequence
<220> FEATURE:
<223> OTHER INFORMATION: Synthetic Sequence
<220> FEATURE:
<221> NAME/KEY: HBV 11-12x.26
<222> LOCATION: (1)..(354)
<223> OTHER INFORMATION: full sequence

<400> SEQUENCE: 33

```
Met Asn Thr Lys Tyr Asn Lys Glu Phe Leu Leu Tyr Leu Ala Gly Phe
1               5                   10                  15

Val Asp Gly Asp Gly Ser Ile Asn Ala Ser Ile Ala Pro Arg Gln Ser
            20                  25                  30

Phe Lys Phe Lys His Gly Leu Lys Leu Arg Phe Glu Val Gly Gln Lys
        35                  40                  45

Thr Gln Arg Arg Trp Phe Leu Asp Lys Leu Val Asp Glu Ile Gly Val
    50                  55                  60

Gly Tyr Val Tyr Asp Asn Gly Ser Val Ser Val Tyr Ser Leu Ser Gln
65                  70                  75                  80

Ile Lys Pro Leu His Asn Phe Leu Thr Gln Leu Gln Pro Phe Leu Lys
                85                  90                  95

Leu Lys Gln Lys Gln Ala Asn Leu Val Leu Lys Ile Ile Glu Gln Leu
            100                 105                 110

Pro Ser Ala Lys Glu Ser Pro Asp Lys Phe Leu Glu Val Cys Thr Trp
        115                 120                 125
```

```
Val Asp Gln Ile Ala Ala Leu Asn Asp Ser Lys Thr Arg Lys Thr Thr
    130                 135                 140

Ser Glu Thr Val Arg Ala Val Leu Asp Ser Leu Pro Gly Ser Val Gly
145                 150                 155                 160

Gly Leu Ser Pro Ser Gln Ala Ser Ser Ala Ala Ser Ser Ala Ser Ser
                165                 170                 175

Ser Pro Gly Ser Gly Ile Ser Glu Ala Leu Arg Ala Gly Ala Gly Ser
            180                 185                 190

Gly Thr Gly Tyr Asn Lys Glu Phe Leu Leu Tyr Leu Ala Gly Phe Val
        195                 200                 205

Asp Gly Asp Gly Ser Ile Tyr Ala Ser Ile Arg Pro Arg Gln Tyr Ala
    210                 215                 220

Lys Phe Lys His Asp Leu Glu Leu Arg Phe Asn Val Arg Gln Lys Thr
225                 230                 235                 240

Gln Arg Arg Trp Phe Leu Asp Lys Leu Val Asp Glu Ile Gly Val Gly
                245                 250                 255

Tyr Val Val Asp Trp Gly Ser Val Ser Thr Tyr Gln Leu Ser Gln Ile
            260                 265                 270

Lys Pro Leu His Asn Phe Leu Thr Gln Leu Gln Pro Phe Leu Lys Leu
        275                 280                 285

Lys Gln Lys Gln Ala Asn Leu Val Leu Lys Ile Ile Glu Gln Leu Pro
    290                 295                 300

Ser Ala Lys Glu Ser Pro Asp Lys Phe Leu Glu Val Cys Thr Trp Val
305                 310                 315                 320

Asp Gln Ile Ala Ala Leu Asn Asp Ser Lys Thr Arg Lys Thr Thr Ser
                325                 330                 335

Glu Thr Val Arg Ala Val Leu Asp Ser Leu Ser Glu Lys Lys Lys Ser
            340                 345                 350

Ser Pro
```

```
<210> SEQ ID NO 34
<211> LENGTH: 354
<212> TYPE: PRT
<213> ORGANISM: Artificial Sequence
<220> FEATURE:
<223> OTHER INFORMATION: Synthetic Sequence
<220> FEATURE:
<221> NAME/KEY: HBV 11-12x.9
<222> LOCATION: (1)..(354)
<223> OTHER INFORMATION: full sequence

<400> SEQUENCE: 34

Met Asn Thr Lys Tyr Asn Lys Glu Phe Leu Leu Tyr Leu Ala Gly Phe
1               5                   10                  15

Val Asp Gly Asp Gly Ser Ile His Ala Cys Ile Arg Pro Arg Gln Thr
            20                  25                  30

Ala Lys Phe Lys His Ser Leu Leu Leu Arg Phe Gln Val Gly Gln Lys
        35                  40                  45

Thr Gln Arg Arg Trp Phe Leu Asp Lys Leu Val Asp Glu Ile Gly Val
    50                  55                  60

Gly Tyr Val Tyr Asp Asn Gly Ser Val Ser Val Tyr Glu Leu Ser Gln
65                  70                  75                  80

Ile Lys Pro Leu His Asn Phe Leu Thr Gln Leu Gln Pro Phe Leu Lys
                85                  90                  95

Leu Lys Gln Lys Gln Ala Asn Leu Val Leu Lys Ile Ile Glu Gln Leu
            100                 105                 110
```

```
Pro Ser Ala Lys Glu Ser Pro Asp Lys Phe Leu Glu Val Cys Thr Trp
        115                 120                 125

Val Asp Gln Ile Ala Ala Leu Asn Asp Ser Lys Thr Arg Lys Thr Thr
    130                 135                 140

Ser Glu Thr Val Arg Ala Val Leu Asp Ser Leu Pro Gly Ser Val Gly
145                 150                 155                 160

Gly Leu Ser Pro Ser Gln Ala Ser Ser Ala Ala Ser Ser Ala Ser Ser
                165                 170                 175

Ser Pro Gly Ser Gly Ile Ser Glu Ala Leu Arg Ala Gly Ala Gly Ser
            180                 185                 190

Gly Thr Gly Tyr Asn Lys Glu Phe Leu Leu Tyr Leu Ala Gly Phe Val
        195                 200                 205

Asp Gly Asp Gly Ser Ile Tyr Ala Ala Ile Arg Pro Lys Gln Thr Arg
    210                 215                 220

Lys Phe Lys His Glu Leu Gln Leu Thr Phe Asn Val Arg Gln Lys Ser
225                 230                 235                 240

Gln Arg Arg Trp Phe Leu Asp Lys Leu Val Asp Glu Ile Gly Val Gly
                245                 250                 255

Tyr Val Leu Asp Trp Gly Ser Val Ser Thr Tyr Ile Leu Ser Gln Ile
            260                 265                 270

Lys Pro Leu His Asn Phe Leu Thr Gln Leu Gln Pro Phe Leu Lys Leu
        275                 280                 285

Lys Gln Lys Gln Ala Asn Leu Val Leu Lys Ile Ile Glu Gln Leu Pro
    290                 295                 300

Ser Ala Lys Glu Ser Pro Asp Lys Phe Leu Glu Val Cys Thr Trp Val
305                 310                 315                 320

Asp Gln Ile Ala Ala Leu Asn Asp Ser Lys Thr Arg Lys Thr Thr Ser
                325                 330                 335

Glu Thr Val Arg Ala Val Leu Asp Ser Leu Ser Glu Lys Lys Lys Ser
            340                 345                 350

Ser Pro


<210> SEQ ID NO 35
<211> LENGTH: 354
<212> TYPE: PRT
<213> ORGANISM: Artificial Sequence
<220> FEATURE:
<223> OTHER INFORMATION: Synthetic Sequence
<220> FEATURE:
<221> NAME/KEY: HBV 11-12x.13
<222> LOCATION: (1)..(354)
<223> OTHER INFORMATION: full sequence

<400> SEQUENCE: 35

Met Asn Thr Lys Tyr Asn Lys Glu Phe Leu Leu Tyr Leu Ala Gly Phe
1               5                   10                  15

Val Asp Gly Asp Gly Ser Ile His Ala Cys Ile Arg Pro Arg Gln Thr
            20                  25                  30

Ala Lys Phe Lys His Ser Leu Leu Leu Arg Phe Gln Val Gly Gln Lys
        35                  40                  45

Thr Gln Arg Arg Trp Phe Leu Asp Lys Leu Val Asp Glu Ile Gly Val
    50                  55                  60

Gly Tyr Val Tyr Asp Asn Gly Ser Val Ser Val Tyr Glu Leu Ser Gln
65                  70                  75                  80

Ile Lys Pro Leu His Asn Phe Leu Thr Gln Leu Gln Pro Phe Leu Lys
                85                  90                  95
```

-continued

```
Leu Lys Gln Lys Gln Ala Asn Leu Val Leu Lys Ile Ile Glu Gln Leu
            100                 105                 110

Pro Ser Ala Lys Glu Ser Pro Asp Lys Phe Leu Glu Val Cys Thr Trp
        115                 120                 125

Val Asp Gln Ile Ala Ala Leu Asn Asp Ser Lys Thr Arg Lys Thr Thr
    130                 135                 140

Ser Glu Thr Val Arg Ala Val Leu Asp Ser Leu Pro Gly Ser Val Gly
145                 150                 155                 160

Gly Leu Ser Pro Ser Gln Ala Ser Ser Ala Ala Ser Ser Ala Ser Ser
                165                 170                 175

Ser Pro Gly Ser Gly Ile Ser Glu Ala Leu Arg Ala Gly Ala Gly Ser
            180                 185                 190

Gly Thr Gly Tyr Asn Lys Glu Phe Leu Leu Tyr Leu Ala Gly Phe Val
        195                 200                 205

Asp Gly Asp Gly Ser Ile Tyr Ala Ala Ile Arg Pro Lys Gln Thr Arg
    210                 215                 220

Lys Phe Lys His Glu Leu Gln Leu Thr Phe Asn Val Arg Gln Lys Thr
225                 230                 235                 240

Gln Arg Arg Trp Phe Leu Asp Lys Leu Val Asp Glu Ile Gly Val Gly
                245                 250                 255

Tyr Val Leu Asp Trp Gly Ser Val Ser Thr Tyr Ile Leu Ser Gln Ile
            260                 265                 270

Lys Pro Leu His Asn Phe Leu Thr Gln Leu Gln Pro Phe Leu Lys Leu
        275                 280                 285

Lys Gln Lys Gln Ala Asn Leu Val Leu Lys Ile Ile Glu Gln Leu Pro
    290                 295                 300

Ser Ala Lys Glu Ser Pro Asp Lys Phe Leu Glu Val Cys Thr Trp Val
305                 310                 315                 320

Asp Gln Ile Ala Ala Leu Asn Asp Ser Lys Thr Arg Lys Thr Thr Ser
                325                 330                 335

Glu Thr Val Arg Ala Val Leu Asp Ser Leu Ser Glu Lys Lys Lys Ser
            340                 345                 350

Ser Pro


<210> SEQ ID NO 36
<211> LENGTH: 354
<212> TYPE: PRT
<213> ORGANISM: Artificial Sequence
<220> FEATURE:
<223> OTHER INFORMATION: Synthetic Sequence
<220> FEATURE:
<221> NAME/KEY: HBV 11-12x.16
<222> LOCATION: (1)..(354)
<223> OTHER INFORMATION: full sequence

<400> SEQUENCE: 36

Met Asn Thr Lys Tyr Asn Lys Glu Phe Leu Leu Tyr Leu Ala Gly Phe
1               5                   10                  15

Val Asp Gly Asp Gly Ser Ile His Ala Thr Ile Ser Pro Arg Gln Thr
            20                  25                  30

Phe Lys Phe Lys His Gly Leu Arg Leu Arg Phe Glu Val Gly Gln Lys
        35                  40                  45

Thr Gln Arg Arg Trp Phe Leu Asp Lys Leu Val Asp Glu Ile Gly Gly
    50                  55                  60

Gly Tyr Val Tyr Asp Asn Gly Ser Val Ser Val Tyr Ser Leu Ser Gln
65                  70                  75                  80
```

```
Ile Lys Pro Leu His Asn Phe Leu Thr Gln Leu Gln Pro Phe Leu Lys
                85                  90                  95

Leu Lys Gln Lys Gln Ala Asn Leu Val Leu Lys Ile Ile Glu Gln Leu
            100                 105                 110

Pro Ser Ala Lys Glu Ser Pro Asp Lys Phe Leu Glu Val Cys Thr Trp
        115                 120                 125

Val Asp Gln Ile Ala Ala Leu Asn Asp Ser Lys Thr Arg Lys Thr Thr
    130                 135                 140

Ser Glu Thr Val Arg Ala Val Leu Asp Ser Leu Pro Gly Ser Val Gly
145                 150                 155                 160

Gly Leu Ser Pro Ser Gln Ala Ser Ser Ala Ala Ser Ser Ala Ser Ser
                165                 170                 175

Ser Pro Gly Ser Gly Ile Ser Glu Ala Leu Arg Ala Gly Ala Gly Ser
            180                 185                 190

Gly Thr Gly Tyr Asn Lys Glu Phe Leu Leu Tyr Leu Ala Gly Phe Val
        195                 200                 205

Asp Gly Asp Gly Ser Ile Tyr Ala Ser Ile Arg Pro Arg Gln Gln Ala
    210                 215                 220

Lys Phe Lys His Ser Leu Glu Leu His Phe Asn Val Arg Gln Lys Thr
225                 230                 235                 240

Gln Arg Arg Trp Phe Leu Asp Lys Leu Val Asp Glu Ile Gly Val Gly
                245                 250                 255

Tyr Val Val Asp Glu Gly Ser Val Ser Thr Tyr Leu Leu Ser Glu Ile
            260                 265                 270

Lys Pro Leu His Asn Phe Leu Thr Gln Leu Gln Pro Phe Leu Lys Leu
        275                 280                 285

Lys Gln Lys Gln Ala Asn Leu Val Leu Lys Ile Ile Glu Gln Leu Pro
    290                 295                 300

Ser Ala Lys Glu Ser Pro Asp Lys Phe Leu Glu Val Cys Thr Trp Val
305                 310                 315                 320

Asp Gln Ile Ala Ala Leu Asn Asp Ser Lys Thr Arg Lys Thr Thr Ser
                325                 330                 335

Glu Thr Val Arg Ala Val Leu Asp Ser Leu Ser Glu Lys Lys Lys Ser
            340                 345                 350

Ser Pro


<210> SEQ ID NO 37
<211> LENGTH: 354
<212> TYPE: PRT
<213> ORGANISM: Artificial Sequence
<220> FEATURE:
<223> OTHER INFORMATION: Synthetic Sequence
<220> FEATURE:
<221> NAME/KEY: HBV 11-12x.27
<222> LOCATION: (1)..(354)
<223> OTHER INFORMATION: full sequence

<400> SEQUENCE: 37

Met Asn Thr Lys Tyr Asn Lys Glu Phe Leu Leu Tyr Leu Ala Gly Phe
1               5                   10                  15

Val Asp Gly Asp Gly Ser Ile His Ala Cys Ile Arg Pro Arg Gln Thr
            20                  25                  30

Ala Lys Phe Lys His Ser Leu Leu Leu Arg Phe Gln Val Gly Gln Lys
        35                  40                  45

Thr Gln Arg Arg Trp Phe Leu Asp Lys Leu Val Asp Glu Ile Gly Val
    50                  55                  60
```

-continued

```
Gly Tyr Val Tyr Asp Asn Gly Ser Val Ser Val Tyr Glu Leu Ser Glu
65                  70                  75                  80

Ile Lys Pro Leu His Asn Phe Leu Thr Gln Leu Gln Pro Phe Leu Lys
                85                  90                  95

Leu Lys Gln Lys Gln Ala Asn Leu Val Leu Lys Ile Ile Glu Gln Leu
            100                 105                 110

Pro Ser Ala Lys Glu Ser Pro Asp Lys Phe Leu Glu Val Cys Thr Trp
        115                 120                 125

Val Asp Gln Ile Ala Ala Leu Asn Asp Ser Lys Thr Arg Lys Thr Thr
    130                 135                 140

Ser Glu Thr Val Arg Ala Val Leu Asp Ser Leu Pro Gly Ser Val Gly
145                 150                 155                 160

Gly Leu Ser Pro Ser Gln Ala Ser Ser Ala Ala Ser Ser Ala Ser Ser
                165                 170                 175

Ser Pro Gly Ser Gly Ile Ser Glu Ala Leu Arg Ala Gly Ala Gly Ser
            180                 185                 190

Gly Thr Gly Tyr Asn Lys Glu Phe Leu Leu Tyr Leu Ala Gly Phe Val
        195                 200                 205

Asp Gly Asp Gly Ser Ile Tyr Ala Ser Ile Arg Pro Arg Gln Tyr Ala
    210                 215                 220

Lys Phe Lys His Asp Leu Glu Leu Arg Phe Asn Val Arg Gln Lys Thr
225                 230                 235                 240

Gln Arg Arg Trp Phe Leu Asp Lys Leu Val Asp Glu Ile Gly Val Gly
                245                 250                 255

Tyr Val Val Asp Trp Gly Ser Val Ser Thr Tyr Gln Leu Ser Gln Ile
            260                 265                 270

Lys Pro Leu His Asn Phe Leu Thr Gln Leu Gln Pro Phe Leu Lys Leu
        275                 280                 285

Lys Gln Lys Gln Ala Asn Leu Val Leu Lys Ile Ile Glu Gln Leu Pro
    290                 295                 300

Ser Ala Lys Glu Ser Pro Asp Lys Phe Leu Glu Val Cys Thr Trp Val
305                 310                 315                 320

Asp Gln Ile Ala Ala Leu Asn Asp Ser Lys Thr Arg Lys Thr Thr Ser
                325                 330                 335

Glu Thr Val Arg Ala Val Leu Asp Ser Leu Ser Glu Lys Lys Lys Ser
            340                 345                 350

Ser Pro


<210> SEQ ID NO 38
<211> LENGTH: 354
<212> TYPE: PRT
<213> ORGANISM: Artificial Sequence
<220> FEATURE:
<223> OTHER INFORMATION: Synthetic Sequence
<220> FEATURE:
<221> NAME/KEY: HBV 11-12x.41
<222> LOCATION: (1)..(354)
<223> OTHER INFORMATION: full sequence

<400> SEQUENCE: 38

Met Asn Thr Lys Tyr Asn Lys Glu Phe Leu Leu Tyr Leu Ala Gly Phe
1               5                   10                  15

Val Asp Gly Asp Gly Ser Ile His Ala Cys Ile Arg Pro Arg Gln Thr
            20                  25                  30

Ala Lys Phe Lys His Ser Leu Leu Leu Arg Phe Gln Val Gly Gln Lys
        35                  40                  45
```

```
Thr Gln Arg Arg Trp Phe Leu Asp Lys Leu Val Asp Glu Ile Gly Val
    50                  55                  60

Gly Tyr Val Tyr Asp Asn Gly Ser Val Ser Val Tyr Glu Leu Ser Lys
65                  70                  75                  80

Ile Lys Pro Leu His Asn Phe Leu Thr Gln Leu Gln Pro Phe Leu Lys
                85                  90                  95

Leu Lys Gln Lys Gln Ala Asn Leu Val Leu Lys Ile Ile Glu Gln Leu
            100                 105                 110

Pro Ser Ala Lys Glu Ser Pro Asp Lys Phe Leu Glu Val Cys Thr Trp
        115                 120                 125

Val Asp Gln Ile Ala Ala Leu Asn Asp Ser Lys Thr Arg Lys Thr Thr
    130                 135                 140

Ser Glu Thr Val Arg Ala Val Leu Asp Ser Leu Pro Gly Ser Val Gly
145                 150                 155                 160

Gly Leu Ser Pro Ser Gln Ala Ser Ser Ala Ala Ser Ser Ala Ser Ser
                165                 170                 175

Ser Pro Gly Ser Gly Ile Ser Glu Ala Leu Arg Ala Gly Ala Gly Ser
            180                 185                 190

Gly Thr Gly Tyr Asn Lys Glu Phe Leu Leu Tyr Leu Ala Gly Phe Val
        195                 200                 205

Asp Gly Asp Gly Ser Ile Tyr Ala Ser Ile Arg Pro Arg Gln Leu Ala
    210                 215                 220

Lys Phe Lys His Thr Leu Glu Leu His Phe Asn Val Arg Gln Lys Thr
225                 230                 235                 240

Gln Arg Arg Trp Phe Leu Asp Lys Leu Val Asp Glu Ile Gly Val Gly
                245                 250                 255

Tyr Val Leu Asp Ser Gly Ser Val Ser Thr Tyr Leu Leu Ser Gln Ile
            260                 265                 270

Lys Pro Leu His Asn Phe Leu Thr Gln Leu Gln Pro Phe Leu Lys Leu
        275                 280                 285

Lys Gln Lys Gln Ala Asn Leu Val Leu Lys Ile Ile Glu Gln Leu Pro
    290                 295                 300

Ser Ala Lys Glu Ser Pro Asp Lys Phe Leu Glu Val Cys Thr Trp Val
305                 310                 315                 320

Asp Gln Ile Ala Ala Leu Asn Asp Ser Lys Thr Arg Lys Thr Thr Ser
                325                 330                 335

Glu Thr Val Arg Ala Val Leu Asp Ser Leu Ser Glu Lys Lys Lys Ser
            340                 345                 350

Ser Pro


<210> SEQ ID NO 39
<211> LENGTH: 354
<212> TYPE: PRT
<213> ORGANISM: Artificial Sequence
<220> FEATURE:
<223> OTHER INFORMATION: Synthetic Sequence
<220> FEATURE:
<221> NAME/KEY: HBV 11-12x.48
<222> LOCATION: (1)..(354)
<223> OTHER INFORMATION: full sequence

<400> SEQUENCE: 39

Met Asn Thr Lys Tyr Asn Lys Glu Phe Leu Leu Tyr Leu Ala Gly Phe
1               5                   10                  15

Val Asp Gly Asp Gly Ser Ile His Ala Cys Ile Arg Pro Arg Gln Thr
            20                  25                  30
```

```
Ala Lys Phe Lys His Ser Leu Leu Leu Arg Phe Gln Val Gly Gln Lys
        35                  40                  45

Thr Gln Arg Arg Trp Phe Leu Asp Lys Leu Val Asp Glu Ile Gly Val
    50                  55                  60

Gly Tyr Val Tyr Asp Asn Gly Ser Val Ser Val Tyr Glu Leu Ser Lys
65                  70                  75                  80

Ile Lys Pro Leu His Asn Phe Leu Thr Gln Leu Gln Pro Phe Leu Lys
                85                  90                  95

Leu Lys Gln Lys Gln Ala Asn Leu Val Leu Lys Ile Ile Glu Gln Leu
            100                 105                 110

Pro Ser Ala Lys Glu Ser Pro Asp Lys Phe Leu Glu Val Cys Thr Trp
        115                 120                 125

Val Asp Gln Ile Ala Ala Leu Asn Asp Ser Lys Thr Arg Lys Thr Thr
    130                 135                 140

Ser Glu Thr Val Arg Ala Val Leu Asp Ser Leu Pro Gly Ser Val Gly
145                 150                 155                 160

Gly Leu Ser Pro Ser Gln Ala Ser Ser Ala Ala Ser Ser Ala Ser Ser
                165                 170                 175

Ser Pro Gly Ser Gly Ile Ser Glu Ala Leu Arg Ala Gly Ala Gly Ser
            180                 185                 190

Gly Thr Gly Tyr Asn Lys Glu Phe Leu Leu Tyr Leu Ala Gly Phe Val
        195                 200                 205

Asp Gly Asp Gly Ser Ile Tyr Ala Ala Ile Arg Pro Lys Gln Thr Arg
    210                 215                 220

Lys Phe Lys His Glu Leu Gln Leu Thr Phe Asn Val Arg Gln Lys Thr
225                 230                 235                 240

Gln Arg Arg Trp Phe Leu Asp Lys Leu Val Asp Glu Ile Gly Val Gly
                245                 250                 255

Tyr Val Leu Asp Trp Gly Ser Val Ser Thr Tyr Ile Leu Ser Gln Ile
            260                 265                 270

Lys Pro Leu His Asn Phe Leu Thr Gln Leu Gln Pro Phe Leu Lys Leu
        275                 280                 285

Lys Gln Lys Gln Ala Asn Leu Val Leu Lys Ile Ile Glu Gln Leu Pro
    290                 295                 300

Ser Ala Lys Glu Ser Pro Asp Lys Phe Leu Glu Val Cys Thr Trp Val
305                 310                 315                 320

Asp Gln Ile Ala Ala Leu Asn Asp Ser Lys Thr Arg Lys Thr Thr Ser
                325                 330                 335

Glu Thr Val Arg Ala Val Leu Asp Ser Leu Ser Glu Lys Lys Lys Ser
            340                 345                 350

Ser Pro


<210> SEQ ID NO 40
<211> LENGTH: 147
<212> TYPE: PRT
<213> ORGANISM: Artificial Sequence
<220> FEATURE:
<223> OTHER INFORMATION: Synthetic Sequence
<220> FEATURE:
<221> NAME/KEY: HBV 1-2x.2-2
<222> LOCATION: (1)..(147)
<223> OTHER INFORMATION: HBV1-binding subunit

<400> SEQUENCE: 40

Lys Glu Phe Leu Leu Tyr Leu Ala Gly Phe Val Asp Gly Asp Gly Ser
1               5                   10                  15
```

-continued

```
Ile Phe Ala Cys Ile Arg Pro Val Gln Trp Ser Lys Phe Lys His Ser
            20                  25                  30

Leu Glu Leu Cys Phe Thr Val Thr Gln Lys Thr Gln Arg Arg Trp Phe
        35                  40                  45

Leu Asp Lys Leu Val Asp Glu Ile Gly Val Gly Tyr Val His Asp Tyr
    50                  55                  60

Gly Ser Val Ser Ala Tyr Arg Leu Ser Gln Ile Lys Pro Leu His Asn
65                  70                  75                  80

Phe Leu Thr Gln Leu Gln Pro Phe Leu Lys Leu Lys Gln Lys Gln Ala
                85                  90                  95

Asn Leu Val Leu Lys Ile Ile Glu Gln Leu Pro Ser Ala Lys Glu Ser
            100                 105                 110

Pro Asp Lys Phe Leu Glu Val Cys Thr Trp Val Asp Gln Ile Ala Ala
        115                 120                 125

Leu Asn Asp Ser Lys Thr Arg Lys Thr Thr Ser Glu Thr Val Arg Ala
    130                 135                 140

Val Leu Asp
145


<210> SEQ ID NO 41
<211> LENGTH: 147
<212> TYPE: PRT
<213> ORGANISM: Artificial Sequence
<220> FEATURE:
<223> OTHER INFORMATION: Synthetic Sequence
<220> FEATURE:
<221> NAME/KEY: HBV 1-2x.14-2
<222> LOCATION: (1)..(147)
<223> OTHER INFORMATION: HBV1-binding subunit

<400> SEQUENCE: 41

Lys Glu Phe Leu Leu Tyr Leu Ala Gly Phe Val Asp Gly Asp Gly Ser
1               5                   10                  15

Ile Tyr Ala Cys Ile Ala Pro Arg Gln Trp Ser Lys Phe Lys His Ser
            20                  25                  30

Leu Glu Leu Arg Phe Ala Val Phe Gln Lys Thr Gln Arg Arg Trp Phe
        35                  40                  45

Leu Asp Lys Leu Val Asp Glu Ile Gly Val Gly Tyr Val Ser Asp Tyr
    50                  55                  60

Gly Ser Val Ser Arg Tyr His Leu Ser Glu Ile Lys Pro Leu His Asn
65                  70                  75                  80

Phe Leu Thr Gln Leu Gln Pro Phe Leu Lys Leu Lys Gln Lys Gln Ala
                85                  90                  95

Asn Leu Val Leu Lys Ile Ile Glu Gln Leu Pro Ser Ala Lys Glu Ser
            100                 105                 110

Pro Asp Lys Phe Leu Glu Val Cys Thr Trp Val Asp Gln Ile Ala Ala
        115                 120                 125

Leu Asn Asp Ser Lys Thr Arg Lys Thr Thr Ser Glu Thr Val Arg Ala
    130                 135                 140

Val Leu Asp
145


<210> SEQ ID NO 42
<211> LENGTH: 147
<212> TYPE: PRT
<213> ORGANISM: Artificial Sequence
<220> FEATURE:
<223> OTHER INFORMATION: Synthetic Sequence
<220> FEATURE:
```

<221> NAME/KEY: HBV 1-2x.68-2
<222> LOCATION: (1)..(147)
<223> OTHER INFORMATION: HBV1-binding subunit

<400> SEQUENCE: 42

Lys Glu Phe Leu Leu Tyr Leu Ala Gly Phe Val Asp Gly Asp Gly Ser
1 5 10 15

Ile Tyr Ala Cys Ile Ala Pro Arg Gln Trp Ser Lys Phe Lys His Ser
20 25 30

Leu Glu Leu Arg Phe Ala Val Phe Gln Lys Thr Gln Arg Arg Trp Phe
35 40 45

Leu Asp Lys Leu Val Asp Glu Ile Gly Val Gly Tyr Val Ser Asp Tyr
50 55 60

Gly Ser Val Ser Arg Tyr His Leu Ser Glu Ile Lys Pro Leu His Asn
65 70 75 80

Phe Leu Thr Gln Leu Gln Pro Phe Leu Lys Leu Lys Gln Lys Gln Ala
85 90 95

Asn Leu Val Leu Lys Ile Ile Glu Gln Leu Pro Ser Ala Lys Glu Ser
100 105 110

Pro Asp Lys Phe Leu Glu Val Cys Thr Trp Val Asp Gln Ile Ala Ala
115 120 125

Leu Asn Asp Ser Lys Thr Arg Lys Thr Thr Ser Glu Thr Val Arg Ala
130 135 140

Val Leu Asp
145

<210> SEQ ID NO 43
<211> LENGTH: 147
<212> TYPE: PRT
<213> ORGANISM: Artificial Sequence
<220> FEATURE:
<223> OTHER INFORMATION: Synthetic Sequence
<220> FEATURE:
<221> NAME/KEY: HBV 1-2x.93-2
<222> LOCATION: (1)..(147)
<223> OTHER INFORMATION: HBV1-binding subunit

<400> SEQUENCE: 43

Lys Glu Phe Leu Leu Tyr Leu Ala Gly Phe Val Asp Gly Asp Gly Ser
1 5 10 15

Ile Phe Ala Cys Ile Arg Pro Val Gln Trp Ser Lys Phe Lys His Ser
20 25 30

Leu Glu Leu Cys Phe Thr Val Thr Gln Lys Thr Gln Arg Arg Trp Phe
35 40 45

Leu Asp Lys Leu Val Asp Glu Ile Gly Val Gly Tyr Val His Asp Tyr
50 55 60

Gly Ser Val Ser Ala Tyr Arg Leu Ser Gln Ile Lys Pro Leu His Asn
65 70 75 80

Phe Leu Thr Gln Leu Gln Pro Phe Leu Lys Leu Lys Gln Lys Gln Ala
85 90 95

Asn Leu Val Leu Lys Ile Ile Glu Gln Leu Pro Ser Ala Lys Glu Ser
100 105 110

Pro Asp Lys Phe Leu Glu Val Cys Thr Trp Val Asp Gln Ile Ala Ala
115 120 125

Leu Asn Asp Ser Lys Thr Arg Lys Thr Thr Ser Glu Thr Val Arg Ala
130 135 140

Val Leu Asp
145

<210> SEQ ID NO 44
<211> LENGTH: 147
<212> TYPE: PRT
<213> ORGANISM: Artificial Sequence
<220> FEATURE:
<223> OTHER INFORMATION: Synthetic Sequence
<220> FEATURE:
<221> NAME/KEY: HBV 1-2x.2-3
<222> LOCATION: (1)..(147)
<223> OTHER INFORMATION: HBV2-binding subunit

<400> SEQUENCE: 44

```
Lys Glu Phe Leu Leu Tyr Leu Ala Gly Phe Val Asp Gly Asp Gly Ser
1               5                   10                  15

Ile Tyr Ala Ser Ile Arg Pro Ser Gln Asp Gln Lys Phe Lys His Arg
            20                  25                  30

Leu Ile Leu Val Phe Ala Val Ser Gln Lys Thr Gln Arg Arg Trp Phe
        35                  40                  45

Leu Asp Lys Leu Val Asp Glu Ile Gly Val Gly Tyr Val Arg Asp Thr
    50                  55                  60

Gly Ser Val Ser Glu Tyr Arg Leu Ser Glu Ile Lys Pro Leu His Asn
65                  70                  75                  80

Phe Leu Thr Gln Leu Gln Pro Phe Leu Lys Leu Lys Gln Lys Gln Ala
                85                  90                  95

Asn Leu Val Leu Lys Ile Ile Glu Gln Leu Pro Ser Ala Lys Glu Ser
            100                 105                 110

Pro Asp Lys Phe Leu Glu Val Cys Thr Trp Val Asp Gln Ile Ala Ala
        115                 120                 125

Leu Asn Asp Ser Lys Thr Arg Lys Thr Thr Ser Glu Thr Val Arg Ala
    130                 135                 140

Val Leu Asp
145
```

<210> SEQ ID NO 45
<211> LENGTH: 147
<212> TYPE: PRT
<213> ORGANISM: Artificial Sequence
<220> FEATURE:
<223> OTHER INFORMATION: Synthetic Sequence
<220> FEATURE:
<221> NAME/KEY: HBV 1-2x.14-3
<222> LOCATION: (1)..(147)
<223> OTHER INFORMATION: HBV2-binding subunit

<400> SEQUENCE: 45

```
Lys Glu Phe Leu Leu Tyr Leu Ala Gly Phe Val Asp Gly Asp Gly Ser
1               5                   10                  15

Ile Tyr Ala Cys Ile Arg Pro Ala Gln Asp Ser Lys Phe Lys His Arg
            20                  25                  30

Leu Ile Leu Ala Leu Glu Val Gly Gln Lys Thr Arg Arg Arg Trp Phe
        35                  40                  45

Leu Asp Lys Leu Val Asp Glu Ile Gly Val Gly Tyr Val Val Asp Asn
    50                  55                  60

Gly Ser Val Ser Arg Tyr Ile Leu Ser Gln Ile Lys Pro Leu His Asn
65                  70                  75                  80

Phe Leu Thr Gln Leu Gln Pro Phe Leu Lys Leu Lys Gln Lys Gln Ala
                85                  90                  95

Asn Leu Val Leu Lys Ile Ile Glu Gln Leu Pro Ser Ala Lys Glu Ser
            100                 105                 110
```

Pro Asp Lys Phe Leu Glu Val Cys Thr Trp Val Asp Gln Ile Ala Ala
115 120 125

Leu Asn Asp Ser Lys Thr Arg Lys Thr Thr Ser Glu Thr Val Arg Ala
130 135 140

Val Leu Asp
145

<210> SEQ ID NO 46
<211> LENGTH: 147
<212> TYPE: PRT
<213> ORGANISM: Artificial Sequence
<220> FEATURE:
<223> OTHER INFORMATION: Synthetic Sequence
<220> FEATURE:
<221> NAME/KEY: HBV 1-2x.68-3
<222> LOCATION: (1)..(147)
<223> OTHER INFORMATION: HBV2-binding subunit

<400> SEQUENCE: 46

Lys Glu Phe Leu Leu Tyr Leu Ala Gly Phe Val Asp Gly Asp Gly Ser
1 5 10 15

Ile Tyr Ala Cys Ile Arg Pro Asp Gln Ser Ser Lys Phe Lys His Arg
20 25 30

Leu Val Leu Gly Phe Glu Val Gly Gln Lys Thr Arg Arg Arg Trp Phe
35 40 45

Leu Asp Lys Leu Val Asp Glu Ile Gly Val Gly Tyr Val Val Asp Asn
50 55 60

Gly Ser Val Ser Arg Tyr Ile Leu Ser Glu Ile Lys Pro Leu His Asn
65 70 75 80

Phe Leu Thr Gln Leu Gln Pro Phe Leu Lys Leu Lys Gln Lys Gln Ala
85 90 95

Asn Leu Val Leu Lys Ile Ile Glu Gln Leu Pro Ser Ala Lys Glu Ser
100 105 110

Pro Asp Lys Phe Leu Glu Val Cys Thr Trp Val Asp Gln Ile Ala Ala
115 120 125

Leu Asn Asp Ser Lys Thr Arg Lys Thr Thr Ser Glu Thr Val Arg Ala
130 135 140

Val Leu Asp
145

<210> SEQ ID NO 47
<211> LENGTH: 147
<212> TYPE: PRT
<213> ORGANISM: Artificial Sequence
<220> FEATURE:
<223> OTHER INFORMATION: Synthetic Sequence
<220> FEATURE:
<221> NAME/KEY: HBV 1-2x.93-3
<222> LOCATION: (1)..(147)
<223> OTHER INFORMATION: HBV2-binding subunit

<400> SEQUENCE: 47

Lys Glu Phe Leu Leu Tyr Leu Ala Gly Phe Val Asp Gly Asp Gly Ser
1 5 10 15

Ile Tyr Ala Thr Ile Arg Pro Asp Gln Thr Tyr Lys Phe Lys His Arg
20 25 30

Leu Ile Leu Gln Phe Ala Val Ser Gln Lys Thr Gln Arg Arg Trp Phe
35 40 45

Leu Asp Lys Leu Val Asp Glu Ile Gly Val Gly Tyr Val Arg Asp Thr
50 55 60

```
Gly Ser Val Ser Glu Tyr Arg Leu Ser Gln Ile Lys Pro Leu His Asn
65                  70                  75                  80

Phe Leu Thr Gln Leu Gln Pro Phe Leu Lys Leu Lys Gln Lys Gln Ala
                85                  90                  95

Asn Leu Val Leu Lys Ile Ile Glu Gln Leu Pro Ser Ala Lys Glu Ser
            100                 105                 110

Pro Asp Lys Phe Leu Glu Val Cys Thr Trp Val Asp Gln Ile Ala Ala
        115                 120                 125

Leu Asn Asp Ser Lys Thr Arg Lys Thr Thr Ser Glu Thr Val Arg Ala
    130                 135                 140

Val Leu Asp
145


<210> SEQ ID NO 48
<211> LENGTH: 147
<212> TYPE: PRT
<213> ORGANISM: Artificial Sequence
<220> FEATURE:
<223> OTHER INFORMATION: Synthetic Sequence
<220> FEATURE:
<221> NAME/KEY: HBV 5-6x.33-2
<222> LOCATION: (1)..(147)
<223> OTHER INFORMATION: HBV5-binding subunit

<400> SEQUENCE: 48

Lys Glu Phe Leu Leu Tyr Leu Ala Gly Phe Val Asp Gly Asp Gly Ser
1               5                   10                  15

Ile Trp Ala Thr Ile Glu Pro Leu Gln Lys Arg Lys Phe Lys His Ala
            20                  25                  30

Leu His Leu Met Phe Thr Val Ser Gln Lys Thr Gln Arg Arg Trp Phe
        35                  40                  45

Leu Asp Lys Leu Val Asp Glu Ile Gly Val Gly Tyr Val Ile Asp Gln
    50                  55                  60

Gly Ser Val Ser Glu Tyr Arg Leu Ser Gln Ile Lys Pro Leu His Asn
65                  70                  75                  80

Phe Leu Thr Gln Leu Gln Pro Phe Leu Lys Leu Lys Gln Lys Gln Ala
                85                  90                  95

Asn Leu Val Leu Lys Ile Ile Glu Gln Leu Pro Ser Ala Lys Glu Ser
            100                 105                 110

Pro Asp Lys Phe Leu Glu Val Cys Thr Trp Val Asp Gln Ile Ala Ala
        115                 120                 125

Leu Asn Asp Ser Lys Thr Arg Lys Thr Thr Ser Glu Thr Val Arg Ala
    130                 135                 140

Val Leu Asp
145


<210> SEQ ID NO 49
<211> LENGTH: 147
<212> TYPE: PRT
<213> ORGANISM: Artificial Sequence
<220> FEATURE:
<223> OTHER INFORMATION: Synthetic Sequence
<220> FEATURE:
<221> NAME/KEY: HBV 5-6x.84-2
<222> LOCATION: (1)..(147)
<223> OTHER INFORMATION: HBV5-binding subunit

<400> SEQUENCE: 49

Lys Glu Phe Leu Leu Tyr Leu Ala Gly Phe Val Asp Gly Asp Gly Ser
1               5                   10                  15
```

```
Ile Asn Ala Ser Ile Glu Pro Val Gln Lys Pro Lys Phe Lys His Thr
            20                  25                  30

Leu His Leu Arg Phe Glu Val Ser Gln Lys Thr Gln Arg Arg Trp Phe
        35                  40                  45

Leu Asp Lys Leu Val Asp Glu Ile Gly Val Gly Tyr Val Tyr Asp Gln
    50                  55                  60

Gly Ser Val Ser Ser Tyr Arg Leu Ser Glu Ile Lys Pro Leu His Asn
65                  70                  75                  80

Phe Leu Thr Gln Leu Gln Pro Phe Leu Lys Leu Lys Gln Lys Gln Ala
                85                  90                  95

Asn Leu Val Leu Lys Ile Ile Glu Gln Leu Pro Ser Ala Lys Glu Ser
            100                 105                 110

Pro Asp Lys Phe Leu Glu Val Cys Thr Trp Val Asp Gln Ile Ala Ala
        115                 120                 125

Leu Asn Asp Ser Lys Thr Arg Lys Thr Thr Ser Glu Thr Val Arg Ala
    130                 135                 140

Val Leu Asp
145


<210> SEQ ID NO 50
<211> LENGTH: 147
<212> TYPE: PRT
<213> ORGANISM: Artificial Sequence
<220> FEATURE:
<223> OTHER INFORMATION: Synthetic Sequence
<220> FEATURE:
<221> NAME/KEY: HBV 5-6x.90-2
<222> LOCATION: (1)..(147)
<223> OTHER INFORMATION: HBV5-binding subunit

<400> SEQUENCE: 50

Lys Glu Phe Leu Leu Tyr Leu Ala Gly Phe Val Asp Gly Asp Gly Ser
1               5                   10                  15

Ile Val Ala Gln Ile His Pro Ala Gln Lys Asn Lys Phe Lys His Gly
            20                  25                  30

Leu Arg Leu Gln Phe Tyr Val Tyr Gln Lys Thr Gln Arg Arg Trp Phe
        35                  40                  45

Leu Asp Lys Leu Val Asp Glu Ile Gly Val Gly Tyr Val Tyr Asp Gln
    50                  55                  60

Gly Ser Val Ser Cys Tyr Arg Leu Ser Gln Ile Lys Pro Leu His Asn
65                  70                  75                  80

Phe Leu Thr Gln Leu Gln Pro Phe Leu Lys Leu Lys Gln Lys Gln Ala
                85                  90                  95

Asn Leu Val Leu Lys Ile Ile Glu Gln Leu Pro Ser Ala Lys Glu Ser
            100                 105                 110

Pro Asp Lys Phe Leu Glu Val Cys Thr Trp Val Asp Gln Ile Ala Ala
        115                 120                 125

Leu Asn Asp Ser Lys Thr Arg Lys Thr Thr Ser Glu Thr Val Arg Ala
    130                 135                 140

Val Leu Asp
145


<210> SEQ ID NO 51
<211> LENGTH: 147
<212> TYPE: PRT
<213> ORGANISM: Artificial Sequence
<220> FEATURE:
<223> OTHER INFORMATION: Synthetic Sequence
```

<220> FEATURE:
<221> NAME/KEY: HBV 5-6x.4-2
<222> LOCATION: (1)..(147)
<223> OTHER INFORMATION: HBV5-binding subunit

<400> SEQUENCE: 51

```
Lys Glu Phe Leu Leu Tyr Leu Ala Gly Phe Val Asp Gly Asp Gly Ser
1               5                   10                  15

Ile Tyr Ala Thr Ile Gln Pro Val Gln Thr Arg Lys Phe Lys His Ile
            20                  25                  30

Leu Arg Leu Trp Phe Thr Val His Gln Lys Thr Gln Arg Arg Trp Phe
        35                  40                  45

Leu Asp Lys Leu Val Asp Glu Ile Gly Val Gly Tyr Val Val Asp Ala
    50                  55                  60

Gly Ser Val Ser Glu Tyr Arg Leu Ser Glu Ile Lys Pro Leu His Asn
65                  70                  75                  80

Phe Leu Thr Gln Leu Gln Pro Phe Leu Lys Leu Lys Gln Lys Gln Ala
                85                  90                  95

Asn Leu Val Leu Lys Ile Ile Glu Gln Leu Pro Ser Ala Lys Glu Ser
            100                 105                 110

Pro Asp Lys Phe Leu Glu Val Cys Thr Trp Val Asp Gln Ile Ala Ala
        115                 120                 125

Leu Asn Asp Ser Lys Thr Arg Lys Thr Thr Ser Glu Thr Val Arg Ala
    130                 135                 140

Val Leu Asp
145
```

<210> SEQ ID NO 52
<211> LENGTH: 147
<212> TYPE: PRT
<213> ORGANISM: Artificial Sequence
<220> FEATURE:
<223> OTHER INFORMATION: Synthetic Sequence
<220> FEATURE:
<221> NAME/KEY: HBV 5-6x.5-2
<222> LOCATION: (1)..(147)
<223> OTHER INFORMATION: HBV5-binding subunit

<400> SEQUENCE: 52

```
Lys Glu Phe Leu Leu Tyr Leu Ala Gly Phe Val Asp Gly Asp Gly Ser
1               5                   10                  15

Ile Tyr Ala Thr Ile His Pro Thr Gln Lys Ala Lys Phe Lys His Val
            20                  25                  30

Leu Ala Leu Arg Phe Ser Val Cys Gln Lys Thr Gln Arg Arg Trp Phe
        35                  40                  45

Leu Asp Lys Leu Val Asp Glu Ile Gly Val Gly Tyr Val Tyr Asp Leu
    50                  55                  60

Gly Ser Val Ser Glu Tyr Arg Leu Ser Gln Ile Lys Pro Leu His Asn
65                  70                  75                  80

Phe Leu Thr Gln Leu Gln Pro Phe Leu Lys Leu Lys Gln Lys Gln Ala
                85                  90                  95

Asn Leu Val Leu Lys Ile Ile Glu Gln Leu Pro Ser Ala Lys Glu Ser
            100                 105                 110

Pro Asp Lys Phe Leu Glu Val Cys Thr Trp Val Asp Gln Ile Ala Ala
        115                 120                 125

Leu Asn Asp Ser Lys Thr Arg Lys Thr Thr Ser Glu Thr Val Arg Ala
    130                 135                 140

Val Leu Asp
```

145

<210> SEQ ID NO 53
<211> LENGTH: 147
<212> TYPE: PRT
<213> ORGANISM: Artificial Sequence
<220> FEATURE:
<223> OTHER INFORMATION: Synthetic Sequence
<220> FEATURE:
<221> NAME/KEY: HBV 5-6x.68-2
<222> LOCATION: (1)..(147)
<223> OTHER INFORMATION: HBV5-binding subunit

<400> SEQUENCE: 53

```
Lys Glu Phe Leu Leu Tyr Leu Ala Gly Phe Val Asp Gly Asp Gly Ser
1               5                   10                  15

Ile Tyr Ala Gln Ile Met Pro Arg Gln Arg Ala Lys Phe Lys His Val
            20                  25                  30

Leu Lys Leu Asn Phe Ala Val Cys Gln Lys Thr Gln Arg Arg Trp Phe
        35                  40                  45

Leu Asp Lys Leu Val Asp Glu Ile Gly Val Gly Tyr Val Thr Asp Gln
    50                  55                  60

Gly Ser Val Ser Glu Tyr Arg Leu Ser Glu Ile Lys Pro Leu His Asn
65                  70                  75                  80

Phe Leu Thr Gln Leu Gln Pro Phe Leu Lys Leu Lys Gln Lys Gln Ala
                85                  90                  95

Asn Leu Val Leu Lys Ile Ile Glu Gln Leu Pro Ser Ala Lys Glu Ser
            100                 105                 110

Pro Asp Lys Phe Leu Glu Val Cys Thr Trp Val Asp Gln Ile Ala Ala
        115                 120                 125

Leu Asn Asp Ser Lys Thr Arg Lys Thr Thr Ser Glu Thr Val Arg Ala
    130                 135                 140

Val Leu Asp
145
```

<210> SEQ ID NO 54
<211> LENGTH: 147
<212> TYPE: PRT
<213> ORGANISM: Artificial Sequence
<220> FEATURE:
<223> OTHER INFORMATION: Synthetic Sequence
<220> FEATURE:
<221> NAME/KEY: HBV 5-6x.79-2
<222> LOCATION: (1)..(147)
<223> OTHER INFORMATION: HBV5-binding subunit

<400> SEQUENCE: 54

```
Lys Glu Phe Leu Leu Tyr Leu Ala Gly Phe Val Asp Gly Asp Gly Ser
1               5                   10                  15

Ile Tyr Ala Thr Ile Glu Pro Val Gln Lys Asn Lys Phe Lys His Gln
            20                  25                  30

Leu Arg Leu Cys Phe Ala Val Cys Gln Lys Thr Gln Arg Arg Trp Phe
        35                  40                  45

Leu Asp Lys Leu Val Asp Glu Ile Gly Val Gly Tyr Val Cys Asp Thr
    50                  55                  60

Gly Ser Val Ser Glu Tyr Arg Leu Ser Gln Ile Lys Pro Leu His Asn
65                  70                  75                  80

Phe Leu Thr Gln Leu Gln Pro Phe Leu Lys Leu Lys Gln Lys Gln Ala
                85                  90                  95

Asn Leu Val Leu Lys Ile Ile Glu Gln Leu Pro Ser Ala Lys Glu Ser
```

```
            100                 105                 110

Pro Asp Lys Phe Leu Glu Val Cys Thr Trp Val Asp Gln Ile Ala Ala
        115                 120                 125

Leu Asn Asp Ser Lys Thr Arg Lys Thr Thr Ser Glu Thr Val Arg Ala
    130                 135                 140

Val Leu Asp
145


<210> SEQ ID NO 55
<211> LENGTH: 147
<212> TYPE: PRT
<213> ORGANISM: Artificial Sequence
<220> FEATURE:
<223> OTHER INFORMATION: Synthetic Sequence
<220> FEATURE:
<221> NAME/KEY: HBV 5-6x.33-3
<222> LOCATION: (1)..(147)
<223> OTHER INFORMATION: HBV6-binding subunit

<400> SEQUENCE: 55

Lys Glu Phe Leu Leu Tyr Leu Ala Gly Phe Val Asp Gly Asp Gly Ser
1               5                   10                  15

Ile Tyr Ala Arg Ile Arg Pro Ser Gln Ser Ser Lys Phe Lys His Lys
            20                  25                  30

Leu Thr Leu Val Phe Ala Val Ala Gln Lys Thr Gln Arg Arg Trp Phe
        35                  40                  45

Leu Asp Lys Leu Val Asp Glu Ile Gly Val Gly Tyr Val His Asp Glu
    50                  55                  60

Gly Ser Val Ser Gln Tyr Arg Leu Ser Gln Ile Lys Pro Leu His Asn
65                  70                  75                  80

Phe Leu Thr Gln Leu Gln Pro Phe Leu Lys Leu Lys Gln Lys Gln Ala
                85                  90                  95

Asn Leu Val Leu Lys Ile Ile Glu Gln Leu Pro Ser Ala Lys Glu Ser
            100                 105                 110

Pro Asp Lys Phe Leu Glu Val Cys Thr Trp Val Asp Gln Ile Ala Ala
        115                 120                 125

Leu Asn Asp Ser Lys Thr Arg Lys Thr Thr Ser Glu Thr Val Arg Ala
    130                 135                 140

Val Leu Asp
145


<210> SEQ ID NO 56
<211> LENGTH: 147
<212> TYPE: PRT
<213> ORGANISM: Artificial Sequence
<220> FEATURE:
<223> OTHER INFORMATION: Synthetic Sequence
<220> FEATURE:
<221> NAME/KEY: HBV 5-6x.84-3
<222> LOCATION: (1)..(147)
<223> OTHER INFORMATION: HBV6-binding subunit

<400> SEQUENCE: 56

Lys Glu Phe Leu Leu Tyr Leu Ala Gly Phe Val Asp Gly Asp Gly Ser
1               5                   10                  15

Ile Phe Ala Arg Ile Arg Pro Gly Gln Asp Tyr Lys Phe Lys His Asn
            20                  25                  30

Leu Val Leu Thr Phe Arg Val Ala Gln Lys Thr Gln Arg Arg Trp Phe
        35                  40                  45

Leu Asp Lys Leu Val Asp Glu Ile Gly Val Gly Tyr Val Leu Asp Glu
```

```
    50                  55                  60

Gly Ser Val Ser Gln Tyr Tyr Leu Ser Glu Ile Lys Pro Leu His Asn
65                  70                  75                  80

Phe Leu Thr Gln Leu Gln Pro Phe Leu Lys Leu Lys Gln Lys Gln Ala
                85                  90                  95

Asn Leu Val Leu Lys Ile Ile Glu Gln Leu Pro Ser Ala Lys Glu Ser
            100                 105                 110

Pro Asp Lys Phe Leu Glu Val Cys Thr Trp Val Asp Gln Ile Ala Ala
        115                 120                 125

Leu Asn Asp Ser Lys Thr Arg Lys Thr Thr Ser Glu Thr Val Arg Ala
    130                 135                 140

Val Leu Asp
145


<210> SEQ ID NO 57
<211> LENGTH: 147
<212> TYPE: PRT
<213> ORGANISM: Artificial Sequence
<220> FEATURE:
<223> OTHER INFORMATION: Synthetic Sequence
<220> FEATURE:
<221> NAME/KEY: HBV 5-6x.90-3
<222> LOCATION: (1)..(147)
<223> OTHER INFORMATION: HBV6-binding subunit

<400> SEQUENCE: 57

Lys Glu Phe Leu Leu Tyr Leu Ala Gly Phe Val Asp Gly Asp Gly Ser
1               5                   10                  15

Ile Tyr Ala Arg Ile Arg Pro Arg Gln Asn Phe Lys Phe Lys His Ala
            20                  25                  30

Leu Val Leu Gln Phe Arg Val Ser Gln Lys Thr Gln Arg Arg Trp Phe
        35                  40                  45

Leu Asp Lys Leu Val Asp Glu Ile Gly Val Gly Tyr Val Leu Asp Glu
    50                  55                  60

Gly Ser Val Ser Gln Tyr Tyr Leu Ser Gln Ile Lys Pro Leu His Asn
65                  70                  75                  80

Phe Leu Thr Gln Leu Gln Pro Phe Leu Lys Leu Lys Gln Lys Gln Ala
                85                  90                  95

Asn Leu Val Leu Lys Ile Ile Glu Gln Leu Pro Ser Ala Lys Glu Ser
            100                 105                 110

Pro Asp Lys Phe Leu Glu Val Cys Thr Trp Val Asp Gln Ile Ala Ala
        115                 120                 125

Leu Asn Asp Ser Lys Thr Arg Lys Thr Thr Ser Glu Thr Val Arg Ala
    130                 135                 140

Val Leu Asp
145


<210> SEQ ID NO 58
<211> LENGTH: 147
<212> TYPE: PRT
<213> ORGANISM: Artificial Sequence
<220> FEATURE:
<223> OTHER INFORMATION: Synthetic Sequence
<220> FEATURE:
<221> NAME/KEY: HBV 5-6x.4-3
<222> LOCATION: (1)..(147)
<223> OTHER INFORMATION: HBV6-binding subunit

<400> SEQUENCE: 58

Lys Glu Phe Leu Leu Tyr Leu Ala Gly Phe Val Asp Gly Asp Gly Ser
```

```
1               5                   10                  15

Ile Tyr Ala Arg Ile Arg Pro Thr Gln Gly Ser Lys Phe Lys His Lys
            20                  25                  30

Leu Thr Leu Cys Phe Arg Val Ala Gln Lys Thr Gln Arg Arg Trp Phe
        35                  40                  45

Leu Asp Lys Leu Val Asp Glu Ile Gly Val Gly Tyr Val Leu Asp Glu
    50                  55                  60

Gly Ser Val Ser Gln Tyr Tyr Leu Ser Gln Ile Lys Pro Leu His Asn
65                  70                  75                  80

Phe Leu Thr Gln Leu Gln Pro Phe Leu Lys Leu Lys Gln Lys Gln Ala
                85                  90                  95

Asn Leu Val Leu Lys Ile Ile Glu Gln Leu Pro Ser Ala Lys Glu Ser
            100                 105                 110

Pro Asp Lys Phe Leu Glu Val Cys Thr Trp Val Asp Gln Ile Ala Ala
        115                 120                 125

Leu Asn Asp Ser Lys Thr Arg Lys Thr Thr Ser Glu Thr Val Arg Ala
    130                 135                 140

Val Leu Asp
145
```

<210> SEQ ID NO 59
<211> LENGTH: 147
<212> TYPE: PRT
<213> ORGANISM: Artificial Sequence
<220> FEATURE:
<223> OTHER INFORMATION: Synthetic Sequence
<220> FEATURE:
<221> NAME/KEY: HBV 5-6x.5-3
<222> LOCATION: (1)..(147)
<223> OTHER INFORMATION: HBV6-binding subunit

<400> SEQUENCE: 59

```
Lys Glu Phe Leu Leu Tyr Leu Ala Gly Phe Val Asp Gly Asp Gly Ser
1               5                   10                  15

Ile Tyr Ala Arg Ile Arg Pro Leu Gln His Gly Lys Phe Lys His Lys
            20                  25                  30

Leu His Leu Ala Phe Arg Val Ala Gln Lys Thr Gln Arg Arg Trp Phe
        35                  40                  45

Leu Asp Lys Leu Val Asp Glu Ile Gly Val Gly Tyr Val Phe Asp Asp
    50                  55                  60

Gly Ser Val Ser Gln Tyr Thr Leu Ser Gln Ile Lys Pro Leu His Asn
65                  70                  75                  80

Phe Leu Thr Gln Leu Gln Pro Phe Leu Lys Leu Lys Gln Lys Gln Ala
                85                  90                  95

Asn Leu Val Leu Lys Ile Ile Glu Gln Leu Pro Ser Ala Lys Glu Ser
            100                 105                 110

Pro Asp Lys Phe Leu Glu Val Cys Thr Trp Val Asp Gln Ile Ala Ala
        115                 120                 125

Leu Asn Asp Ser Lys Thr Arg Lys Thr Thr Ser Glu Thr Val Arg Ala
    130                 135                 140

Val Leu Asp
145
```

<210> SEQ ID NO 60
<211> LENGTH: 147
<212> TYPE: PRT
<213> ORGANISM: Artificial Sequence
<220> FEATURE:

<223> OTHER INFORMATION: Synthetic Sequence
<220> FEATURE:
<221> NAME/KEY: HBV 5-6x.68-3
<222> LOCATION: (1)..(147)
<223> OTHER INFORMATION: HBV6-binding subunit

<400> SEQUENCE: 60

```
Lys Glu Phe Leu Leu Tyr Leu Ala Gly Phe Val Asp Gly Asp Gly Ser
1               5                   10                  15

Ile Tyr Ala Arg Ile Arg Pro Arg Gln Ser Ser Lys Phe Lys His Arg
            20                  25                  30

Leu Leu Leu Phe Phe Arg Val Ser Gln Lys Thr Gln Arg Arg Trp Phe
        35                  40                  45

Leu Asp Lys Leu Val Asp Glu Ile Gly Val Gly Tyr Val Leu Asp Glu
    50                  55                  60

Gly Ser Val Ser Gln Tyr Tyr Leu Ser Glu Ile Lys Pro Leu His Asn
65                  70                  75                  80

Phe Leu Thr Gln Leu Gln Pro Phe Leu Lys Leu Lys Gln Lys Gln Ala
                85                  90                  95

Asn Leu Val Leu Lys Ile Ile Glu Gln Leu Pro Ser Ala Lys Glu Ser
            100                 105                 110

Pro Asp Lys Phe Leu Glu Val Cys Thr Trp Val Asp Gln Ile Ala Ala
        115                 120                 125

Leu Asn Asp Ser Lys Thr Arg Lys Thr Thr Ser Glu Thr Val Arg Ala
    130                 135                 140

Val Leu Asp
145
```

<210> SEQ ID NO 61
<211> LENGTH: 147
<212> TYPE: PRT
<213> ORGANISM: Artificial Sequence
<220> FEATURE:
<223> OTHER INFORMATION: Synthetic Sequence
<220> FEATURE:
<221> NAME/KEY: HBV 5-6x.79-3
<222> LOCATION: (1)..(147)
<223> OTHER INFORMATION: HBV6-binding subunit

<400> SEQUENCE: 61

```
Lys Glu Phe Leu Leu Tyr Leu Ala Gly Phe Val Asp Gly Asp Gly Ser
1               5                   10                  15

Ile Tyr Ala Arg Ile Arg Pro Cys Gln Gly Cys Lys Phe Lys His Ala
            20                  25                  30

Leu Lys Leu Thr Phe Arg Val Ala Gln Lys Thr Gln Arg Arg Trp Phe
        35                  40                  45

Leu Asp Lys Leu Val Asp Glu Ile Gly Val Gly Tyr Val Cys Asp Glu
    50                  55                  60

Gly Ser Val Ser Gln Tyr Tyr Leu Ser Gln Ile Lys Pro Leu His Asn
65                  70                  75                  80

Phe Leu Thr Gln Leu Gln Pro Phe Leu Lys Leu Lys Gln Lys Gln Ala
                85                  90                  95

Asn Leu Val Leu Lys Ile Ile Glu Gln Leu Pro Ser Ala Lys Glu Ser
            100                 105                 110

Pro Asp Lys Phe Leu Glu Val Cys Thr Trp Val Asp Gln Ile Ala Ala
        115                 120                 125

Leu Asn Asp Ser Lys Thr Arg Lys Thr Thr Ser Glu Thr Val Arg Ala
    130                 135                 140
```

Val Leu Asp
145

<210> SEQ ID NO 62
<211> LENGTH: 147
<212> TYPE: PRT
<213> ORGANISM: Artificial Sequence
<220> FEATURE:
<223> OTHER INFORMATION: Synthetic Sequence
<220> FEATURE:
<221> NAME/KEY: HBV 7-8x.2-2
<222> LOCATION: (1)..(147)
<223> OTHER INFORMATION: HBV7-binding subunit

<400> SEQUENCE: 62

Lys Glu Phe Leu Leu Tyr Leu Ala Gly Phe Val Asp Gly Asp Gly Ser
1 5 10 15

Ile Tyr Ala Arg Ile Val Pro Cys Gln Arg Ser Lys Phe Lys His Ala
20 25 30

Leu Arg Leu Glu Phe Thr Val Arg Gln Lys Thr Arg Arg Arg Trp Ile
35 40 45

Leu Asp Lys Leu Val Asp Glu Ile Gly Val Gly Tyr Val Tyr Asp Ser
50 55 60

Gly Ser Val Ser Arg Tyr Tyr Leu Ser Gln Ile Lys Pro Leu His Asn
65 70 75 80

Phe Leu Thr Gln Leu Gln Pro Phe Leu Lys Leu Lys Gln Lys Gln Ala
85 90 95

Asn Leu Val Leu Lys Ile Ile Glu Gln Leu Pro Ser Ala Lys Glu Ser
100 105 110

Pro Asp Lys Phe Leu Glu Val Cys Thr Trp Val Asp Gln Ile Ala Ala
115 120 125

Leu Asn Asp Ser Lys Thr Arg Lys Thr Thr Ser Glu Thr Val Arg Ala
130 135 140

Val Leu Asp
145

<210> SEQ ID NO 63
<211> LENGTH: 147
<212> TYPE: PRT
<213> ORGANISM: Artificial Sequence
<220> FEATURE:
<223> OTHER INFORMATION: Synthetic Sequence
<220> FEATURE:
<221> NAME/KEY: HBV 7-8x.9-2
<222> LOCATION: (1)..(147)
<223> OTHER INFORMATION: HBV7-binding subunit

<400> SEQUENCE: 63

Lys Glu Phe Leu Leu Tyr Leu Ala Gly Phe Val Asp Gly Asp Gly Ser
1 5 10 15

Ile Tyr Ala Arg Ile Val Pro Cys Gln Arg Ser Lys Phe Lys His Ala
20 25 30

Leu Arg Leu Glu Phe Thr Val Arg Gln Lys Thr Arg Arg Arg Trp Ile
35 40 45

Leu Asp Lys Leu Val Asp Glu Ile Gly Val Gly Tyr Val Phe Asp Asp
50 55 60

Gly Ser Val Ser Arg Tyr Tyr Leu Ser Gln Ile Lys Pro Leu His Asn
65 70 75 80

Phe Leu Thr Gln Leu Gln Pro Phe Leu Lys Leu Lys Gln Lys Gln Ala
85 90 95

```
Asn Leu Val Leu Lys Ile Ile Glu Gln Leu Pro Ser Ala Lys Glu Ser
            100                 105                 110

Pro Asp Lys Phe Leu Glu Val Cys Thr Trp Val Asp Gln Ile Ala Ala
        115                 120                 125

Leu Asn Asp Ser Lys Thr Arg Lys Thr Thr Ser Glu Thr Val Arg Ala
    130                 135                 140

Val Leu Asp
145


<210> SEQ ID NO 64
<211> LENGTH: 147
<212> TYPE: PRT
<213> ORGANISM: Artificial Sequence
<220> FEATURE:
<223> OTHER INFORMATION: Synthetic Sequence
<220> FEATURE:
<221> NAME/KEY: HBV 7-8x.17-2
<222> LOCATION: (1)..(147)

<400> SEQUENCE: 64

Lys Glu Phe Leu Leu Tyr Leu Ala Gly Phe Val Asp Gly Asp Gly Ser
1               5                   10                  15

Ile Tyr Ala Arg Ile Val Pro Cys Gln Arg Ser Lys Phe Lys His Ala
            20                  25                  30

Leu Arg Leu Glu Phe Thr Val Arg Gln Lys Thr Arg Arg Arg Trp Ile
        35                  40                  45

Leu Asp Lys Leu Val Asp Glu Ile Gly Val Gly Tyr Val Phe Asp Asp
    50                  55                  60

Gly Ser Val Ser Arg Tyr Tyr Leu Ser Gln Ile Lys Pro Leu His Asn
65                  70                  75                  80

Phe Leu Thr Gln Leu Gln Pro Phe Leu Lys Leu Lys Gln Lys Gln Ala
                85                  90                  95

Asn Leu Val Leu Lys Ile Ile Glu Gln Leu Pro Ser Ala Lys Glu Ser
            100                 105                 110

Pro Asp Lys Phe Leu Glu Val Cys Thr Trp Val Asp Gln Ile Ala Ala
        115                 120                 125

Leu Asn Asp Ser Lys Thr Arg Lys Thr Thr Ser Glu Thr Val Arg Ala
    130                 135                 140

Val Leu Asp
145


<210> SEQ ID NO 65
<211> LENGTH: 147
<212> TYPE: PRT
<213> ORGANISM: Artificial Sequence
<220> FEATURE:
<223> OTHER INFORMATION: Synthetic Sequence
<220> FEATURE:
<221> NAME/KEY: HBV 7-8x.44-2
<222> LOCATION: (1)..(147)
<223> OTHER INFORMATION: HBV7-binding subunit

<400> SEQUENCE: 65

Lys Glu Phe Leu Leu Tyr Leu Ala Gly Phe Val Asp Gly Asp Gly Ser
1               5                   10                  15

Ile Tyr Ala Arg Ile Val Pro Cys Gln Arg Ser Lys Phe Lys His Ala
            20                  25                  30

Leu Arg Leu Glu Phe Ala Val Arg Gln Lys Thr Gln Arg Arg Trp Ile
        35                  40                  45

Leu Asp Lys Leu Val Asp Glu Ile Gly Val Gly Tyr Val Phe Asp Asp
```

```
    50                  55                  60

Gly Ser Val Ser Arg Tyr Tyr Leu Ser Glu Ile Lys Pro Leu His Asn
65                  70                  75                  80

Phe Leu Thr Gln Leu Gln Pro Phe Leu Lys Leu Lys Gln Lys Gln Ala
                85                  90                  95

Asn Leu Val Leu Lys Ile Ile Glu Gln Leu Pro Ser Ala Lys Glu Ser
            100                 105                 110

Pro Asp Lys Phe Leu Glu Val Cys Thr Trp Val Asp Gln Ile Ala Ala
        115                 120                 125

Leu Asn Asp Ser Lys Thr Arg Lys Thr Thr Ser Glu Thr Val Arg Ala
    130                 135                 140

Val Leu Asp
145


<210> SEQ ID NO 66
<211> LENGTH: 147
<212> TYPE: PRT
<213> ORGANISM: Artificial Sequence
<220> FEATURE:
<223> OTHER INFORMATION: Synthetic Sequence
<220> FEATURE:
<221> NAME/KEY: HBV 7-8x.2-3
<222> LOCATION: (1)..(147)
<223> OTHER INFORMATION: HBV8-binding subunit

<400> SEQUENCE: 66

Lys Glu Phe Leu Leu Tyr Leu Ala Gly Phe Val Asp Gly Asp Gly Ser
1               5                   10                  15

Ile Tyr Ala Thr Ile Ser Pro Ala Gln Ala Tyr Lys Phe Lys His Arg
            20                  25                  30

Leu Gly Leu Phe Phe Glu Val Asp Gln Lys Thr Gln Arg Arg Trp Phe
        35                  40                  45

Leu Asp Lys Leu Val Asp Glu Ile Gly Val Gly Tyr Val His Asp Arg
    50                  55                  60

Gly Ser Val Ser Arg Tyr Lys Leu Ser Glu Ile Lys Pro Leu His Asn
65                  70                  75                  80

Phe Leu Thr Gln Leu Gln Pro Phe Leu Lys Leu Lys Gln Lys Gln Ala
                85                  90                  95

Asn Leu Val Leu Lys Ile Ile Glu Gln Leu Pro Ser Ala Lys Glu Ser
            100                 105                 110

Pro Asp Lys Phe Leu Glu Val Cys Thr Trp Val Asp Gln Ile Ala Ala
        115                 120                 125

Leu Asn Asp Ser Lys Thr Arg Lys Thr Thr Ser Glu Thr Val Arg Ala
    130                 135                 140

Val Leu Asp
145


<210> SEQ ID NO 67
<211> LENGTH: 147
<212> TYPE: PRT
<213> ORGANISM: Artificial Sequence
<220> FEATURE:
<223> OTHER INFORMATION: Synthetic Sequence
<220> FEATURE:
<221> NAME/KEY: HBV 7-8x.9-3
<222> LOCATION: (1)..(147)
<223> OTHER INFORMATION: HBV8-binding subunit

<400> SEQUENCE: 67

Lys Glu Phe Leu Leu Tyr Leu Ala Gly Phe Val Asp Gly Asp Gly Ser
```

-continued

```
1               5                   10                  15

Ile Tyr Ala Thr Ile Ser Pro Ala Gln Ala Tyr Lys Phe Lys His Arg
            20                  25                  30

Leu Gly Leu Phe Phe Glu Val Asp Gln Lys Thr Gln Arg Arg Trp Phe
        35                  40                  45

Leu Asp Lys Leu Val Asp Glu Ile Gly Val Gly Tyr Val His Asp Arg
    50                  55                  60

Gly Ser Val Ser Arg Tyr Lys Leu Ser Gln Ile Lys Pro Leu His Asn
65                  70                  75                  80

Phe Leu Thr Gln Leu Gln Pro Phe Leu Lys Leu Lys Gln Lys Gln Ala
                85                  90                  95

Asn Leu Val Leu Lys Ile Ile Glu Gln Leu Pro Ser Ala Lys Glu Ser
            100                 105                 110

Pro Asp Lys Phe Leu Glu Val Cys Thr Trp Val Asp Gln Ile Ala Ala
        115                 120                 125

Leu Asn Asp Ser Lys Thr Arg Lys Thr Thr Ser Glu Thr Val Arg Ala
    130                 135                 140

Val Leu Asp
145


<210> SEQ ID NO 68
<211> LENGTH: 147
<212> TYPE: PRT
<213> ORGANISM: Artificial Sequence
<220> FEATURE:
<223> OTHER INFORMATION: Synthetic Sequence
<220> FEATURE:
<221> NAME/KEY: HBV 7-8x.17-3
<222> LOCATION: (1)..(147)
<223> OTHER INFORMATION: HBV8-binding subunit

<400> SEQUENCE: 68

Lys Glu Phe Leu Leu Tyr Leu Ala Gly Phe Val Asp Gly Asp Gly Ser
1               5                   10                  15

Ile Tyr Ala Thr Ile Ser Pro Ala Gln Ala Tyr Lys Phe Lys His Arg
            20                  25                  30

Leu Gly Leu Phe Phe Glu Val Asp Gln Lys Thr Gln Arg Arg Trp Phe
        35                  40                  45

Leu Asp Lys Leu Val Asp Glu Ile Gly Val Gly Tyr Val His Asp Arg
    50                  55                  60

Gly Ser Val Ser Arg Tyr Lys Leu Ser Gln Ile Lys Pro Leu His Asn
65                  70                  75                  80

Phe Leu Thr Gln Leu Gln Pro Phe Leu Lys Leu Lys Gln Lys Gln Ala
                85                  90                  95

Asn Leu Val Leu Lys Ile Ile Glu Gln Leu Pro Ser Ala Lys Glu Ser
            100                 105                 110

Pro Asp Lys Phe Leu Glu Val Cys Thr Trp Val Asp Gln Ile Ala Ala
        115                 120                 125

Leu Asn Asp Ser Lys Thr Arg Lys Thr Thr Ser Glu Thr Val Arg Ala
    130                 135                 140

Val Leu Asp
145


<210> SEQ ID NO 69
<211> LENGTH: 147
<212> TYPE: PRT
<213> ORGANISM: Artificial Sequence
<220> FEATURE:
```

```
<223> OTHER INFORMATION: Synthetic Sequence
<220> FEATURE:
<221> NAME/KEY: HBV 7-8x.44-3
<222> LOCATION: (1)..(147)
<223> OTHER INFORMATION: HBV8-binding subunit

<400> SEQUENCE: 69

Lys Glu Phe Leu Leu Tyr Leu Ala Gly Phe Val Asp Gly Asp Gly Ser
1               5                   10                  15

Ile Tyr Ala Thr Ile Ser Pro Ala Gln Ala Tyr Lys Phe Lys His Arg
            20                  25                  30

Leu Gly Leu Phe Phe Glu Val Asp Gln Lys Thr Gln Arg Arg Trp Phe
        35                  40                  45

Leu Asp Lys Leu Val Asp Glu Ile Gly Val Gly Tyr Val His Asp Arg
    50                  55                  60

Gly Ser Val Ser Arg Tyr Lys Leu Ser Gln Ile Lys Pro Leu His Asn
65                  70                  75                  80

Phe Leu Thr Gln Leu Gln Pro Phe Leu Lys Leu Lys Gln Lys Gln Ala
                85                  90                  95

Asn Leu Val Leu Lys Ile Ile Glu Gln Leu Pro Ser Ala Lys Glu Ser
            100                 105                 110

Pro Asp Lys Phe Leu Glu Val Cys Thr Trp Val Asp Gln Ile Ala Ala
        115                 120                 125

Leu Asn Asp Ser Lys Thr Arg Lys Thr Thr Ser Glu Thr Val Arg Ala
    130                 135                 140

Val Leu Asp
145


<210> SEQ ID NO 70
<211> LENGTH: 147
<212> TYPE: PRT
<213> ORGANISM: Artificial Sequence
<220> FEATURE:
<223> OTHER INFORMATION: Synthetic Sequence
<220> FEATURE:
<221> NAME/KEY: HBV 11-12x.26-2
<222> LOCATION: (1)..(147)
<223> OTHER INFORMATION: HBV11-binding subunit

<400> SEQUENCE: 70

Lys Glu Phe Leu Leu Tyr Leu Ala Gly Phe Val Asp Gly Asp Gly Ser
1               5                   10                  15

Ile Tyr Ala Ser Ile Arg Pro Arg Gln Tyr Ala Lys Phe Lys His Asp
            20                  25                  30

Leu Glu Leu Arg Phe Asn Val Arg Gln Lys Thr Gln Arg Arg Trp Phe
        35                  40                  45

Leu Asp Lys Leu Val Asp Glu Ile Gly Val Gly Tyr Val Val Asp Trp
    50                  55                  60

Gly Ser Val Ser Thr Tyr Gln Leu Ser Gln Ile Lys Pro Leu His Asn
65                  70                  75                  80

Phe Leu Thr Gln Leu Gln Pro Phe Leu Lys Leu Lys Gln Lys Gln Ala
                85                  90                  95

Asn Leu Val Leu Lys Ile Ile Glu Gln Leu Pro Ser Ala Lys Glu Ser
            100                 105                 110

Pro Asp Lys Phe Leu Glu Val Cys Thr Trp Val Asp Gln Ile Ala Ala
        115                 120                 125

Leu Asn Asp Ser Lys Thr Arg Lys Thr Thr Ser Glu Thr Val Arg Ala
    130                 135                 140
```

```
Val Leu Asp
145


<210> SEQ ID NO 71
<211> LENGTH: 147
<212> TYPE: PRT
<213> ORGANISM: Artificial Sequence
<220> FEATURE:
<223> OTHER INFORMATION: Synthetic Sequence
<220> FEATURE:
<221> NAME/KEY: HBV 11-12x.9-2
<222> LOCATION: (1)..(147)
<223> OTHER INFORMATION: HBV11-binding subunit

<400> SEQUENCE: 71

Lys Glu Phe Leu Leu Tyr Leu Ala Gly Phe Val Asp Gly Asp Gly Ser
1               5                   10                  15

Ile Tyr Ala Ala Ile Arg Pro Lys Gln Thr Arg Lys Phe Lys His Glu
            20                  25                  30

Leu Gln Leu Thr Phe Asn Val Arg Gln Lys Ser Gln Arg Arg Trp Phe
        35                  40                  45

Leu Asp Lys Leu Val Asp Glu Ile Gly Val Gly Tyr Val Leu Asp Trp
    50                  55                  60

Gly Ser Val Ser Thr Tyr Ile Leu Ser Gln Ile Lys Pro Leu His Asn
65                  70                  75                  80

Phe Leu Thr Gln Leu Gln Pro Phe Leu Lys Leu Lys Gln Lys Gln Ala
                85                  90                  95

Asn Leu Val Leu Lys Ile Ile Glu Gln Leu Pro Ser Ala Lys Glu Ser
            100                 105                 110

Pro Asp Lys Phe Leu Glu Val Cys Thr Trp Val Asp Gln Ile Ala Ala
        115                 120                 125

Leu Asn Asp Ser Lys Thr Arg Lys Thr Thr Ser Glu Thr Val Arg Ala
    130                 135                 140

Val Leu Asp
145


<210> SEQ ID NO 72
<211> LENGTH: 147
<212> TYPE: PRT
<213> ORGANISM: Artificial Sequence
<220> FEATURE:
<223> OTHER INFORMATION: Synthetic Sequence
<220> FEATURE:
<221> NAME/KEY: HBV 11-12x.13-2
<222> LOCATION: (1)..(147)
<223> OTHER INFORMATION: HBV11-binding subunit

<400> SEQUENCE: 72

Lys Glu Phe Leu Leu Tyr Leu Ala Gly Phe Val Asp Gly Asp Gly Ser
1               5                   10                  15

Ile Tyr Ala Ala Ile Arg Pro Lys Gln Thr Arg Lys Phe Lys His Glu
            20                  25                  30

Leu Gln Leu Thr Phe Asn Val Arg Gln Lys Thr Gln Arg Arg Trp Phe
        35                  40                  45

Leu Asp Lys Leu Val Asp Glu Ile Gly Val Gly Tyr Val Leu Asp Trp
    50                  55                  60

Gly Ser Val Ser Thr Tyr Ile Leu Ser Gln Ile Lys Pro Leu His Asn
65                  70                  75                  80

Phe Leu Thr Gln Leu Gln Pro Phe Leu Lys Leu Lys Gln Lys Gln Ala
                85                  90                  95
```

```
Asn Leu Val Leu Lys Ile Ile Glu Gln Leu Pro Ser Ala Lys Glu Ser
            100                 105                 110

Pro Asp Lys Phe Leu Glu Val Cys Thr Trp Val Asp Gln Ile Ala Ala
        115                 120                 125

Leu Asn Asp Ser Lys Thr Arg Lys Thr Thr Ser Glu Thr Val Arg Ala
    130                 135                 140

Val Leu Asp
145


<210> SEQ ID NO 73
<211> LENGTH: 147
<212> TYPE: PRT
<213> ORGANISM: Artificial Sequence
<220> FEATURE:
<223> OTHER INFORMATION: Synthetic Sequence
<220> FEATURE:
<221> NAME/KEY: HBV 11-12x.16-2
<222> LOCATION: (1)..(147)
<223> OTHER INFORMATION: HBV11-binding subunit

<400> SEQUENCE: 73

Lys Glu Phe Leu Leu Tyr Leu Ala Gly Phe Val Asp Gly Asp Gly Ser
1               5                   10                  15

Ile Tyr Ala Ser Ile Arg Pro Arg Gln Gln Ala Lys Phe Lys His Ser
            20                  25                  30

Leu Glu Leu His Phe Asn Val Arg Gln Lys Thr Gln Arg Arg Trp Phe
        35                  40                  45

Leu Asp Lys Leu Val Asp Glu Ile Gly Val Gly Tyr Val Val Asp Glu
    50                  55                  60

Gly Ser Val Ser Thr Tyr Leu Leu Ser Glu Ile Lys Pro Leu His Asn
65                  70                  75                  80

Phe Leu Thr Gln Leu Gln Pro Phe Leu Lys Leu Lys Gln Lys Gln Ala
                85                  90                  95

Asn Leu Val Leu Lys Ile Ile Glu Gln Leu Pro Ser Ala Lys Glu Ser
            100                 105                 110

Pro Asp Lys Phe Leu Glu Val Cys Thr Trp Val Asp Gln Ile Ala Ala
        115                 120                 125

Leu Asn Asp Ser Lys Thr Arg Lys Thr Thr Ser Glu Thr Val Arg Ala
    130                 135                 140

Val Leu Asp
145


<210> SEQ ID NO 74
<211> LENGTH: 147
<212> TYPE: PRT
<213> ORGANISM: Artificial Sequence
<220> FEATURE:
<223> OTHER INFORMATION: Synthetic Sequence
<220> FEATURE:
<221> NAME/KEY: HBV 11-12x.27-2
<222> LOCATION: (1)..(147)
<223> OTHER INFORMATION: HBV11-binding subunit

<400> SEQUENCE: 74

Lys Glu Phe Leu Leu Tyr Leu Ala Gly Phe Val Asp Gly Asp Gly Ser
1               5                   10                  15

Ile Tyr Ala Ser Ile Arg Pro Arg Gln Tyr Ala Lys Phe Lys His Asp
            20                  25                  30

Leu Glu Leu Arg Phe Asn Val Arg Gln Lys Thr Gln Arg Arg Trp Phe
        35                  40                  45
```

Leu Asp Lys Leu Val Asp Glu Ile Gly Val Gly Tyr Val Val Asp Trp
    50                  55                  60

Gly Ser Val Ser Thr Tyr Gln Leu Ser Gln Ile Lys Pro Leu His Asn
65                  70                  75                  80

Phe Leu Thr Gln Leu Gln Pro Phe Leu Lys Leu Lys Gln Lys Gln Ala
                85                  90                  95

Asn Leu Val Leu Lys Ile Ile Glu Gln Leu Pro Ser Ala Lys Glu Ser
            100                 105                 110

Pro Asp Lys Phe Leu Glu Val Cys Thr Trp Val Asp Gln Ile Ala Ala
        115                 120                 125

Leu Asn Asp Ser Lys Thr Arg Lys Thr Thr Ser Glu Thr Val Arg Ala
    130                 135                 140

Val Leu Asp
145

<210> SEQ ID NO 75
<211> LENGTH: 147
<212> TYPE: PRT
<213> ORGANISM: Artificial Sequence
<220> FEATURE:
<223> OTHER INFORMATION: Synthetic Sequence
<220> FEATURE:
<221> NAME/KEY: HBV 11-12x.41-2
<222> LOCATION: (1)..(147)
<223> OTHER INFORMATION: HBV11-binding subunit

<400> SEQUENCE: 75

Lys Glu Phe Leu Leu Tyr Leu Ala Gly Phe Val Asp Gly Asp Gly Ser
1               5                   10                  15

Ile Tyr Ala Ser Ile Arg Pro Arg Gln Leu Ala Lys Phe Lys His Thr
            20                  25                  30

Leu Glu Leu His Phe Asn Val Arg Gln Lys Thr Gln Arg Arg Trp Phe
        35                  40                  45

Leu Asp Lys Leu Val Asp Glu Ile Gly Val Gly Tyr Val Leu Asp Ser
    50                  55                  60

Gly Ser Val Ser Thr Tyr Leu Leu Ser Gln Ile Lys Pro Leu His Asn
65                  70                  75                  80

Phe Leu Thr Gln Leu Gln Pro Phe Leu Lys Leu Lys Gln Lys Gln Ala
                85                  90                  95

Asn Leu Val Leu Lys Ile Ile Glu Gln Leu Pro Ser Ala Lys Glu Ser
            100                 105                 110

Pro Asp Lys Phe Leu Glu Val Cys Thr Trp Val Asp Gln Ile Ala Ala
        115                 120                 125

Leu Asn Asp Ser Lys Thr Arg Lys Thr Thr Ser Glu Thr Val Arg Ala
    130                 135                 140

Val Leu Asp
145

<210> SEQ ID NO 76
<211> LENGTH: 147
<212> TYPE: PRT
<213> ORGANISM: Artificial Sequence
<220> FEATURE:
<223> OTHER INFORMATION: Synthetic Sequence
<220> FEATURE:
<221> NAME/KEY: HBV 11-12x.48-2
<222> LOCATION: (1)..(147)
<223> OTHER INFORMATION: HBV11-binding subunit

<400> SEQUENCE: 76

Lys Glu Phe Leu Leu Tyr Leu Ala Gly Phe Val Asp Gly Asp Gly Ser
1 5 10 15

Ile Tyr Ala Ala Ile Arg Pro Lys Gln Thr Arg Lys Phe Lys His Glu
20 25 30

Leu Gln Leu Thr Phe Asn Val Arg Gln Lys Thr Gln Arg Arg Trp Phe
35 40 45

Leu Asp Lys Leu Val Asp Glu Ile Gly Val Gly Tyr Val Leu Asp Trp
50 55 60

Gly Ser Val Ser Thr Tyr Ile Leu Ser Gln Ile Lys Pro Leu His Asn
65 70 75 80

Phe Leu Thr Gln Leu Gln Pro Phe Leu Lys Leu Lys Gln Lys Gln Ala
85 90 95

Asn Leu Val Leu Lys Ile Ile Glu Gln Leu Pro Ser Ala Lys Glu Ser
100 105 110

Pro Asp Lys Phe Leu Glu Val Cys Thr Trp Val Asp Gln Ile Ala Ala
115 120 125

Leu Asn Asp Ser Lys Thr Arg Lys Thr Thr Ser Glu Thr Val Arg Ala
130 135 140

Val Leu Asp
145

<210> SEQ ID NO 77
<211> LENGTH: 147
<212> TYPE: PRT
<213> ORGANISM: Artificial Sequence
<220> FEATURE:
<223> OTHER INFORMATION: Synthetic Sequence
<220> FEATURE:
<221> NAME/KEY: HBV 11-12x.26-3
<222> LOCATION: (1)..(147)
<223> OTHER INFORMATION: HBV12-binding subunit

<400> SEQUENCE: 77

Lys Glu Phe Leu Leu Tyr Leu Ala Gly Phe Val Asp Gly Asp Gly Ser
1 5 10 15

Ile Asn Ala Ser Ile Ala Pro Arg Gln Ser Phe Lys Phe Lys His Gly
20 25 30

Leu Lys Leu Arg Phe Glu Val Gly Gln Lys Thr Gln Arg Arg Trp Phe
35 40 45

Leu Asp Lys Leu Val Asp Glu Ile Gly Val Gly Tyr Val Tyr Asp Asn
50 55 60

Gly Ser Val Ser Val Tyr Ser Leu Ser Gln Ile Lys Pro Leu His Asn
65 70 75 80

Phe Leu Thr Gln Leu Gln Pro Phe Leu Lys Leu Lys Gln Lys Gln Ala
85 90 95

Asn Leu Val Leu Lys Ile Ile Glu Gln Leu Pro Ser Ala Lys Glu Ser
100 105 110

Pro Asp Lys Phe Leu Glu Val Cys Thr Trp Val Asp Gln Ile Ala Ala
115 120 125

Leu Asn Asp Ser Lys Thr Arg Lys Thr Thr Ser Glu Thr Val Arg Ala
130 135 140

Val Leu Asp
145

<210> SEQ ID NO 78
<211> LENGTH: 147
<212> TYPE: PRT
<213> ORGANISM: Artificial Sequence
<220> FEATURE:
<223> OTHER INFORMATION: Synthetic Sequence
<220> FEATURE:
<221> NAME/KEY: HBV 11-12x.9-3
<222> LOCATION: (1)..(147)
<223> OTHER INFORMATION: HBV12-binding subunit

<400> SEQUENCE: 78

```
Lys Glu Phe Leu Leu Tyr Leu Ala Gly Phe Val Asp Gly Asp Gly Ser
1               5                   10                  15

Ile His Ala Cys Ile Arg Pro Arg Gln Thr Ala Lys Phe Lys His Ser
            20                  25                  30

Leu Leu Leu Arg Phe Gln Val Gly Gln Lys Thr Gln Arg Arg Trp Phe
        35                  40                  45

Leu Asp Lys Leu Val Asp Glu Ile Gly Val Gly Tyr Val Tyr Asp Asn
    50                  55                  60

Gly Ser Val Ser Val Tyr Glu Leu Ser Gln Ile Lys Pro Leu His Asn
65                  70                  75                  80

Phe Leu Thr Gln Leu Gln Pro Phe Leu Lys Leu Lys Gln Lys Gln Ala
                85                  90                  95

Asn Leu Val Leu Lys Ile Ile Glu Gln Leu Pro Ser Ala Lys Glu Ser
            100                 105                 110

Pro Asp Lys Phe Leu Glu Val Cys Thr Trp Val Asp Gln Ile Ala Ala
        115                 120                 125

Leu Asn Asp Ser Lys Thr Arg Lys Thr Thr Ser Glu Thr Val Arg Ala
    130                 135                 140

Val Leu Asp
145
```

<210> SEQ ID NO 79
<211> LENGTH: 147
<212> TYPE: PRT
<213> ORGANISM: Artificial Sequence
<220> FEATURE:
<223> OTHER INFORMATION: Synthetic Sequence
<220> FEATURE:
<221> NAME/KEY: HBV 11-12x.13-3
<222> LOCATION: (1)..(147)
<223> OTHER INFORMATION: HBV12-binding subunit

<400> SEQUENCE: 79

```
Lys Glu Phe Leu Leu Tyr Leu Ala Gly Phe Val Asp Gly Asp Gly Ser
1               5                   10                  15

Ile His Ala Cys Ile Arg Pro Arg Gln Thr Ala Lys Phe Lys His Ser
            20                  25                  30

Leu Leu Leu Arg Phe Gln Val Gly Gln Lys Thr Gln Arg Arg Trp Phe
        35                  40                  45

Leu Asp Lys Leu Val Asp Glu Ile Gly Val Gly Tyr Val Tyr Asp Asn
    50                  55                  60

Gly Ser Val Ser Val Tyr Glu Leu Ser Gln Ile Lys Pro Leu His Asn
65                  70                  75                  80

Phe Leu Thr Gln Leu Gln Pro Phe Leu Lys Leu Lys Gln Lys Gln Ala
                85                  90                  95

Asn Leu Val Leu Lys Ile Ile Glu Gln Leu Pro Ser Ala Lys Glu Ser
            100                 105                 110

Pro Asp Lys Phe Leu Glu Val Cys Thr Trp Val Asp Gln Ile Ala Ala
        115                 120                 125

Leu Asn Asp Ser Lys Thr Arg Lys Thr Thr Ser Glu Thr Val Arg Ala
    130                 135                 140
```

```
Val Leu Asp
145


<210> SEQ ID NO 80
<211> LENGTH: 147
<212> TYPE: PRT
<213> ORGANISM: Artificial Sequence
<220> FEATURE:
<223> OTHER INFORMATION: Synthetic Sequence
<220> FEATURE:
<221> NAME/KEY: HBV 11-12x.16-3
<222> LOCATION: (1)..(147)
<223> OTHER INFORMATION: HBV12-binding subunit

<400> SEQUENCE: 80

Lys Glu Phe Leu Leu Tyr Leu Ala Gly Phe Val Asp Gly Asp Gly Ser
1               5                   10                  15

Ile His Ala Thr Ile Ser Pro Arg Gln Thr Phe Lys Phe Lys His Gly
            20                  25                  30

Leu Arg Leu Arg Phe Glu Val Gly Gln Lys Thr Gln Arg Arg Trp Phe
        35                  40                  45

Leu Asp Lys Leu Val Asp Glu Ile Gly Gly Gly Tyr Val Tyr Asp Asn
    50                  55                  60

Gly Ser Val Ser Val Tyr Ser Leu Ser Gln Ile Lys Pro Leu His Asn
65                  70                  75                  80

Phe Leu Thr Gln Leu Gln Pro Phe Leu Lys Leu Lys Gln Lys Gln Ala
                85                  90                  95

Asn Leu Val Leu Lys Ile Ile Glu Gln Leu Pro Ser Ala Lys Glu Ser
            100                 105                 110

Pro Asp Lys Phe Leu Glu Val Cys Thr Trp Val Asp Gln Ile Ala Ala
        115                 120                 125

Leu Asn Asp Ser Lys Thr Arg Lys Thr Thr Ser Glu Thr Val Arg Ala
    130                 135                 140

Val Leu Asp
145


<210> SEQ ID NO 81
<211> LENGTH: 147
<212> TYPE: PRT
<213> ORGANISM: Artificial Sequence
<220> FEATURE:
<223> OTHER INFORMATION: Synthetic Sequence
<220> FEATURE:
<221> NAME/KEY: HBV 11-12x.27-3
<222> LOCATION: (1)..(147)
<223> OTHER INFORMATION: HBV12-binding subunit

<400> SEQUENCE: 81

Lys Glu Phe Leu Leu Tyr Leu Ala Gly Phe Val Asp Gly Asp Gly Ser
1               5                   10                  15

Ile His Ala Cys Ile Arg Pro Arg Gln Thr Ala Lys Phe Lys His Ser
            20                  25                  30

Leu Leu Leu Arg Phe Gln Val Gly Gln Lys Thr Gln Arg Arg Trp Phe
        35                  40                  45

Leu Asp Lys Leu Val Asp Glu Ile Gly Val Gly Tyr Val Tyr Asp Asn
    50                  55                  60

Gly Ser Val Ser Val Tyr Glu Leu Ser Glu Ile Lys Pro Leu His Asn
65                  70                  75                  80

Phe Leu Thr Gln Leu Gln Pro Phe Leu Lys Leu Lys Gln Lys Gln Ala
                85                  90                  95
```

```
Asn Leu Val Leu Lys Ile Ile Glu Gln Leu Pro Ser Ala Lys Glu Ser
            100                 105                 110

Pro Asp Lys Phe Leu Glu Val Cys Thr Trp Val Asp Gln Ile Ala Ala
        115                 120                 125

Leu Asn Asp Ser Lys Thr Arg Lys Thr Thr Ser Glu Thr Val Arg Ala
    130                 135                 140

Val Leu Asp
145
```

<210> SEQ ID NO 82
<211> LENGTH: 147
<212> TYPE: PRT
<213> ORGANISM: Artificial Sequence
<220> FEATURE:
<223> OTHER INFORMATION: Synthetic Sequence
<220> FEATURE:
<221> NAME/KEY: HBV 11-12x.41-3
<222> LOCATION: (1)..(147)
<223> OTHER INFORMATION: HBV12-binding subunit

<400> SEQUENCE: 82

```
Lys Glu Phe Leu Leu Tyr Leu Ala Gly Phe Val Asp Gly Asp Gly Ser
1               5                   10                  15

Ile His Ala Cys Ile Arg Pro Arg Gln Thr Ala Lys Phe Lys His Ser
            20                  25                  30

Leu Leu Leu Arg Phe Gln Val Gly Gln Lys Thr Gln Arg Arg Trp Phe
        35                  40                  45

Leu Asp Lys Leu Val Asp Glu Ile Gly Val Gly Tyr Val Tyr Asp Asn
    50                  55                  60

Gly Ser Val Ser Val Tyr Glu Leu Ser Lys Ile Lys Pro Leu His Asn
65                  70                  75                  80

Phe Leu Thr Gln Leu Gln Pro Phe Leu Lys Leu Lys Gln Lys Gln Ala
                85                  90                  95

Asn Leu Val Leu Lys Ile Ile Glu Gln Leu Pro Ser Ala Lys Glu Ser
            100                 105                 110

Pro Asp Lys Phe Leu Glu Val Cys Thr Trp Val Asp Gln Ile Ala Ala
        115                 120                 125

Leu Asn Asp Ser Lys Thr Arg Lys Thr Thr Ser Glu Thr Val Arg Ala
    130                 135                 140

Val Leu Asp
145
```

<210> SEQ ID NO 83
<211> LENGTH: 147
<212> TYPE: PRT
<213> ORGANISM: Artificial Sequence
<220> FEATURE:
<223> OTHER INFORMATION: Synthetic Sequence
<220> FEATURE:
<221> NAME/KEY: HBV 11-12x.48-3
<222> LOCATION: (1)..(147)
<223> OTHER INFORMATION: HBV12-binding subunit

<400> SEQUENCE: 83

```
Lys Glu Phe Leu Leu Tyr Leu Ala Gly Phe Val Asp Gly Asp Gly Ser
1               5                   10                  15

Ile His Ala Cys Ile Arg Pro Arg Gln Thr Ala Lys Phe Lys His Ser
            20                  25                  30

Leu Leu Leu Arg Phe Gln Val Gly Gln Lys Thr Gln Arg Arg Trp Phe
        35                  40                  45
```

-continued

```
Leu Asp Lys Leu Val Asp Glu Ile Gly Val Gly Tyr Val Tyr Asp Asn
    50                  55                  60

Gly Ser Val Ser Val Tyr Glu Leu Ser Lys Ile Lys Pro Leu His Asn
65                  70                  75                  80

Phe Leu Thr Gln Leu Gln Pro Phe Leu Lys Leu Lys Gln Lys Gln Ala
                85                  90                  95

Asn Leu Val Leu Lys Ile Ile Glu Gln Leu Pro Ser Ala Lys Glu Ser
            100                 105                 110

Pro Asp Lys Phe Leu Glu Val Cys Thr Trp Val Asp Gln Ile Ala Ala
        115                 120                 125

Leu Asn Asp Ser Lys Thr Arg Lys Thr Thr Ser Glu Thr Val Arg Ala
    130                 135                 140

Val Leu Asp
145


<210> SEQ ID NO 84
<211> LENGTH: 22
<212> TYPE: DNA
<213> ORGANISM: Hepatitis B virus

<400> SEQUENCE: 84

ccccttctcg tgttacaggc gg                                              22


<210> SEQ ID NO 85
<211> LENGTH: 22
<212> TYPE: DNA
<213> ORGANISM: Hepatitis B virus

<400> SEQUENCE: 85

gatgatctgg tattgggggc ca                                              22


<210> SEQ ID NO 86
<211> LENGTH: 22
<212> TYPE: DNA
<213> ORGANISM: Hepatitis B virus

<400> SEQUENCE: 86

tttgctgatg caaccccac tg                                               22
```

ENGINEERED MEGANUCLEASES SPECIFIC FOR RECOGNITION SEQUENCES IN THE HEPATITIS B VIRUS GENOME

RELATED APPLICATIONS

This application is a continuation of U.S. application Ser. No. 16/342,169, filed Apr. 15, 2019, which is a national stage filing under 35 U.S.C. § 371 of international application number PCT/US2017/056638, filed Oct. 13, 2017, which claims the benefit of U.S. Provisional Application No. 62/527,159, filed Jun. 30, 2017, U.S. Provisional Application No. 62/527,196, filed Jun. 30, 2017, U.S. Provisional Application No. 62/452,506, filed Jan. 31, 2017, and U.S. Provisional Application No. 62/408,356, filed Oct. 14, 2016. The entire contents of each of these referenced applications are incorporated by reference herein.

FIELD OF THE INVENTION

The invention relates to the fields of oncology, molecular biology and recombinant nucleic acid technology. In particular, the invention relates to engineered meganucleases having specificity for a recognition sequence within at least two genotypes of the Hepatitis B virus genome. Such engineered meganucleases are useful in methods for treating Hepatitis B virus infections and hepatocellular carcinoma caused by Hepatitis B virus.

REFERENCE TO A SEQUENCE LISTING SUBMITTED AS A TEXT FILE VIA EFS-WEB

The instant application contains a Sequence Listing which has been submitted in ASCII format via EFS-Web and is hereby incorporated by reference in its entirety. Said ASCII copy, created on Apr. 17, 2020, is named P109070018US05-SEQ-MJT.txt, and is 165 kilobytes in size.

BACKGROUND OF THE INVENTION

The Hepatitis B virus (HBV) is a major health problem worldwide and more than 350 million people are chronic carriers. HBV infection is a serious and common infectious disease of the liver. Chronic infection is associated with an increased risk to develop severe liver diseases, including liver cirrhosis and hepatocellular carcinoma (HCC), one of the most common forms of human cancer. The estimated risk of HCC in chronic HBV carriers is approximately 100 times greater than in uninfected individuals. About a third of the world population has been infected at one point in their lives, including 240 million to 350 million who have chronic infections. Over 750,000 people die of hepatitis B each year. About 300,000 of these are due to liver cancer. Currently available anti-HBV drugs have limitations. For example, interferon alpha administration is associated with severe adverse reactions. Nucleoside analogues are virostatic and require long-term administration.

The HBV genome exhibits genetic variability with an estimated rate of 1.4-3.2$\times$10$^{-5}$ nucleotide substitutions per site per year. A large number of virus variants arise during replication as a result of nucleotide misincorporations in the absence of any proof reading capacity by the viral polymerase. This variability has resulted in well-recognized subtypes of the virus. HBV has been classified into well-defined genotypes on the basis of an inter-group divergence of 8% or more in the complete genomic sequence, each having a distinct geographical distribution. For example, Genotype A is widespread in sub-Saharan Africa, Northern Europe, and Western Africa; genotypes B and C are common in Asia; genotype C is primarily observed in Southeast Asia; genotype D is dominant in Africa, Europe, Mediterranean countries, and India; genotype G is reported in France, Germany, and the United States; and genotype H is commonly encountered in Central and South America. Genotype I has recently been reported in Vietnam and Laos. The newest HBV genotype, genotype J, has been identified in the Ryukyu Islands in Japan.

HBV is an enveloped DNA virus that belongs to the Hepadnaviridae family. It contains a small, partially double-stranded (DS), relaxed-circular DNA (rcDNA) genome that replicates by reverse transcription of an RNA intermediate, the pregenomic RNA (pgRNA). The circular DNA genome of HBV is unusual because the DNA is not fully double-stranded. One end of the full length strand is linked to the viral DNA polymerase. The genome is approximately 3020-3320 nucleotides long (for the full-length strand) and 1700-2800 nucleotides long (for the short length-strand). The negative-sense (non-coding) is complementary to the viral mRNA.

There are four known genes encoded by the genome, referred to as C, X, P, and S. The core protein is coded for by gene C (HBcAg), and its start codon is preceded by an upstream in-frame AUG start codon from which the pre-core protein is produced. The HBeAg is produced by proteolytic processing of the pre-core protein. The DNA polymerase is encoded by gene P. Gene S codes for the surface antigen (HBsAg). The HBsAg gene is one long open reading frame but contains three in frame "start" (ATG) codons that divide the gene into three sections: pre-S1, pre-S2, and S. Because of the multiple start codons, polypeptides of three different sizes called Large (the order from surface to the inside: pre-S1/pre-S2/S), Middle (pre-S2/S), and Small (S) are produced. The function of the protein coded for by gene X is not fully understood but it is associated with the development of liver cancer. It stimulates genes that promote cell growth and inactivates growth regulating molecules.

The viral DNA is found in the nucleus soon after infection of the cell. The partially double-stranded DNA is rendered fully double-stranded by completion of the (+) sense strand and removal of a protein molecule from the (−) sense strand and a short sequence of RNA from the (+) sense strand. Non-coding bases are removed from the ends of the (−) sense strand and the ends are rejoined.

The HBV life cycle begins when the virus attaches to the host cell and is internalized. Recent studies have demonstrated that sodium-taurocholate co-transporting polypeptide (NTCP) is a functional receptor in HBV infection. The virion relaxed circular DNA (rcDNA) is delivered to the nucleus, where it is repaired to form a covalently closed-circular DNA (cccDNA). The episomal cccDNA serves as the template for the transcription of the pregenomic RNA (pgRNA) and the other viral mRNAs by the host RNA polymerase II. The transcripts are then exported to the cytoplasm, where translation of the viral proteins occurs. Reverse transcriptase (RT) binds to pgRNA and triggers assembly of the core proteins into immature, RNA-containing nucleocapsids. The immature nucleocapsids then undergo a process of maturation whereby pgRNA is reversed transcribed by RT to make the mature rcDNA. A unique feature of hepadnavirus reverse transcription is the RT primed initiation of minus-strand DNA synthesis, which leads to the covalent linkage of RT to the 5' end of the minus-strand DNA.

The mature, rcDNA-containing nucleocapsids are then enveloped by the viral surface proteins and secreted as virions (secretion pathway) or, alternatively, are recycled back to the nucleus to further amplify the pool of cccDNA (recycling pathway). Persistence of cccDNA in hepatocytes plays a key role in viral persistence, reactivation of viral replication after cessation of antiviral therapy, and resistance to therapy.

Homing endonucleases are a group of naturally-occurring nucleases which recognize 15-40 base-pair cleavage sites commonly found in the genomes of plants and fungi. They are frequently associated with parasitic DNA elements, such as group I self-splicing introns and inteins. They naturally promote homologous recombination or gene insertion at specific locations in the host genome by producing a double-stranded break in the chromosome, which recruits the cellular DNA-repair machinery (Stoddard (2006), *Q. Rev. Biophys.* 38: 49-95). Homing endonucleases are commonly grouped into four families: the LAGLIDADG (SEQ ID NO: 2) family, the GIY-YIG family, the His-Cys box family and the HNH family. These families are characterized by structural motifs, which affect catalytic activity and recognition sequence. For instance, members of the LAGLIDADG (SEQ ID NO: 2) family are characterized by having either one or two copies of the conserved LAGLIDADG (SEQ ID NO: 2) motif (see Chevalier et al. (2001), *Nucleic Acids Res.* 29(18): 3757-3774). The LAGLIDADG (SEQ ID NO: 2) homing endonucleases with a single copy of the LAGLIDADG (SEQ ID NO: 2) motif form homodimers, whereas members with two copies of the LAGLIDADG (SEQ ID NO: 2) motif are found as monomers. Methods for producing homing endonucleases are known in the art.

I-CreI (SEQ ID NO: 1) is a member of the LAGLIDADG (SEQ ID NO: 2) family of homing endonucleases which recognizes and cuts a 22 basepair recognition sequence in the chloroplast chromosome of the algae *Chlamydomonas reinhardtii*. Genetic selection techniques have been used to modify the wild-type I-CreI cleavage site preference (Sussman el al. (2004), *J. Mol. Biol.* 342: 31-41; Chames et al. (2005), *Nucleic Acids Res.* 33: e178; Seligman et al. (2002), *Nucleic Acids Res.* 30: 3870-9, Arnould et al. (2006), *J. Mol. Biol.* 355: 443-58). Methods for rationally-designing mono-LAGLIDADG (SEQ ID NO: 2) homing endonucleases were described which are capable of comprehensively redesigning I-CreI and other homing endonucleases to target widely-divergent DNA sites, including sites in mammalian, yeast, plant, bacterial, and viral genomes (WO 2007/047859).

As first described in WO 2009/059195, I-CreI and its engineered derivatives are normally dimeric but can be fused into a single polypeptide using a short peptide linker that joins the C-terminus of a first subunit to the N-terminus of a second subunit (Li et al. (2009). *Nucleic Acids Res.* 37:1650-62; Grizot et al. (2009), *Nucleic Acids Res.* 37:5405-19). Thus, a functional "single-chain" meganuclease can be expressed from a single transcript.

The use of engineered meganucleases for treatment of HBV infections has been suggested. For example, WO2010/136841 suggests the use of engineered meganucleases for cleaving the genome of non-genomically integrating viruses. Such meganucleases include variants of I-CreI. The '841 application discloses a number of 22 base pair meganuclease recognition sequences present in the genome of one HBV strain. However, the '841 application does not identify any recognition sequences that are present within multiple genotypes of the HBV genome.

SUMMARY OF THE INVENTION

The present invention depends, in part, upon the development of site-specific, rare-cutting endonucleases that are engineered to recognize DNA sequences within at least one open reading frame (ORF) of the HBV genome and within at least two different genotypes of the HBV genome. The inventors have identified specific recognition sequences conserved across genotypes that can be targeted by recombinant meganucleases in order to inactivate multiple genotypes of the virus.

The present invention improves on the prior art in several aspects. The inventors surprisingly found that recognition sequences can be identified within an ORF of several genotypes of the HBV genome. By targeting several genotypes of the virus, a single pharmaceutical composition can be prepared that can be used against different genotypes present in localized regions of the world. Thus, the methods and compositions disclosed herein are useful in treating or reducing the proliferation of HBV in infected individuals worldwide. Suppression or eradication of the replication of HBV in the liver leads to improved liver pathology and decreased progression to liver cirrhosis and hepatocellular carcinoma. Accordingly, the present invention fulfills a need in the art for further gene therapy approaches to HBV infections. In addition, the invention provides a method of treatment for hepatocellular carcinoma by providing a means of targeting the insertion by homologous recombination of a "suicide gene" into an HBV genome in an HCC cell. The suicide gene can encode a toxin or pro-apoptotic protein which directly kills the cancer cell, or a cell surface antigen or an MHC Class I antigenic polypeptide which directs the subject's own immune system to kill the cancer cell.

The present invention provides engineered meganucleases useful for the treatment of Hepatitis B virus (HBV) infection. The engineered meganucleases of the invention recognize and cleave a recognition sequence within an open reading frame (ORF) of the genome of at least two genotypes of the Hepatitis B virus. Cleavage at such a recognition sequence by an engineered meganuclease disclosed herein can disrupt expression of one or more viral proteins due to non-homologous end joining (NHEJ) at the cleavage site. NHEJ can result in insertions, deletions, or result in a frameshift mutation that can interfere with gene expression. Accordingly, by interrupting normal gene expression, the infection and proliferation of HBV can be reduced or eliminated according to the methods disclosed herein. The present invention also provides pharmaceutical compositions and methods for treatment of HBV which utilize an engineered meganuclease having specificity for a recognition sequence positioned within an ORF of the genome of at least two genotypes of the Hepatitis B virus. The present invention further provides methods of delivering the engineered meganucleases disclosed herein to a subject infected with HBV in order to reduce the level of HBV and/or reduce the symptoms associated with an HBV infection.

Thus, in one aspect, the invention provides an engineered meganuclease that recognizes and cleaves a recognition sequence within an open reading frame (ORF) of the genome of at least two genotypes of the Hepatitis B virus. The engineered meganuclease comprises a first subunit and a second subunit, wherein the first subunit binds to a first recognition half-site of the recognition sequence and comprises a first hypervariable (HVR1) region, and wherein the second subunit binds to a second recognition half-site of the recognition sequence and comprises a second hypervariable (HVR2) region.

In some embodiments, the recognition sequence is found within an ORF of at least 3, at least 4, at least 5, or at least 6 genotypes of the Hepatitis B virus. In one such embodiment the recognition sequence is within an ORF of genotype A (SEQ ID NO: 3) of the Hepatitis B virus. Such an embodiment includes Hepatitis B virus isolates of genotype A which differ from SEQ ID NO: 3 but comprise one or more HBV meganuclease recognition sequences described herein. In further such embodiments, the recognition sequence is within an ORF of genotype A and one or more of genotypes B, C, D, E, F, and G (SEQ ID NOs: 4-9, respectively). Such embodiments include Hepatitis B virus isolates of genotype A, B, C, D, E, F, and G which differ from SEQ ID NOs: 3-9 but comprise one or more HBV meganuclease recognition sequences described herein.

In some embodiments, the recognition sequence is within at least one ORF encoding a protein selected from the group consisting of: the polymerase (P) protein, the large surface (preS1/preS2/S) protein, the middle surface (preS2/S) protein, and the small surface (S) protein. In some embodiments, the recognition sequence can comprise SEQ ID NO: 10 (i.e., the HBV 1-2 recognition sequence), SEQ ID NO: 12 (i.e., the HBV 5-6 recognition sequence), SEQ ID NO: 14 (i.e., the HBV 7-8 recognition sequence), or SEQ ID NO: 16 (i.e., the HBV 11-12 recognition sequence).

In some embodiments, wherein the recognition sequence comprises SEQ ID NO: 10, the HVR1 region can comprise an amino acid sequence having at least 80%, at least 85%, at least 90%, at least 95%, or more, sequence identity to an amino acid sequence corresponding to residues 24-79 of SEQ ID NO: 18 or 19 or residues 215-270 of SEQ ID NO: 20 or 21. In some such embodiments, the HVR1 region can comprise residues corresponding to residues 24, 26, 28, 30, 32, 33, 38, 40, 42, 44, 46, 68, 70, 75, and 77 of SEQ ID NO: 18 or 19, or residues corresponding to residues 215, 217, 219, 221, 223, 224, 229, 231, 233, 235, 237, 259, 261, 266, and 268 of SEQ ID NO: 20 or 21. In particular embodiments, the HVR1 region can comprise residues 24-79 of SEQ ID NO: 18 or 19, or residues 215-270 of SEQ ID NO: 20 or 21.

In some such embodiments, wherein the recognition sequence comprises SEQ ID NO: 10, the HVR2 region can comprise an amino acid sequence having at least 80%, at least 85%, at least 90%, at least 95%, or more, sequence identity to an amino acid sequence corresponding to residues 215-270 of SEQ ID NO: 18 or 19 or residues 24-79 of SEQ ID NO: 20 or 21. In some such embodiments, the HVR2 region can comprise residues corresponding to residues 215, 217, 219, 221, 223, 224, 229, 231, 233, 235, 237, 259, 261, 266, and 268 of SEQ ID NO: 18 or 19, or residues corresponding to residues 24, 26, 28, 30, 32, 33, 38, 40, 42, 44, 46, 68, 70, 75, and 77 of SEQ ID NO: 20 or 21. In particular embodiments, the HVR2 region can comprise residues 215-270 of SEQ ID NO: 18 or 19, or residues 24-79 of SEQ ID NO: 20 or 21.

In such embodiments, wherein the recognition sequence comprises SEQ ID NO: 10, the first subunit can comprise an amino acid sequence having at least 80%, at least 85%, at least 90%, at least 95%, or more, sequence identity to residues 7-153 of SEQ ID NO: 18 or 19 or residues 198-344 of SEQ ID NO: 20 or 21, and the second subunit can comprise an amino acid sequence having at least 80%, at least 85%, at least 90%, at least 95%, or more, sequence identity to residues 198-344 of SEQ ID NO: 18 or 19 or residues 7-153 of SEQ ID NO: 20 or 21. In some embodiments, the first subunit can comprise residues 7-153 of SEQ ID NO: 18 or 19 or residues 198-344 of SEQ ID NO: 20 or 21. Likewise, in some embodiments, the second subunit can comprise residues 198-344 of SEQ ID NO: 18 or 19 or residues 7-153 of SEQ ID NO: 20 or 21.

In certain such embodiments, wherein the recognition sequence comprises SEQ ID NO: 10, the engineered meganuclease can comprise a linker, wherein the linker covalently joins the first subunit and the second subunit. In particular embodiments, the engineered meganuclease can comprise the amino acid sequence of any one of SEQ ID NOs: 18-21.

In other embodiments, wherein the recognition sequence comprises SEQ ID NO: 12, the HVR1 region can comprise an amino acid sequence having at least 80%, at least 85%, at least 90%, at least 95%, or more, sequence identity to an amino acid sequence corresponding to residues 215-270 of any one of SEQ ID NOs: 22-24 or residues 24-79 of any one of SEQ ID NOs: 25-28. In some such embodiments, the HVR1 region can comprise residues corresponding to residues 215, 217, 219, 221, 223, 224, 229, 231, 233, 235, 237, 259, 261, 266, and 268 of any one of SEQ ID NOs: 22-24, or residues corresponding to residues 24, 26, 28, 30, 32, 33, 38, 40, 42, 44, 46, 68, 70, 75, and 77 of any one of SEQ ID NOs: 25-28. In particular embodiments, the HVR1 region can comprise residues 215-270 of any one of SEQ ID NOs: 22-24 or residues 24-79 of any one of SEQ ID NOs: 25-28.

In some such embodiments, wherein the recognition sequence comprises SEQ ID NO: 12, the HVR2 region can comprise an amino acid sequence having at least 80%, at least 85%, at least 90%, at least 95%, or more, sequence identity to an amino acid sequence corresponding to residues 24-79 of any one of SEQ ID NOs: 22-24 or residues 215-270 of any one of SEQ ID NOs: 25-28. In some such embodiments, the HVR2 region can comprise residues corresponding to residues 24, 26, 28, 30, 32, 33, 38, 40, 42, 44, 46, 68, 70, 75, and 77 of any one of SEQ ID NOs: 22-24, or residues corresponding to residues 215, 217, 219, 221, 223, 224, 229, 231, 233, 235, 237, 259, 261, 266, and 268 of any one of SEQ ID NOs: 25-28. In particular embodiments, the HVR2 region can comprise residues 24-79 of any one of SEQ ID NOs: 22-24 or residues 215-270 of any one of SEQ ID NOs: 25-28.

In some such embodiments, wherein the recognition sequence comprises SEQ ID NO: 12, the first subunit can comprise an amino acid sequence having at least 80%, at least 85%, at least 90%, at least 95%, or more, sequence identity to residues 198-344 of any one of SEQ ID NOs: 22-24 or residues 7-153 of any one of SEQ ID NOs: 25-28, and the second subunit can comprise an amino acid sequence having at least 80%, at least 85%, at least 90%, at least 95%, or more, sequence identity to residues 7-153 of any one of SEQ ID NOs: 22-24 or residues 198-344 of any one of SEQ ID NOs: 25-28. In some embodiments, the first subunit can comprise residues 198-344 of any one of SEQ ID NOs: 22-24 or residues 7-153 of any one of SEQ ID NOs: 25-28. Likewise, in some embodiments, the second subunit can comprise residues 7-153 of any one of SEQ ID NOs: 22-24 or residues 198-344 of any one of SEQ ID NOs: 25-28.

In certain such embodiments, wherein the recognition sequence comprises SEQ ID NO: 12, the engineered meganuclease can comprise a linker, wherein the linker covalently joins the first subunit and the second subunit. In particular embodiments, the engineered meganuclease can comprise the amino acid sequence of any one of SEQ ID NOs: 22-28.

In some embodiments, wherein the recognition sequence comprises SEQ ID NO: 14, the HVR1 region can comprise an amino acid sequence having at least 80%, at least 85%, at least 90%, at least 95%, or more, sequence identity to an amino acid sequence corresponding to residues 215-270 of any one of SEQ ID NOs: 29-32. In some such embodiments, the HVR1 region can comprise residues corresponding to residues 215, 217, 219, 221, 223, 224, 229, 231, 233, 235, 237, 259, 261, 266, and 268 of any one of SEQ ID NOs: 29-32. In particular embodiments, the HVR1 region can comprise residues 215-270 of any one of SEQ ID NOs: 29-32.

In some such embodiments, wherein the recognition sequence comprises SEQ ID NO: 14, the HVR2 region can comprise an amino acid sequence having at least 80%, at least 85%, at least 90%, at least 95%, or more, sequence identity to an amino acid sequence corresponding to residues 24-79 of any one of SEQ ID NOs: 29-32. In some such embodiments, the HVR2 region can comprise residues corresponding to residues 24, 26, 28, 30, 32, 33, 38, 40, 42, 44, 46, 68, 70, 75, and 77 of any one of SEQ ID NOs: 29-32. In particular embodiments, the HVR2 region can comprise residues 24-79 of any one of SEQ ID NOs: 29-32.

In some such embodiments, wherein the recognition sequence comprises SEQ ID NO: 14, the first subunit can comprise an amino acid sequence having at least 80%, at least 85%, at least 90%, at least 95%, or more, sequence identity to residues 198-344 of any one of SEQ ID NOs: 29-32, and the second subunit can comprise an amino acid sequence having at least 80%, at least 85%, at least 90%, at least 95%, or more, sequence identity to residues 7-153 of any one of SEQ ID NOs: 29-32. In some embodiments, the first subunit can comprise residues 198-344 of any one of SEQ ID NOs: 29-32. Likewise, in some embodiments, the second subunit can comprise residues 7-153 of any one of SEQ ID NOs: 29-32.

In certain such embodiments, wherein the recognition sequence comprises SEQ ID NO: 14, the engineered meganuclease can comprise a linker, wherein the linker covalently joins the first subunit and the second subunit. In particular embodiments, the engineered meganuclease can comprise the amino acid sequence of any one of SEQ ID NOs: 29-32.

In some embodiments, wherein the recognition sequence comprises SEQ ID NO: 16, the HVR1 region can comprise an amino acid sequence having at least 80%, at least 85%, at least 90%, at least 95%, or more, sequence identity to residues 215-270 of any one of SEQ ID NOs: 33-39. In some such embodiments, the HVR1 region can comprise residues corresponding to residues 215, 217, 219, 221, 223, 224, 229, 231, 233, 235, 237, 259, 261, 266, and 268 of any one of SEQ ID NOs: 33-39. In particular embodiments, the HVR1 region can comprise residues 215-270 of any one of SEQ ID NOs: 33-39.

In some such embodiments, wherein the recognition sequence comprises SEQ ID NO: 16, the HVR2 region can comprise an amino acid sequence having at least 80%, at least 85%, at least 90%, at least 95%, or more, sequence identity to residues 24-79 of any one of SEQ ID NOs: 33-39. In some such embodiments, the HVR2 region can comprise residues corresponding to residues 24, 26, 28, 30, 32, 33, 38, 40, 42, 44, 46, 68, 70, 75, and 77 of any one of SEQ ID NOs: 33-39. In particular embodiments, the HVR2 region can comprise residues 24-79 of any one of SEQ ID NOs: 33-39.

In such embodiments, wherein the recognition sequence comprises SEQ ID NO: 16, the first subunit can comprise an amino acid sequence having at least 80%, at least 85%, at least 90%, at least 95%, or more, sequence identity to residues 198-344 of any one of SEQ ID NOs: 33-39, and the second subunit can comprise an amino acid sequence having at least 80%, at least 85%, at least 90%, at least 95%, or more, sequence identity to residues 7-153 of any one of SEQ ID NOs: 33-39. In some embodiments, the first subunit can comprise residues 198-344 of any one of SEQ ID NOs: 33-39. Likewise, in some embodiments, the second subunit can comprise residues 7-153 of any one of SEQ ID NOs: 33-39.

In certain embodiments, the engineered meganuclease can comprise a linker, wherein the linker covalently joins the first subunit and the second subunit. In particular embodiments, the engineered meganuclease can comprise the amino acid sequence of any one of SEQ ID NOs: 33-39.

In another aspect, the invention provides an isolated polynucleotide comprising a nucleic acid sequence encoding any engineered meganuclease disclosed herein. In a particular embodiment, the isolated polynucleotide can be an mRNA.

In further embodiments, the mRNA can be a polycistronic mRNA encoding one or more engineered meganucleases described herein. In certain embodiments, polycistronic mRNA of the invention can be, without limitation, a bicistronic mRNA encoding two engineered meganucleases described herein, a tricistronic mRNA encoding three engineered meganucleases described herein, or a quadcistronic mRNA encoding four engineered meganucleases described herein. In such embodiments wherein two or more engineered meganucleases are encoded by a polycistronic mRNA, each encoded engineered meganuclease has specificity for a different HBV recognition sequence. Further, in such embodiments, a polycistronic mRNA of the invention can encode any combination of engineered meganucleases described herein. In a particular embodiment, a polycistronic mRNA can encode an HBV 1-2 meganuclease, an HBV 5-6 meganuclease, an HBV 7-8 meganuclease, and an HBV 11-12 meganuclease. In another particular embodiment, a polycistronic mRNA can be a bicistronic mRNA encoding an HBV 5-6 meganuclease and an HBV 11-12 meganuclease.

In further embodiments, a polycistronic mRNA of the invention can encode one or more engineered meganucleases described herein and one or more additional proteins that induce a therapeutically beneficial effect in an HBV-infected cell and/or HBV-infected subject.

In another aspect, the invention provides a recombinant DNA construct comprising a nucleic acid sequence which encodes any engineered meganuclease of the invention. In some embodiments, the recombinant DNA construct comprises a cassette comprising a promoter and a nucleic acid sequence encoding an engineered meganuclease described herein. In other embodiments, the recombinant DNA construct comprises two or more cassettes, wherein each cassette comprises a promoter and a nucleic acid sequence encoding an engineered meganuclease described herein, and wherein each engineered meganuclease has specificity for a different HBV recognition sequence disclosed herein. In particular embodiments, the recombinant DNA construct can comprise two cassettes, three cassettes, four cassettes, or more.

In other embodiments, the recombinant DNA construct comprises a cassette comprising a promoter and a polycistronic nucleic acid sequence, wherein the promoter drives expression of the polycistronic nucleic acid sequence to generate a polycistronic mRNA described herein in a target cell.

In a particular embodiment, the recombinant DNA construct encodes a viral vector comprising a nucleic acid sequence encoding any engineered meganuclease disclosed herein. In such an embodiment, the viral vector can be a retrovirus, a lentivirus, an adenovirus, or an adeno-associated virus (AAV) vector. In a particular embodiment, the viral vector can be a recombinant AAV vector.

In some embodiments, the viral vector comprises a cassette comprising a promoter and a nucleic acid sequence encoding an engineered meganuclease described herein. In other embodiments, the viral vector comprises two or more cassettes, wherein each cassette comprises a promoter and a nucleic acid sequence encoding an engineered meganuclease described herein, and wherein each engineered meganuclease has specificity for a different HBV recognition sequence disclosed herein.

In other embodiments, the viral vector comprises one cassette comprising a promoter and a polycistronic nucleic acid sequence, wherein the promoter drives expression of the polycistronic nucleic acid sequence to generate a polycistronic mRNA described herein in a target cell.

In another aspect, the invention provides a viral vector comprising a nucleic acid sequence which encodes any engineered meganuclease of the invention. In some embodiments, the viral vector can be a retrovirus, a lentivirus, an adenovirus, or an adeno-associated virus (AAV) vector. In a particular embodiment, the viral vector can be a recombinant AAV vector. In some embodiments, the viral vector comprises a cassette comprising a promoter and a nucleic acid sequence encoding an engineered meganuclease described herein. In other embodiments, the viral vector comprises two or more cassettes, wherein each cassette comprises a promoter and a nucleic acid sequence encoding an engineered meganuclease described herein, and wherein each engineered meganuclease has specificity for a different HBV recognition sequence disclosed herein.

In further embodiments, the viral vector comprises one cassette comprising a promoter and a polycistronic nucleic acid sequence, wherein the promoter drives expression of the polycistronic nucleic acid sequence to generate a polycistronic mRNA described herein in a target cell.

In another aspect, the invention provides a pharmaceutical composition for treatment of a subject having hepatitis B virus (HBV) or hepatocellular carcinoma caused by HBV, the pharmaceutical composition comprising a pharmaceutically acceptable carrier and: (a) a nucleic acid encoding an engineered meganuclease described herein; or (b) an engineered meganuclease protein described herein; wherein the engineered meganuclease has specificity for a recognition sequence within an open reading frame (ORF) of the genome of at least two genotypes of the Hepatitis B virus. In some embodiments, the recognition sequence is within an ORF of at least 3, at least 4, at least 5, or at least 6 genotypes of the Hepatitis B virus. In one such embodiment the recognition sequence is within an ORF of HBV genotype A (SEQ ID NO: 3), or isolates thereof which comprise the recognition sequence, and at least 1, at least 2, at least 3, at least 4, at least 5, or at least 6 other genotypes of HBV. In various embodiments, additional HBV genotypes can include genotype B, C, D, E, F, and/or G (SEQ ID NOs: 4-9, respectively), or isolates thereof which comprise one or more HBV recognition sequences described herein.

In some embodiments, the engineered meganuclease of the pharmaceutical composition, or encoded by a nucleic acid sequence of the pharmaceutical composition, has specificity for a recognition sequence within at least one ORF encoding a protein selected from the group consisting of: the polymerase (P) protein, the large surface (preS1/preS2/S) protein, the middle surface (preS2/S) protein, and the small surface (S) protein. In some embodiments, the recognition sequence can comprise SEQ ID NO: 10, 12, 14, or 16.

In one embodiment, the nucleic acid sequence of the pharmaceutical composition encoding an engineered meganuclease disclosed herein can be an mRNA described herein. In some such embodiments, the mRNA can be a polycistronic mRNA described herein, such that two or more engineered meganucleases described herein are expressed in the target cell in vivo.

In another embodiment, the pharmaceutical composition comprises a recombinant DNA construct described herein comprising the nucleic acid sequence encoding an engineered meganuclease disclosed herein. In some such embodiments, the recombinant DNA construct comprises a cassette comprising a promoter and a nucleic acid sequence encoding an engineered meganuclease of the invention. In other embodiments, the recombinant DNA construct of the pharmaceutical composition comprises two or more cassettes, wherein each cassette comprises a promoter and a nucleic acid sequence encoding an engineered meganuclease described herein, and wherein each engineered meganuclease has specificity for a different HBV recognition sequence disclosed herein. In particular embodiments, the recombinant DNA construct of the pharmaceutical composition can comprise two cassettes, three cassettes, four cassettes, or more.

In other embodiments, the recombinant DNA construct of the pharmaceutical composition comprises a cassette comprising a promoter and a polycistronic nucleic acid sequence, wherein the promoter drives expression of the polycistronic nucleic acid sequence to generate a polycistronic mRNA described herein in the target cell in vivo, such that two or more engineered meganucleases described herein are expressed in the target cell.

In another embodiment, the pharmaceutical composition comprises a viral vector comprising the nucleic acid sequence encoding an engineered meganuclease disclosed herein. In one such embodiment, the viral vector can be a retrovirus, a lentivirus, an adenovirus, or an AAV. In a particular embodiment, the viral vector can be a recombinant AAV vector.

In some such embodiments, the viral vector comprises a cassette comprising a promoter and a nucleic acid sequence encoding an engineered meganuclease described herein. In other embodiments, the viral vector comprises two or more cassettes, wherein each cassette comprises a promoter and a nucleic acid sequence encoding an engineered meganuclease described herein, and wherein each engineered meganuclease has specificity for a different HBV recognition sequence disclosed herein.

In other such embodiments, the viral vector comprises one cassette comprising a promoter and a polycistronic nucleic acid sequence, wherein the promoter drives expression of the polycistronic nucleic acid sequence to generate a polycistronic mRNA described herein in the target cell in vivo, such that two or more engineered meganucleases described herein are expressed in the target cell.

In one such embodiment, the pharmaceutical composition can comprise an engineered meganuclease disclosed herein (or a nucleic acid encoding the same) which recognizes and cleaves SEQ ID NO: 10. In particular embodiments, the engineered meganuclease can comprise the amino acid sequence of any one of SEQ ID NOs: 18-21.

In another embodiment, the pharmaceutical composition can comprise an engineered meganuclease disclosed herein (or a nucleic acid encoding the same) which recognizes and cleaves SEQ ID NO: 12. In particular embodiments, the engineered meganuclease can comprise the amino acid sequence of any one of SEQ ID NOs: 22-28.

In another embodiment, the pharmaceutical composition can comprise an engineered meganuclease disclosed herein (or a nucleic acid encoding the same) which recognizes and cleaves SEQ ID NO: 14. In particular embodiments, the engineered meganuclease can comprise the amino acid sequence of any one of SEQ ID NOs: 29-32.

In another embodiment, the pharmaceutical composition can comprise an engineered meganuclease disclosed herein (or a nucleic acid encoding the same) which recognizes and cleaves SEQ ID NO: 16. In particular embodiments, the engineered meganuclease can comprise the amino acid sequence of any one of SEQ ID NOs: 33-39.

In various embodiments, the pharmaceutical composition can comprise two or more engineered meganuclease proteins described herein, wherein the engineered meganucleases have specificity for different HBV recognition sequences described herein. In other embodiments, the pharmaceutical composition can comprise two or more nucleic acids encoding engineered meganucleases described herein, wherein the engineered meganucleases have specificity for different HBV recognition sequences described herein. In such embodiments, the two or more nucleic acids may be comprised by mRNAs described herein, recombinant DNA constructs described herein, and/or viral vectors described herein. In other embodiments, the pharmaceutical composition can comprise one or more engineered meganuclease proteins described herein and one or more nucleic acids encoding an engineered meganuclease described herein (i.e., mRNA, recombinant DNA construct, or viral vector), wherein the engineered meganucleases and encoded engineered meganucleases have specificity for different HBV recognition sequences described herein.

In further embodiments, the pharmaceutical composition can comprise a combination of engineered meganuclease proteins described herein, a combination of nucleic acids encoding engineered meganucleases described herein (i.e., mRNAs, recombinant DNA constructs, viral vectors), or a combination of engineered meganuclease proteins and nucleic acids encoding engineered meganuclease proteins, wherein the combination of engineered meganucleases and/or encoded engineered meganucleases in the pharmaceutical composition can recognize and cleave a recognition sequence in each of HBV genotypes A, B, C, D, E, F, and G (SEQ ID NOs: 3-9), and isolates of each genotype which comprise HBV recognition sequences described herein.

In some embodiments, the pharmaceutical composition can comprise one or more mRNAs described herein encapsulated within lipid nanoparticles. In particular embodiments, the lipid nanoparticles of the pharmaceutical composition can comprise two or more mRNAs described herein, each encoding an engineered meganuclease of the invention having specificity for a different HBV recognition sequence described herein. In specific embodiments, the lipid nanoparticles can comprise two, three, or four mRNAs described herein, each encoding an engineered meganuclease of the invention having specificity for a different HBV recognition sequence. In other embodiments, the lipid nanoparticles of the pharmaceutical composition can comprise one or more polycistronic mRNAs described herein, wherein each polycistronic mRNA encodes two or more engineered meganucleases of the invention having specificity for different HBV recognition sequences described herein. In particular embodiments, the lipid nanoparticles can comprise a polycistronic mRNA encoding two, three, or four engineered meganucleases described herein. In other particular embodiments, the lipid nanoparticles can comprise two or more polycistronic mRNAs described herein, each encoding two or more engineered meganucleases of the invention. In some embodiments, the lipid nanoparticles have a composition which enhances delivery and uptake in the liver, and specifically within hepatocytes.

In another aspect, the invention provides a method for treating a subject having HBV. Likewise, provided herein is a method for reducing the level and/or proliferation of HBV, or reducing the symptoms associated with HBV. The methods comprise delivering to a target cell in the subject: (a) a nucleic acid encoding an engineered meganuclease, wherein the engineered meganuclease is expressed in the target cell in vivo; or (b) an engineered meganuclease protein; wherein the engineered meganuclease has specificity for a recognition sequence in an ORF of the genome of at least two genotypes of the Hepatitis B virus, and wherein the engineered meganuclease recognizes and cleaves the recognition sequence, thus cleaving the HBV genome in the target cell. The method can reduce or eliminate the infection and/or proliferation of HBV in the subject.

In another aspect, the invention provides a method for treating a subject having HCC caused by HBV. The methods comprise delivering to a target cell in the subject: (1) (a) a nucleic acid encoding an engineered meganuclease, wherein the engineered meganuclease is expressed in the target cell in vivo; or (b) an engineered meganuclease protein; and (2) a nucleic acid comprising a polynucleotide sequence encoding a suicide gene and sequences homologous to sequences flanking the meganuclease cleavage site; wherein the engineered meganuclease has specificity for a recognition sequence in an ORF of the genome of at least two genotypes of the Hepatitis B virus, wherein the engineered meganuclease recognizes and cleaves the recognition sequence, thus cleaving the HBV genome in the target cell; wherein the suicide gene is inserted into the cleaved HBV genome by homologous recombination; and wherein expression of the suicide gene kills the target cell.

In some embodiments, the suicide gene is directly lethal to the target cell. In some such embodiments, the directly lethal suicide gene encodes a toxic polypeptide or a pro-apoptotic protein. In some embodiments, the suicide gene is indirectly lethal to the target cell, and directs the subject's own immune system to kill the target cell. In some such embodiments, the indirectly lethal suicide gene encodes a cell surface protein which is recognized as foreign by the subject's immune system and is targeted by a humoral or cellular immune response. In other such embodiments, the indirectly lethal suicide gene encodes a polypeptide which is presented by an MHC Class I molecule, is recognized as foreign by the subject's immune system, and is targeted by a cytotoxic immune response.

In some embodiments of the methods of treatment for HBV infection or HCC, the recognition sequence is found within an ORF of at least 3, at least 4, at least 5, or at least 6 genotypes of the Hepatitis B virus. In one such embodiment the recognition sequence is within an ORF of genotype A (SEQ ID NO: 3) of the Hepatitis B virus. Such an embodiment includes Hepatitis B virus isolates of genotype A which differ from SEQ ID NO: 3 but comprise one or more HBV meganuclease recognition sequences described herein. In further such embodiments, the recognition sequence is within an ORF of genotype A and one or more of genotypes B, C, D, E, F, and G (SEQ ID NOs: 4-9, respectively). Such embodiments include Hepatitis B virus isolates of genotype A, B, C, D, E, F, and G which differ from SEQ ID NOs: 3-9 but comprise one or more HBV meganuclease recognition sequences described herein.

In such embodiments of the methods of treatment for HBV infection or HCC, the recognition sequence can be within at least one ORF encoding a protein selected from the group consisting of: the polymerase (P) protein, the large surface (preS1/preS2/S) protein, the middle surface (preS2/S) protein, and the small surface (S) protein. In some embodiments, the recognition sequence can comprise SEQ ID NO: 10 (i.e., the HBV 1-2 recognition sequence), SEQ ID NO: 12 (i.e., the HBV 5-6 recognition sequence), SEQ ID NO: 14 (i.e., the HBV 7-8 recognition sequence), or SEQ ID NO: 16 (i.e., the HBV 11-12 recognition sequence).

In particular embodiments of the methods of treatment for HBV infection or HCC, the engineered meganuclease protein, or the encoded engineered meganuclease, is an engineered meganuclease described herein.

In further embodiments, the methods of treatment for HBV infection or HCC comprise administering to the subject any pharmaceutical composition of the invention described herein which comprises, at least, a pharmaceutically acceptable carrier and (a) a nucleic acid encoding an engineered meganuclease described herein, wherein the engineered meganuclease is expressed in a target cell in vivo; or (b) an engineered meganuclease protein described herein.

In some embodiments of the methods of treatment for HBV infection or HCC, the engineered meganuclease, or the nucleic acid encoding the engineered meganuclease, can be delivered to a target hepatocyte cell. In particular embodiments, an effective amount of the engineered meganuclease, or the nucleic acid encoding the engineered meganuclease, can be delivered to a target hepatocyte cell.

In particular embodiments, delivery to a hepatocyte cell occurs ex vivo, wherein an effective amount of the hepatocyte cells having been delivered the engineered meganuclease, or the nucleic acid encoding the engineered meganuclease, are administered to a subject.

In some embodiments, a hepatotoxic protein, or a nucleic acid or AAV encoding a hepatotoxic protein, is administered with the pharmaceutical compositions disclosed herein.

In particular embodiments of the methods, the first recognition sequence can comprise SEQ ID NO: 10. In some such embodiments, the engineered meganuclease can be any engineered meganuclease of the invention which recognizes and cleaves SEQ ID NO: 10. In particular embodiments, the engineered meganuclease can comprise the amino acid sequence of any one of SEQ ID NOs: 18-21.

In another embodiment of the methods, the first recognition sequence can comprise SEQ ID NO: 12. In some such embodiments, the engineered meganuclease can be any engineered meganuclease of the invention which recognizes and cleaves SEQ ID NO: 12. In particular embodiments, the engineered meganuclease can comprise the amino acid sequence of any one of SEQ ID NOs: 22-28.

In other embodiments of the methods, the first recognition sequence can comprise SEQ ID NO: 14. In some such embodiments, the engineered meganuclease can be any engineered meganuclease of the invention which recognizes and cleaves SEQ ID NO: 14. In particular embodiments, the engineered meganuclease can comprise the amino acid sequence of any one of SEQ ID NOs: 29-32.

In other embodiments of the methods, the first recognition sequence can comprise SEQ ID NO: 16. In some such embodiments, the engineered meganuclease can be any engineered meganuclease of the invention which recognizes and cleaves SEQ ID NO: 16. In particular embodiments, the engineered meganuclease can comprise the amino acid sequence of any one of SEQ ID NOs: 33-39.

In particular embodiments of the methods, the subject can be a mammal, such as a human.

In another aspect, the invention provides an engineered meganuclease described herein for use as a medicament. The invention further provides the use of an engineered meganuclease, described herein in the manufacture of a medicament for treating HBV, for reducing the level or proliferation of HBV, reducing the symptoms associated with HBV, or treating HCC.

In another aspect, the invention provides an isolated polynucleotide for use as a medicament, wherein the isolated polynucleotide comprises a nucleic acid sequence encoding an engineered meganuclease disclosed herein. The invention further provides the use of an isolated polynucleotide in the manufacture of a medicament for treating HBV, for reducing the level or proliferation of HBV, reducing the symptoms associated with HBV, or treating HCC.

In another aspect, the invention provides a recombinant AAV vector for use as a medicament, wherein the recombinant AAV vector comprises an isolated polynucleotide, and wherein the isolated polynucleotide comprises a nucleic acid sequence encoding an engineered meganuclease disclosed herein. The invention further provides the use of a recombinant AAV vector in the manufacture of a medicament for treating HBV, for reducing the level or proliferation of HBV, reducing the symptoms associated with HBV, or treating HCC, wherein the recombinant AAV vector comprises an isolated polynucleotide, and wherein the isolated polynucleotide comprises a nucleic acid sequence encoding an engineered meganuclease disclosed herein.

The foregoing and other aspects and embodiments of the present invention can be more fully understood by reference to the following detailed description and claims. Certain features of the invention, which are, for clarity, described in the context of separate embodiments, may also be provided in combination in a single embodiment. All combinations of the embodiments are specifically embraced by the present invention and are disclosed herein just as if each and every combination was individually and explicitly disclosed. Conversely, various features of the invention, which are, for brevity, described in the context of a single embodiment, may also be provided separately or in any suitable sub-combination. All sub-combinations of features listed in the embodiments are also specifically embraced by the present invention and are disclosed herein just as if each and every such sub-combination was individually and explicitly disclosed herein. Embodiments of each aspect of the present invention disclosed herein apply to each other aspect of the invention mutatis mutandis.

BRIEF DESCRIPTION OF THE FIGURES

FIG. 2. Engineered meganuclease recognition sequences in the HBV genome. A) Each recognition sequence targeted by an engineered meganuclease of the invention comprises two recognition half-sites. Each recognition half-site comprises 9 base pairs, separated by a 4 base pair central sequence. The HBV 1-2 recognition sequence (SEQ ID NO: 10) comprises two recognition half-sites referred to as HBV1 and HBV2. The HBV 5-6 recognition sequence (SEQ ID NO: 12) comprises two recognition half-sites referred to as HBV5 and HBV6. The HBV 7-8 recognition sequence (SEQ ID NO: 14) comprises two recognition half-sites referred to as HBV7 and HBV8. The HBV 11-12 recognition sequence (SEQ ID NO: 16) comprises two recognition half-sites referred to as HBV11 and HBV12.

FIG. 4. Alignment of HBV recognition sequences in HBV genotypes A-G. The recognition sequences targeted by the invention are conserved across multiple HBV genotypes. The HBV 1-2 recognition sequence spans residues 185-206 of HBV genotype A set forth in SEQ ID NO: 3, and this recognition sequence is fully conserved in genotypes B, C, E, F, and G. Genotype D comprises a single nucleotide difference of G to T at position −4 of the first half-site. The HBV 5-6 recognition sequence spans residues 742-763 of HBV genotype A set forth in SEQ ID NO: 3, and this recognition sequence is fully conserved in genotypes B, C, D, E, and G. Genotype F comprises a single nucleotide difference of G to C at position −3 of the first half-site. The HBV 7-8 recognition sequence spans residues 1183-1204 of HBV genotype A set forth in SEQ ID NO: 3, and this recognition sequence is fully conserved in genotypes B, C, D, F, and G. Genotype E comprises a single nucleotide difference of G to C at position −1 of the first half-site. The HBV 11-12 recognition sequence spans residues 1259-1280 of HBV genotype A set forth in SEQ ID NO: 3, and this recognition sequence is fully conserved in genotypes B, C, D, E, F, and G.

FIG. 7A shows meganucleases targeting the HBV 1-2 recognition sequence. FIG. 7B shows meganucleases targeting the HBV 5-6 recognition sequence. FIG. 7C shows meganucleases targeting the HBV 7-8 recognition sequence. FIG. 7D shows meganucleases targeting the HBV 11-12 recognition sequence.

FIG. 8. Efficiency of engineered meganucleases for recognizing and cleaving recognition sequences in an ORF of the genome of at least two genotypes of the Hepatitis B virus, gene in a CHO cell reporter assay. Engineered meganucleases set forth in SEQ ID NOs: 18-39 were engineered to target the HBV 1-2 recognition sequence (SEQ ID NO: 10), the HBV 5-6 recognition sequence (SEQ ID NO: 12), the HBV 7-8 recognition sequence (SEQ ID NO: 14), or the HBV 11-12 recognition sequence (SEQ ID NO: 16), and were screened for efficacy in the CHO cell reporter assay at multiple time points over 12 days after nucleofection. The results shown provide the percentage of GFP-expressing cells observed in each assay over the 12 day period of analysis, which indicates the efficacy of each meganuclease for cleaving a target recognition sequence or the CHO-23/24 recognition sequence as a function of time. FIG. 8A shows meganucleases targeting the HBV 1-2 recognition sequence. FIG. 8B shows meganucleases targeting the HBV 5-6 recognition sequence. FIG. 8C shows meganucleases targeting the HBV 7-8 recognition sequence. FIG. 8D shows meganucleases targeting the HBV 11-12 recognition sequence.

FIG. 9A shows plasmid pARCUS and plasmid pHBVa. FIG. 9B shows the number of colonies present on each selective plate, providing evidence of the ability of HBV meganucleases to cleave the pHBVa plasmid.

FIG. 12A shows HBsAg concentrations in cell culture medium. FIG. 12B shows extracellular HBV DNA copy numbers in cell culture medium. FIG. 12C shows intracellular HBV cccDNA copy numbers in cell lysates.

FIG. 13A shows that transduction with a lentivirus encoding an RFP had little impact on HBsAg expression at an MOI or 1.25, 2.5, or 5. FIG. 13B shows that transduction with a lentivirus encoding an RFP had little impact on HBeAg expression at an MOI or 1.25, 2.5, or 5. FIG. 13C shows that transduction with a lentivirus encoding an RFP had little impact on HBV DNA expression at an MOI or 1.25, 2.5, or 5.

FIG. 14. Evaluation of HBV meganucleases in HBV-infected primary human hepatocytes. Lentiviruses were generated that expressed either RFP, HBV 5-6x.33, or HBV 11-12x.26, and HBV-infected primary human hepatocytes were transduced to determine the impact of the meganucleases on HBsAg and HBeAg production. Primary human hepatocytes were seeded and 24 hours later infected with HBV. 1 day post-infection, the cells were washed and 24 hours later (day 2 post-infection) were transduced with either a lentivirus encoding RFP. HBV 5-6x.33, HBV 11-12x.26, or a 1:1 mixture of the lentiviruses encoding the HBV meganucleases. As an additional control, infected cells were treated with DMSO. Cell supernatants were harvested and medium was replaced on days 4, 8, 11, and 13 post-transduction. At each time point. HBsAg and HBeAg was measured in the cell supernatants by ELISA. FIG. 14A shows HBsAg in cell culture medium following transduction at an MOI of 2.5. FIG. 14B shows HBsAg in cell culture medium following transduction at an MOI of 1.25. FIG. 14C shows HBeAg in cell culture medium following transduction at an MOI of 2.5. FIG. 14D shows HBeAg in cell culture medium following transduction at an MOI of 1.25.

BRIEF DESCRIPTION OF THE SEQUENCES

Figure 1:
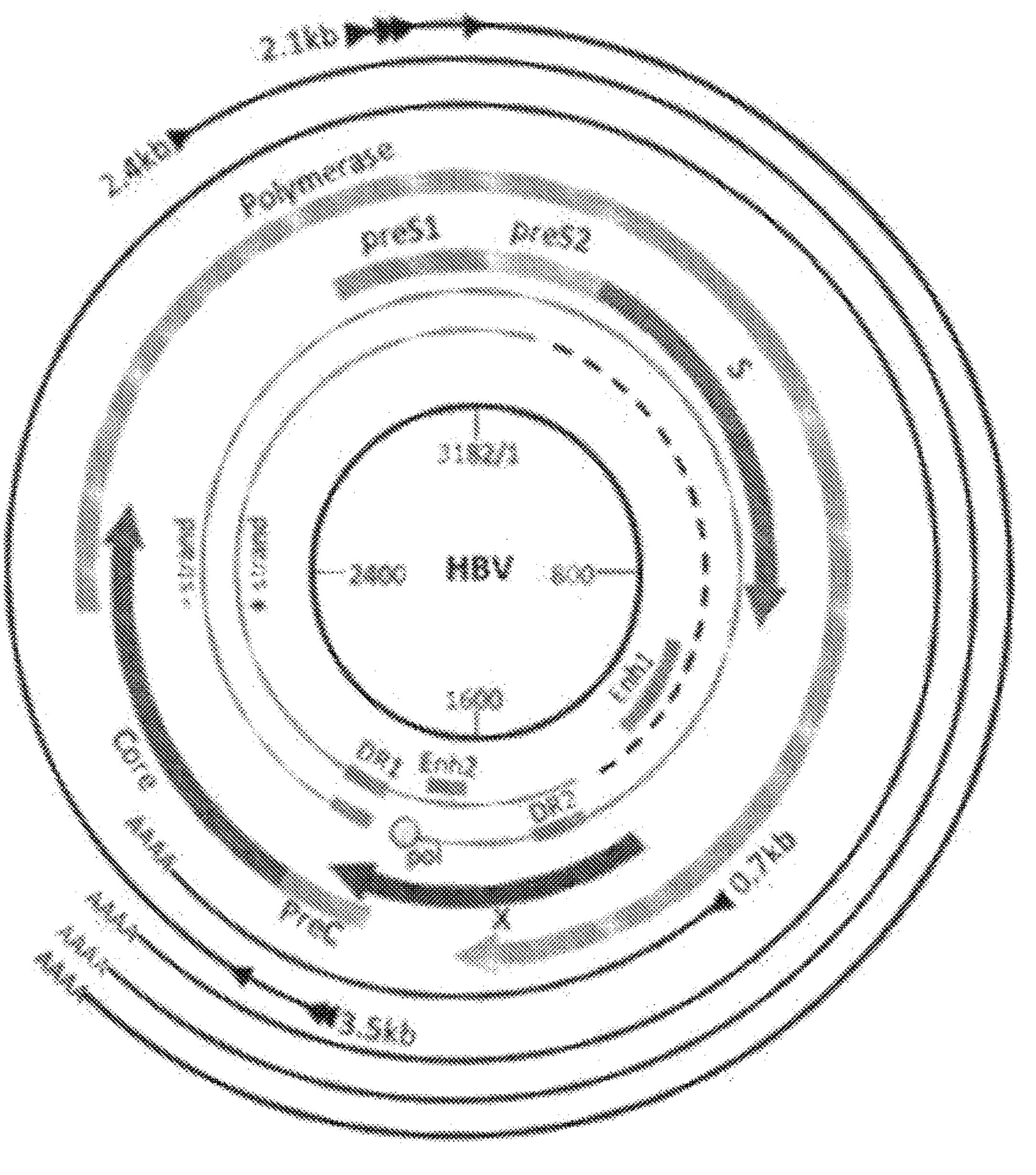
FIG. 1 shows a genomic map of the HBV genome and identifies all ORFs. Virus particles have a partially double-stranded genome (indicated by a dashed line) with a cohesive overlap that spans the 5' regions of each strand and that is flanked by direct repeat sequences (DR1 and DR2). The gene S encodes the major hepatitis B surface antigen (HBsAg) protein and its glycosylated partner, which are transmembrane proteins in the virus envelope. In-frame sequences upstream from the S gene encode the pre-S domains, which are translated with the S sequences to make the pre-S and S polypeptides (middle and large proteins) that contain the virus receptor for infection of hepatocytes. Gene C encodes the hepatitis B core antigen (HBcAg) which forms the nucleocapsid of the virus. The P region encodes the virus reverse transcriptase that also has DNA-dependent DNA polymerase activity and RNase H activity required for virus replication. Although HBV is a DNA virus, it replicates through a pre-genomic RNA intermediate. Finally, the X gene encodes the small regulatory protein of the virus, the hepatitis B x (HBx) antigen. HBx is a transactivating protein that stimulates virus gene expression and replication, protects virus-infected cells against immune-mediated destruction and contributes to the development of hepatocellular carcinoma.
Figure 3:
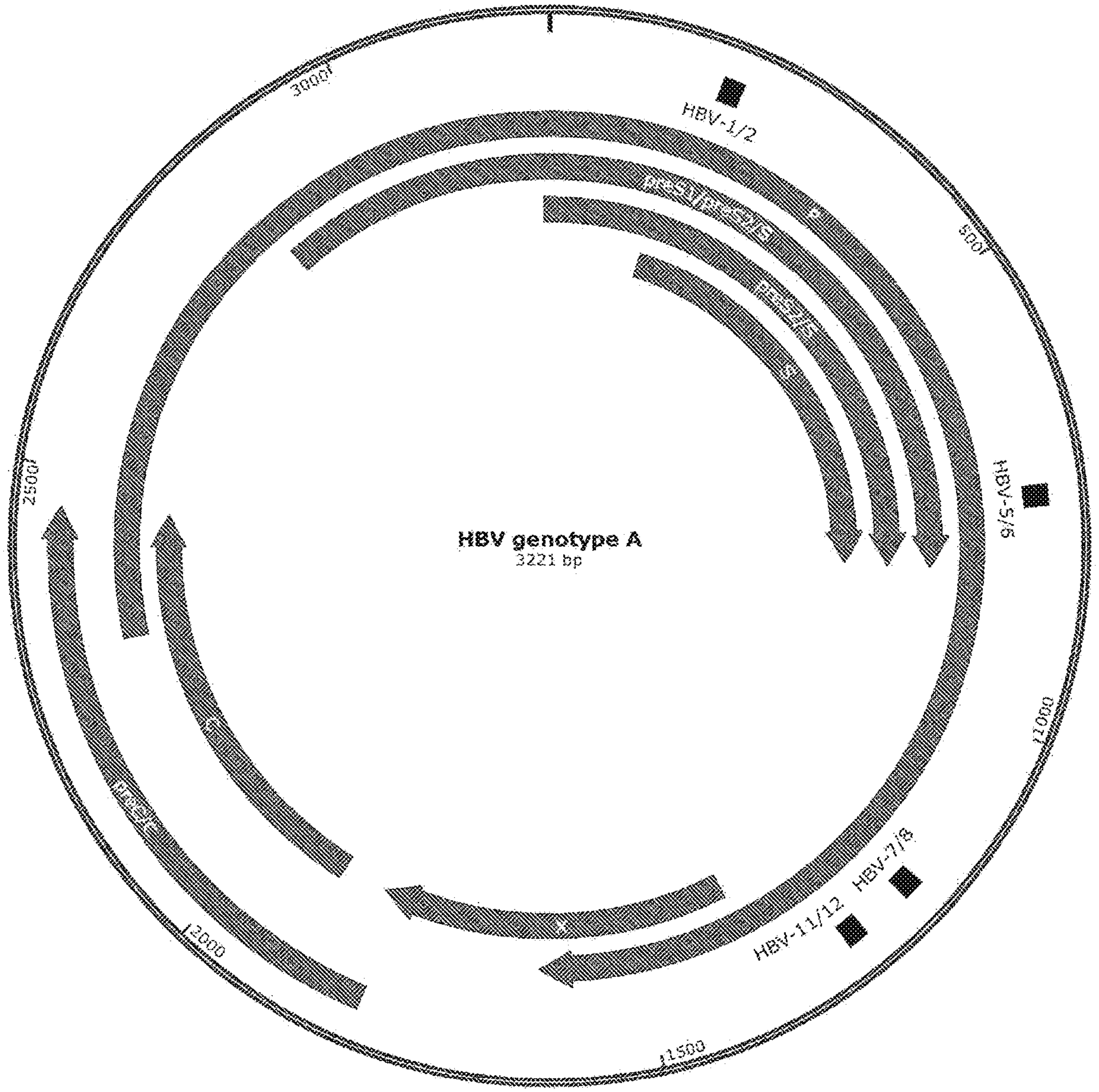
FIG. 3. Illustration of the genome of HBV genotype A and the position of the HBV 1-2, HBV 5-6, HBV 7-8, and HBV 11-12 recognition sequences within the genome. Both the HBV 1-2 and HBV 5-6 recognition sequences are positioned within four ORFs of the HBV genome: P, preS1/preS2/S, preS2/S, and S. The HBV 7-8 and HBV 11-12 recognition sequences are each positioned within the ORF encoding the polymerase.
Figure 5:
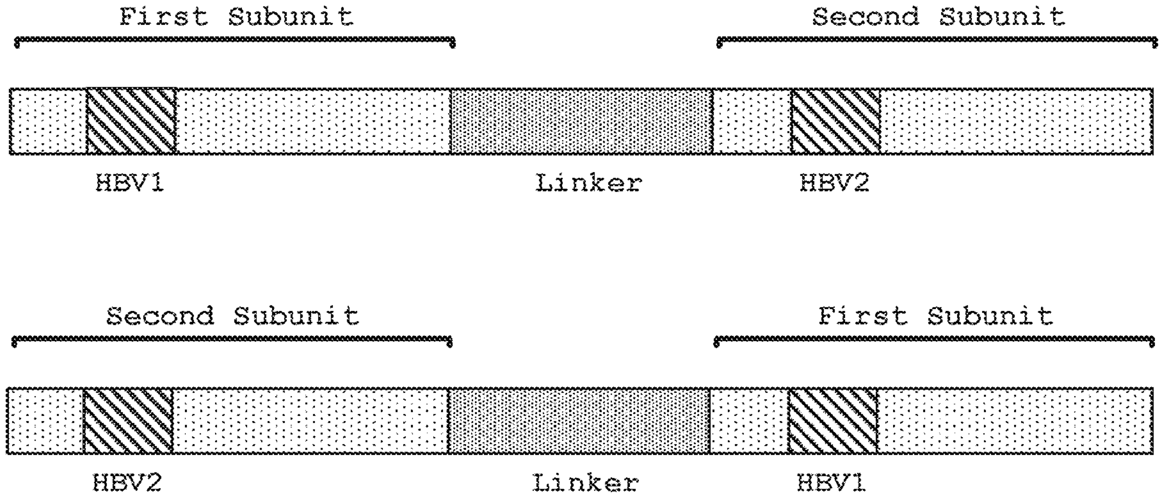
FIG. 5. The engineered meganucleases of the invention comprise two subunits, wherein the first subunit comprising the HVR1 region binds to a first recognition half-site (e.g., HBV1, HBV5, HBV7, or HBV 11) and the second subunit comprising the HVR2 region binds to a second recognition half-site (e.g., HBV2, HBV6, HBV8, or HBV 12). In embodiments where the engineered meganuclease is a single-chain meganuclease, the first subunit comprising the HVR1 region can be positioned as either the N-terminal or C-terminal subunit. Likewise, the second subunit comprising the HVR2 region can be positioned as either the N-terminal or C-terminal subunit.

SEQ ID NO: 1 sets forth the amino acid sequence of wild-type I-CreI meganuclease from *Chlamydomonas reinhardtii.*

SEQ ID NO: 2 sets forth the amino acid sequence of LAGLIDADG.

SEQ ID NO: 3 sets forth the amino acid sequence of HBV genotype A.

SEQ ID NO: 4 sets forth the amino acid sequence of HBV genotype B.

SEQ ID NO: 5 sets forth the amino acid sequence of HBV genotype C.

SEQ ID NO: 6 sets forth the amino acid sequence of HBV genotype D.

SEQ ID NO: 7 sets forth the amino acid sequence of HBV genotype E.

SEQ ID NO: 8 sets forth the amino acid sequence of HBV genotype F.

SEQ ID NO: 9 sets forth the amino acid sequence of HBV genotype G.

SEQ ID NO: 10 sets forth the amino acid sequence of the HBV 1-2 recognition sequence (sense).

SEQ ID NO: 11 sets forth the amino acid sequence of the HBV 1-2 recognition sequence (antisense).

SEQ ID NO: 12 sets forth the amino acid sequence of the HBV 5-6 recognition sequence (sense).

SEQ ID NO: 13 sets forth the amino acid sequence of the HBV 5-6 recognition sequence (antisense).

SEQ ID NO: 14 sets forth the amino acid sequence of the HBV 7-8 recognition sequence (sense).

SEQ ID NO: 15 sets forth the amino acid sequence of the HBV 7-8 recognition sequence (antisense).

SEQ ID NO: 16 sets forth the amino acid sequence of the HBV 11-12 recognition sequence (sense).

SEQ ID NO: 17 sets forth the amino acid sequence of the HBV 11-12 recognition sequence (antisense).

SEQ ID NO: 18 sets forth the amino acid sequence of the HBV 1-2x.2 meganuclease.

SEQ ID NO: 19 sets forth the amino acid sequence of the HBV 1-2x.14 meganuclease.

SEQ ID NO: 20 sets forth the amino acid sequence of the HBV 1-2x.68 meganuclease.

SEQ ID NO: 21 sets forth the amino acid sequence of the HBV 1-2x.93 meganuclease.

SEQ ID NO: 22 sets forth the amino acid sequence of the HBV 5-6x.33 meganuclease.

SEQ ID NO: 23 sets forth the amino acid sequence of the HBV 5-6x.84 meganuclease.

SEQ ID NO: 24 sets forth the amino acid sequence of the HBV 5-6x.90 meganuclease.

SEQ ID NO: 25 sets forth the amino acid sequence of the HBV 5-6x.4 meganuclease.

SEQ ID NO: 26 sets forth the amino acid sequence of the HBV 5-6x.5 meganuclease.

SEQ ID NO: 27 sets forth the amino acid sequence of the HBV 5-6x.68 meganuclease.

SEQ ID NO: 28 sets forth the amino acid sequence of the HBV 5-6x.79 meganuclease.

SEQ ID NO: 29 sets forth the amino acid sequence of the HBV 7-8x.2 meganuclease.

SEQ ID NO: 30 sets forth the amino acid sequence of the HBV 7-8x.9 meganuclease.

SEQ ID NO: 31 sets forth the amino acid sequence of the HBV 7-8x.17 meganuclease.

SEQ ID NO: 32 sets forth the amino acid sequence of the HBV 7-8x.44 meganuclease.

SEQ ID NO: 33 sets forth the amino acid sequence of the HBV 11-12x.26 meganuclease.

SEQ ID NO: 34 sets forth the amino acid sequence of the HBV 11-12x.9 meganuclease.

SEQ ID NO: 35 sets forth the amino acid sequence of the HBV 11-12x.13 meganuclease.

SEQ ID NO: 36 sets forth the amino acid sequence of the HBV 11-12x.16 meganuclease.

SEQ ID NO: 37 sets forth the amino acid sequence of the HBV 11-12x.27 meganuclease.

SEQ ID NO: 38 sets forth the amino acid sequence of the HBV 11-12x.41 meganuclease.

SEQ ID NO: 39 sets forth the amino acid sequence of the HBV 11-12x.48 meganuclease.

SEQ ID NO: 40 sets forth the amino acid sequence of the HBV 1-2x.2 meganuclease HBV-binding subunit.

SEQ ID NO: 41 sets forth the amino acid sequence of the HBV 1-2x.14 meganuclease HBV 1-binding subunit.

SEQ ID NO: 42 sets forth the amino acid sequence of the HBV 1-2x.68 meganuclease HBV 1-binding subunit.

SEQ ID NO: 43 sets forth the amino acid sequence of the HBV 1-2x.93 meganuclease HBV 1-binding subunit.

SEQ ID NO: 44 sets forth the amino acid sequence of the HBV 1-2x.2 meganuclease HBV2-binding subunit.

SEQ ID NO: 45 sets forth the amino acid sequence of the HBV 1-2x.14 meganuclease HBV2-binding subunit.

SEQ ID NO: 46 sets forth the amino acid sequence of the HBV 1-2x.68 meganuclease HBV2-binding subunit.

SEQ ID NO: 47 sets forth the amino acid sequence of the HBV 1-2x.93 meganuclease HBV2-binding subunit.

SEQ ID NO: 48 sets forth the amino acid sequence of the HBV 5-6x.33 meganuclease HBV5-binding subunit.

SEQ ID NO: 49 sets forth the amino acid sequence of the HBV 5-6x.84 meganuclease HBV5-binding subunit.

SEQ ID NO: 50 sets forth the amino acid sequence of the HBV 5-6x.90 meganuclease HBV5-binding subunit.

SEQ ID NO: 51 sets forth the amino acid sequence of the HBV 5-6x.4 meganuclease HBV5-binding subunit.

SEQ ID NO: 52 sets forth the amino acid sequence of the HBV 5-6x.5 meganuclease HBV5-binding subunit.

SEQ ID NO: 53 sets forth the amino acid sequence of the HBV 5-6x.68 meganuclease HBV5-binding subunit.

SEQ ID NO: 54 sets forth the amino acid sequence of the HBV 5-6x.79 meganuclease HBV5-binding subunit.

SEQ ID NO: 55 sets forth the amino acid sequence of the HBV 5-6x.33 meganuclease HBV6-binding subunit.

SEQ ID NO: 56 sets forth the amino acid sequence of the HBV 5-6x.84 meganuclease HBV6-binding subunit.

SEQ ID NO: 57 sets forth the amino acid sequence of the HBV 5-6x.90 meganuclease HBV6-binding subunit.

SEQ ID NO: 58 sets forth the amino acid sequence of the HBV 5-6x.4 meganuclease HBV6-binding subunit.

SEQ ID NO: 59 sets forth the amino acid sequence of the HBV 5-6x.5 meganuclease HBV6-binding subunit.

SEQ ID NO: 60 sets forth the amino acid sequence of the HBV 5-6x.68 meganuclease HBV6-binding subunit.

SEQ ID NO: 61 sets forth the amino acid sequence of the HBV 5-6x.79 meganuclease HBV6-binding subunit.

SEQ ID NO: 62 sets forth the amino acid sequence of the HBV 7-8x.2 meganuclease HBV7-binding subunit.

SEQ ID NO: 63 sets forth the amino acid sequence of the HBV 7-8x.9 meganuclease HBV7-binding subunit.

SEQ ID NO: 64 sets forth the amino acid sequence of the HBV 7-8x.17 meganuclease HBV7-binding subunit.

SEQ ID NO: 65 sets forth the amino acid sequence of the HBV 7-8x.44 meganuclease HBV7-binding subunit.

SEQ ID NO: 66 sets forth the amino acid sequence of the HBV 7-8x.2 meganuclease HBV8-binding subunit.

SEQ ID NO: 67 sets forth the amino acid sequence of the HBV 7-8x.9 meganuclease HBV8-binding subunit.

SEQ ID NO: 68 sets forth the amino acid sequence of the HBV 7-8x.17 meganuclease HBV8-binding subunit.

SEQ ID NO: 69 sets forth the amino acid sequence of the HBV 7-8x.44 meganuclease HBV8-binding subunit.

SEQ ID NO: 70 sets forth the amino acid sequence of the HBV 11-12x.26 meganuclease HBV1-binding subunit.

SEQ ID NO: 71 sets forth the amino acid sequence of the HBV 11-12x.9 meganuclease HBV 1-binding subunit.

SEQ ID NO: 72 sets forth the amino acid sequence of the HBV 11-12x.13 meganuclease HBV1-binding subunit.

SEQ ID NO: 73 sets forth the amino acid sequence of the HBV 11-12x.16 meganuclease HBV 1-binding subunit.

SEQ ID NO: 74 sets forth the amino acid sequence of the HBV 11-12x.27 meganuclease HBV 11-binding subunit.

SEQ ID NO: 75 sets forth the amino acid sequence of the HBV 11-12x.41 meganuclease HBV 11-binding subunit.

SEQ ID NO: 76 sets forth the amino acid sequence of the HBV 11-12x.48 meganuclease HBV 11-binding subunit.

SEQ ID NO: 77 sets forth the amino acid sequence of the HBV 11-12x.26 meganuclease HBV 12-binding subunit.

SEQ ID NO: 78 sets forth the amino acid sequence of the HBV 11-12x.9 meganuclease HBV 12-binding subunit.

SEQ ID NO: 79 sets forth the amino acid sequence of the HBV 11-12x.13 meganuclease HBV12-binding subunit.

SEQ ID NO: 80 sets forth the amino acid sequence of the HBV 11-12x.16 meganuclease HBV 12-binding subunit.

SEQ ID NO: 81 sets forth the amino acid sequence of the HBV 11-12x.27 meganuclease HBV 12-binding subunit.

SEQ ID NO: 82 sets forth the amino acid sequence of the HBV 11-12x.41 meganuclease HBV 12-binding subunit.

SEQ ID NO: 83 sets forth the amino acid sequence of the HBV 11-12x.48 meganuclease HBV 12-binding subunit.

SEQ ID NO: 84 sets forth the nucleic acid sequence of the recognition sequence present in HBV genotype D that corresponds to the HBV 1-2 recognition sequence in HBV genotype A with a G to C substitution at position −4 of the first half-site.

SEQ ID NO: 85 sets forth the nucleic acid sequence of the recognition sequence present in HBV genotype F that corresponds to the HBV 5-6 recognition sequence in HBV genotype A with a G to C substitution at position −3 of the first half-site.

SEQ ID NO: 86 sets forth the nucleic acid sequence of the recognition sequence present in HBV genotype E that corresponds to the HBV 7-8 recognition sequence in HBV genotype A with a C to T substitution at position −1 of the first half-site.

DETAILED DESCRIPTION OF THE INVENTION

1.1 References and Definitions

The patent and scientific literature referred to herein establishes knowledge that is available to those of skill in the art. The issued US patents, allowed applications, published foreign applications, and references, including GenBank database sequences, which are cited herein are hereby incorporated by reference to the same extent as if each was specifically and individually indicated to be incorporated by reference.

The present invention can be embodied in different forms and should not be construed as limited to the embodiments set forth herein. Rather, these embodiments are provided so that this disclosure will be thorough and complete, and will fully convey the scope of the invention to those skilled in the art. For example, features illustrated with respect to one embodiment can be incorporated into other embodiments, and features illustrated with respect to a particular embodiment can be deleted from that embodiment. In addition, numerous variations and additions to the embodiments suggested herein will be apparent to those skilled in the art in light of the instant disclosure, which do not depart from the instant invention.

Unless otherwise defined, all technical and scientific terms used herein have the same meaning as commonly understood by one of ordinary skill in the art to which this invention belongs. The terminology used in the description of the invention herein is for the purpose of describing particular embodiments only and is not intended to be limiting of the invention.

All publications, patent applications, patents, and other references mentioned herein are incorporated by reference herein in their entirety.

As used herein, "a," "an," or "the" can mean one or more than one. For example, "a" cell can mean a single cell or a multiplicity of cells.

As used herein, unless specifically indicated otherwise, the word "or" is used in the inclusive sense of "and/or" and not the exclusive sense of "either/or."

As used herein, the terms "nuclease" and "endonuclease" are used interchangeably to refer to naturally-occurring or engineered enzymes which cleave a phosphodiester bond within a polynucleotide chain.

As used herein, the term "meganuclease" refers to an endonuclease that binds double-stranded DNA at a recognition sequence that is greater than 12 base pairs. Preferably, the recognition sequence for a meganuclease of the invention is 22 base pairs. A meganuclease can be an endonuclease that is derived from I-CreI, and can refer to an engineered variant of I-CreI that has been modified relative to natural 1-CreI with respect to, for example, DNA-binding specificity, DNA cleavage activity, DNA-binding affinity, or dimerization properties. Methods for producing such modified variants of I-CreI are known in the art (e.g. WO 2007/047859). A meganuclease as used herein binds to double-stranded DNA as a heterodimer. A meganuclease may also be a "single-chain meganuclease" in which a pair of DNA-binding domains are joined into a single polypeptide using a peptide linker. The term "homing endonuclease" is synonymous with the term "meganuclease." Meganucleases of the invention are substantially non-toxic when expressed in cells without observing deleterious effects on cell viability or significant reductions in meganuclease cleavage activity when measured using the methods described herein.

As used herein, the term "single-chain meganuclease" refers to a polypeptide comprising a pair of nuclease subunits joined by a linker. A single-chain meganuclease has the organization: N-terminal subunit—Linker—C-terminal subunit. The two meganuclease subunits will generally be non-identical in amino acid sequence and will recognize non-identical DNA sequences. Thus, single-chain meganucleases typically cleave pseudo-palindromic or non-palindromic recognition sequences. A single-chain meganuclease may be referred to as a "single-chain heterodimer" or "single-chain heterodimeric meganuclease" although it is not, in fact, dimeric. For clarity, unless otherwise specified, the term "meganuclease" can refer to a dimeric or single-chain meganuclease.

As used herein, the term "linker" refers to an exogenous peptide sequence used to join two meganuclease subunits into a single polypeptide. A linker may have a sequence that is found in natural proteins, or may be an artificial sequence that is not found in any natural protein. A linker may be flexible and lacking in secondary structure or may have a propensity to form a specific three-dimensional structure under physiological conditions. A linker can include, without limitation, those encompassed by U.S. Pat. Nos. 8,445,251 and 9,434,931. In some embodiments, a linker may have an amino acid sequence comprising residues 154-195 of any one of SEQ ID NOs: 18-39.

As used herein, with respect to a protein, the term "recombinant" or "engineered" means having an altered amino acid sequence as a result of the application of genetic engineering techniques to nucleic acids which encode the protein, and cells or organisms which express the protein. With respect to a nucleic acid, the term "recombinant" or "engineered" means having an altered nucleic acid sequence as a result of the application of genetic engineering techniques. Genetic engineering techniques include, but are not limited to, PCR and DNA cloning technologies; transfection, transformation and other gene transfer technologies; homologous recombination; site-directed mutagenesis; and gene fusion. In accordance with this definition, a protein having an amino acid sequence identical to a naturally-occurring protein, but produced by cloning and expression in a heterologous host, is not considered recombinant.

As used herein, the term "wild-type" refers to the most common naturally occurring allele (i.e., polynucleotide sequence) in the allele population of the same type of gene, wherein a polypeptide encoded by the wild-type allele has its original functions. The term "wild-type" also refers a polypeptide encoded by a wild-type allele. Wild-type alleles (i.e., polynucleotides) and polypeptides are distinguishable from mutant or variant alleles and polypeptides, which comprise one or more mutations and/or substitutions relative to the wild-type sequence(s). Whereas a wild-type allele or polypeptide can confer a normal phenotype in an organism, a mutant or variant allele or polypeptide can, in some instances, confer an altered phenotype. Wild-type nucleases are distinguishable from recombinant or non-naturally-occurring nucleases. The term "wild-type" can also refer to a cell, an organism, and/or a subject which possesses a wild-type allele of a particular gene, or a cell, an organism, and/or a subject used for comparative purposes.

As used herein, the term "genetically-modified" refers to a cell or organism in which, or in an ancestor of which, a genomic DNA sequence has been deliberately modified by recombinant technology. As used herein, the term "genetically-modified" encompasses the term "transgenic."

As used herein with respect to recombinant proteins, the term "modification" means any insertion, deletion, or substitution of an amino acid residue in the recombinant sequence relative to a reference sequence (e.g., a wild-type or a native sequence).

As used herein, the term "recognition sequence" refers to a DNA sequence that is bound and cleaved by an endonuclease. In the case of a meganuclease, a recognition sequence comprises a pair of inverted, 9 basepair "half sites" which are separated by four basepairs. In the case of a single-chain meganuclease, the N-terminal domain of the protein contacts a first half-site and the C-terminal domain of the protein contacts a second half-site. Cleavage by a meganuclease produces four basepair 3' "overhangs". "Overhangs", or "sticky ends" are short, single-stranded DNA segments that can be produced by endonuclease cleavage of a double-stranded DNA sequence. In the case of meganucleases and single-chain meganucleases derived from 1-CreI, the overhang comprises bases 10-13 of the 22 basepair recognition sequence.

As used herein, the term "target site" or "target sequence" refers to a region of the chromosomal DNA of a cell comprising a recognition sequence for a nuclease.

As used herein, the term "DNA-binding affinity" or "binding affinity" means the tendency of a meganuclease to non-covalently associate with a reference DNA molecule (e.g., a recognition sequence or an arbitrary sequence). Binding affinity is measured by a dissociation constant, $K_d$. As used herein, a nuclease has "altered" binding affinity if the $K_d$ of the nuclease for a reference recognition sequence is increased or decreased by a statistically significant ($p<0.05$) amount relative to a reference nuclease.

As used herein, the term "specificity" means the ability of a meganuclease to recognize and cleave double-stranded DNA molecules only at a particular sequence of base pairs referred to as the recognition sequence, or only at a particular set of recognition sequences. The set of recognition sequences will share certain conserved positions or sequence motifs, but may be degenerate at one or more positions. A highly-specific meganuclease is capable of cleaving only one or a very few recognition sequences. Specificity can be determined by any method known in the art. As used herein, a meganuclease has "altered" specificity if it binds to and cleaves a recognition sequence which is not bound to and cleaved by a reference meganuclease (e.g., a wild-type) under physiological conditions, or if the rate of cleavage of a recognition sequence is increased or decreased by a biologically significant amount (e.g., at least 2×, or 2×-10×) relative to a reference meganuclease.

As used herein, the term "homologous recombination" or "HR" refers to the natural, cellular process in which a double-stranded DNA-break is repaired using a homologous DNA sequence as the repair template (see, e.g. Cahill et al. (2006), *Front. Biosci.* 11:1958-1976). The homologous DNA sequence may be an endogenous chromosomal sequence or an exogenous nucleic acid that was delivered to the cell.

As used herein, the term "non-homologous end-joining" or "NHEJ" refers to the natural, cellular process in which a double-stranded DNA-break is repaired by the direct joining of two non-homologous DNA segments (see, e.g. Cahill et al. (2006), *Front. Biosci.* 11:1958-1976). DNA repair by non-homologous end-joining is error-prone and frequently results in the untemplated addition or deletion of DNA sequences at the site of repair. In some instances, cleavage at a target recognition sequence results in NHEJ at a target recognition site. Nuclease-induced cleavage of a target site in the coding sequence of a gene followed by DNA repair by NHEJ can introduce mutations into the coding sequence, such as frameshift mutations, that disrupt gene function. Thus, engineered meganucleases can be used to effectively knock-out a gene in a population of cells.

As used herein with respect to both amino acid sequences and nucleic acid sequences, the terms "percent identity," "sequence identity," "percentage similarity," "sequence similarity" and the like refer to a measure of the degree of similarity of two sequences based upon an alignment of the sequences which maximizes similarity between aligned amino acid residues or nucleotides, and which is a function of the number of identical or similar residues or nucleotides, the number of total residues or nucleotides, and the presence and length of gaps in the sequence alignment. A variety of algorithms and computer programs are available for determining sequence similarity using standard parameters. As used herein, sequence similarity is measured using the BLASTp program for amino acid sequences and the BLASTn program for nucleic acid sequences, both of which are available through the National Center for Biotechnology Information (www.ncbi.nlm.nih.gov/), and are described in, for example, Altschul et al. (1990), *J. Mol. Biol.* 215:403-410; Gish and States (1993), *Nature Genet.* 3:266-272; Madden et al. (1996), *Meth. Enzymol.* 266:131-141; Altschul et al. (1997), *Nucleic Acids Res.* 25:33 89-3402); Zhang et al. (2000), *J. Comput. Biol.* 7(1-2):203-14. As used herein, percent similarity of two amino acid sequences is the score based upon the following parameters for the BLASTp algorithm: word size=3; gap opening penalty=−1; gap extension penalty=−1; and scoring matrix=BLOSUM62. As used herein, percent similarity of two nucleic acid sequences is the score based upon the following parameters for the BLASTn algorithm: word size=11; gap opening penalty=−5; gap extension penalty=−2; match reward=1; and mismatch penalty=−3.

As used herein with respect to modifications of two proteins or amino acid sequences, the term "corresponding to" is used to indicate that a specified modification in the first protein is a substitution of the same amino acid residue as in the modification in the second protein, and that the amino acid position of the modification in the first proteins corresponds to or aligns with the amino acid position of the modification in the second protein when the two proteins are subjected to standard sequence alignments (e.g., using the BLASTp program). Thus, the modification of residue "X" to amino acid "A" in the first protein will correspond to the modification of residue "Y" to amino acid "A" in the second protein if residues X and Y correspond to each other in a sequence alignment, and despite the fact that X and Y may be different numbers.

As used herein, the term "recognition half-site," "recognition sequence half-site," or simply "half-site" means a nucleic acid sequence in a double-stranded DNA molecule which is recognized by a monomer of a homodimeric or heterodimeric meganuclease, or by one subunit of a single-chain meganuclease.

As used herein, the term "hypervariable region" refers to a localized sequence within a meganuclease monomer or subunit that comprises amino acids with relatively high variability. A hypervariable region can comprise about 50-60 contiguous residues, about 53-57 contiguous residues, or preferably about 56 residues. In some embodiments, the residues of a hypervariable region may correspond to positions 24-79 or positions 215-270 of any one of SEQ ID NOs: 18-39. A hypervariable region can comprise one or more residues that contact DNA bases in a recognition sequence and can be modified to alter base preference of the monomer or subunit. A hypervariable region can also comprise one or more residues that bind to the DNA backbone when the meganuclease associates with a double-stranded DNA recognition sequence. Such residues can be modified to alter the binding affinity of the meganuclease for the DNA backbone and the target recognition sequence. In different embodiments of the invention, a hypervariable region may comprise between 1-20 residues that exhibit variability and can be modified to influence base preference and/or DNA-binding affinity. In some embodiments, variable residues within a hypervariable region correspond to one or more of positions 24, 26, 28, 30, 32, 33, 38, 40, 42, 44, 46, 49, 50, 54, 64, 68, 70, 75, and 77 of any one of SEQ ID NOs: 18-39. In other embodiments, variable residues within a hypervariable region correspond to one or more of positions 215, 217, 219, 221, 223, 224, 229, 231, 233, 235, 237, 240, 241, 245, 255, 259, 261, 266, and 268 of any one of SEQ ID NOs: 18-39.

The terms "recombinant DNA construct," "recombinant construct," "expression cassette," "expression construct," "chimeric construct," "construct," and "recombinant DNA fragment" are used interchangeably herein and are nucleic acid fragments. A recombinant construct comprises an artificial combination of nucleic acid fragments, including, without limitation, regulatory and coding sequences that are not found together in nature. For example, a recombinant DNA construct may comprise regulatory sequences and coding sequences that are derived from different sources, or regulatory sequences and coding sequences derived from the same source and arranged in a manner different than that found in nature. Such a construct may be used by itself or may be used in conjunction with a vector.

As used herein, a "vector" or "recombinant DNA vector" may be a construct that includes a replication system and sequences that are capable of transcription and translation of a polypeptide-encoding sequence in a given host cell. If a vector is used then the choice of vector is dependent upon the method that will be used to transform host cells as is well known to those skilled in the art. Vectors can include, without limitation, plasmid vectors and recombinant AAV vectors, or any other vector known in that art suitable for delivering a gene encoding a meganuclease of the invention to a target cell. The skilled artisan is well aware of the genetic elements that must be present on the vector in order to successfully transform, select and propagate host cells comprising any of the isolated nucleotides or nucleic acid sequences of the invention.

As used herein, a "vector" can also refer to a viral vector. Viral vectors can include, without limitation, retroviral vectors, lentiviral vectors, adenoviral vectors, and adeno-associated viral vectors (AAV).

As used herein, a "polycistronic" mRNA refers to a single messenger RNA which comprises two or more coding sequences (i.e., cistrons) and encodes more than one protein. A polycistronic mRNA can comprise any element known in the art to allow for the translation of two or more genes from the same mRNA molecule including, but not limited to, an IRES element, a T2A element, a P2A element, an E2A element, and an F2A element.

As used herein, a "control" or "control cell" refers to a cell that provides a reference point for measuring changes in genotype or phenotype of a genetically-modified cell. A control cell may comprise, for example: (a) a wild-type cell, i.e., of the same genotype as the starting material for the genetic alteration which resulted in the genetically-modified cell; (b) a cell of the same genotype as the genetically-modified cell but which has been transformed with a null construct (i.e., with a construct which has no known effect on the trait of interest); or, (c) a cell genetically identical to the genetically-modified cell but which is not exposed to conditions or stimuli or further genetic modifications that would induce expression of altered genotype or phenotype.

As used herein with respect to modifications of two proteins or amino acid sequences, the term "corresponding to" is used to indicate that a specified modification in the first protein is a substitution of the same amino acid residue as in the modification in the second protein, and that the amino acid position of the modification in the first proteins corresponds to or aligns with the amino acid position of the modification in the second protein when the two proteins are subjected to standard sequence alignments (e.g., using the BLASTp program). Thus, the modification of residue "X" to amino acid "A" in the first protein will correspond to the modification of residue "Y" to amino acid "A" in the second protein if residues X and Y correspond to each other in a sequence alignment, and despite the fact that X and Y may be different numbers.

As used herein, the terms "treatment" or "treating a subject" refers to the administration of an engineered meganuclease of the invention, or a nucleic acid encoding an engineered meganuclease of the invention, to a subject infected with HBV for the purpose of slowing or stopping the rate of HBV proliferation of the virus by cleaving the genome of at least one HBV particle. Such treatment reduces or prevents transfection and replication of HBV in the subject, and either partial or complete relief of one or more symptoms of HBV in the subject. Means to assess alleviation of symptoms of HBV infection may include measurement of liver functions by determining levels of the enzyme alanine aminotransferase (ALT) or by measuring sero conversion, namely disappearance of the HbeAg. Further, alleviation or reduction of symptoms of HBV can be determined by examining liver biopsies and measuring the level of tissue fibrosis by methods well known in the art. The number of circulating viral particles can be determined for example by measuring HBV DNA levels using PCR or by detecting HBsAg levels in the blood. The terms "treatment" or "treating a subject" can further refer to the administration of a cell (e.g., hepatocyte cell) comprising a nucleic acid encoding an engineered meganuclease, wherein the cell is delivered to a target tissue (e.g., liver) and produces the engineered meganuclease in an amount sufficient to treat an HBV infection in the subject, thereby resulting in either partial or complete relief of one or more symptoms of HBV. In some aspects, an engineered meganuclease of the invention, a nucleic acid encoding the same, or a genetically-modified cell of the invention is administered during treatment in the form of a pharmaceutical composition of the invention.

The term "Hepatitis B Virus infection" refers to any condition related to or resulting from infection with a Hepatitis B virus, such as chronic liver diseases/disorders, inflammations, fibrotic conditions and proliferative disorders, such as liver cancers. Chronic persistent HBV infection can cause fatigue, liver damage, cirrhosis of the liver, and hepatocellular carcinoma, a primary liver cancer.

The term "proliferating" and "proliferation" as used herein refer to HBV cells actively dividing and infecting human cells. Thus, reduction in proliferation refers to any decrease in the proliferation of HBV including reduction of at least 1%, 2%, 3%, 4%, 5%, 10%, 15%, 20%, 25%, 30%, 40%, 50%, 60%, 70%, 80%, 90%, 95%, or 100% when compared to an appropriate control not having been administered the engineered meganuclease, or nucleic acid encoding the engineered meganuclease, disclosed herein. Throughout this application, the term "proliferative disorder" refers to any disease/disorder marked by unwanted or aberrant proliferation of tissue. As used herein, the term "proliferative disorder" also refers to conditions in which the unregulated and/or abnormal growth of cells can lead to the development of an unwanted condition or disease, which can be cancerous or non-cancerous.

The term "effective amount" or "therapeutically effective amount" refers to an amount sufficient to effect beneficial or desirable biological and/or clinical results. The therapeutically effective amount will vary depending on the meganuclease formulation or composition, the disease and its severity and the age, weight, physical condition and responsiveness of the subject to be treated. In specific embodiments, an effective amount of the engineered meganuclease or pharmaceutical compositions disclosed herein reduces the level or proliferation of HBV or reduces at least one symptom of HBV in a subject with an HBV infection.

The term "lipid nanoparticle" refers to a lipid composition having a typically spherical structure with an average diameter between 10 and 1000 nanometers. In some formulations, lipid nanoparticles can comprise at least one cationic lipid, at least one non-cationic lipid, and at least one conjugated lipid. Lipid nanoparticles known in the art that are suitable for encapsulating nucleic acids, such as mRNA, are contemplated for use in the invention.

As used herein, the recitation of a numerical range for a variable is intended to convey that the invention may be practiced with the variable equal to any of the values within that range. Thus, for a variable which is inherently discrete, the variable can be equal to any integer value within the numerical range, including the end-points of the range. Similarly, for a variable which is inherently continuous, the variable can be equal to any real value within the numerical range, including the end-points of the range. As an example, and without limitation, a variable which is described as having values between 0 and 2 can take the values 0, 1 or 2 if the variable is inherently discrete, and can take the values 0.0, 0.1, 0.01, 0.001, or any other real values ≥20 and ≤2 if the variable is inherently continuous.

2.1 Principle of the Invention

The present invention is based, in part, on the hypothesis that engineered meganucleases can be used to reduce the level of HBV or slow the proliferation of HBV by cleaving an ORF within the HBV genome. More specifically, meganucleases can be engineered to recognize and cleave a recognition sequence present within the genome of multiple HBV genotypes. Thus, a single engineered meganuclease can be used to reduce the level or proliferation of HBV, or reduce the symptoms of an HBV infection, of multiple genotypes of the Hepatitis B virus.

Thus, the present invention encompasses engineered meganucleases which recognize and cleave a recognition sequence within an ORF of at least 2 genotypes of the HBV genome. The present invention also encompasses methods of using such engineered meganucleases in a pharmaceutical composition and in methods for treating HBV infection. Further, the invention encompasses pharmaceutical compositions comprising engineered meganuclease proteins, or nucleic acids encoding engineered meganucleases, and the use of such compositions for the treatment of HBV infection.

2.2 Meganucleases for Recognizing and Cleaving Recognition Sequences within the Genome of HBV It is known in the art that it is possible to use a site-specific nuclease to make a DNA break in the genome of a virus, and that such a DNA break can result in permanent modification of the genome via NHEJ such that the HBV virion can no longer divide or infect human cells. Thus, in one embodiment, the invention can be practiced using engineered recombinant meganucleases.

In preferred embodiments, the nucleases used to practice the invention are single-chain meganucleases. A single-chain meganuclease comprises an N-terminal subunit and a C-terminal subunit joined by a linker peptide. Each of the two domains recognizes half of the recognition sequence (i.e., a recognition half-site) and the site of DNA cleavage is at the middle of the recognition sequence near the interface of the two subunits. DNA strand breaks are offset by four base pairs such that DNA cleavage by a meganuclease generates a pair of four base pair, 3' single-strand overhangs.

In some examples, engineered meganucleases of the invention have been engineered to recognize and cleave the HBV 1-2 recognition sequence (SEQ ID NO: 10). The HBV 1-2 recognition sequence is positioned within the P protein, S, preS2/S. and preS1/preS2 ORFs of multiple HBV genotypes. The HBV 1-2 recognition sequence can at least be found in the genome of multiple HBV genotypes including genotype A, B, C, E, F. and G (e.g., SEQ ID NOs: 3-5 and 7-9, respectively). Such engineered meganucleases are collectively referred to herein as "HBV 1-2 meganucleases." Exemplary HBV 1-2 meganucleases are provided in SEQ ID NOs: 18-21.

In additional examples, engineered meganucleases of the invention have been engineered to recognize and cleave the HBV 5-6 recognition sequence (SEQ ID NO: 12). The HBV 5-6 recognition sequence is positioned within the P protein. S, preS2S. and preS1/preS2 ORFs of multiple HBV genotypes. The HBV 5-6 recognition sequence can at least be found in the genome of multiple HBV genotypes including genotype A, B, C, D, E, and G (e.g., SEQ ID NOs: 3-7 and 9, respectively). Such engineered meganucleases are collectively referred to herein as "HBV 5-6 meganucleases." Exemplary HBV 5-6 meganucleases are provided in SEQ ID NOs: 22-28.

In additional examples, engineered meganucleases of the invention have been engineered to recognize and cleave the HBV 7-8 recognition sequence (SEQ ID NO: 14). The HBV 7-8 recognition sequence is positioned within the P protein ORF of multiple HBV genotypes. The HBV 7-8 recognition sequence can at least be found in the genome of multiple HBV genotypes including genotype A, B, C, D, F, and G (e.g., SEQ ID NOs: 3-6, 8, and 9, respectively). Such engineered meganucleases are collectively referred to herein as "HBV 7-8 meganucleases." Exemplary HBV 7-8 meganucleases are provided in SEQ ID NOs: 29-32.

In additional examples, engineered meganucleases of the invention have been engineered to recognize and cleave the HBV 11-12 recognition sequence (SEQ ID NO: 16). The HBV 11-12 recognition sequence is positioned within the P protein ORF of multiple HBV genotypes. The HBV 11-12 recognition sequence can at least be found in the genome of multiple HBV genotypes including genotype A, B, C, D, E. F. and G (e.g., SEQ ID NOs: 3-9, respectively). Such engineered meganucleases are collectively referred to herein as "HBV 11-12 meganucleases." Exemplary HBV 11-12 meganucleases are provided in SEQ ID NOs: 34-40.

Engineered meganucleases of the invention comprise a first subunit, comprising a first hypervariable (HVR1) region, and a second subunit, comprising a second hypervariable (HVR2) region. Further, the first subunit binds to a first recognition half-site in the recognition sequence (e.g., the HBV1, HBV5. HBV7, or HBV11 half-site), and the second subunit binds to a second recognition half-site in the recognition sequence (e.g., the HBV2, HBV6, HBV8, or HBV 12 half-site). In embodiments where the engineered meganuclease is a single-chain meganuclease, the first and second subunits can be oriented such that the first subunit, which comprises the HVR1 region and binds the first half-site, is positioned as the N-terminal subunit, and the second subunit, which comprises the HVR2 region and binds the second half-site, is positioned as the C-terminal subunit. In alternative embodiments, the first and second subunits can be oriented such that the first subunit, which comprises the HVR1 region and binds the first half-site, is positioned as the C-terminal subunit, and the second subunit, which comprises the HVR2 region and binds the second half-site, is positioned as the N-terminal subunit. Exemplary HBV 1-2 meganucleases of the invention are provided in Table 1. Exemplary HBV 5-6 meganucleases of the invention are provided in Table 2. Exemplary HBV 7-8 meganucleases of the invention are provided in Table 3. Exemplary HBV 11-12 meganucleases of the invention are provided in Table 4.

TABLE 1

Exemplary engineered meganucleases engineered to recognize and cleave the HBV 1-2 recognition sequence (SEQ ID NO: 10)

| Meganuclease | AA SEQ ID | HBV1 Subunit Residues | HBV1 Subunit SEQ ID | *HBV1 Subunit % | HBV2 Subunit Residues | HBV2 Subunit SEQ ID | *HBV2 Subunit % |
|---|---|---|---|---|---|---|---|
| HBV 1-2x.2 | 18 | 7-153 | 40 | 100 | 198-344 | 44 | 100 |
| HBV 1-2x.14 | 19 | 7-153 | 41 | 93.2 | 198-344 | 45 | 91.16 |
| HBV 1-2x.68 | 20 | 198-344 | 42 | 93.2 | 7-153 | 46 | 91.16 |
| HBV 1-2x.93 | 21 | 198-344 | 43 | 100 | 7-153 | 47 | 95.92 |

*"HBV1 Subunit %" and "HBV2 Subunit %" represent the amino acid sequence identity between the HBV1-binding and HBV2-binding subunit regions of each meganuclease and the HBV1-binding and HBV2-binding subunit regions, respectively, of the HBV 1-2x.2 meganuclease.

TABLE 2

Exemplary engineered meganucleases engineered to recognize and cleave the HBV 5-6 recognition sequence (SEQ ID NO: 12)

| Meganuclease | AA SEQ ID | HBV5 Subunit Residues | HBV5 Subunit SEQ ID | *HBV5 Subunit % | HBV6 Subunit Residues | HBV6 Subunit SEQ ID | *HBV6 Subunit % |
|---|---|---|---|---|---|---|---|
| HBV 5-6x.33 | 22 | 198-344 | 48 | 100 | 7-153 | 55 | 100 |
| HBV 5-6x.84 | 23 | 198-344 | 49 | 93.2 | 7-153 | 56 | 92.52 |
| HBV 5-6x.90 | 24 | 198-344 | 50 | 91.84 | 7-153 | 57 | 93.2 |
| HBV 5-6x.4 | 25 | 7-153 | 51 | 92.52 | 198-344 | 58 | 95.92 |
| HBV 5-6x 5 | 26 | 7-153 | 52 | 92.52 | 198-344 | 59 | 93.88 |
| HBV 5-6x.68 | 27 | 7-153 | 53 | 91.16 | 198-344 | 60 | 93.88 |
| HBV 5-6x.79 | 28 | 7-153 | 54 | 93.2 | 198-344 | 61 | 93.88 |

*"HBV5 Subunit %" and "HBV6 Subunit %" represent the amino acid sequence identity between the HBV5-binding and HBV6-binding subunit regions of each meganuclease and the HBV 5-binding and HBV6-binding subunit regions, respectively, of the HBV 5-6x.33 meganuclease.

TABLE 3

Exemplary engineered meganucleases engineered to recognize and cleave the HBV 7-8 recognition sequence (SEQ ID NO: 14)

| Meganuclease | AA SEQ ID | HBV7 Subunit Residues | HBV7 Subunit SEQ ID | *HBV7 Subunit % | HBV8 Subunit Residues | HBV8 Subunit SEQ ID | *HBV8 Subunit % |
|---|---|---|---|---|---|---|---|
| HBV 7-8x.2 | 29 | 198-344 | 62 | 100 | 7-153 | 66 | 100 |
| HBV 7-8x.9 | 30 | 198-344 | 63 | 98.64 | 7-153 | 67 | 99.32 |
| HBV 7-8x.17 | 31 | 198-344 | 64 | 98.64 | 7-153 | 68 | 99.32 |
| HBV 7-8x.44 | 32 | 198-344 | 65 | 96.6 | 7-153 | 69 | 99.32 |

*"HBV7 Subunit %" and "HBV8 Subunit %" represent the amino acid sequence identity between the HBV7-binding and HBV8-binding subunit regions of each meganuclease and the HBV7-binding and HBV8-binding subunit regions, respectively, of the HBV 7-8x.2 meganuclease.

TABLE 4

Exemplary engineered meganucleases engineered to recognize and cleave the HBV 11-12 recognition sequence (SEQ ID NO: 16)

| Meganuclease | AA SEQ ID | HBV11 Subunit Residues | HBV11 Subunit SEQ ID | *HBV11 Subunit % | HBV12 Subunit Residues | HBV12 Subunit SEQ ID | *HBV12 Subunit % |
|---|---|---|---|---|---|---|---|
| HBV 11-12x.26 | 33 | 198-344 | 70 | 100 | 7-153 | 77 | 100 |
| HBV 11-12x.9 | 34 | 198-344 | 71 | 93.2 | 7-153 | 78 | 93.88 |
| HBV 11-12x.13 | 35 | 198-344 | 72 | 93.88 | 7-153 | 79 | 93.88 |
| HBV 11-12x.16 | 36 | 198-344 | 73 | 95.92 | 7-153 | 80 | 95.92 |
| HBV 11-12x.27 | 37 | 198-344 | 74 | 100 | 7-153 | 81 | 93.2 |
| HBV 11-12x.41 | 38 | 198-344 | 75 | 95.92 | 7-153 | 82 | 93.2 |
| HBV 11-12x.48 | 39 | 198-344 | 76 | 93.88 | 7-153 | 83 | 93.2 |

*"HBV11 Subunit %" and "HBV12 Subunit %" represent the amino acid sequence identity between the HBV11-binding and HBV12-binding subunit regions of each meganuclease and the HBV11-binding and HBV12-binding subunit regions, respectively, of the HBV 11-12x.26 meganuclease.

2.3 Methods for Delivering and Expressing Endonucleases

Disclosed herein are methods for treating an HBV infection or HCC in a subject. Likewise, methods are provided for reducing the symptoms of an HBV infection and reducing the amount of HBV, reducing the rate of proliferation of HBV or treating HCC in a subject comprising administering a pharmaceutical composition comprising a pharmaceutically acceptable carrier and an engineered meganuclease disclosed herein (or a nucleic acid encoding the engineered meganuclease). In the methods of the invention an engineered meganuclease disclosed herein can be delivered to and/or expressed from DNA/RNA in target cells that can provide the engineered meganuclease to the HBV genome.

Engineered meganucleases disclosed herein can be delivered into a cell in the form of protein or, preferably, as a nucleic acid encoding the engineered meganuclease. Such nucleic acid can be DNA (e.g., circular or linearized plasmid DNA or PCR products) or RNA (e.g., mRNA). For embodiments in which the engineered meganuclease coding sequence is delivered in DNA form, it should be operably linked to a promoter to facilitate transcription of the nuclease gene. Mammalian promoters suitable for the invention include constitutive promoters such as the cytomegalovirus early (CMV) promoter (Thomsen et al. (1984), *Proc Natl Acad Sci USA.* 81(3):659-63) or the SV40 early promoter (Benoist and Chambon (1981), *Nature.* 290(5804):304-10) as well as inducible promoters such as the tetracycline-inducible promoter (Dingermann et al. (1992). *Mol Cell Biol.* 12(9):4038-45). An engineered meganuclease of the invention can also be operably linked to a synthetic promoter. Synthetic promoters can include, without limitation, the JeT promoter (WO 2002/012514). In specific embodiments, a nucleic acid sequence encoding an engineered meganuclease as disclosed herein can be operably linked to a liver-specific promoter. Examples of liver-specific promoters include, without limitation, human alpha-1 antitrypsin promoter and apolipoprotein A-II promoter.

In specific embodiments, a nucleic acid sequence encoding at least one engineered meganuclease is delivered on a recombinant DNA construct or expression cassette. For example, the recombinant DNA construct can comprise an expression cassette (i.e., "cassette") comprising a promoter and a nucleic acid sequence encoding an engineered meganuclease described herein. In other embodiments, the recombinant DNA construct comprises two or more cassettes, wherein each cassette comprises a promoter and a nucleic acid sequence encoding an engineered meganuclease described herein, and wherein each engineered meganuclease has specificity for a different HBV recognition sequence disclosed herein. In particular embodiments, the recombinant DNA construct can comprise two cassettes, three cassettes, four cassettes, or more. For example, a cassette or combination of cassettes can encode any number or combination of an HBV 1-2 meganuclease, an HBV 5-6 meganuclease, an HBV 7-8 meganuclease, and an HBV 11-12 meganuclease. In some embodiments, a single cassette can encode an HBV 1-2 meganuclease, an HBV 5-6 meganuclease, an HBV 7-8 meganuclease, and an HBV 11-12 meganuclease. In another particular embodiment, a cassette or combination of cassettes can encode an HBV 5-6 meganuclease and an HBV 11-12 meganuclease.

In other embodiments, the recombinant DNA construct comprises a cassette comprising a promoter and a polycistronic nucleic acid sequence, wherein the promoter drives expression of the polycistronic nucleic acid sequence to generate a polycistronic mRNA described herein in a target cell.

In some embodiments, mRNA encoding an engineered meganuclease is delivered to a cell because this reduces the likelihood that the gene encoding the engineered meganuclease will integrate into the genome of the cell. Such mRNA encoding an engineered meganuclease can be produced using methods known in the art such as in vitro transcription. In some embodiments, the mRNA is capped using 7-methyl-guanosine. In some embodiments, the mRNA may be polyadenylated.

In particular embodiments, an mRNA encoding an engineered nuclease of the invention can be a polycistronic mRNA encoding two or more nucleases which are simultaneously expressed in a cell. In some embodiments, a polycistronic mRNA can encode two or more meganucleases described herein which target different recognition sequences in the HBV genome, such that the HBV genome is cleaved at multiple sites. In some embodiments, a polycistronic mRNA can encode two or more meganucleases described herein and at least one additional protein which induces a therapeutically beneficial effect in the cell. A polycistronic mRNA of the invention can comprise any element known in the art to allow for the translation of two or more genes from the same mRNA molecule including, but not limited to, an IRES element, a T2A element, a P2A element, an E2A element, and an F2A element. In particular embodiments, the polycistronic mRNA is a bicistronic mRNA encoding two meganucleases described herein, a tricistronic mRNA encoding three meganucleases described herein, or a quadcistronic mRNA encoding four meganucleases described herein, wherein the nucleases encoded by each mRNA have specificity for different recognition sequences in the HBV genome. For example, a polycistronic mRNA can encode any number or combination of an HBV 1-2 meganuclease, an HBV 5-6 meganuclease, an HBV 7-8 meganuclease, and an HBV 11-12 meganuclease. In some embodiments, a polycistronic mRNA can encode an HBV 1-2 meganuclease, an HBV 5-6 meganuclease, an HBV 7-8 meganuclease, and an HBV 11-12 meganuclease. In another particular embodiment, a polycistronic mRNA can be a bicistronic mRNA encoding an HBV 5-6 meganuclease and an HBV 11-12 meganuclease.

In another particular embodiment, a nucleic acid encoding an endonuclease of the invention can be introduced into the cell using a single-stranded DNA template. The single-stranded DNA can further comprise a 5' and/or a 3' AAV inverted terminal repeat (ITR) upstream and/or downstream of the sequence encoding the engineered meganuclease. In other embodiments, the single-stranded DNA can further comprise a 5' and/or a 3' homology arm upstream and/or downstream of the sequence encoding the engineered meganuclease.

In another particular embodiment, genes encoding an endonuclease of the invention can be introduced into a cell using a linearized DNA template. In some examples, a plasmid DNA encoding an endonuclease can be digested by one or more restriction enzymes such that the circular plasmid DNA is linearized prior to being introduced into a cell.

Purified nuclease proteins can be delivered into cells to cleave genomic DNA by a variety of different mechanisms known in the art, including those further detailed herein below.

The target tissue(s) for delivery of engineered meganucleases of the invention include, without limitation, cells of the liver, such as a hepatocyte cell or preferably a primary hepatocyte, more preferably a human hepatocyte or a human primary hepatocyte, a HepG2.2.15 or a HepG2-hNTCP cell. As discussed, meganucleases of the invention can be delivered as purified protein or as RNA or DNA encoding the meganuclease. In one embodiment, meganuclease proteins, or mRNA, or DNA vectors encoding endonucleases, are supplied to target cells (e.g., cells in the liver) via injection directly to the target tissue. Alternatively, endonuclease protein, mRNA, or DNA can be delivered systemically via the circulatory system.

In some embodiments, endonuclease proteins, or DNA/mRNA encoding endonucleases, are formulated for systemic administration, or administration to target tissues, in a pharmaceutically acceptable carrier in accordance with known techniques. See, e.g., Remington, *The Science And Practice of Pharmacy* ($21^{st}$ ed. 2005). In the manufacture of a pharmaceutical formulation according to the invention, proteins/RNA/mRNA are typically admixed with a pharmaceutically acceptable carrier. The carrier must, of course, be acceptable in the sense of being compatible with any other ingredients in the formulation and must not be deleterious to the patient. The carrier can be a solid or a liquid, or both, and can be formulated with the compound as a unit-dose formulation.

In some embodiments, endonuclease proteins, or DNA/mRNA encoding the endonuclease, are coupled to a cell penetrating peptide or targeting ligand to facilitate cellular uptake. Examples of cell penetrating peptides known in the art include poly-arginine (Jearawiriyapaisarn, et al. (2008) *Mol Ther.* 16:1624-9), TAT peptide from the HIV virus (Hudecz et al. (2005). *Med. Res. Rev.* 25: 679-736), MPG (Simeoni, et al. (2003) *Nucleic Acids Res.* 31:2717-2724), Pep-1 (Deshayes et al. (2004) *Biochemistry* 43: 7698-7706, and HSV-1 VP-22 (Deshayes et al. (2005) *Cell Mol Life Sci.* 62:1839-49. In an alternative embodiment, endonuclease proteins, or DNA/mRNA encoding endonucleases, are coupled covalently or non-covalently to an antibody that recognizes a specific cell-surface receptor expressed on target cells such that the endonuclease protein/DNA/mRNA binds to and is internalized by the target cells. Alternatively, endonuclease protein/DNA/mRNA can be coupled covalently or non-covalently to the natural ligand (or a portion of the natural ligand) for such a cell-surface receptor. (McCall, et al. (2014) *Tissue Barriers.* 2(4):e944449; Dinda, et al. (2013) *Curr Pharm Biotechnol.* 14:1264-74; Kang, et al. (2014) *Curr Pharm Biotechnol.* 15(3):220-30; Qian et al. (2014) *Erpert Opin Drug Metab Toxicol.* 10(11):1491-508).

In some embodiments, endonuclease proteins, or DNA/mRNA encoding endonucleases, are encapsulated within biodegradable hydrogels for injection or implantation within the desired region of the liver (e.g., in proximity to hepatic sinusoidal endothelial cells or hematopoietic endothelial cells, or progenitor cells which differentiate into the same). Hydrogels can provide sustained and tunable release of the therapeutic payload to the desired region of the target tissue without the need for frequent injections, and stimuli-responsive materials (e.g., temperature- and pH-responsive hydrogels) can be designed to release the payload in response to environmental or externally applied cues (Kang Derwent et al. (2008) *Trans Am Ophthalmol Soc.* 106:206-214).

In some embodiments, endonuclease proteins, or DNA/mRNA encoding endonucleases, are coupled covalently or, preferably, non-covalently to a nanoparticle or encapsulated within such a nanoparticle using methods known in the art (Sharma, et al. (2014) *Biomed Res Int.* 2014). A nanoparticle is a nanoscale delivery system whose length scale is <1 μm, preferably <100 nm. Such nanoparticles may be designed using a core composed of metal, lipid, polymer, or biological macromolecule, and multiple copies of the endonuclease proteins, mRNA, or DNA can be attached to or encapsulated with the nanoparticle core. This increases the copy number of the protein/mRNA/DNA that is delivered to each cell and, so, increases the intracellular expression of each endonuclease to maximize the likelihood that the target recognition sequences will be cut. The surface of such nanoparticles may be further modified with polymers or lipids (e.g., chitosan, cationic polymers, or cationic lipids) to form a core-shell nanoparticle whose surface confers additional functionalities to enhance cellular delivery and uptake of the payload (Jian et al. (2012) *Biomaterials.* 33(30): 7621-30). Nanoparticles may additionally be advantageously coupled to targeting molecules to direct the nanoparticle to the appropriate cell type and/or increase the likelihood of cellular uptake. Examples of such targeting molecules include antibodies specific for cell-surface receptors and the natural ligands (or portions of the natural ligands) for cell surface receptors.

In some embodiments, the endonuclease proteins or DNA/mRNA encoding the endonucleases are encapsulated within liposomes or complexed using cationic lipids (see, e.g., LIPOFECTAMINE transfection reagent, Life Technologies Corp., Carlsbad, Calif.; Zuris et al. (2015) *Nat Biotechnol.* 33: 73-80; Mishra et al. (2011) *J Drug Deliv.* 2011:863734). The liposome and lipoplex formulations can protect the payload from degradation, enhance accumulation and retention at the target site, and facilitate cellular uptake and delivery efficiency through fusion with and/or disruption of the cellular membranes of the target cells.

In some embodiments, endonuclease proteins, or DNA/mRNA encoding endonucleases, are encapsulated within polymeric scaffolds (e.g., PLGA) or complexed using cationic polymers (e.g., PEI, PLL) (Tamboli et al. (2011) *Ther Deliv.* 2(4): 523-536). Polymeric carriers can be designed to provide tunable drug release rates through control of polymer erosion and drug diffusion, and high drug encapsulation efficiencies can offer protection of the therapeutic payload until intracellular delivery to the desired target cell population.

In some embodiments, endonuclease proteins, or DNA/mRNA encoding engineered meganucleases, are combined with amphiphilic molecules that self-assemble into micelles (Tong et al. (2007) *J Gene Med.* 9(11): 956-66). Polymeric micelles may include a micellar shell formed with a hydrophilic polymer (e.g., polyethyleneglycol) that can prevent aggregation, mask charge interactions, and reduce nonspecific interactions.

In some embodiments, endonuclease proteins, or DNA/mRNA encoding endonucleases, are formulated into an emulsion or a nanoemulsion (i.e., having an average particle diameter of <1 nm) for administration and/or delivery to the target cell. The term "emulsion" refers to, without limitation, any oil-in-water, water-in-oil, water-in-oil-in-water, or oil-in-water-in-oil dispersions or droplets, including lipid structures that can form as a result of hydrophobic forces that drive apolar residues (e.g., long hydrocarbon chains) away from water and polar head groups toward water, when a water immiscible phase is mixed with an aqueous phase. These other lipid structures include, but are not limited to, unilamellar, paucilamellar, and multilamellar lipid vesicles, micelles, and lamellar phases. Emulsions are composed of an aqueous phase and a lipophilic phase (typically containing an oil and an organic solvent). Emulsions also frequently contain one or more surfactants. Nanoemulsion formulations are well known, e.g., as described in US Patent Application Nos. 2002/0045667 and 2004/0043041, and U.S. Pat. Nos. 6,015,832, 6,506,803, 6,635.676, and 6,559,189, each of which is incorporated herein by reference in its entirety.

In some embodiments, endonuclease proteins, or DNA/mRNA encoding endonucleases, are covalently attached to, or non-covalently associated with, multifunctional polymer conjugates, DNA dendrimers, and polymeric dendrimers (Mastorakos et al. (2015) *Nanoscale.* 7(9): 3845-56; Cheng et a. (2008) *J Pharm Sci.* 97(1): 123-43). The dendrimer generation can control the payload capacity and size, and can provide a high drug payload capacity. Moreover, display of multiple surface groups can be leveraged to improve stability, reduce nonspecific interactions, and enhance cell-specific targeting and drug release.

In some embodiments, genes encoding an endonuclease are delivered using a viral vector. Such vectors are known in the art and include retroviral vectors, lentiviral vectors, adenoviral vectors, and adeno-associated virus (AAV) vectors (reviewed in Vannucci, et al. (2013 *New Microbiol.* 36:1-22). In some embodiments, the viral vectors are injected directly into target tissues (e.g., liver tissue). In alternative embodiments, the viral vectors are delivered systemically via the circulatory system. It is known in the art that different AAV vectors tend to localize to different tissues. In liver target tissues, effective transduction of hepatocytes has been shown, for example, with AAV serotypes 2, 8, and 9 (Sands (2011) *Methods Mol. Biol.* 807: 141-157). AAV vectors can also be self-complementary such that they do not require second-strand DNA synthesis in the host cell (McCarty, et al. (2001) *Gene Ther.* 8:1248-54).

In one embodiment, a viral vector used for endonuclease gene delivery is a self-limiting viral vector. A self-limiting viral vector can have limited persistence time in a cell or organism due to the presence of a recognition sequence for an engineered meganuclease within the vector. Thus, a self-limiting viral vector can be engineered to provide coding for a promoter, an endonuclease described herein, and an endonuclease recognition site within the ITRs. The self-limiting viral vector delivers the endonuclease gene to a cell, tissue, or organism, such that the endonuclease is expressed and able to cut the genome of the cell at an endogenous recognition sequence within the genome. The delivered endonuclease will also find its target site within the self-limiting viral vector itself, and cut the vector at this target site. Once cut, the 5' and 3' ends of the viral genome will be exposed and degraded by exonucleases, thus killing the virus and ceasing production of the endonuclease.

If the endonuclease genes are delivered in DNA form (e.g. plasmid) and/or via a viral vector (e.g. AAV) they must be operably linked to a promoter. In some embodiments, this can be a viral promoter such as endogenous promoters from the viral vector (e.g. the LTR of a lentiviral vector) or the well-known cytomegalovirus- or SV40 virus-early promoters. In a preferred embodiment, meganuclease genes are operably linked to a promoter that drives gene expression preferentially in the target cells. Examples of liver-specific promoters include, without limitation, human alpha-1 antitrypsin promoter and apolipoprotein A-II promoter.

In particular embodiments, the viral vector comprises a cassette comprising a promoter and a nucleic acid sequence encoding an engineered meganuclease described herein. The viral vector could also comprise two or more cassettes, wherein each cassette comprises a promoter and a nucleic acid sequence encoding an engineered meganuclease described herein, and wherein each engineered meganuclease has specificity for a different HBV recognition sequence disclosed herein. In some embodiments, the viral vector comprises one cassette comprising a promoter and a polycistronic nucleic acid sequence, wherein the promoter drives expression of the polycistronic nucleic acid sequence to generate a polycistronic mRNA, such as polycistronic mRNA encoding an engineered meganuclease, described herein in a target cell.

Methods and compositions are provided for delivering a meganuclease disclosed herein to the liver of a subject infected with HBV. In one embodiment, native hepatocytes which have been removed from the mammal can be transduced with a vector which encodes the engineered meganuclease. Alternatively, native hepatocytes of the HBV-infected subject can be transduced ex vivo with an adenoviral vector which encodes the engineered meganuclease and/or a molecule that stimulates liver regeneration, such as a hepatotoxin. Preferably the hepatotoxin is uPA, and has been modified to inhibit its secretion from the hepatocyte once expressed by the viral vector. In another embodiment the vector encodes tPA, which can stimulate hepatocyte regeneration de novo. The transduced hepatocytes which have been removed from the mammal can then be returned to the mammal, where conditions are provided which are conducive to expression of the engineered meganuclease. Typically the transduced hepatocytes can be returned to the patient by infusion through the spleen or portal vasculature, and administration may be single or multiple over a period of 1 to 5 or more days.

In an in vivo aspect of the methods of the invention, a retroviral, pseudotype or adenoviral associated vector is constructed which encodes the engineered meganuclease and is administered to the subject. Administration of a vector encoding the engineered meganuclease can occur with administration of an adenoviral vector that encodes a secretion-impaired hepatotoxin, or encodes tPA, which stimulates hepatocyte regeneration without acting as a hepatotoxin.

Appropriate doses will depend, among other factors, on the specifics of any AAV vector chosen (e.g., serotype, etc.), on the route of administration, on the subject being treated (i.e., age, weight, sex, and general condition of the subject), and the mode of administration. Thus, the appropriate dosage may vary from patient to patient. An appropriate effective amount can be readily determined by one of skill in the art. Dosage treatment may be a single dose schedule or a multiple dose schedule. Moreover, the subject may be administered as many doses as appropriate. One of skill in the art can readily determine an appropriate number of doses. The dosage may need to be adjusted to take into consideration an alternative route of administration, or balance the therapeutic benefit against any side effects.

2.4 Pharmaceutical Compositions

In some embodiments, the invention provides a pharmaceutical composition comprising a pharmaceutically acceptable carrier and an engineered meganuclease of the invention, or a pharmaceutically acceptable carrier and an isolated polynucleotide comprising a nucleic acid encoding an engineered meganuclease of the invention. In other embodiments, the invention provides a pharmaceutical composition comprising a pharmaceutically acceptable carrier and a cell of the invention which can be delivered to a target tissue where the cell expresses the engineered meganuclease as disclosed herein. Pharmaceutical compositions of the invention can be useful for treating a subject having HBV, reducing the level or proliferation of HBV, reducing at least one symptom of HBV, or treating HCC.

Pharmaceutical compositions can be designed or selected according to the genotype of the target HBV strain. As described in detail herein, the meganucleases of the invention have been engineered to recognize and cleave recognition sequences in specific genotypes of HBV. For example, HBV 1-2 meganucleases (e.g., SEQ ID NOs: 18-21), recognize and cleave the HBV 1-2 recognition sequence that is at least found in the genome of HBV genotypes A, B, C, E, F, and G (e.g., SEQ ID NOs: 3-5 and 7-9, respectively). Further, recognition sequences of the engineered meganucleases disclosed herein can be found in isolates of HBV genotypes A, B, C, D, E, F, and G that do not share 100% sequence identity to the respective genotype examples provided in SEQ ID NOs: 3-9. As used herein, HBV "isolates" can share at least 90%, at least 91%, at least 92%, at least 93%, at least 94%, at least 95%, at least 96%, at least 97%, at least 98%, at least 99%, or more sequence identity with the corresponding genotype example provided in any of SEQ ID NOs: 3-9. In some embodiments, the pharmaceutical compositions disclosed herein can be administered to a subject having any genotype of HBV comprising a recognition sequence set forth in SEQ ID NO: 10, 12, 14, or 16.

Such pharmaceutical compositions can be prepared in accordance with known techniques. See, e.g., Remington, *The Science And Practice of Pharmacy* ($21^{st}$ ed. 2005). In the manufacture of a pharmaceutical formulation according to the invention, endonuclease polypeptides (or DNA/RNA encoding the same) are typically admixed with a pharmaceutically acceptable carrier and the resulting composition is administered to a subject. The carrier must, of course, be acceptable in the sense of being compatible with any other ingredients in the formulation and must not be deleterious to the subject. In some embodiments, pharmaceutical compositions of the invention can further comprise one or more additional agents or biological molecules useful in the treatment of a disease in the subject. Likewise, the additional agent(s) and/or biological molecule(s) can be co-administered as a separate composition.

In particular embodiments, pharmaceutical compositions of the invention can include combinations of the engineered meganucleases described herein (or nucleic acids encoding engineered meganucleases), wherein each engineered meganuclease has specificity for a different HBV recognition sequence, such that a single pharmaceutical composition is broadly useful for the treatment of a wide array of HBV genotypes and/or genotype isolates in a subject. Likewise, in other embodiments, pharmaceutical compositions of the invention can include polycistronic mRNAs (or recombinant DNA constructs or viral vectors having cassettes which, when expressed, produce polycistronic mRNAs) that encode multiple engineered meganucleases described herein having specificity for different HBV recognition sequences. Such pharmaceutical compositions are also broadly useful for the treatment of a wide array of HBV genotypes and/or genotype isolates in a subject. In either case, such pharmaceutical compositions can be useful as a single treatment when the specific HBV genotype or isolate is known or unknown in the subject.

For example, pharmaceutical compositions comprising multiple different recombinant meganucleases disclosed herein or comprising nucleic molecules encoding multiple different recombinant meganucleases disclosed herein, can be administered to a patient infected with multiple genotypes of HBV, or infected with unknown genotypes of HBV. Accordingly, providing pharmaceutical compositions with multiple different recombinant meganucleases or comprising nucleic molecules encoding multiple different recombinant meganucleases affords a flexible option for treatment and control of HBV infection where resources do not allow for accurate genotyping HBV and where fast and broad treatment solutions are desired.

In particular embodiments of the invention, the pharmaceutical composition can comprise one or more mRNAs described herein encapsulated within lipid nanoparticles, which are described elsewhere herein. In particular embodiments, lipid nanoparticles can comprise two or more mRNAs described herein, each encoding an engineered meganuclease of the invention having specificity for a different HBV recognition sequence described herein. In specific embodiments, lipid nanoparticles can comprise two, three, or four mRNAs described herein, each encoding an engineered meganuclease of the invention having specificity for a different HBV recognition sequence. In other embodiments, lipid nanoparticles can comprise one or more polycistronic mRNAs described herein, wherein each polycistronic mRNA encodes two or more engineered meganucleases of the invention having specificity for different HBV recognition sequences described herein. In particular embodiments, lipid nanoparticles can comprise a polycistronic mRNA encoding two, three, or four engineered meganucleases described herein. In other particular embodiments, lipid nanoparticles can comprise two or more polycistronic mRNAs described herein, each encoding two or more engineered meganucleases of the invention.

Some lipid nanoparticles contemplated for use in the invention comprise at least one cationic lipid, at least one non-cationic lipid, and at least one conjugated lipid. In more particular examples, lipid nanoparticles can comprise from about 50 mol % to about 85 mol % of a cationic lipid, from about 13 mol % to about 49.5 mol % of a non-cationic lipid, and from about 0.5 mol % to about 10 mol % of a lipid conjugate, and are produced in such a manner as to have a non-lamellar (i.e., non-bilayer) morphology. In other particular examples, lipid nanoparticles can comprise from about 40 mol % to about 85 mol % of a cationic lipid, from about 13 mol % to about 49.5 mol % of a non-cationic lipid, and from about 0.5 mol % to about 10 mol % of a lipid conjugate, and are produced in such a manner as to have a non-lamellar (i.e., non-bilayer) morphology.

Cationic lipids can include, for example, one or more of the following: palmitoyi-oleoyl-nor-arginine (PONA), MPDACA, GUADACA, ((6Z,9Z,28Z,31Z)-heptatriaconta-6,9,28,31-tetraen-19-yl 4-(dimethylamino)butanoate) (MC-3),LenMC3, CP-LenMC3, γ-LenMC3, CP-γ-LenMC3, MC3MC, MC2MC, MC3 Ether, MC4 Ether, MC3 Amide, Pan-MC3, Pan-MC4 and Pan MC5, 1,2-dilinoleyloxy-N,N-dimethylaminopropane (DLinDMA), 1,2-dilinolenyloxy-N,N-dimethylaminopropane (DLenDMA), 2,2-dilinoleyl-4-(2-dimethylaminoethyl)-[1,3]-dioxolane (DLin-K-C2-DMA; "XTC2"), 2,2-dilinoleyl-4-(3-dimethylaminopropyl)-[1,3]-dioxolane (DLin-K-C3-DMA), 2,2-dilinoleyl-4-(4-dimethylaminobutyl)-[1,3]-dioxolane (DLin-K-C4-DMA), 2,2-dilinoleyl-5-dimethylaminomethyl-[1,3]-dioxane (DLin-K6-DMA), 2,2-dilinoleyl-4-N-methylpepiazino-[1,3]-dioxolane (DLin-K-MPZ), 2,2-dilinoleyl-4-dimethylaminomethyl-[1,3]-dioxolane (DLin-K-DMA), 1,2-dilinoleylcarbamoyloxy-3-dimethylaminopropane (DLin-C-DAP), 1,2-dilinoleyoxy-3-(dimethylamino)acetoxypropane (DLin-DAC), 1,2-dilinoleyoxy-3-morpholinopropane (DLin-MA), 1,2-dilinoleoyl-3-dimethylaminopropane (DLinDAP), 1,2-dilinoleylthio-3-dimethylaminopropane (DLin-S-DMA), 1-linoleoyl-2-linoleyloxy-3-dimethylaminopropane (DLin-2-DMAP), 1,2-dilinoleyloxy-3-trimethylaminopropane chloride salt (DLin-TMA.Cl), 1,2-dilinoleoyl-3-trimethylaminopropane chloride salt (DLin-TAP.Cl), 1,2-dilinoleyloxy-3-(N-methylpiperazino)propane (DLin-MPZ), 3-(N,N-dilinoleylamino)-1,2-propanediol (DLinAP), 3-(N,N-dioleylamino)-1,2-propanedio (DOAP), 1,2-dilinoleyloxo-3-(2-N,N-dimethylamino)ethoxypropane (DLin-EG-DMA), N,N-dioleyl-N,N-dimethylammonium chloride (DODAC), 1,2-dioleyloxy-N,N-dimethylaminopmpane (DODMA), 1,2-distearyloxy-N,N-dimethylaminopropane (DSDMA), N-(1-(2,3-dioleyloxy)propyl)-N,N,N-trimethylammonium chloride (DOTMA), N,N-distearyl-N,N-dimethylammonium bromide (DDAB), N-(1-(2,3-dioleoyloxy)propyl)-N,N,N-trimethylammonium chloride (DOTAP), 3-(N—(N',N'-dimethylaminoethane)-carbamoyl)cholesterol (DC-Chol), N-(1,2-dimyristyloxyprop-3-yl)-N,N-dimethyl-N-hydroxyethyl ammonium bromide (DMRIE), 2,3-dioleyloxy-N-[2(spermine-carboxamido)ethyl]-N,N-dimethyl-1-propanaminiumtrifluoroacetate (DOSPA), dioctadecylamidoglycyl spermine (DOGS), 3-dimethylamino-2-(cholest-5-en-3-beta-oxybutan-4-oxy)-1-(cis,cis-9,12-octadecadienoxy)propane (CLinDMA), 2-[5'-(cholest-5-en-3-beta-oxy)-3'-oxapentoxy)-3-dimethy-1-(cis,cis-9', 1-2'-octadecadienoxy)propane (CpLinDMA), N,N-dimethyl-3,4-dioleyloxybenzylamine (DMOBA), 1,2-N,N'-dioleylcarbamyl-3-dimethylaminopropane (DOcarbDAP), 1,2-N,N'-dilinoleylcarbamyl-3-dimethylaminopropane (DLincarbDAP), or mixtures thereof. The cationic lipid can also be DLinDMA, DLin-K-C2-DMA ("XTC2"), MC3, LenMC3, CP-LenMC3, γ-LenMC3, CP-γ-LenMC3, MC3MC, MC2MC, MC3 Ether, MC4 Ether, MC3 Amide, Pan-MC3, Pan-MC4, Pan MC5, or mixtures thereof.

In various embodiments, the cationic lipid may comprise from about 50 mol % to about 90 mol %, from about 50 mol % to about 85 mol %, from about 50 mol % to about 80 mol %, from about 50 mol % to about 75 mol %, from about 50 mol % to about 70 mol %, from about 50 mol % to about 65 mol %, or from about 50 mol % to about 60 mol % of the total lipid present in the particle.

In other embodiments, the cationic lipid may comprise from about 40 mol % to about 90 mol %, from about 40 mol % to about 85 mol %, from about 40 mol % to about 80 mol %, from about 40 mol % to about 75 mol %, from about 40 mol % to about 70 mol %, from about 40 mol % to about 65 mol %, or from about 40 mol % to about 60 mol % of the total lipid present in the particle.

The non-cationic lipid may comprise, e.g., one or more anionic lipids and/or neutral lipids. In preferred embodiments, the non-cationic lipid comprises one of the following neutral lipid components: (1) cholesterol or a derivative thereof; (2) a phospholipid; or (3) a mixture of a phospholipid and cholesterol or a derivative thereof. Examples of cholesterol derivatives include, but are not limited to, cholestanol, cholestanone, cholestenone, coprostanol, cholesteryl-2'-hydroxyethyl ether, cholesteryl-4'-hydroxybutyl ether, and mixtures thereof. The phospholipid may be a neutral lipid including, but not limited to, dipalmitoylphosphatidylcholine (DPPC), distearoylphosphatidylcholine (DSPC), dioleoylphosphatidylethanolamine (DOPE), palmitoyloleoyl-phosphatidylcholine (POPC), palmitoyloleoyl-phosphatidylethanolamine (POPE), palmitoyloleyol-phosphatidylglycerol (POPG), dipalmitoyl-phosphatidylethanolamine (DPPE), dimyristoyl-phosphatidylethanolamine (DMPE), distearoyl-phosphatidylethanolamine (DSPE), monomethyl-phosphatidylethanolamine, dimethyl-phosphatidylethanolamine, dielaidoyl-phosphatidylethanolamine (DEPE), stearoyloleoyl-phosphatidylethanolamine (SOPE), egg phosphatidylcholine (EPC), and mixtures thereof. In certain preferred embodiments, the phospholipid is DPPC, DSPC, or mixtures thereof.

In some embodiments, the non-cationic lipid (e.g., one or more phospholipids and/or cholesterol) may comprise from about 10 mol % to about 60 mol %, from about 15 mol % to about 60 mol %, from about 20 mol % to about 60 mol %, from about 25 mol % to about 60 mol %, from about 30 mol % to about 60 mol %, from about 10 mol % to about 55 mol %, from about 15 mol % to about 55 mol %, from about 20 mol % to about 55 mol %, from about 25 mol % to about 55 mol %, from about 30 mol % to about 55 mol %, from about 13 mol % to about 50 mol %, from about 15 mol % to about 50 mol % or from about 20 mol % to about 50 mol % of the total lipid present in the particle. When the non-cationic lipid is a mixture of a phospholipid and cholesterol or a cholesterol derivative, the mixture may comprise up to about 40, 50, or 60 mol % of the total lipid present in the particle.

The conjugated lipid that inhibits aggregation of particles may comprise, e.g., one or more of the following: a polyethyleneglycol (PEG)-lipid conjugate, a polyamide (ATTA)-lipid conjugate, a cationic-polymer-lipid conjugates (CPLs), or mixtures thereof. In one preferred embodiment, the nucleic acid-lipid particles comprise either a PEG-lipid conjugate or an ATTA-lipid conjugate. In certain embodiments, the PEG-lipid conjugate or ATTA-lipid conjugate is used together with a CPL. The conjugated lipid that inhibits aggregation of particles may comprise a PEG-lipid including, e.g., a PEG-diacylglycerol (DAG), a PEG dialkyloxypropyl (DAA), a PEG-phospholipid, a PEG-ceramide (Cer), or mixtures thereof. The PEG-DAA conjugate may be PEG-di lauryloxypropyl (C12), a PEG-dimyristyloxypropyl (C14), a PEG-dipalmityloxypropyl (C16), a PEG-distearyloxypropyl (C18), or mixtures thereof.

Additional PEG-lipid conjugates suitable for use in the invention include, but are not limited to, mPEG2000-1,2-di-O-alkyl-sn3-carbomoylglyceride (PEG-C-DOMG). The synthesis of PEG-C-DOMG is described in PCT Application No. PCT/US08/88676. Yet additional PEG-lipid conjugates suitable for use in the invention include, without limitation, 1-[8'-(1,2-dimyristoyl-3-propanoxy)-carboxamido-3',6'-dioxaoctanyl]carbamoyl-ω-methyl-poly(ethylene glycol) (2KPEG-DMG). The synthesis of 2KPEG-DMG is described in U.S. Pat. No. 7,404,969.

In some cases, the conjugated lipid that inhibits aggregation of particles (e.g., PEG-lipid conjugate) may comprise from about 0.1 mol % to about 2 mol %, from about 0.5 mol % to about 2 mol %, from about 1 mol % to about 2 mol %, from about 0.6 mol % to about 1.9 mol %, from about 0.7 mol % to about 1.8 mol %, from about 0.8 mol % to about 1.7 mol %, from about 1 mol % to about 1.8 mol %, from about 1.2 mol % to about 1.8 mol %, from about 1.2 mol % to about 1.7 mol %, from about 1.3 mol % to about 1.6 mol %, from about 1.4 mol % to about 1.5 mol %, or about 1, 1.1, 1.2, 1.3, 1.4, 1.5, 1.6, 1.7, 1.8, 1.9, or 2 mol % (or any fraction thereof or range therein) of the total lipid present in the particle. Typically, in such instances, the PEG moiety has an average molecular weight of about 2,000 Daltons. In other cases, the conjugated lipid that inhibits aggregation of particles (e.g., PEG-lipid conjugate) may comprise from about 5.0 mol % to about 10 mol %, from about 5 mol % to about 9 mol %, from about 5 mol % to about 8 mol %, from about 6 mol % to about 9 mol %, from about 6 mol % to about 8 mol %, or about 5 mol %, 6 mol %, 7 mol %, 8 mol %, 9 mol %, or 10 mol % (or any fraction thereof or range therein) of the total lipid present in the particle. Typically, in such instances, the PEG moiety has an average molecular weight of about 750 Daltons.

In other embodiments, the composition may comprise amphoteric liposomes, which contain at least one positive and at least one negative charge carrier, which differs from the positive one, the isoelectric point of the liposomes being between 4 and 8. This objective is accomplished owing to the fact that liposomes are prepared with a pH-dependent, changing charge.

Liposomal structures with the desired properties are formed, for example, when the amount of membrane-forming or membrane-based cationic charge carriers exceeds that of the anionic charge carriers at a low pH and the ratio is reversed at a higher pH. This is always the case when the ionizable components have a pKa value between 4 and 9. As the pH of the medium drops, all cationic charge carriers are charged more and all anionic charge carriers lose their charge.

Cationic compounds useful for amphoteric liposomes include those cationic compounds previously described herein above. Without limitation, strongly cationic compounds can include, for example: DC-Chol 3-β-[N—(N',N'-dimethylmethane) carbamoyl] cholesterol, TC-Chol 3-β-[N—(N',N',N'-trimethylaminoethane) carbamoyl cholesterol, BGSC bisguanidinium-spermidine-cholesterol, BGTC bis-guadinium-tren-cholesterol, DOTAP (1,2-dioleoyloxypropyl)-N,N,N-trimethylammonium chloride, DOSPER (1,3-dioleoyloxy-2-(6-carboxy-spermyl)-propylamide, DOTMA (1,2-dioleoyloxypropyl)-N,N,N-trimethylammonium chloride) (Lipofectin®), DORIE 1,2-dioleoyloxypropyl)-3-dimethylhydroxyethylammonium bromide, DOSC (1,2-dioleoyl-3-succinyl-sn-glyceryl choline ester), DOGSDSO (1,2-dioleoyl-sn-glycero-3-succinyl-2-hydroxyethyl disulfide omithine), DDAB dimethyldioctadecylammonium bromide, DOGS ((C18)2GlySper3+) N,N-dioctadecylamido-glycol-spermin (Transfectam®) (C18)2Gly+N, N-dioctadecylamidoglycine, CTAB cetyltrimethylammonium bromide, CpyC cetylpyridinium chloride, DOEPC 1,2-dioleoly-sn-glycero-3-ethylphosphocholine or other O-alkyl-phosphatidylcholine or ethanolamines, amides from lysine, arginine or omithine and phosphatidyl ethanolamine.

Examples of weakly cationic compounds include, without limitation: His-Chol (histaminyl-cholesterol hemisuccinate), Mo-Chol (morpholine-N-ethylamino-cholesterol hemisuccinate), or histidinyl-PE.

Examples of neutral compounds include, without limitation: cholesterol, ceramides, phosphatidyl cholines, phosphatidyl ethanolamines, tetraether lipids, or diacyl glycerols.

Anionic compounds useful for amphoteric liposomes include those non-cationic compounds previously described herein. Without limitation, examples of weakly anionic compounds can include: CHEMS (cholesterol hemisuccinate), alkyl carboxylic acids with 8 to 25 carbon atoms, or diacyl glycerol hemisuccinate. Additional weakly anionic compounds can include the amides of aspartic acid, or glutamic acid and PE as well as PS and its amides with glycine, alanine, glutamine, asparagine, serine, cysteine, threonine, tyrosine, glutamic acid, aspartic acid or other amino acids or aminodicarboxylic acids. According to the same principle, the esters of hydroxycarboxylic acids or hydroxydicarboxylic acids and PS are also weakly anionic compounds.

In some embodiments, amphoteric liposomes may contain a conjugated lipid, such as those described herein above. Particular examples of useful conjugated lipids include, without limitation, PEG-modified phosphatidylethanolamine and phosphatidic acid, PEG-ceramide conjugates (e.g., PEG-CerC14 or PEG-CerC20), PEG-modified dialkylamines and PEG-modified 1,2-diacyloxypropan-3-amines. Particularly preferred are PEG-modified diacylglycerols and dialkylglycerols.

In some embodiments, the neutral lipids may comprise from about 10 mol % to about 60 mol %, from about 15 mol % to about 60 mol %, from about 20 mol % to about 60 mol %, from about 25 mol % to about 60 mol %, from about 30 mol % to about 60 mol %, from about 10 mol % to about 55 mol %, from about 15 mol % to about 55 mol %, from about 20 mol % to about 55 mol %, from about 25 mol % to about 55 mol %, from about 30 mol % to about 55 mol %, from about 13 mol % to about 50 mol %, from about 15 mol % to about 50 mol % or from about 20 mol % to about 50 mol % of the total lipid present in the particle.

In some cases, the conjugated lipid that inhibits aggregation of particles (e.g., PEG-lipid conjugate) may comprise from about 0.1 mol % to about 2 mol %, from about 0.5 mol % to about 2 mol %, from about 1 mol % to about 2 mol %, from about 0.6 mol % to about 1.9 mol %, from about 0.7 mol % to about 1.8 mol %, from about 0.8 mol % to about 1.7 mol %, from about 1 mol % to about 1.8 mol %, from about 1.2 mol % to about 1.8 mol %, from about 1.2 mol % to about 1.7 mol %, from about 1.3 mol % to about 1.6 mol %, from about 1.4 mol % to about 1.5 mol %, or about 1, 1.1, 1.2, 1.3, 1.4, 1.5, 1.6, 1.7, 1.8, 1.9, or 2 mol % (or any fraction thereof or range therein) of the total lipid present in the particle. Typically, in such instances, the PEG moiety has an average molecular weight of about 2,000 Daltons. In other cases, the conjugated lipid that inhibits aggregation of particles (e.g., PEG-lipid conjugate) may comprise from about 5.0 mol % to about 10 mol %, from about 5 mol % to about 9 mol %, from about 5 mol % to about 8 mol %, from about 6 mol % to about 9 mol %, from about 6 mol % to about 8 mol %, or about 5 mol %, 6 mol %, 7 mol %, 8 mol %, 9 mol %, or 10 mol % (or any fraction thereof or range therein) of the total lipid present in the particle. Typically, in such instances, the PEG moiety has an average molecular weight of about 750 Daltons.

Considering the total amount of neutral and conjugated lipids, the remaining balance of the amphoteric liposome can comprise a mixture of cationic compounds and anionic compounds formulated at various ratios. The ratio of cationic to anionic lipid may selected in order to achieve the desired properties of nucleic acid encapsulation, zeta potential, pKa, or other physicochemical property that is at least in part dependent on the presence of charged lipid components.

In some embodiments, the lipid nanoparticles have a composition which specifically enhances delivery and uptake in the liver, and specifically within hepatocytes.

2.5 Methods for Producing Recombinant AAV Vectors

In some embodiments, the invention provides recombinant AAV vectors for use in the methods of the invention. Recombinant AAV vectors are typically produced in mammalian cell lines such as HEK-293. Because the viral cap and rep genes are removed from the vector to prevent its self-replication to make room for the therapeutic gene(s) to be delivered (e.g. the endonuclease gene), it is necessary to provide these in trans in the packaging cell line. In addition, it is necessary to provide the "helper" (e.g. adenoviral) components necessary to support replication (Cots D, Bosch A, Chillon M (2013) *Curr. Gene Ther.* 13(5): 370-81). Frequently, recombinant AAV vectors are produced using a triple-transfection in which a cell line is transfected with a first plasmid encoding the "helper" components, a second plasmid comprising the cap and rep genes, and a third plasmid comprising the viral ITRs containing the intervening DNA sequence to be packaged into the virus. Viral particles comprising a genome (ITRs and intervening gene(s) of interest) encased in a capsid are then isolated from cells by freeze-thaw cycles, sonication, detergent, or other means known in the art. Particles are then purified using cesium-chloride density gradient centrifugation or affinity chromatography and subsequently delivered to the gene(s) of interest to cells, tissues, or an organism such as a human patient.

Because recombinant AAV particles are typically produced (manufactured) in cells, precautions must be taken in practicing the current invention to ensure that the site-specific endonuclease is not expressed in the packaging cells. Because the viral genomes of the invention comprise a recognition sequence for the endonuclease, any endonuclease expressed in the packaging cell line will be capable of cleaving the viral genome before it can be packaged into viral particles. This will result in reduced packaging efficiency and/or the packaging of fragmented genomes. Several approaches can be used to prevent endonuclease expression in the packaging cells, including:

The endonuclease can be placed under the control of a tissue-specific promoter that is not active in the packaging cells. For example, if a viral vector is developed for delivery of (an) endonuclease gene(s) to muscle tissue, a muscle-specific promoter can be used. Examples of muscle-specific promoters include C5-12 (Liu, et al. (2004) *Hum Gene Ther.* 15:783-92), the muscle-specific creatine kinase (MCK) promoter (Yuasa, et al. (2002) *Gene Ther.* 9:1576-88), or the smooth muscle 22 (SM22) promoter (Haase, et al. (2013) *BMC Biotechnol.* 13:49-54). Examples of CNS (neuron)-specific promoters include the NSE, Synapsin, and MeCP2 promoters (Lentz, et al. (2012) *Neurobiol Dis.* 48:179-88). Examples of liver-specific promoters include albumin promoters (such as Palb), human α1-antitrypsin (such as PalAT), and hemopexin (such as Phpx) (Kramer, M G et al., (2003) *Mol. Therapy* 7:375-85). Examples of eye-specific promoters include opsin, and corneal epithelium-specific K12 promoters (Martin K R G, Klein R L, and Quigley H A (2002) Methods (28): 267-75) (Tong Y, et al., (2007) *J Gene Med,* 9:956-66). These promoters, or other tissue-specific promoters known in the art, are not highly-active in HEK-293 cells and, thus, will not expected to yield significant levels of endonuclease gene expression in packaging cells when incorporated into viral vectors of the present invention. Similarly, the viral vectors of the present invention contemplate the use of other cell lines with the use of incompatible tissue specific promoters (i.e., the well-known HeLa cell line (human epithelial cell) and using the liver-specific hemopexin promoter). Other examples of tissue specific promoters include: synovial sarcomas PDZD4 (cerebellum), C6 (liver), ASB5 (muscle), PPP1R12B (heart), SLC5A12 (kidney), cholesterol regulation APOM (liver), ADPRHL1 (heart), and monogenic malformation syndromes TP73L (muscle). (Jacox E, et al., (2010) *PLoS One* v.5(8):e12274).

Alternatively, the vector can be packaged in cells from a different species in which the endonuclease is not likely to be expressed. For example, viral particles can be produced in microbial, insect, or plant cells using mammalian promoters, such as the well-known cytomegalovirus- or SV40 virus-early promoters, which are not active in the non-mammalian packaging cells. In a preferred embodiment, viral particles are produced in insect cells using the baculovirus system as described by Gao, et al. (Gao, H., et al. (2007) *J. Biotechnol.* 131(2):138-43). An endonuclease under the control of a mammalian promoter is unlikely to be expressed in these cells (Airenne, K J, et al. (2013) *Mol. Ther.* 21(4):739-49). Moreover, insect cells utilize different mRNA splicing motifs than mammalian cells. Thus, it is possible to incorporate a mammalian intron, such as the human growth hormone (HGH) intron or the SV40 large T antigen intron, into the coding sequence of an endonuclease. Because these introns are not spliced efficiently from pre-mRNA transcripts in insect cells, insect cells will not express a functional endonuclease and will package the full-length genome. In contrast, mammalian cells to which the resulting recombinant AAV particles are delivered will properly splice the pre-mRNA and will express functional endonuclease protein. Haifeng Chen has reported the use of the HGH and SV40 large T antigen introns to attenuate expression of the toxic proteins barnase and diphtheria toxin fragment A in insect packaging cells, enabling the production of recombinant AAV vectors carrying these toxin genes (Chen, H (2012) *Mol Ther Nucleic Acids.* 1(11): e57).

The endonuclease gene can be operably linked to an inducible promoter such that a small-molecule inducer is required for endonuclease expression. Examples of inducible promoters include the Tet-On system (Clontech; Chen H., el al., (2015) *BMC Biotechnol.* 15(1):4)) and the RheoSwitch system (Intrexon; Sowa G., et al., (2011) *Spine,* 36(10): E623-8). Both systems, as well as similar systems known in the art, rely on ligand-inducible transcription factors (variants of the Tet Repressor and Ecdysone receptor, respectively) that activate transcription in response to a small-molecule activator (Doxycycline or Ecdysone, respectively). Practicing the current invention using such ligand-inducible transcription activators includes: 1) placing the endonuclease gene under the control of a promoter that responds to the corresponding transcription factor, the endonuclease gene having (a) binding site(s) for the transcription factor; and 2) including the gene encoding the transcription factor in the packaged viral genome The latter step is necessary because the endonuclease will not be expressed in the target cells or tissues following recombinant AAV delivery if the transcription activator is not also provided to the same cells. The transcription activator then induces endonuclease gene expression only in cells or tissues that are treated with the cognate small-molecule activator. This approach is advantageous because it enables endonuclease gene expression to be regulated in a spatio-temporal manner by selecting when and to which tissues the small-molecule inducer is delivered. However, the requirement to include the inducer in the viral genome, which has significantly limited carrying capacity, creates a drawback to this approach.

In another preferred embodiment, recombinant AAV particles are produced in a mammalian cell line that expresses a transcription repressor that prevents expression of the endonuclease. Transcription repressors are known in the art and include the Tet-Repressor, the Lac-Repressor, the Cro repressor, and the Lambda-repressor. Many nuclear hormone receptors such as the ecdysone receptor also act as transcription repressors in the absence of their cognate hormone ligand. To practice the current invention, packaging cells are transfected/transduced with a vector encoding a transcription repressor and the endonuclease gene in the viral genome (packaging vector) is operably linked to a promoter that is modified to comprise binding sites for the repressor such that the repressor silences the promoter. The gene encoding the transcription repressor can be placed in a variety of positions. It can be encoded on a separate vector; it can be incorporated into the packaging vector outside of the ITR sequences; it can be incorporated into the cap/rep vector or the adenoviral helper vector; or, most preferably, it can be stably integrated into the genome of the packaging cell such that it is expressed constitutively. Methods to modify common mammalian promoters to incorporate transcription repressor sites are known in the art. For example, Chang and Roninson modified the strong, constitutive CMV and RSV promoters to comprise operators for the Lac repressor and showed that gene expression from the modified promoters was greatly attenuated in cells expressing the repressor (Chang B D, and Roninson I B (1996) *Gene* 183:137-42). The use of a non-human transcription repressor ensures that transcription of the endonuclease gene will be repressed only in the packaging cells expressing the repressor and not in target cells or tissues transduced with the resulting recombinant AAV vector.

2.6 Engineered Meganuclease Variants

Embodiments of the invention encompass the engineered meganucleases described herein, and variants thereof. Further embodiments of the invention encompass isolated polynucleotides comprising a nucleic acid sequence encoding the endonucleases described herein, and variants of such polynucleotides.

As used herein. "variants" is intended to mean substantially similar sequences. A "variant" polypeptide is intended to mean a polypeptide derived from the "native" polypeptide by deletion or addition of one or more amino acids at one or more internal sites in the native protein and/or substitution of one or more amino acids at one or more sites in the native polypeptide. As used herein, a "native" polynucleotide or polypeptide comprises a parental sequence from which variants are derived. Variant polypeptides encompassed by the embodiments are biologically active. That is, they continue to possess the desired biological activity of the native protein; i.e., the ability to recognize and cleave a recognition sequence within an ORF of the genome of at least two genotypes of the Hepatitis B virus, for example, the HBV 1-2 recognition sequence (SEQ ID NO: 10), the HBV 5-6 recognition sequence (SEQ ID NO: 12), the HBV 7-8 recognition sequence (SEQ ID NO: 14), or the HBV 11-12 recognition sequence (SEQ ID NO: 16). Such variants may result, for example, from human manipulation. Biologically active variants of a native polypeptide of the embodiments (e.g., SEQ ID NOs: 18-39), or biologically active variants of the recognition half-site binding subunits described herein, will have at least about 40%, about 45%, about 50%, about 55%, about 60%, about 65%, about 70%, about 75%, about 80%, about 85%, about 90%, about 91%, about 92%, about 93%, about 94%, about 95%, about 96%, about 97%, about 98%, or about 99%, sequence identity to the amino acid sequence of the native polypeptide or native subunit, as determined by sequence alignment programs and parameters described elsewhere herein. A biologically active variant of a polypeptide or subunit of the embodiments may differ from that polypeptide or subunit by as few as about 1-40 amino acid residues, as few as about 1-20, as few as about 1-10, as few as about 5, as few as 4, 3, 2, or even 1 amino acid residue.

The polypeptides of the embodiments may be altered in various ways including amino acid substitutions, deletions, truncations, and insertions. Methods for such manipulations are generally known in the art. For example, amino acid sequence variants can be prepared by mutations in the DNA. Methods for mutagenesis and polynucleotide alterations are well known in the art. See, for example, Kunkel (1985) *Proc. Natl. Acad. Sci. USA* 82:488-492; Kunkel et al. (1987) *Methods in Enzymol.* 154:367-382; U.S. Pat. No. 4,873,192; Walker and Gaastra, eds. (1983) *Techniques in Molecular Biology* (MacMillan Publishing Company, New York) and the references cited therein. Guidance as to appropriate amino acid substitutions that do not affect biological activity of the protein of interest may be found in the model of Dayhoff et al. (1978) *Atlas of Protein Sequence and Structure* (Natl. Biomed. Res. Found, Washington, D.C.), herein incorporated by reference. Conservative substitutions, such as exchanging one amino acid with another having similar properties, may be optimal.

In some embodiments, engineered meganucleases of the invention can comprise variants of the HVR1 and HVR2 regions disclosed herein. Parental HVR regions can comprise, for example, residues 24-79 or residues 215-270 of the exemplified engineered meganucleases. Thus, variant HVRs can comprise an amino acid sequence having at least 80%, at least 85%, at least 90%, at least 95%, or more, sequence identity to an amino acid sequence corresponding to residues 24-79 or residues 215-270 of the engineered meganucleases exemplified herein, such that the variant HVR regions maintain the biological activity of the engineered meganuclease (i.e., binding to and cleaving the recognition sequence). Further, in some embodiments of the invention, a variant HVR1 region or variant HVR2 region can comprise residues corresponding to the amino acid residues found at specific positions within the parental HVR. In this context, "corresponding to" means that an amino acid residue in the variant HVR is the same amino acid residue (i.e., a separate identical residue) present in the parental HVR sequence in the same relative position (i.e., in relation to the remaining amino acids in the parent sequence). By way of example, if a parental HVR sequence comprises a serine residue at position 26, a variant HVR that "comprises a residue corresponding to" residue 26 will also comprise a serine at a position that is relative to parental position 26.

A substantial number of amino acid modifications to the DNA recognition domain of the wild-type I-CreI meganuclease have previously been identified (e.g., U.S. Pat. No. 8,021,867) which, singly or in combination, result in engineered meganucleases with specificities altered at individual bases within the DNA recognition sequence half-site, such that the resulting rationally-designed meganucleases have half-site specificities different from the wild-type enzyme. Table 5 provides potential substitutions that can be made in an engineered meganuclease monomer or subunit to enhance specificity based on the base present at each half-site position (−1 through −9) of a recognition half-site.

TABLE 5

| | Favored Sense-Strand Base | | | | | | | | | | |
|---|---|---|---|---|---|---|---|---|---|---|---|
| Posn. | A | C | G | T | A/T | A/C | A/G | C/T | G/T | A/G/T | A/C/G/T |
| −1 | Y75 | **R70*** | K70 | Q70* | | | | **T46*** | | | G70 |
| | L75* | H75* | E70* | C70 | | | | | | | A70 |
| | C75* | R75* | E75* | L70 | | | | | | | S70 |
| | Y139* | H46* | E46* | Y75* | | | | | | | G46* |
| | C46* | K46* | D46* | Q75* | | | | | | | |
| | A46* | R46* | | H75* | | | | | | | |
| | | | | H139 | | | | | | | |
| | | | | Q46* | | | | | | | |
| | | | | H46* | | | | | | | |
| −2 | Q70 | E70 | H70 | **Q44*** | C44* | | | | | | |
| | T44* | D70 | D44* | | | | | | | | |
| | A44* | K44* | E44* | | | | | | | | |
| | V44* | R44* | | | | | | | | | |
| | I44* | | | | | | | | | | |
| | L44* | | | | | | | | | | |
| | N44* | | | | | | | | | | |
| −3 | Q68 | E68 | **R68** | M68 | | H68 | | Y68 | K68 | | |
| | C24* | F68 | | C68 | | | | | | | |
| | **I24*** | K24* | | L68 | | | | | | | |
| | | R24* | | F68 | | | | | | | |
| −4 | A26* | E77 | R77 | | | | | S77 | | | S26* |
| | Q77 | K26* | E26* | | | | | **Q26*** | | | |
| −5 | | E42 | R42 | | | **K28*** | C28* | | | | M66 |
| | | | | | | | Q42 | | | | K66 |
| −6 | Q40 | E40 | R40 | C40 | A40 | | | | | | **S40** |
| | C28* | R28* | | I40 | A79 | | | | | | S28* |
| | | | | V40 | A28* | | | | | | |
| | | | | C79 | H28* | | | | | | |
| | | | | I79 | | | | | | | |
| | | | | V79 | | | | | | | |
| | | | | Q28* | | | | | | | |
| −7 | **N30*** | E38 | K38 | I38 | | | C38 | | | | H38 |
| | **Q38** | K30* | R38 | L38 | | | | | | | N38 |
| | | R30* | E30* | | | | | | | | Q30* |
| −8 | F33 | E33 | F33 | L33 | | R32* | R33 | | | | |
| | **Y33** | D33 | H33 | V33 | | | | | | | |
| | | | | I33 | | | | | | | |
| | | | | F33 | | | | | | | |
| | | | | C33 | | | | | | | |
| −9 | | E32 | R32 | L32 | | | | D32 | | | **S32** |
| | | | K32 | V32 | | | | I32 | | | N32 |
| | | | | A32 | | | | | | | H32 |
| | | | | C32 | | | | | | | Q32 |
| | | | | | | | | | | | T32 |

Bold entries are wild-type contact residues and do not constitute "modifications" as used herein.
An asterisk indicates that the residue contacts the base on the antisense strand.

For polynucleotides, a "variant" comprises a deletion and/or addition of one or more nucleotides at one or more sites within the native polynucleotide. One of skill in the art will recognize that variants of the nucleic acids of the embodiments will be constructed such that the open reading frame is maintained. For polynucleotides, conservative variants include those sequences that, because of the degeneracy of the genetic code, encode the amino acid sequence of one of the polypeptides of the embodiments. Variant polynucleotides include synthetically derived polynucleotides, such as those generated, for example, by using site-directed mutagenesis but which still encode an engineered meganuclease of the embodiments. Generally, variants of a particular polynucleotide of the embodiments will have at least about 40%, about 45%, about 50%, about 55%, about 60%, about 65%, about 70%, about 75%, about 80%, about 85%, about 90%, about 91%, about 92%, about 93%, about 94%, about 95%, about 96%, about 97%, about 98%, about 99% or more sequence identity to that particular polynucleotide as determined by sequence alignment programs and parameters described elsewhere herein. Variants of a particular polynucleotide of the embodiments (i.e., the reference polynucleotide) can also be evaluated by comparison of the percent sequence identity between the polypeptide encoded by a variant polynucleotide and the polypeptide encoded by the reference polynucleotide.

The deletions, insertions, and substitutions of the protein sequences encompassed herein are not expected to produce radical changes in the characteristics of the polypeptide. However, when it is difficult to predict the exact effect of the substitution, deletion, or insertion in advance of doing so, one skilled in the art will appreciate that the effect will be evaluated by screening the polypeptide for its ability to preferentially recognize and cleave a recognition sequence within an ORF of the genome of at least two genotypes of the Hepatitis B virus.

EXAMPLES

This invention is further illustrated by the following examples, which should not be construed as limiting. Those skilled in the art will recognize, or be able to ascertain, using no more than routine experimentation, numerous equivalents to the specific substances and procedures described herein. Such equivalents are intended to be encompassed in the scope of the claims that follow the examples below.

Example 1

Characterization of Meganucleases that Recognize and Cleave HBV Recognition Sequences Meganucleases that Recognize and Cleave the HBV 1-2 Recognition Sequence Engineered meganucleases (SEQ ID NOs: 18-21), collectively referred to herein as "HBV 1-2 meganucleases," were engineered to recognize and cleave the HBV 1-2 recognition sequence (SEQ ID NO: 10), which is positioned within the P protein, S, preS2/S, and preS1/preS2 ORFs of multiple HBV genotypes including genotype A, B, C, E, F, and G (e.g., SEQ ID NOs: 3-5 and 7-9, respectively). Each HBV 1-2 engineered meganuclease comprises an N-terminal nuclease-localization signal derived from SV40, a first meganuclease subunit, a linker sequence, and a second meganuclease subunit. A first subunit in each HBV 1-2 meganuclease binds to the HBV 1 recognition half-site of SEQ ID NO: 10, while a second subunit binds to the HBV2 recognition half-site (see, FIG. 2).

The HBV1-binding subunits and HBV2-binding subunits each comprise a 56 base pair hypervariable region, referred to as HVR1 and HVR2, respectively. HBV-binding subunits are highly conserved outside of the HVR1 region. Similarly, HBV2-binding subunits are also highly conserved outside of the HVR2 region. The HBV1-binding regions of SEQ ID NOs: 18-21 are provided as SEQ ID NOs: 40-43, respectively. Each of SEQ ID NOs: 40-43 share at least 90% sequence identity to SEQ ID NO: 40, which is the HBV1-binding region of the meganuclease HBV 1-2x.2 (SEQ ID NO: 18). HBV2-binding regions of SEQ ID NOs: 18-21 are provided as SEQ ID NOs: 44-47, respectively. Each of SEQ ID NOs: 44-47 share at least 90% sequence identity to SEQ ID NO: 44, which is the HBV2-binding region of the meganuclease HBV 1-2x.2 (SEQ ID NO: 18).

Meganucleases that Recognize and Cleave the HBV 5-6 Recognition Sequence

Engineered meganucleases (SEQ ID NOs: 22-28), collectively referred to herein as "HBV 5-6 meganucleases," were engineered to recognize and cleave the HBV 5-6 recognition sequence (SEQ ID NO: 12), which is positioned within the P protein, S, preS2/S, and preS1/preS2 ORFs of multiple HBV genotypes, including genotype A, B, C, D, E, and G (e.g., SEQ ID NOs: 3-7 and 9, respectively). Each HBV 5-6 engineered meganuclease comprises an N-terminal nuclease-localization signal derived from SV40, a first meganuclease subunit, a linker sequence, and a second meganuclease subunit. A first subunit in each HBV 5-6 meganuclease binds to the HBV5 recognition half-site of SEQ ID NO: 12, while a second subunit binds to the HBV6 recognition half-site (see, FIG. 2).

The HBV5-binding subunits and HBV6-binding subunits each comprise a 56 base pair hypervariable region, referred to as HVR1 and HVR2, respectively. HBV5-binding subunits are highly conserved outside of the HVR1 region. Similarly, HBV6-binding subunits are also highly conserved outside of the HVR2 region. The HBV5-binding regions of SEQ ID NOs: 22-28 are provided as SEQ ID NOs: 48-54, respectively. Each of SEQ ID NOs: 48-54 share at least 90% sequence identity to SEQ ID NO: 49, which is the HBV5-binding region of the meganuclease HBV 5-6x.33 (SEQ ID NO: 22). HBV6-binding regions of SEQ ID NOs: 22-28 are provided as SEQ ID NOs: 55-61, respectively. Each of SEQ ID NOs: 55-61 share at least 90% sequence identity to SEQ ID NO: 55, which is the HBV5-binding region of the meganuclease HBV 5-6x.33 (SEQ ID NO: 22).

Meganucleases that Recognize and Cleave the HBV 7-8 Recognition Sequence

Engineered meganucleases (SEQ ID NOs: 29-32), collectively referred to herein as "HBV 7-8 meganucleases," were engineered to recognize and cleave the HBV 7-8 recognition sequence (SEQ ID NO: 14), which is positioned within the P protein ORF of multiple HBV genotypes, including genotype A, B, C, D, F, and G (e.g., SEQ ID NOs: 3-6, 8, and 9, respectively). Each HBV 7-8 engineered meganuclease comprises an N-terminal nuclease-localization signal derived from SV40, a first meganuclease subunit, a linker sequence, and a second meganuclease subunit. A first subunit in each HBV 7-8 meganuclease binds to the HBV7 recognition half-site of SEQ ID NO: 14, while a second subunit binds to the HBV8 recognition half-site (see, FIG. 2).

The HBV7-binding subunits and HBV8-binding subunits each comprise a 56 base pair hypervariable region, referred to as HVR1 and HVR2, respectively. HBV7-binding subunits are highly conserved outside of the HVR1 region. Similarly, HBV8-binding subunits are also highly conserved outside of the HVR2 region. The HBV7-binding regions of SEQ ID NOs: 29-32 are provided as SEQ ID NOs: 62-65, respectively. Each of SEQ ID NOs: 62-65 share at least 90% sequence identity to SEQ ID NO: 62, which is the HBV7-binding region of the meganuclease HBV 7-8x.2 (SEQ ID NO: 29). HBV8-binding regions of SEQ ID NOs: 29-32 are provided as SEQ ID NOs: 66-69, respectively. Each of SEQ ID NOs: 66-69 share at least 90% sequence identity to SEQ ID NO: 66, which is the HBV8-binding region of the meganuclease HBV 7-8x.2 (SEQ ID NO: 29).

Meganucleases that Recognize and Cleave the HBV 11-12 Recognition Sequence

Engineered meganucleases (SEQ ID NOs: 33-39), collectively referred to herein as "HBV 11-12 meganucleases," were engineered to recognize and cleave the HBV 11-12 recognition sequence (SEQ ID NO: 16), which is positioned within the P protein ORF of multiple HBV genotypes, including genotype A, B, C, D, E, F, and G (e.g., SEQ ID NOs: 3-9, respectively). Each HBV 11-12 engineered meganuclease comprises an N-terminal nuclease-localization signal derived from SV40, a first meganuclease subunit, a linker sequence, and a second meganuclease subunit. A first subunit in each HBV 11-12 meganuclease binds to the HBV 11 recognition half-site of SEQ ID NO: 16, while a second subunit binds to the HBV 12 recognition half-site (see, FIG. 2).

The HBV 11-binding subunits and HBV 12-binding subunits each comprise a 56 base pair hypervariable region, referred to as HVR1 and HVR2, respectively. HBV11-binding subunits are highly conserved outside of the HVR1 region. Similarly, HBV12-binding subunits are also highly conserved outside of the HVR2 region. The HBV 11-binding regions of SEQ ID NOs: 33-39 are provided as SEQ ID NOs: 70-76, respectively. Each of SEQ ID NOs: 70-76 share at least 90% sequence identity to SEQ ID NO: 70, which is the HBV 11-binding region of the meganuclease HBV 11-12x.26 (SEQ ID NO: 33). HBV12-binding regions of SEQ ID NOs: 33-39 are provided as SEQ ID NOs: 77-83, respectively. Each of SEQ ID NOs: 77-83 share at least 90% sequence identity to SEQ ID NO: 77, which is the HBV 2-binding region of the meganuclease HBV 11-12x.26 (SEQ ID NO: 33).

Cleavage of HBV Recognition Sequences in a CHO Cell Reporter Assay

Figure 6:
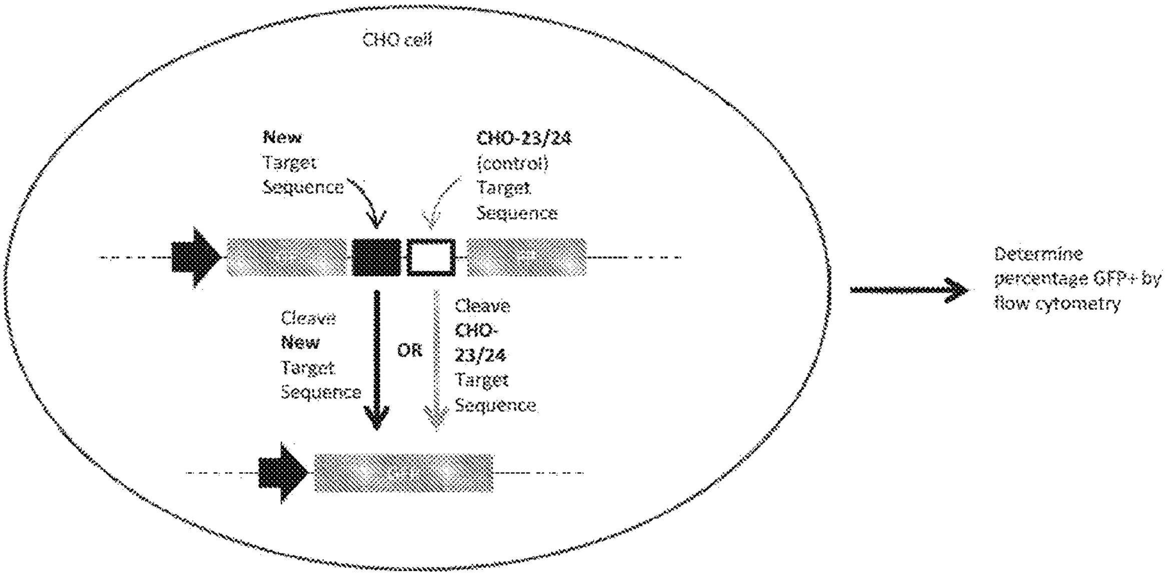
FIG. 6. Schematic of reporter assay in CHO cells for evaluating engineered meganucleases targeting an ORF of the genome of at least two genotypes of the Hepatitis B virus. For the engineered meganucleases described herein, a CHO cell line was produced in which a reporter cassette was integrated stably into the genome of the cell. The reporter cassette comprised, in 5' to 3' order; an SV40 Early Promoter, the 5' 2/3 of the GFP gene; the recognition sequence for an engineered meganuclease of the invention (e.g., the HBV 1-2 recognition sequence); the recognition sequence for the CHO-23/24 meganuclease (WO/2012/167192); and the 3' 2/3 of the GFP gene. Cells stably transfected with this cassette did not express GFP in the absence of a DNA break-inducing agent. Meganucleases were introduced by transduction of plasmid DNA or mRNA encoding each meganuclease. When a DNA break was induced at either of the meganuclease recognition sequences, the duplicated regions of the GFP gene recombined with one another to produce a functional GFP gene. The percentage of GFP-expressing cells could then be determined by flow cytometry as an indirect measure of the frequency of genome cleavage by the meganucleases.
Figure 7:
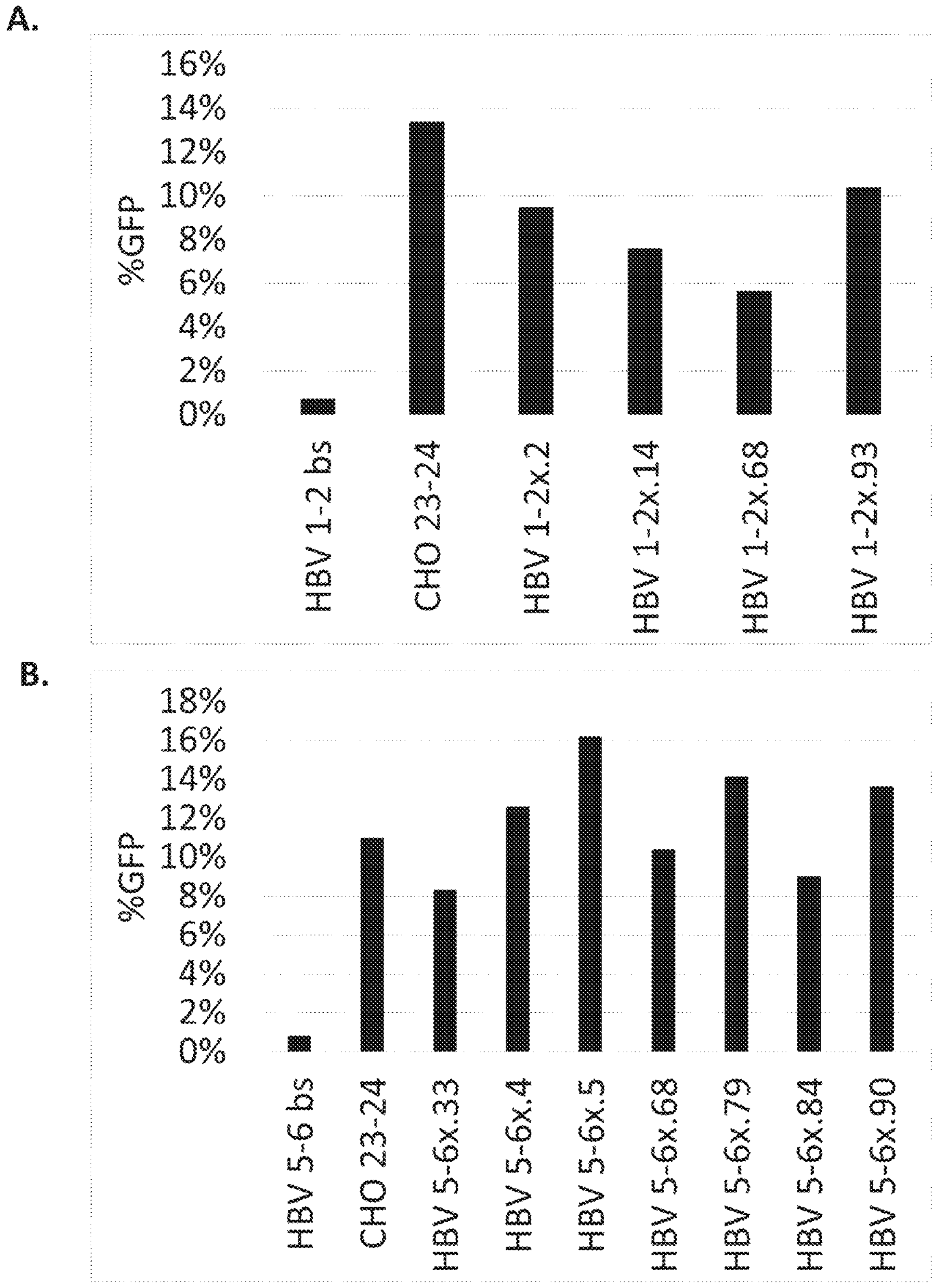
FIG. 7. Efficiency of engineered meganucleases for recognizing and cleaving recognition sequences in an ORF of the genome of at least two genotypes of the Hepatitis B virus, gene in a CHO cell reporter assay. Engineered meganucleases set forth in SEQ ID NOs: 18-39 were engineered to target the HBV 1-2 recognition sequence (SEQ ID NO: 10), the HBV 5-6 recognition sequence (SEQ ID NO: 12), the HBV 7-8 recognition sequence (SEQ ID NO: 14), or the HBV 11-12 recognition sequence (SEQ ID NO: 16), and were screened for efficacy in the CHO cell reporter assay. The results shown provide the percentage of GFP-expressing cells observed in each assay, which indicates the efficacy of each meganuclease for cleaving a target recognition sequence or the CHO-23/24 recognition sequence. A negative control (bs) was further included in each assay.

To determine whether HBV 1-2, HBV 5-6, HBV 7-8, and HBV 11-12 meganucleases could recognize and cleave their respective recognition sequences (SEQ ID NOs: 10, 12, 14, and 16, respectively), each engineered meganuclease was evaluated using the CHO cell reporter assay previously described (see, WO/2012/167192 and FIG. 6). To perform the assays, CHO cell reporter lines were produced which carried a non-functional Green Fluorescent Protein (GFP) gene expression cassette integrated into the genome of the cells. The GFP gene in each cell line was interrupted by a pair of recognition sequences such that intracellular cleavage of either recognition sequence by a meganuclease would stimulate a homologous recombination event resulting in a functional GFP gene.

In CHO reporter cell lines developed for this study, one recognition sequence inserted into the GFP gene was the HBV 1-2 recognition sequence (SEQ ID NO: 10), the HBV 5-6 recognition sequence (SEQ ID NO: 12), the HBV 7-8 recognition sequence (SEQ ID NO: 12), and the HBV 11-12 recognition sequence (SEQ ID NO: 16). The second recognition sequence inserted into the GFP gene was a CHO-23/24 recognition sequence, which is recognized and cleaved by a control meganuclease called "CHO-23/24". CHO reporter cells comprising the HBV 1-2 recognition sequence and the CHO-23/24 recognition sequence are referred to as "HBV 1-2 cells." CHO reporter cells comprising the HBV 5-6 recognition sequence and the CHO-23/24 recognition sequence are referred to as "HBV 5-6 cells." CHO reporter cells comprising the HBV 7-8 recognition sequence and the CHO-23/24 recognition sequence are referred to as "HBV 7-8 cells." CHO reporter cells comprising the HBV 11-12 recognition sequence and the CHO-23/24 recognition sequence are referred to as "HBV 11-12 cells."

CHO reporter cells were transfected with plasmid DNA encoding their corresponding engineered meganucleases (e.g., HBV 1-2 cells were transfected with plasmid DNA encoding HBV 1-2 meganucleases) or encoding the CHO-23/34 meganuclease. In each assay, $4e^5$ CHO reporter cells were transfected with 50 ng of plasmid DNA in a 96-well plate using Lipofectamine 2000 (ThermoFisher) according to the manufacturer's instructions. At 48 hours post-transfection, cells were evaluated by flow cytometry to determine the percentage of GFP-positive cells compared to an untransfected negative control (HBV bs). As shown in FIGS. 7A-7D, all HBV meganucleases were found to produce GFP-positive cells in cell lines comprising their corresponding recognition sequence at frequencies significantly exceeding the negative control.

The efficacy of HBV 1-2, HBV 5-6, HBV 7-8, and HBV 11-12 meganucleases was also determined in a time-dependent manner 2, 5, 7, 9, and 12 days after introduction of the meganucleases into CHO reporter cells. In this study, HBV 1-2, HBV 5-6, HBV 7-8, or HB 11-12 cells ($1.0\times10^6$) were electroporated with $1\times10^6$ copies of meganuclease mRNA per cell using a BioRad Gene Pulser Xcell according to the manufacturer's instructions. At the designated time points post-transfection, cells were evaluated by flow cytometry to determine the percentage of GFP-positive cells. A CHO-23/24 meganuclease was also included at each time point as a positive control.

As shown in FIGS. 8A-8D, the % GFP produced by different HBV meganucleases varied over time. HBV 5-6 and HBV 11-12 meganucleases were substantially consistent over the 12 day period of analysis (FIGS. 8B and 8D), whereas HBV 1-2 and HBV 7-8 meganucleases produced a high level of GFP-positive cells at early time points which decreased during the course of the experiment.

Conclusions

These studies demonstrated that HBV meganucleases encompassed by the invention can efficiently target and cleave their respective recognition sequences in cells and that this effect can either be consistent or transient over time.

Example 2

HBV-Specific Nucleases Eliminate Plasmid DNA in *E. coli*

Bacterial Reporter System Utilizing Episomal DNA

The purpose of this experiment was to evaluate HBV meganucleases of the invention for their ability to recognize and cleave recognition sequences within episomal DNA plasmids in an *E. coli* reporter system.

Figure 9:
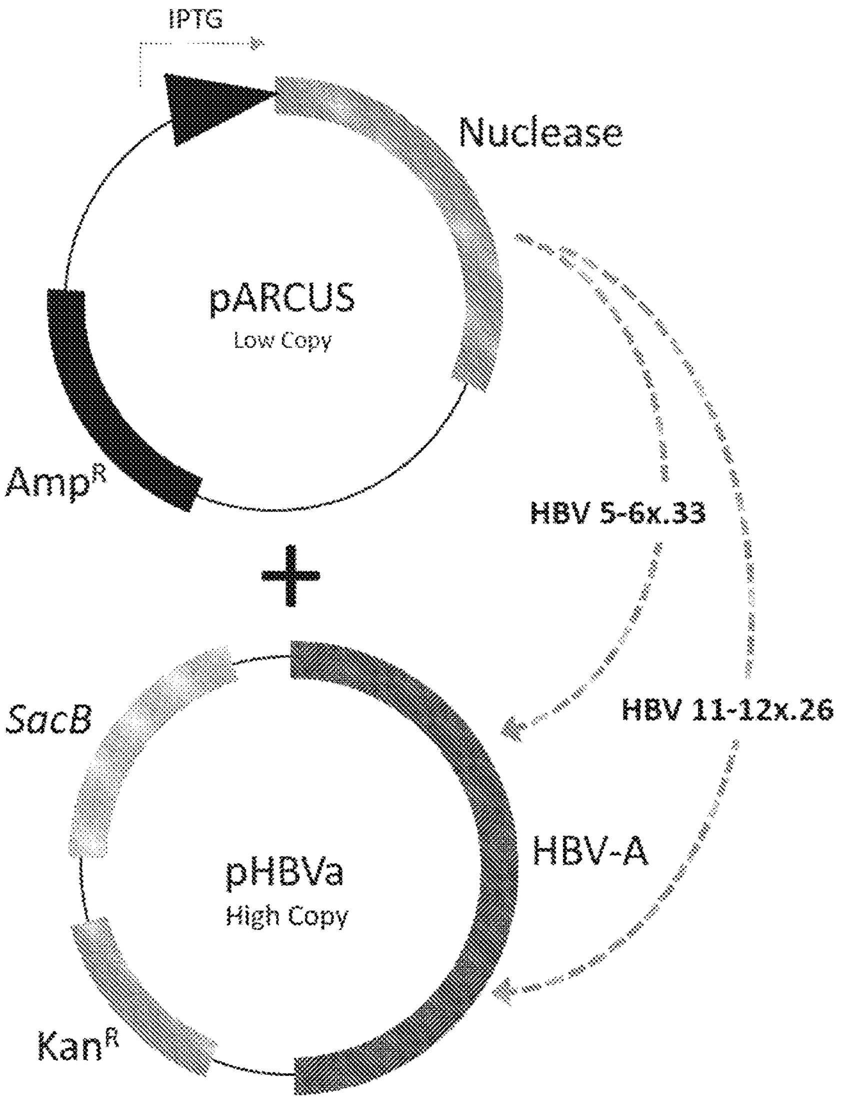
FIG. 9. Evaluation of HBV meganucleases for their ability to recognize and cleave recognition sequences within episomal DNA plasmids in an *E. coli* reporter system.
Figure 9:
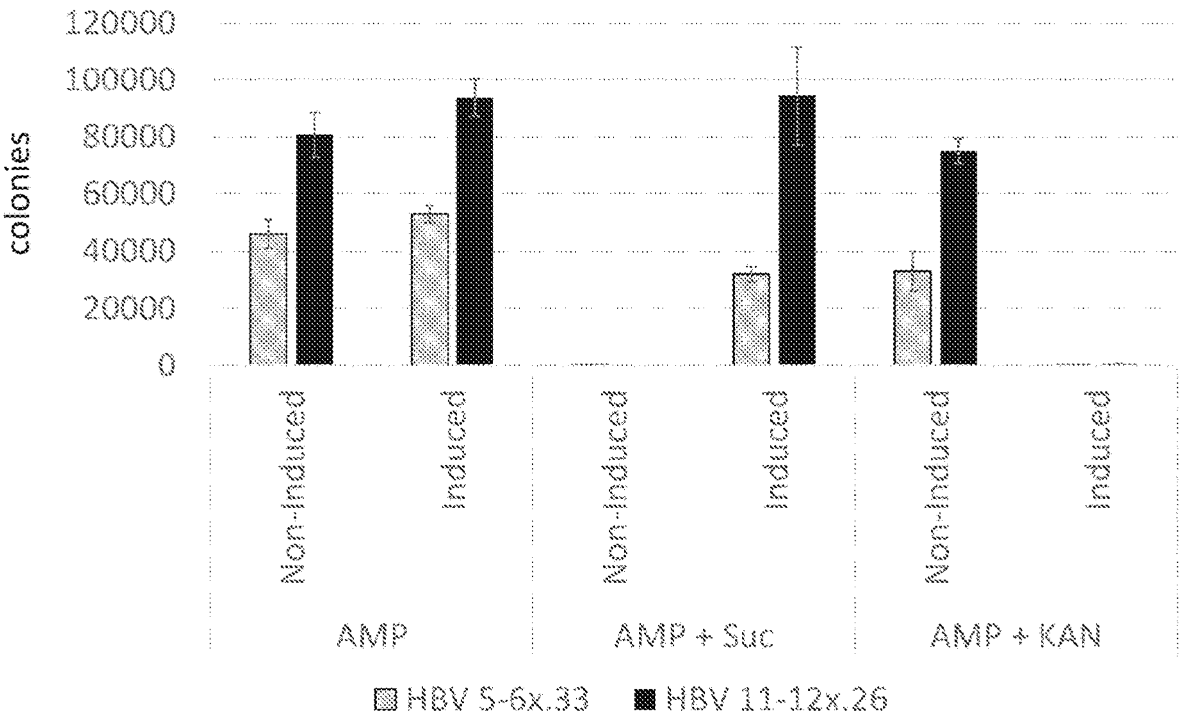

A plasmid called "pARCUS" was generated to drive inducible expression of an ARCUS nuclease (FIG. 9A). In pARCUS, an ARCUS nuclease (here, either HBV 5-6x.33 or HBV 11-12x) is placed under the control of an IPTG-inducible promoter. Additionally, to allow for selection of transformed bacteria, pARCUS encodes an ampicillin resistance gene. pARCUS is a low copy plasmid so that induced expression of an ARCUS nuclease does not result in over-expression.

An additional plasmid called "pHBVa" was generated (FIG. 9A). pHBVa carries a large fragment of the HBV genome, including the recognition sequences for HBV 5-6 and HBV 11-12. The plasmid also encodes a kanamycin resistance gene and a SacB gene. The kanamycin resistance gene allows for selection of transformed bacteria and the SacB gene is a toxin that is active in the presence of sucrose. Thus, bacteria transformed with pHBVa will survive in the presence of kanamycin in the medium, but will not survive in the presence of kanamycin and sucrose. pHBVa was designed to be a high copy plasmid in an attempt to replicate an HBV-infected cell in which there may be many copies of the HBV genome. Importantly, pHBVa utilizes a different origin of replication than pARCUS, allowing for co-transformation of bacteria with both plasmids.

When bacteria are co-transformed with these plasmids and grown in medium containing various combinations of selective pressure (ampicillin, kanamycin, or sucrose), there are a number of possible outcomes. Bacteria transformed with pARCUS and grown in the presence of ampicillin will carry the pARCUS plasmid, but will not express the encoded nuclease unless the growth medium is supplemented with IPTG. When induced with IPTG, the encoded nuclease will be expressed. Bacteria transformed with pHBVa will grow in the presence of kanamycin, but not kanamycin and sucrose. Bacteria co-transformed with pARCUS and pHBVa in the presence of ampicillin and/or kanamycin will be sensitive to sucrose. It was predicted that in bacteria co-transformed with pARCUS and pHBV, induction of the ARCUS nuclease with IPTG will result in expression of the nuclease, which could then cleave the target site encoded on pHBVa. Cleavage at that site was expected to result in linearization of the pHBVa plasmid, which should be rapidly degraded by bacterial nucleases. Degradation of the pHBV plasmid will result in two outcomes: bacteria will lose resistance to kanamycin, but will be able to survive in the presence of sucrose.

To test the outcomes of co-transformation, bacteria were co-transformed (by electroporation) with pARCUS and pHBVa and cultured in the presence of ampicillin for 3 hours prior to plating. In parallel cultures, co-transformed cells were treated with IPTG (3 hours) to induce nuclease expression and allow for cleavage of pHBVa. Cells were then plated on agar plates in the presence of ampicillin, ampicillin and sucrose, or ampicillin and kanamycin. Plates were incubated overnight, and colonies were counted to assess bacterial survival.

Results

The number of colonies present on each selective plate provided dramatic evidence of the ability of ARCUS nucleases to cleave the pHBVa plasmid. On control ampicillin plates, the number of colonies from either non-induced or IPTG-induced cultures were equal for cells co-transformed with pHBVa and either pARCUS plasmids (FIG. 9B). There was a difference in colony number between bacteria co-transformed with pARCUS encoding HBV 5-6x.33 and bacteria co-transformed with pARCUS encoding HBV 11-12x.26, but that likely reflects transformation efficiency.

In sharp contrast, the number of colonies from non-IPTG induced cultures on plates containing both ampicillin and sucrose were dramatically reduced, indicating that the SacB gene was effective at killing cells when sucrose was available (FIG. 9B). However, cultures that were induced with IPTG, grew quite well on plates containing both ampicillin and sucrose, indicating elimination of the SacB gene. Colony counts for bacteria co-transformed (but not induced with IPTG) with pHBVa and pARCUS encoding HBV 11-12x.26 were the same as on ampicillin control plates, and bacteria co-transformed with pARCUS 5-6x.33 were only slightly reduced compared to control plates.

Non-IPTG induced cultures were able to grow on plates containing both ampicillin and kanamycin (FIG. 9B). Colony counts from bacteria co-transformed with pARCUS encoding HBV 11-12x.26 were approximately equal to control ampicillin-only plates, and cells co-transformed with pARCUS HBV 5-6x.33 were only slightly reduced compared to controls. However, when IPTG-induced cells were grown on plates containing ampicillin and kanamycin, colony counts were close to zero, indicating elimination of plasmids carrying a kanamycin resistance gene (FIG. 9B).

Conclusions

These data clearly demonstrate that HBV meganucleases of the invention recognizing sites in the HBV genome are capable of cutting the pHBVa plasmid, resulting in elimination of the pHBVa plasmid. In IPTG-induced cultures, cells grew in the presence of sucrose, indicating efficient elimination of the SacB-containing plasmid. Similarly, in IPTG-induced cultures, cells died in the presence of kanamycin, also strongly indicating destruction of the pHBVa plasmid. It is possible that similar outcomes could occur in HBV-infected mammalian cells, using HBV meganucleases of the invention to cleave HBV cccDNA. In bacteria, linear DNA is quickly eliminated. It is conceivable that linearized cccDNA in mammalian cells will be digested by cellular nucleases as well. Even if cleavage does not lead to linearization and elimination of cccDNA, it is likely that indel mutations caused by the HBV ARCUS nucleases will disrupt coding regions and render the cccDNA unable to produce functional HBV proteins. Thus, meganucleases of the invention targeting sites in the HBV genome should be an effective method to eliminate, or inactivate, HBV cccDNA.

Example 3

Targeting HBV Viral Genomes in Cells

Treatment of AD38 Cells Expressing an HBV Genome

A primary purpose of these Examples was to evaluate whether meganucleases of the invention were capable of inactivating and/or eliminating HBV genomes in HBV-infected mammalian cells.

In a first study, meganuclease effectiveness was evaluated in an AD38 cell line which stably expresses an HBV genome under a Tet promoter. This AD38 cell line does not generate active viral particles but does generate HBV S antigen (HBsAg) which is detectable in the cell medium. In this study, cells were transfected with a DNA plasmid encoding either HBV 5-6x.33 or HBV 11-12x.26. Both of these engineered meganucleases target a sequence specific to the HBV genome, with HBV 5-6x.33 targeting a sequence within the overlapping S (HBsAg gene) and P (polymerase gene) reading frames and HBV 11-12x.26 targeting the P gene. As a control, AD38 cells were transfected with a plasmid encoding the red fluorescent protein (RFP) gene. Cells were seeded and 24 hours later were transfected with plasmids using a liposome-based transfection protocol. 24 hours post-transfection, the AD38 cells were washed to remove remaining liposome complexes. On days 3 and 7 post-transfection, cell supernatant was harvested and assayed for the presence of HBsAg by ELISA.

Results

Figure 10:
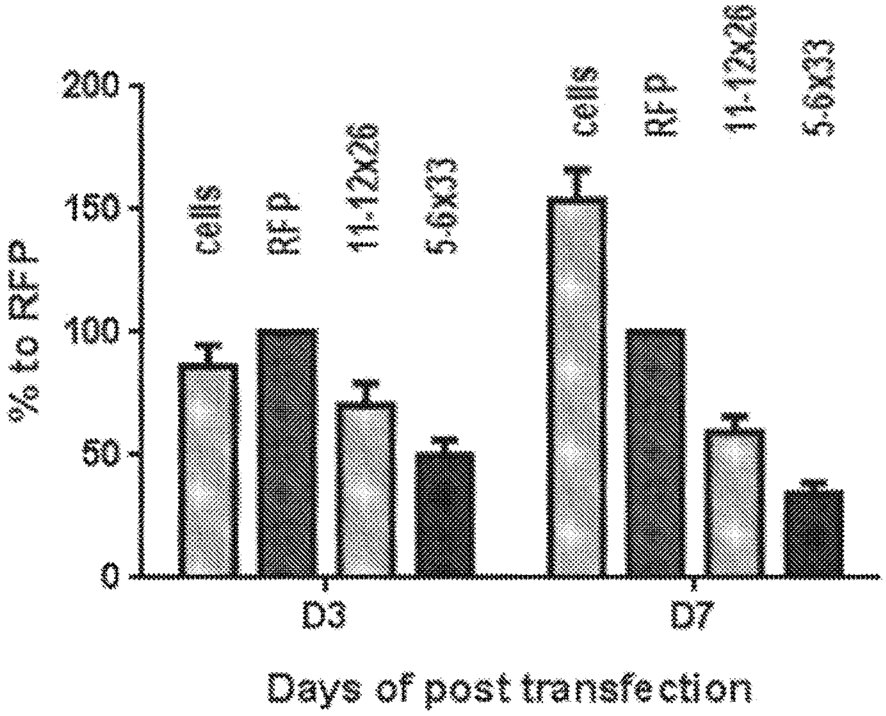
FIG. 10. Evaluation of HBV meganucleases in AD38 cells. AD38 cells, which express an HBV genome and secrete HBsAg, were transfected with plasmid DNA encoding the HBV 5-6x.33 or HBV 11-12x.26 meganucleases. Plasmid DNA encoding a red fluorescent protein was used in this experiment as a control. On days 3 and 7 post-transfection, cell supernatant was harvested and assayed for the presence of HBsAg by ELISA.

ELISA data was normalized to the amount of HBsAg present in the supernatant of RFP-transfected AD38 cells at day 3 and day 7 post-transfection. At day 3 post-transfection, cells transfected with a plasmid encoding HBV 11-12x.26 showed approximately 25% less HBsAg in the supernatant compared to RFP-transfected cells (FIG. 10). At the same timepoint, cells transfected with a plasmid encoding HBV 5-6x.33 showed approximately 50% less HBsAg in the supernatant compared to RFP-transfected cells (FIG. 10). Non-transfected control cells were essentially the same as RFP-transfected cells. The reduction in HBsAg was even more apparent at day 7 post-transfection. AD38 cells transfected with HBV 11-12x.26 showed HBsAg levels approximately 50% less than cells transfected with RFP, and cells transfected with HBV 5-6x.33 had levels approximately 75% less than the RFP control (FIG. 10). At day 7 post-transfection, cells transfected with RFP had significantly less HBsAg in the supernatant compared with non-transfected cells, suggesting that the transfection process had a negative impact on the ability of the cells to produce HBsAg. Nonetheless, the impact was far more pronounced in cells transfected with plasmids encoding the HBV meganucleases, strongly suggesting that the reduction in supernatant HBsAg levels was due to meganuclease activity.

Conclusions

These data demonstrate that AD38 cells transfected with plasmids encoding either the HBV 5-6x.33 or HBV 11-12x.26 show a dramatic reduction in HBsAg in the supernatant compared to either non-transfected cells or cells transfected with an RFP reporter gene. The reduction in supernatant HBsAg levels in cells transfected with either of the HBV meganucleases strongly suggests that the reduction is due to meganuclease activity against the HBV genome in AD38 cells.

Example 4

Targeting HBV Viral Genomes in Cells

Treatment of AD38 Cells Expressing an HBV Genome

The studies in Example 3 above demonstrate meganuclease effectiveness in reducing the secretion of HBsAg from the HBV genome-expressing AD38 cell line. To determine if a greater reduction in HBsAg secretion could be achieved using lentiviral delivery instead of plasmid transfection, this study was repeated with lentiviral delivery using the HBV 11-12x.26 and HBV5-6x.33 meganucleases individually or in combination.

Lentiviruses were generated that expressed either RFP, HBV 5-6x.33 or HBV 11-12x.26, and AD38 cells were transduced to determine the impact of the meganucleases on HBsAg production. AD38 cells were seeded and 24 hours later were transduced with either a lentivirus encoding RFP, HBV 5-6x.33, HBV 11-12x.26, or a 1:1 mixture of the lentiviruses encoding the HBV meganucleases. Cells were transduced with single lentiviruses at an MOI of 1, 2, or 4. Cells that were transduced with the 1:1 mixture of HBV meganuclease-encoding lentiviruses were transduced at total MOIs of 2 and 4. The media on the transduced cells was changed on day 1 and day 3 post-transduction. On day 7 post-transduction, cell supernatants were harvested and assayed for the presence of HBsAg by ELISA.

Results

Figure 11:
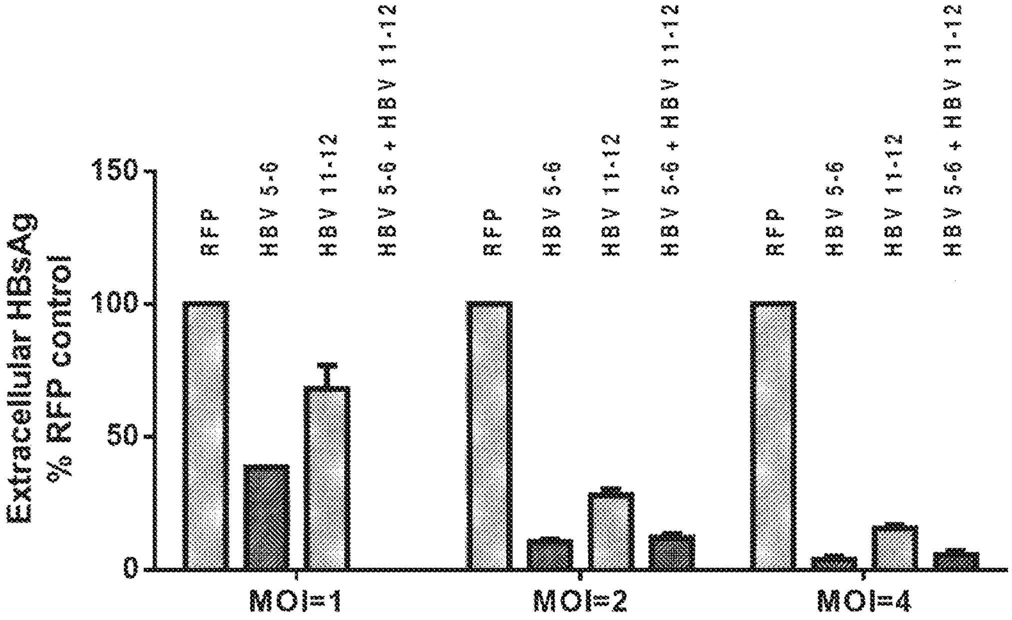
FIG. 11. Evaluation of HBV meganucleases in AD38 cells. AD38 cells, which express an HBV genome and secrete HBsAg, were transduced with lentivirus encoding the HBV 5-6x.33 meganuclease or the HBV 11-12x.26 meganuclease, or were transduced with a combination of the two. Lentivirus encoding a red fluorescent protein was used in this experiment as a control. MOIs of 1, 2, and 4 were examined. On day 7 post-transduction, cell supernatant was harvested and assayed for the presence of HBsAg by ELISA.

ELISA data was normalized to the amount of HBsAg present in the supernatant of RFP-transduced AD38 cells at day 7 post-transfection. At an MOI of 1, AD38 cells transduced with HBV 5-6x.33 showed approximately 60% less HBsAg in the supernatant than AD38 cells transduced with RFP-expressing lentivirus (FIG. 11). Also at an MOI of 1, HBV 11-12x.26 showed about 40% less HBsAg than RFP. At higher MOIs, the impact of the HBV meganucleases was more pronounced. At an MOI of 2, cells transduced with lentivirus encoding HBV 5-6x.33 showed a reduction in HBsAg of about 80% compared to RFP-transduced cells and, at an MOI of 4, the reduction was around 90% compared. Similarly, at an MOI of 2, cells transduced with lentivirus encoding HBV 11-12x.26 showed about 70% less HBsAg than the RFP-transduced cells and, at an MOI of 4, HBsAg was lower by approximately 80%. Lastly, cells transduced with a 1:1 mixture of lentiviruses encoding the HBV meganucleases also showed dramatically reduced levels of HBsAg in the supernatant compared to RFP-transduced control cells (FIG. 11). At a total MOI of 2, the HBV-expressing lentiviruses reduced expression of HBsAg by about 80% and, at a total MOI of 4, expression was reduced by approximately 90%.

Conclusions

These data demonstrate that AD38 cells transduced with lentiviruses encoding either the HBV 5-6x.33 or HBV 11-12x.26, or a combination of both, show a dramatic reduction in HBsAg in the supernatant compared to cells transduced with a lentivirus expressing RFP. The reduction in supernatant HBsAg levels in cells transduced with lentiviruses expressing either or both of the HBV meganucleases strongly suggests that the reduction is due to meganuclease activity against the HBV genome in AD38 cells. Further, these data demonstrate that co-expression of the HBV meganucleases effectively reduce expression of HBsAg, strongly suggesting that co-expressed meganucleases can effectively the HBV genome.

Example 5

Targeting HBV Viral Genomes in Cells

Treatment of AD38 Cells Expressing an HBV Genome

In a further study, AD38 cells were transduced with lentiviruses encoding the HBV 5-6x.33 or HBV 11-12x.26 meganucleases in order to observe the effect of meganuclease treatment on HBsAg secretion. HBV DNA copies present in the cell culture medium, and intracellular HBV cccDNA copies.

Similar to Example 4 above, lentiviruses were generated that expressed either RFP (LV212), HBV 5-6x.33 (LV224), or HBV 11-12x.26 (LV225), and AD38 cells were transduced to determine the impact of the meganucleases on each experimental outcome. AD38 cells were seeded in the presence of tetracycline and 24 hours later were transduced with lentivirus encoding RFP, HBV 5-6x.33, or HBV 11-12x.26 at an MOI of 4. The media on the transduced cells was changed 24 hours post-transduction. On day 7 post-transduction, cell supernatants were harvested and assayed for the presence of HBsAg by ELISA. Copies of extracellular HBV DNA per 5 μL of cell culture were determined by quantitative PCR. Cell lysates were obtained and intracellular copies of HBV cccDNA per 5 μL of cell lysate were determined by quantitative PCR.

Results

Figure 12:
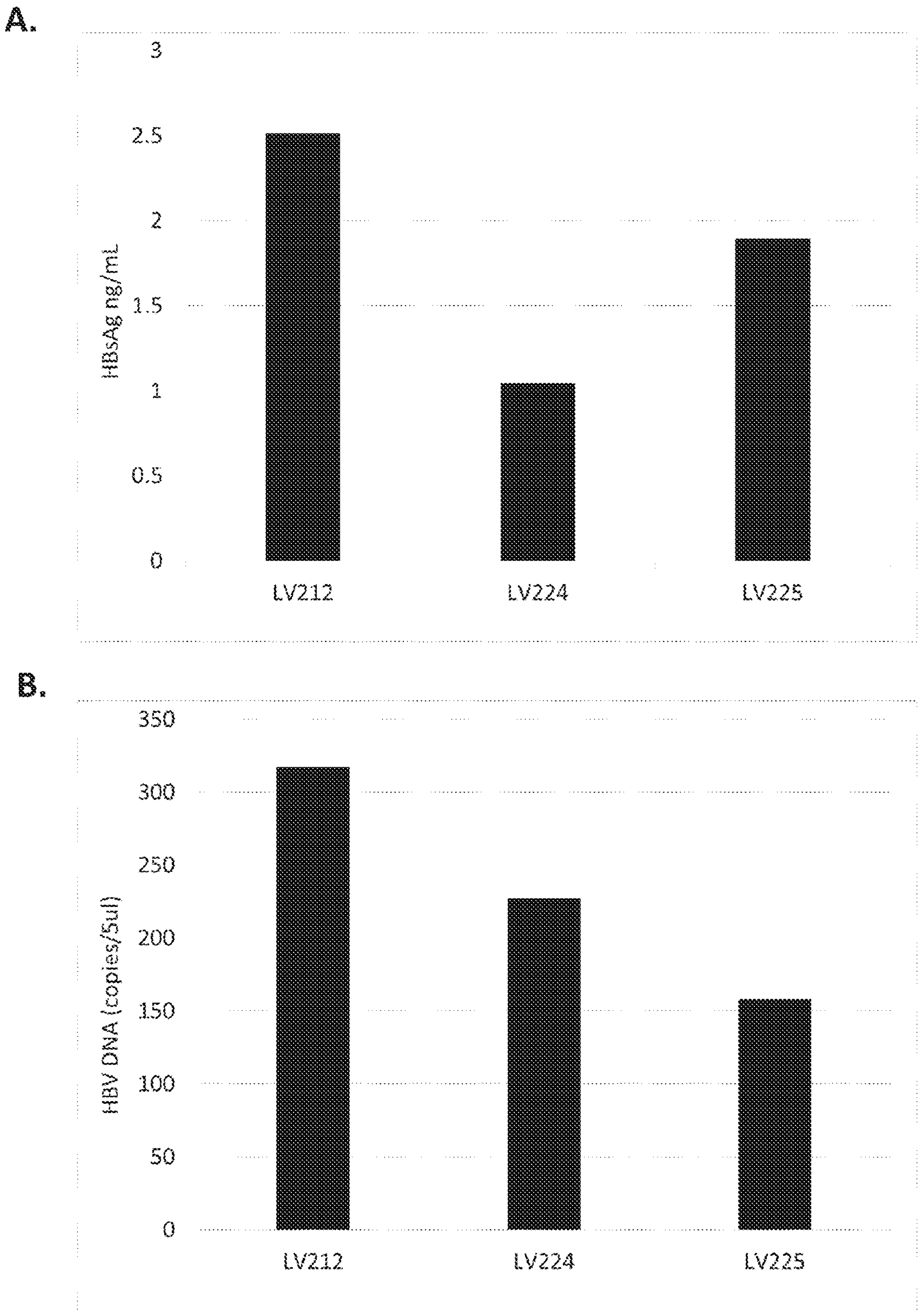
FIG. 12. Evaluation of HBV meganucleases in AD38 cells. AD38 cells, which express an HBV genome and secrete HBsAg, were transduced with lentivirus encoding the HBV 5-6x.33 meganuclease (LV224), the HBV 11-12x.26 meganuclease (LV225), or a red fluorescent protein (LV212). An MOI of 4 was examined, and on day 7 post-transduction, cell supernatant was harvested and assayed for the presence of HBsAg and extracellular HBV DNA copy number. Additionally, cell lysates were obtained on day 7 post-transduction and analyzed for intracellular copy number of HBV cccDNA.
Figure 12:
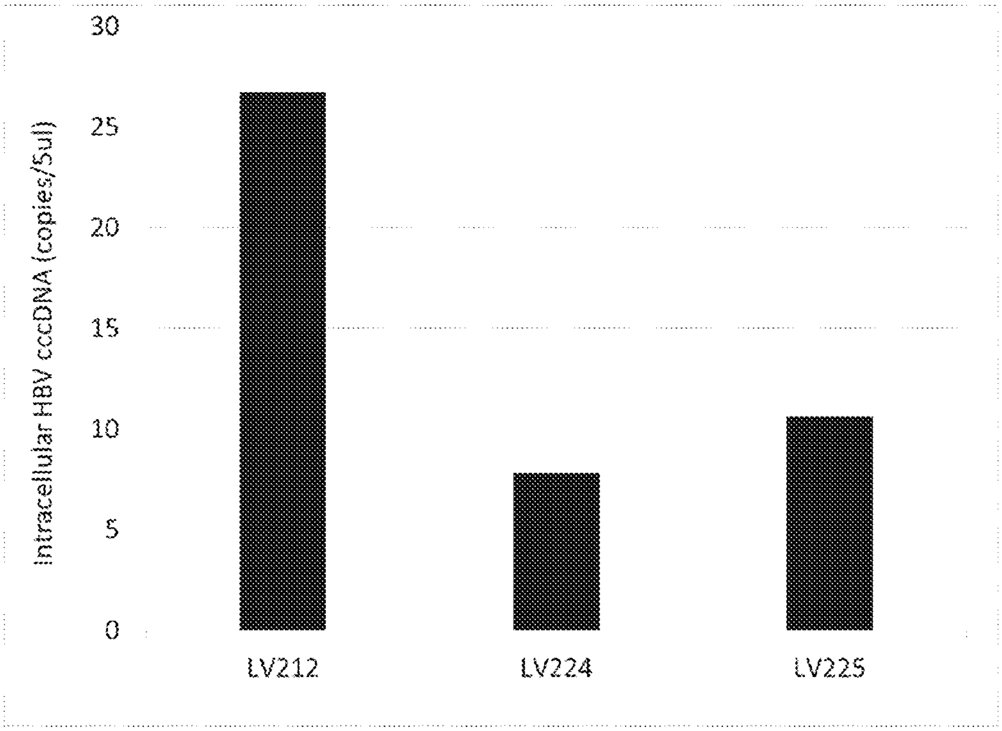

At an MOI of 4, AD38 cells transduced with HBV 5-6x.33 and HBV 11-12x.26 showed approximately 58% and 25% less HBsAg in the cell culture medium, respectively, 7 days after transduction than AD38 cells transduced with RFP-expressing lentivirus (FIG. 12A). Extracellular HBV DNA copy number was also reduced by transduction with HBV 5-6x.33 and HBV 11-12x.26 meganucleases by approximately 28% and 50%, respectively, when compared to transduction with RFP-expressing lentivirus (FIG. 12B). Finally, intracellular HBV cccDNA copy number was also reduced by transduction with HBV 5-6x.33 and HBV 11-12x.26 meganucleases by approximately 71% and 60%, respectively, when compared to transduction with RFP-expressing lentivirus (FIG. 12C).

Conclusions

These data further demonstrate that AD38 cells transduced with lentiviruses encoding either the HBV 5-6x.33 or HBV 11-12x.26 meganucleases show a dramatic reduction in HBsAg in the supernatant compared to cells transduced with a lentivirus expressing RFP. Additionally, these data demonstrate that HBV meganucleases of the invention also reduce extracellular HBV DNA copy number and, importantly, significantly reduce intracellular copy number of HBV cccDNA.

Example 6

Treatment of HBV-Infected Primary Human Hepatocytes

Treatment of HBV-Infected Primary Human Hepatocytes

The studies in the Examples above demonstrate meganuclease effectiveness in reducing the secretion of HBsAg from the HBV genome-expressing AD38 cell line. The studies of the present Example were conducted to determine the effectiveness of HBV meganucleases of the invention in HBV-infected primary human hepatocytes.

Lentiviruses were generated that expressed either RFP, HBV 5-6x.33, or HBV 11-12x.26, and HBV-infected primary human hepatocytes were transduced to determine the impact of the meganucleases on HBsAg and HBeAg production. Briefly, primary human hepatocytes were seeded and 24 hours later infected with HBV. 1 day post-infection, the cells were washed and 24 hours later (day 2 post-infection) were transduced with either a lentivirus encoding RFP, HBV 5-6x.33, HBV 11-12x.26, or a 1:1 mixture of the lentiviruses encoding the HBV meganucleases. As an additional control, infected cells were treated with DMSO. Cell supernatants were harvested and medium was replaced on days 4, 8, 11, and 13 post-transduction. At each time point, HBsAg and HBeAg was measured in the cell supernatants by ELISA. Extracellular DNA in the supernatant was also measured at day 13 post-infection.

Results

Figure 13:
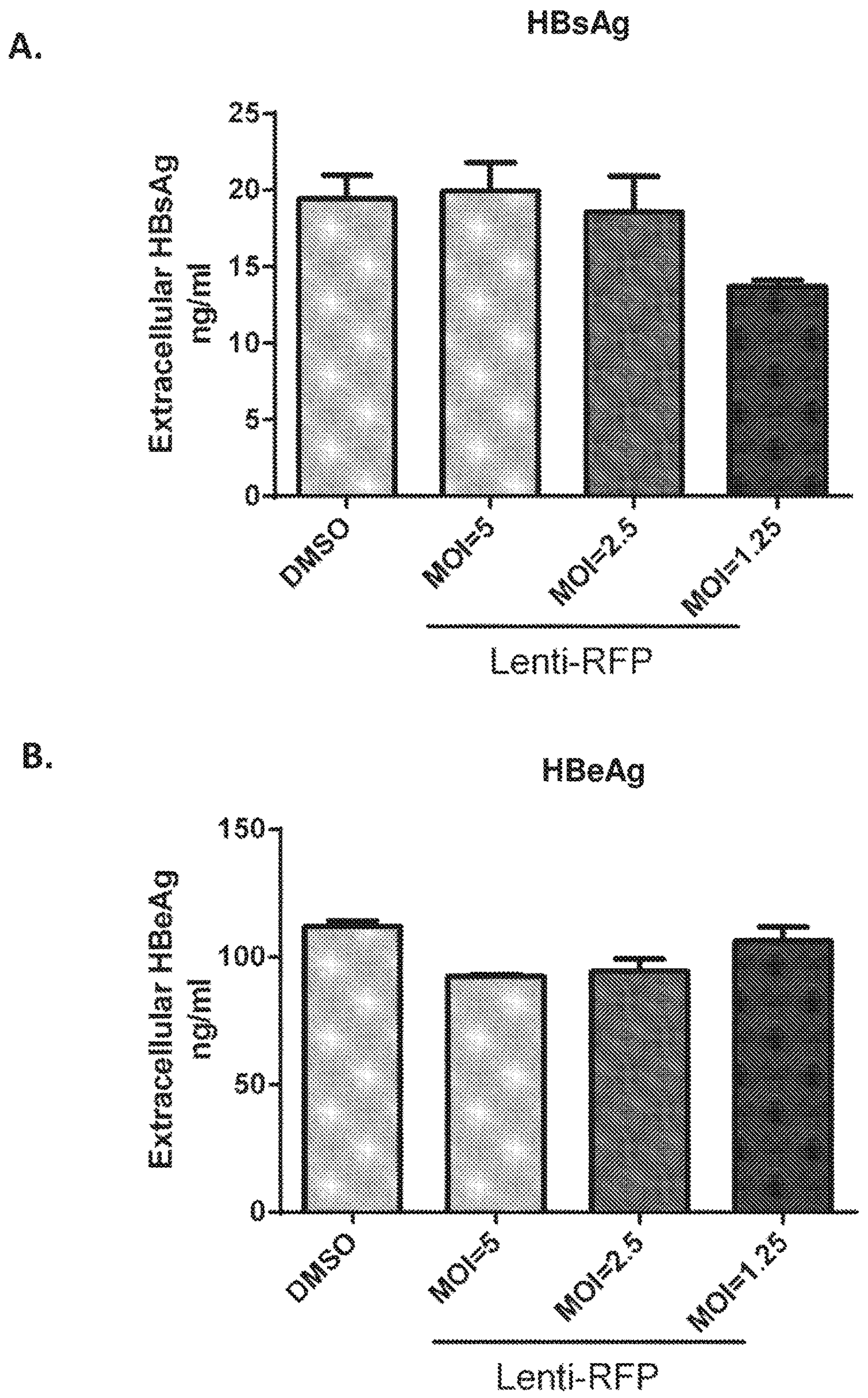
FIG. 13. Evaluation of HBV meganucleases in HBV-infected primary human hepatocytes. Lentiviruses were generated that expressed either RFP, HBV 5-6x.33, or HBV 11-12x.26, and HBV-infected primary human hepatocytes were transduced to determine the impact of the meganucleases on HBsAg and HBeAg production. Primary human hepatocytes were seeded and 24 hours later infected with HBV. One day post-infection, the cells were washed and 24 hours later (day 2 post-infection) were transduced with either a lentivirus encoding RFP, HBV 5-6x.33, HBV 11-12x.26, or a 1:1 mixture of the lentiviruses encoding the HBV meganucleases. As an additional control, infected cells were treated with DMSO. Cell supernatants were harvested and medium was replaced on days 4, 8, 11, and 13 post-transduction. At each time point. HBsAg and HBeAg was measured in the cell supernatants by ELISA. Extracellular DNA in the supernatant was also measured at day 13 post-infection. To determine whether lentivirus transduction, in general, impacted secretion of either HBsAg or HBeAg, cell supernatants from cells transduced with an RFP-encoding lentivirus were compared to cells treated with DMSO.
Figure 13:
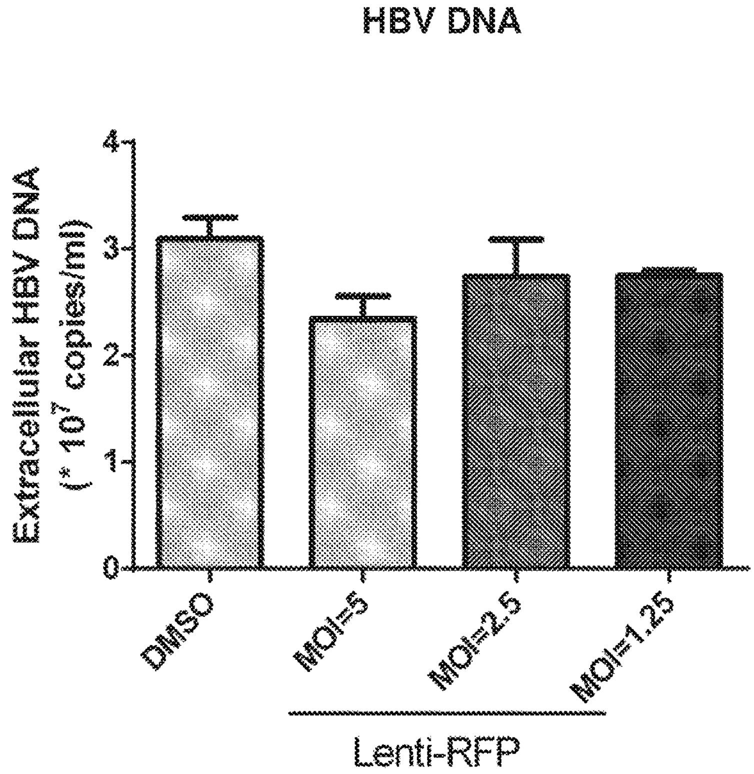

To determine whether lentivirus transduction, in general, impacted secretion of either HBsAg or HBeAg, cell supernatants from cells transduced with an RFP-encoding lentivirus were compared to cells treated with DMSO (FIG. 13). Transduction of HBV-infected primary human hepatocytes with a lentivirus encoding RFP had minor, if any, impact on secretion of HBsAg or HBeAg (FIGS. 13A and 13B). At an MOI of 5 or 2.5, HBsAg levels are identical to cells treated with DMSO, and at an MOI of 1.25, there is only a modest decrease (FIG. 13A). Similarly, HBeAg levels in supernatants of RFP-lentivirus transduced cells show only modest decreases at an MOI of 1.25, 2.5 or 5, when compared to DMSO treated cells (FIG. 13B). Additionally, the amount of extracellular HBV detected in the supernatant of HBV-infected primary human hepatocytes shows little difference between DMSO treated cells and cells transduced with RFP-encoding lentivirus (FIG. 13C).

Having shown that lentiviral transduction, in general, did not impact HBV function in infected primary human hepatocytes, lentiviruses encoding HBV meganucleases were compared to RFP lentivirus. HBsAg ELISA data was normalized to the amount of HBsAg present in the supernatant of RFP-transduced, HBV-infected primary human hepatocytes at days 3, 8, 11, and 13 post-transduction (FIG. 14). At both an MOI of 2.5 and 1.25, cells transduced with lentivirus encoding HBV 5-6x.33 showed a steady decrease in HBsAg over the time course of the experiment, showing slightly reduced levels at day 3, a reduction of approximately 50-60% by day 8, and a reduction of around 90% by days 11 and 13 when compared to the RFP control (FIGS. 14A and 14B). Infected cells transduced with HBV 11-12x.26 showed a similar pattern at both an MOI of 2.5 and 1.25, with a more noticeable reduction at the day 3 time point (around 50% reduction), and still achieving around 90% reduction by days 11 and 13 post-transduction (FIGS. 14A and 14B). When infected cells were transduced with a 1:1 mix of the HBV meganuclease-encoding lentiviruses, a similar reduction in HBsAg was observed over the time course. At an MOI of 2.5, levels were reduced by approximately 50% at day 3 post-transduction, and the reduction continued, reaching 90% by days 11 and 13 post-transduction (FIGS. 14A and 14B).

HBeAg ELISA data was also normalized to the amount of HBeAg present in the supernatant of RFP-transduced, HBV-infected primary human hepatocytes at days 3, 8, 11 and 13 post-transduction (FIG. 14). At both an MOI of 2.5 and 1.25, cells transduced with lentivirus encoding HBV 5-6x.33 showed a steady decrease in HBeAg over the time course of the experiment, showing levels reduced by around 25% at day 3, a reduction of approximately 50% by day 8, and a reduction of around 90% by days 11 and 13 when compared to the RFP control (FIGS. 14C and 14D). Infected cells transduced with HBV 11-12x.26 showed a similar pattern at both an MOI of 2.5 and 1.25, with a similar reduction at the day 3 time point (around 30% reduction), and still achieving around 90% reduction in HBeAg by days 11 and 13 post-transduction (FIGS. 14C and 14D). When infected cells were transduced with a 1:1 mix of the HBV meganuclease-encoding lentiviruses, a similar reduction in HBeAg was observed over the time course. At an MOI of 2.5 and 1.25, levels were reduced by approximately 50% at day 3 post-transduction, and the reduction continued, reaching 90% by days 11 and 13 post-transduction (FIGS. 14C and 14D).

Conclusions

These data demonstrate that HBV-infected primary human hepatocytes, transduced with lentiviruses encoding either the HBV 5-6x.33 or HBV 11-12x.26, or a combination of the two, show a dramatic reduction in HBsAg and HBeAg in the supernatant compared to cells transduced with a lentivirus expressing RFP. The reduction in supernatant HBsAg and HBeAg levels in infected cells, transduced with lentiviruses expressing either or both of the HBV meganucleases, strongly suggests that the reduction is due to meganuclease activity against the infectious virus.

Example 7

Delivery of LNP-Encapsulated Nuclease mRNA to Liver

Encapsulation of mRNA in lipid nanoparticles and delivery to mice

The purpose of this study was to demonstrate that lipid nanoparticle (LNP)-encapsulated mRNA encoding an engineered meganuclease could be prepared and administered in vivo, and that gene editing in the liver occurs and could be observed.

An engineered meganuclease was developed which has specificity for a recognition sequence in the mouse CMP-NeuAc hydrolase (Cmah) gene, which is expressed in the mouse liver. ARCA-capped mRNA encoding the Cmah meganuclease was prepared by TriLink BioTechnologies LLC (San Diego, Calif.) and encapsulated in three different commercial LNP formulations, each comprising various ratios of an ionizable cationic lipid, a PEG lipid, and cholesterol. The LNP-encapsulated mRNA was administered to CD-1 mice by IV injection at a dose of 1.0 mg/kg. Livers were harvested 6 days after administration. Prior to organ collection, animals were perfused with saline. Whole-liver genomic DNA (gDNA) was isolated and the frequency of insertion/deletion (indel) mutations in the Cmah gene were determined using a T7 endonuclease I (T7E) assay and deep sequencing. In the T7E assay, the genomic region containing the Cmah recognition sequence was PCR amplified, resulting in a heterogenous mix of wild-type and mutant amplified alleles. The PCR product was denatured and allowed to slowly reanneal, allowing for the formation of heteroduplexes between wild-type and mutant alleles. Such heteroduplexes are susceptible to cleavage by the T7 endonuclease I, which cuts at mismatches. When the T7E-cleaved products are visualized on a gel, multiple bands are present due to T7E cleavage of heteroduplexes, whereas a single band is present in wild-type samples. The ratio of cleaved to uncleaved product provides a measure of the level of nuclease cleavage activity.

Results

Figure 15:
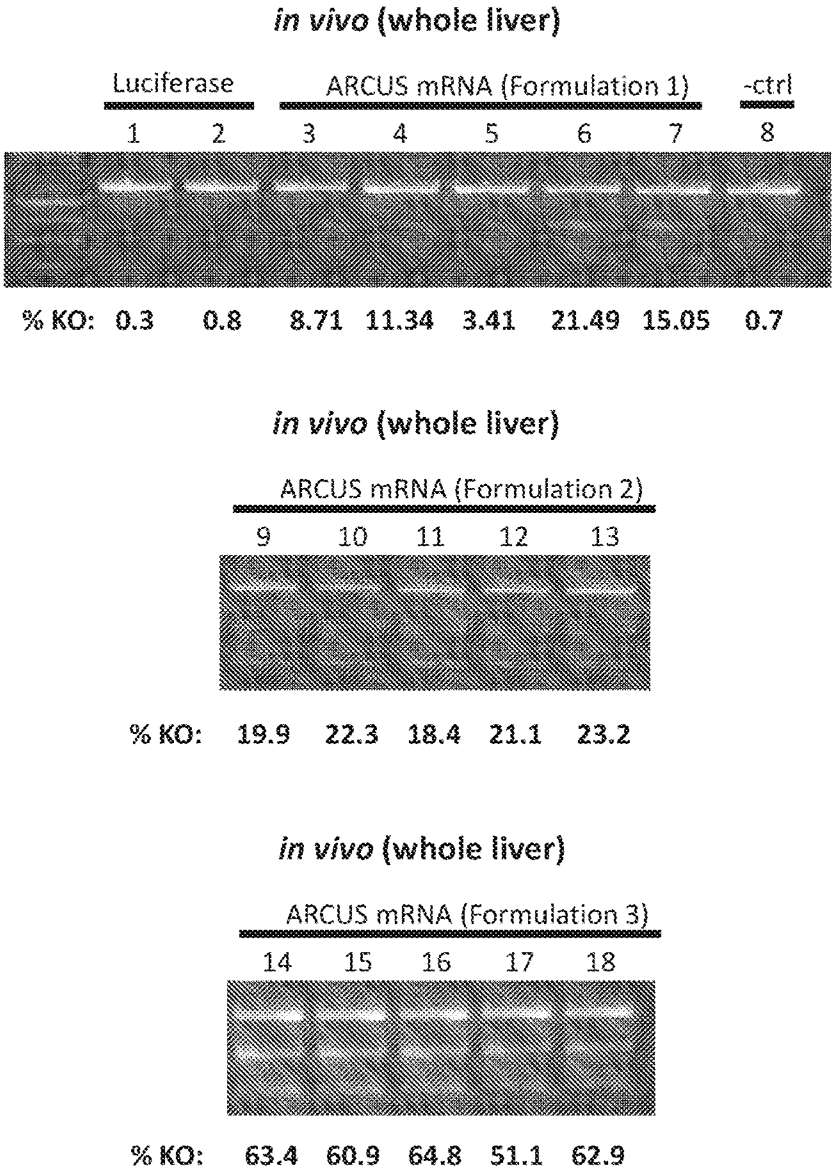
FIG. 15. Delivery of lipid nanoparticle-encapsulated mRNA to liver. An engineered meganuclease was developed which has specificity for a recognition sequence in the mouse CMP-NeuAc hydrolase (Cmah) gene, which is expressed in the mouse liver. ARCA-capped mRNA encoding the Cmah meganuclease was encapsulated in three different commercial LNP formulations. The LNP-encapsulated mRNA was administered to CD-1 mice by IV injection and livers were harvested 6 days later. Whole-liver genomic DNA (gDNA) was isolated and the frequency of insertion/deletion (indel) mutations in the Cmah gene were determined using a T7 endonuclease I (T7E) assay and deep sequencing.

The results of the present study are presented in FIG. 15. As shown in lanes 1 and 2, gDNA obtained from control mice, which were administered LNP-encapsulated mRNA encoding luciferase, showed no evidence of cleavage at the Cmah recognition sequence. The cleaved:uncleaved ratio observed in the luciferase mRNA-treated animals was comparable to the ratio observed in animals that were administered no mRNA (lane 8). By contrast, lanes 3-7 and 9-18 each demonstrate modification at the Cmah recognition sequence when animals were administered LNP-encapsulated mRNA encoding a Cmah meganuclease, as indicated by the presence of multiple bands in each lane. Deep sequencing was also performed on gDNA obtained from each liver in order to confirm and quantitate the percentage of gene modification at the Cmah recognition sequence. Percentages obtained by deep sequencing are shown in FIG. 15 beneath each lane as % KO. Lanes 3-7 show modifications ranging from 3.41% to 21.49% in replicate animals administered LNP formulation #1. Lanes 9-13 show modifications ranging from 18.4% to 23.2% in replicate animals administered LNP formulation #2. Lanes 14-18 show modifications ranging from 51.1% to 64.8% in replicate animals administered LNP formulation #3.

Conclusions

This study clearly demonstrates that mRNA encoding an engineered meganuclease, such as the HBV-specific meganucleases of the invention, can be encapsulated in an LNP, delivered to target liver cells (i.e., hepatocytes) in vivo, and can induce gene editing at the targeted recognition sequence in the genome.

What is claimed:

1. A recombinant adeno-associated viral (AAV) vector comprising a polynucleotide, wherein said polynucleotide comprises a nucleic acid sequence encoding an engineered meganuclease, wherein said engineered meganuclease binds and cleaves a recognition sequence consisting of SEQ ID NO: 16, wherein said engineered meganuclease comprises a first subunit and a second subunit, wherein said first subunit binds a first recognition half-site of said recognition sequence, wherein said second subunit binds a second recognition half-site of said recognition sequence, wherein said engineered meganuclease comprises an amino acid sequence having at least 96% sequence identity to SEQ ID NO: 33, and wherein said nucleic acid sequence encoding said engineered meganuclease is operably linked to a promoter.

2. The recombinant AAV vector of claim 1, wherein said recombinant AAV vector comprises serotype 2, 8, or 9.

3. The recombinant AAV vector of claim 1, wherein said recombinant AAV vector is serotype 8.

4. The recombinant AAV vector of claim 1, wherein said recombinant AAV vector is a self-limiting AAV vector.

5. The recombinant AAV vector of claim 1, wherein said recombinant AAV vector is a self-complementary AAV vector.

6. The recombinant AAV vector of claim 1, wherein said first subunit comprises an amino acid sequence having at least 96% sequence identity to residues 198-344 of SEQ ID NO: 33, and wherein said second subunit comprises an amino acid sequence having at least 96% sequence identity to residues 7-153 of SEQ ID NO: 33.

7. The recombinant AAV vector of claim 1, wherein said first subunit comprises residues 198-344 of SEQ ID NO: 33.

8. The recombinant AAV vector of claim 1, wherein said second subunit comprises residues 7-153 of SEQ ID NO: 33.

9. The recombinant AAV vector of claim 1, wherein said engineered meganuclease comprises the amino acid sequence of SEQ ID NO: 33.

10. The recombinant AAV vector of claim 1, wherein said promoter is a liver-specific promoter.

11. The recombinant AAV vector of claim 1, wherein said recombinant AAV vector is serotype 8, and wherein said recombinant AAV vector is a self-complementary AAV vector.

12. The recombinant AAV vector of claim 1, wherein said recombinant AAV vector is serotype 8, and wherein said promoter is a liver-specific promoter.

13. The recombinant AAV vector of claim 1, wherein said recombinant AAV vector is serotype 8, wherein said promoter is a liver-specific promoter, and wherein said recombinant AAV vector is a self-complementary AAV vector.

* * * * *